US007919279B2

(12) United States Patent
Trachtenberg et al.

(10) Patent No.: US 7,919,279 B2

(45) Date of Patent: Apr. 5, 2011

(54) METHODS AND COMPOSITIONS FOR KIR GENOTYPING

(75) Inventors: Elizabeth A. Trachtenberg, Oakland, CA (US); Kathleen Houtchens, Oakland, CA (US); Robert J. Nichols, Oakland, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 0 days.

(21) Appl. No.: 12/088,229

(22) PCT Filed: Sep. 21, 2006

(86) PCT No.: PCT/US2006/037279

§ 371 (c)(1),
(2), (4) Date: May 12, 2008

(87) PCT Pub. No.: WO2007/041067

PCT Pub. Date: Apr. 12, 2007

(65) Prior Publication Data

US 2008/0213787 A1 Sep. 4, 2008

Related U.S. Application Data

(60) Provisional application No. 60/722,673, filed on Sep. 29, 2005.

(51) Int. Cl.
*C12P 19/34* (2006.01)
*C07H 21/04* (2006.01)

(52) U.S. Cl. .................................... 435/91.2; 536/24.33

(58) Field of Classification Search ........................ None
See application file for complete search history.

(56) References Cited

U.S. PATENT DOCUMENTS

| | | | | |
|---|---|---|---|---|
| 5,777,324 | A | 7/1998 | Hillenkamp | |
| 6,104,028 | A | 8/2000 | Hunter et al. | |
| 6,111,251 | A | 8/2000 | Hillenkamp | |
| 6,258,538 | B1 | 7/2001 | Koster et al. | |
| 6,300,076 | B1 | 10/2001 | Koster | |
| 6,423,966 | B2 | 7/2002 | Hillenkamp et al. | |
| 6,500,621 | B2 | 12/2002 | Koster | |
| 6,558,902 | B1 | 5/2003 | Hillenkamp | |
| 6,569,385 | B1 | 5/2003 | Little et al. | |
| 6,706,530 | B2 | 3/2004 | Hillenkamp | |
| 6,723,564 | B2 | 4/2004 | Hillenkamp | |
| 2001/0016320 | A1* | 8/2001 | He et al. | 435/6 |
| 2004/0146866 | A1* | 7/2004 | Fu | 435/6 |

OTHER PUBLICATIONS

Norman et al., SNP haplotypes and allele frequencies show evidence for disruptive and balancing selection in the human leukocyte receptor complex, Immunogenetics (2004) 56: 225-237.*
Parham et al., Alloreactive Killer Cells: Hindrance and Help for Haematopoietic Transplants, Nature Reviews, Immunology vol. 3, Feb. 2003, pp. 108-122.*
Parham et al., Text Version, Alloreactive Killer Cells: Hindrance and Help for Haematopoietic Transplants, Nature Reviews, Immunology vol. 3, Feb. 2003, pp. 108-122.*
Tost et al., Molecular haplotyping at high throughput, Nucleic Acids Research, 2002, vol. 30 No. 19 e96, pp. 1-8.*
Stratagene, 1988 catalog, p. 39.*
Shilling et al., Allelic Polymorphism Synergizes with Variable Gene Content to Individualize Human KIR Genotype, The Journal of Immunology, 2002, 168: 2307-2315.*
Uhrberg et al., Immunity, 7:753-763 (1997).
Gomez-Lozano et al., Tissue Antigens, 59:184-193 (2002).
Cook et al., Hum. Immunology, 64:567-571 (2003).
Crum et al., Tissue Antigens, 56:313-326 (2000).
Middleton et al., Transplant Immunology, 10:147-164 (2002).
Ross et al., Nature Biotech., 16:1347-1351 (1998).
Fei et al., Rapid Comm. Mass. Spec., 14:950-959 (2000).
Fei et al., NAR 26(11):2827-2828 (1998).
Amexis et al., PNAS 98(21)12097-12102 (2001).
Li et al., Electrophoresis 20:1258-1265 (1999).
Buetow et al., PNAS 98(2)581-584 (2001).
Storm et al., Methods in Mol. Biol., 212:241-262 (2003).
Parham, Immunology Lett. 92:11-13 (2004).
Parham, Nature Reviews, Immunology, 3:108-122 (2003).
Biassoni et al. 1996 J Exp Med 184:645-650.
Carrington et al. The KIR Gene Cluster 2003: National Library of Medicine (U.S.), National Center for Biotechnology Information, Bethesda, MD.
Middleton et al. (2002) Transplant Immunol 10:147-164.

* cited by examiner

*Primary Examiner* — Mark Staples
(74) *Attorney, Agent, or Firm* — Edward J. Baba; Bozicevic, Field & Francis LLP

(57) ABSTRACT

The present invention provides methods for single nucleotide polymorphism (SNP)-based killer cell immunoglobulin-like receptor (KIR) gene cluster genotyping using the matrix-assisted laser desorption/ionization time-of-flight (MALDI-TOF) mass spectrometer. In general, the methods involve amplifying a plurality of target sequences of a plurality of KIR genes, and detecting the presence or absence of a plurality of single SNPs of the plurality of KIR genes by MALDI-TOF mass spectrometry. The invention also features compositions, including arrays of capture primers and optionally extension primers on a substrate surface, and kits, for use in the methods of the invention.

12 Claims, 82 Drawing Sheets

FIG. 1A

```
                      | Exon 1                                           Exon 1 | Exon 2                                                   Exon 2 |
                      |  -20                                                    |-10                                                     1        |
                      |   |                                                     | |                                                      |        |
consensus               ATG TCG CTC ATG GTC GTC AGC ATG GCG TGT GTT G | GG TTC TTC TTG CTG CAG GGG GCC TGG CCA CAC GAG G |
                   Uhrberg 2DL1a-5' ->
3DL2*001Ref             ATG TCG CTC ACG GTC GTC AGC ATG GCG TGC GTT G | GG TTC TTC TTG CTG CAG GGG GCC TGG CCA CTC ATG G |
2DL1*001                --- --- --- TT- --- --- --- --- --- --T --- - | -- --- --- --- --- --- --- --- --- --- -AT GA- - |
2DL1*002                --- --- --- TT- T-- --- --- --- --- --T --- - | -- --- --- --- --- --- --- --- --- --- -AT GA- - |
2DL1*00301              --- --- --- TT- --- --- --- --- --- --T --- - | -- --- --- --- --- --- --- --- --- --- -AT GA- - |
2DL1*00302              --- --- --- TT- --- --- --- --- --- --T --- - | -- --- --- --- --- --- --- --- --- --- -AT GA- - |
2DL1*004                --- --- --- TT- --- --- --- --- --- --T --- - | -- --- --- --- --- --- --- --- --- --- -AT GA- - |
2DL1*005                *** *** *** *** *** *** *** *** *** *** *** * | ** *** *-- --- --- --- --- --- --- --- -AT GA- - |

2DL2*001                --- --- --- -T- --- --- --- --- --- --T --- - | -- --- --- --- --- --- --- --- --- --- -AT GA- - |
2DL2*002                --- --- --- -T- --- --- --- --- --- --T --- - | -- --- --- --- --- --- --- --- --- --- -AT GA- - |
2DL2*003                *** *** *** *** *** *** *** *** *** *** *** * | ** *** *-- --- --- --- --- --- --- --- -AT GA- - |
2DL2*004                *** *** *** *** *** *** *** *** *** *** *** * | ** *** *-- --- --- --- --- --- --- --- -AT GA- - |

2DL3*001                --- --- --- -T- --- --- --- --- -T- --T --- - | -- --- --- --- --- --- --- --- --- --- -AT GA- - |
2DL3*002                --- --- --- -T- --- --- --- --- -T- --T --- - | -- --- --- --- --- --- --- --- --- --- -AT GA- - |
2DL3*003                --- --- --- -T- --- --- --- --- -T- --T --- - | -- --- --- --- --- --- --- --- --- --- -AT GA- - |
2DL3*004                --- --- --- -T- --- --- --- --- --- --T --- - | -- --- --- --- --- --- --- --- --- --- -AT GA- - |
2DL3*005                --- --- --- -T- --- --- --- --- --- --T --- - | -- --- --- --- --- --- --- --- --- --- -AT GA- - |
2DL3*006                *** *** *** *** *** *** *** *** *** *** *** * | ** *** *-- --- --- --- --- --- --- --- -AT GA- - |


3DL2*001Ref             ATG TCG CTC ACG GTC GTC AGC ATG GCG TGC GTT G | GG TTC TTC TTG CTG CAG GGG GCC TGG CCA CTC ATG G |
2DL4*00101      ATG TCC --- --A -C- --- --- A-- -T- C-- --A --T C-- - | -- --- --- --- GAC --- A-T -TG --- G-- -A- G-- - |
2DL4*00102      --- --- --- --A -C- --- --- A-- -T- C-- --A --T C-- - | -- --- --- --- GAC --- A-T -TG --- G-- -A- G-- - |
2DL4*00201      --- --- --- --A -C- --- --- A-- -T- C-- --A --T C-- - | -- --- --- --- GAC --- A-T -TG --- G-- -A- G-- - |
2DL4*00202      --- --- --- --A -C- --- --- A-- -T- C-- --A --T C-- - | -- --- --- --- GAC --- A-T -TG --- G-- -A- G-- - |
2DL4*003        --- --- --- --A -C- --- --- A-- -T- C-- --A --T C-- - | -- --- --- --- GAC --- A-T -TG --- G-- -A- G-- - |
2DL4*004        --- --- --- --A -C- --- --- A-- -T- C-- --A --T C-- - | -- --- --- --- GAC --- A-T -TG --- G-- -A- G-- - |
2DL4*005        --- --- --- --A -C- --- --- A-- -T- C-- --A --T C-- - | -- --- --- --- GAC --- A-T -TG --- G-- -A- G-- - |
2DL4*006        --- --- --- --A -C- --- --- A-- -T- C-- --A --T C-- - | -- --- --- --- GAC --- A-T -TG --- G-- -A- G-- - |
2DL4*007        --- --- --- --A -C- --- --- A-- -T- C-- --A --T C-- - | -- --- --- --- GAC --- A-T -TG --- G-- -A- G-- - |
```

FIG. 1C

```
                    40                                                    50
                     |                                                     |
consensus    AGG TTT AAC AAT TTC ATG CTA TAC AAA GAA GAC AGA ATC CAC GTT CCC ATC TTC CAT GGC AGA ATA TTC CAG GAG

3DL2*001Ref  GGG TTT AAC AAT TTC ATG CTG TAC AAA GAA GAC AGA AGC CAC GTT CCC ATC TTC CAC GGC AGA ATA TTC CAG GAG
2DL1*001     *** *** *** *** *** *** *** *** *** *** *** *** *** *** *** *** *** *** *** *** *** *** *** *** ***
2DL1*002     *** *** *** *** *** *** *** *** *** *** *** *** *** *** *** *** *** *** *** *** *** *** *** *** ***
2DL1*00301   *** *** *** *** *** *** *** *** *** *** *** *** *** *** *** *** *** *** *** *** *** *** *** *** ***
2DL1*00302   *** *** *** *** *** *** *** *** *** *** *** *** *** *** *** *** *** *** *** *** *** *** *** *** ***
2DL1*004     --- --- --- --C --- -GT --- --A --G --- --T G-G GTG -CT --C --T GAG C-- T-- AA- -T- --- --- TG- A-C
2DL1*005     *** *** *** *** *** *** *** *** *** *** *** *** *** *** *** *** *** *** *** *** *** *** *** *** ***

2DL2*001     --- --- --- --C --- -GT --- --- --G --- -GT G-G GTG -CT --C --T GAG C-- T-- AA- --- --- --- TG- A-C
2DL2*002     *** *** *** *** *** *** *** *** *** *** *** *** *** *** *** *** *** *** *** *** *** *** *** *** ***
2DL2*003     *** *** *** *** *** *** *** *** *** *** *** *** *** *** *** *** *** *** *** *** *** *** *** *** ***
2DL2*004     *** *** *** *** *** *** *** *** *** *** *** *** *** *** *** *** *** *** *** *** *** *** *** *** ***

2DL3*001     *** *** *** *** *** *** *** *** *** *** *** *** *** *** *** *** *** *** *** *** *** *** *** *** ***
2DL3*002     --- --- --- --C --- -GT --- --- --G --- -GT G-G GTG -CT --C --T GAG C-- T-- AA- --- --- --- TG- A-C
2DL3*003     *** *** *** *** *** *** *** *** *** *** *** *** *** *** *** *** *** *** *** *** *** *** *** *** ***
2DL3*004     *** *** *** *** *** *** *** *** *** *** *** *** *** *** *** *** *** *** *** *** *** *** *** *** ***
2DL3*005     --- --- --- --C --- -GT --- --- --G --- -GT G-G GTG -CT --C --T GAG C-- T-- AA- --- --- --- TG- A-C
2DL3*006     *** *** *** *** *** *** *** *** *** *** *** *** *** *** *** *** *** *** *** *** *** *** *** *** ***

                                                                    5' cap2DL4.D0.G->
consensus    AGG TTT AAC AAT TTC ATG CTA TAC AAA GAA GAC AGA ATC CAC GTT CCC ATC TTC CAT GGC AGA ATA TTC CAG GAG
                             Ig3 2DL4                                   Uhrberg 2DL4 5' ->
3DL2*001Ref  GGG TTT AAC AAT TTC ATG CTG TAC AAA GAA GAC AGA AGC CAC GTT CCC ATC TTC CAC GGC AGA ATA TTC CAG GAG
2DL4*00101   --- --- --- -TC --- -C- --- --- --G A-- --T G-G GT- -CT --C --T GAG C-- T-- AA- --- --- --- TG- A-C
2DL4*00102   --- --- --- -TC --- -C- --- --- --G A-- --T G-G GT- -CT --C --T GAG C-- T-- AA- --- --- --- TG- A-C
2DL4*00201   --- --- --- -TC --- -C- --- --- --G A-- --T G-G GT- -CT --C --T GAG C-- T-- AA- --- --- --- TG- A-C
2DL4*00202   --- --- --- -TC --- -C- --- --- --G A-- --T G-G GT- -CT --C --T GAG C-- T-- AA- --- --- --- TG- A-C
2DL4*003     --- --- --- -TC --- -C- --- --- --G A-- --T G-G GT- -CT --C --T GAG C-- T-- AA- --- --- --- TG- A-C
2DL4*004     --- --- --- -TC --- -C- --- --- --G A-- --T G-G GT- -CT --C --T GAG C-- T-- AA- --- --- --- TG- A-C
2DL4*005     --- --- --- -TC --- -C- --- --- --G A-- --T G-G GT- -CT --C --T GAG C-- T-- AA- --- --- --- TG- A-C
2DL4*006     --- --- --- -TC --- -C- --- --- --G A-- --T G-G GT- -CT --C --T GAG C-- T-- AA- --- --- --- TG- A-C
2DL4*007     --- --- --- -TC --- -C- --- --- --G A-- --T G-G GT- -CT --C --T GAG C-- T-- AA- --- --- --- TG- A-C
```

FIG. 1E

```
                                   (Pseudo)Exon 3  |  Exon 4
                 90                                |      100                                   110
                 |                                 |       |                                     |
consensus        CCC AGC AAC CCC GTG GTG ATC ATG GTC ACA G | GA ATC CAC AGA AAA CCT TCC CTC CTG GCC CAC CCA GGT

3DL2*001Ref      CCC AGC AAC CCC CTG GTG ATC ATG GTC ACA G | GA AAC CAC AGA AAA CCT TCC CTC CTG GCC CAC CCA GGG
2DL1*001         *** *** *** *** *** *** *** *** *** *** * | -- GT- --- --- --- --- --- --- --- --- --- --- --T
2DL1*002         *** *** *** *** *** *** *** *** *** *** * | -- GT- --- --- --- --- --- --- --- --- --- --- --T
2DL1*00301       *** *** *** *** *** *** *** *** *** *** * | -- GT- --- --- --- --- --- --- --- --- --- --- --T
2DL1*00302       *** *** *** *** *** *** *** *** *** *** * | -- GT- --- --- --- --- --- --- --- --- --- --- --T
2DL1*004         --- --- --- --- --- -A- --- -C- --- --- - | -- GT- --- --- --- --- --- --- --- --- --- --- --T
2DL1*005         *** *** *** *** *** *** *** *** *** *** * | -- GT- --- --- --- --- --- --- --- --- --- --- --T

consensus        CCC AGC AAC CCC GTG GTG ATC ATG GTC ACA G | GA ATC CAC AGA AAA CCT TCC CTC CTG GCC CAC CCA GGT

2DL2*001         --- --- --- --- --- --- --- G-- --- -T- - | -- GT- --- --- --- --- --- --- --- --- --- --- --T
2DL2*002         *** *** *** *** *** *** *** *** *** *** * | -- GT- --- --- --- --- --- --- --- --- --- --- --T
2DL2*003         *** *** *** *** *** *** *** *** *** *** * | -- GT- --- --- --- --- --- --- --- --- --- --- --T
2DL2*004         *** *** *** *** *** *** *** *** *** *** * | -- GT- --- --- --- --- --- --- --- --- --- --- --T

                                                                  5' cap2DL3.2DL2.D1.S->
consensus        CCC AGC AAC CCC GTG GTG ATC ATG GTC ACA G | GA ATC CAC AGA AAA CCT TCC CTC CTG GCC CAC CCA GGT

3DL2*001Ref      CCC AGC AAC CCC CTG GTG ATC ATG GTC ACA G | GA AAC CAC AGA AAA CCT TCC CTC CTG GCC CAC CCA GGG
2DL3*001         *** *** *** *** *** *** *** *** *** *** * | -- GT- --- --- --- --- --- --- --- --- --- --- --T
2DL3*002         --- --- --- --- --- --- --- G-- --- -T- - | -- GT- --- --- --- --- --- --- --- --- --- --- --T
2DL3*003         *** *** *** *** *** *** *** *** *** *** * | -- GT- --- --- --- --- --- --- --- --- --- --- --T
2DL3*004         *** *** *** *** *** *** *** *** *** *** * | -- GT- --- --- --- --- --- --- -G- --- --- --- --T
2DL3*005         --- --- --- --- --- --- --- G-- --- -T- - | -- GT- --- --- --- --- --- --- -G- --- --- --- --T
2DL3*006         *** *** *** *** *** *** *** *** *** *** * | -- GT- --- --- --- --- --- --- --- --- --- --- --T

2DL4*00101       --- --- --- --- --- --- --- --- --- --- - | .. ... ... ... ... ... ... ... ... ... ... ... ...
2DL4*00102       --- --- --- --- --- --- --- --- --- --- - | .. ... ... ... ... ... ... ... ... ... ... ... ...
2DL4*00201       --- --- --- --- --- --- --- --- --- --- - | .. ... ... ... ... ... ... ... ... ... ... ... ...
2DL4*00202       --- --- --- --- --- --- --- --- --- --- - | .. ... ... ... ... ... ... ... ... ... ... ... ...
2DL4*003         --- --- --- --- --- --- --- --- --- --- - | .. ... ... ... ... ... ... ... ... ... ... ... ...
2DL4*004         --- --- --- --- --- --- --- --- --- --- - | .. ... ... ... ... ... ... ... ... ... ... ... ...
2DL4*005         --- --- --- --- --- --- --- --- --- --- - | .. ... ... ... ... ... ... ... ... ... ... ... ...
2DL4*006         --- --- --- --- --- --- --- --- --- --- - | .. ... ... ... ... ... ... ... ... ... ... ... ...
2DL4*007         --- --- --- --- --- --- --- --- --- --- - | .. ... ... ... ... ... ... ... ... ... ... ... ...
```

FIG. 1H

```
         170                                    180                                    190
          |                                      |                                      |
                 <-3' cap2DL1.2DS1.D1.S.tri                    Ig2 2DL1
CAT GAC CTT GCA GGG ACC TAC AGA TGC TAC GGT TCT GTT ACT CAC TCC CCC TAT CAG TTG TCA GCT CCC AGT GAC CCT CTG GAC ATC GTG
                                                               Cook 2DL1-a,b 5' ->
<-2DL1.2DS1.D1.S.tri                    Norman 2DL1vPJN -> Uhrberg 2DL1-b 5' ->   <- Uhrberg 2DL1-a 3'
CCT GTC CTT GCA GGA ACC TAC AGA TGT TAT GGT TCT GTT CCT CAC TCC CCC TAT CAG TTG TCA GCT CCC AGT GAC CCC CTG GAC ATC GTG
-AA -A- --G --- --G --- --- --- --C --C --- --- --- A-- --- --- --- --- --- G-- --- --- --- --- --- --T --- --- --- ---
-AA -A- --G --- --G --- --- --- --C --C --- --- --- A-- --- --- --- --- --- G-- --- --- --- --- --- --T --- --- --- ---
-AA -A- --G --- --G --- --- --- --C --C --- --- --- A-- --- --- --- --- --- G-- --- --- --- --- --- --T --- --- --- ---
-AA -A- --G --- --G --- --- --- --C --C --- --- --- A-- --- --- --- --- --- G-- --- --- --- --- --- --T --- --- --- ---
-AA -A- --G --- --G --- --- --- --C --C --- --- --- A-- --- --- --- --- --- G-- --- --- --- --- --- --T --- --- --- ---
-AA -A- --G --- --G --- --- --- --C --C --- --- --- A-- --- --- --- --- --- G-- --- --- --- --- --- --T --- --- --- ---
                                                                                <-3' cap2DL2.001.2.3.D1.G
CAT GAC CTT GCA GGG ACC TAC AGA TGC TAC GGT TCT GTT ACT CAC TCC CCC TAT CAG TTG TCA GCT CCC AGT GAC CCT CTG GAC ATC GTG

CCT GTC CTT GCA GGA ACC TAC AGA TGT TAT GGT TCT GTT CCT CAC TCC CCC TAT CAG TTG TCA GCT CCC AGT GAC CCC CTG GAC ATC GTG
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C

CAT GAC CTT GCA GGG ACC TAC AGA TGC TAC GGT TCT GTT ACT CAC TCC CCC TAT CAG TTG TCA GCT CCC AGT GAC CCT CTG GAC ATC GTG
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C
-AA -A- --- --- --G --- --- --- --C --C --- --- --- A-- --- --- --- --- --- --- --- --- --- --- --- --T --- --- --- --C
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
... ... ... ... ... ... ... ... ... ... ... ... ... ... ... ... ... ... ... ... ... ... ... ... ... ... ... ... ... ... ...
```

FIG. 1I

```
                Exon 4  | Exon 5
                        |    200                                      210
                        |     |                                        |
consensus       ATC ACA G | GT CTA TAT GAG AAA CCT TCT CTC TCA GCC CAG CCG GGC CCC ACG GTT CAG GCA GGA
3DL2*001Ref     ATC ACA G | GT CTA TAT GAG AAA CCT TCT CTC TCA GCC CAG CCG GGC CCC ACG GTT CAG GCA GGA
2DL1*001        --- -T- - | -- --- --- --- --- --- --- --- --- --- --- --- --- --- --- --- -T- --- ---
2DL1*002        --- -T- - | -- --- --- --- --- --- --- --- --- --- --- --- --- --- --- --- -T- --- ---
2DL1*00301      --- -T- - | -- --- --- --- --- --- --- --- --- --- --- -T- --- --- --- --- -T- --- ---
2DL1*00302      --- -T- - | -- --- --- --- --- --- --- --- --- --- --- -T- --- --- --- --- -T- --- ---
2DL1*004        --- -T- - | -- --- --- --- --- --- --- --- --- --- --- --- --- --- --- --- -T- --- ---
2DL1*005        --- -T- - | -- --- --- --- --- --- --- --- --- --- --- -T- --- --- --- --- -T- --- ---

consensus       ATC ACA G | GT CTA TAT GAG AAA CCT TCT CTC TCA GCC CAG CCG GGC CCC ACG GTT CAG GCA GGA

3DL2*001Ref     ATC ACA G | GT CTA TAT GAG AAA CCT TCT CTC TCA GCC CAG CCG GGC CCC ACG GTT CAG GCA GGA
2DL2*001        --- --- - | -- --- --- --- --- --- --- --- --- --- --- --- --- --- --- --- -T- --- ---
2DL2*002        --- --- - | -- --- --- --- --- --- --- --- --- --- --- --- --- --- --- --- -T- --- ---
2DL2*003        --- --- - | -- --- --- --- --- --- --- --- --- --- --- --- --- --- --- --- -T- --- ---
2DL2*004        --- --- - | -- --- --- --- --- --- --- --- --- --- --- --- --- --- --- --- -T- --- ---

3DL2*001Ref     ATC ACA G | GT CTA TAT GAG AAA CCT TCT CTC TCA GCC CAG CCG GGC CCC ACG GTT CAG GCA GGA
2DL3*001        --- --- - | -- --- --- --- --- --- --- --- --- --- --- --- --- --- --- --- -T- --- ---
2DL3*002        --- --- - | -- --- --- --- --- --- --- --- --- --- --- --- --- --- --- --- -T- --- ---
2DL3*003        --- --- - | -- --- --- --- --- --- --- --- --- --- --- --- --- --- --- --- -T- --- ---
2DL3*004        --- --- - | -- --- --- --- --- --- --- --- --- --- --- --- --- --- --- --- -T- --- ---
2DL3*005        --- --- - | -- --- --- --- --- --- --- --- --- --- --- --- --- --- --- --- -T- --- ---
2DL3*006        --- --- - | -- --- --- --- --- --- --- --- --- --- --- --- --- --- --- --- -T- --- ---
                                          Cook 2DL4 5' ->
consensus       ATC ACA G | GT CTA TAT GAG AAA CCT TCT CTC TCA GCC CAG CCG GGC CCC ACG GTT CAG GCA GGA
                                               Igl 2DL4
3DL2*001Ref     ATC ACA G | GT CTA TAT GAG AAA CCT TCT CTC TCA GCC CAG CCG GGC CCC ACG GTT CAG GCA GGA
2DL4*00101      ... ... . | -- --- --- --- --- --- --G --T A-- --- -G- --- --- --- --- --- -GC A-- ---
2DL4*00102      ... ... . | -- --- --- --- --- --- --G --T A-- --- -G- --- --- --- --- --- -GC A-- ---
2DL4*00201      ... ... . | -- --- --- --- --- --- --G --T A-- --- -G- --- --- --- --- --- -GC --- ---
2DL4*00202      ... ... . | -- --- --- --- --- --- --G --T A-- --- -G- --- --- --- --- --- -GC --- ---
2DL4*003        ... ... . | -- --- --- --- --- --- --G --T A-- --- -G- --- --- --- --- --- -GC A-- ---
2DL4*004        ... ... . | -- --- --- --- --- --- --G --T A-- --- -G- --- --- --- --- --- -GC --- ---
2DL4*005        ... ... . | -- --- --- --- --- --- --G --T A-- --- -G- --- --- --- --- --- -GC --- ---
2DL4*006        ... ... . | -- --- --- --- --- --- --G --T A-- --- -G- -T- --- --- --- --- -GC --- ---
2DL4*007        ... ... . | -- --- --- --- --- --- --G --T A-- --- -G- --- --- --- --- --- -GC --- ---
```

FIG. 1K

```
                  250                                     260                                     270
                   |                                       |                                       |
              5' cap2DL1.D2.G.no004->
consensus     AAG GTC AAC GGA ACA TTC CAG GCC GAC TTT CCT CTG GGC CCT GCC ACC CAC GGA GGG ACC TAC AGA TGC TTC GGC TCT TTC CGT GAC
                                                 <- Cook 2DL1-b 3'
               <- GL 2DL1 Ra872 (continues above) <- Uhrberg 2DL1-b 3'                                   2DL1.D2.G.no004->  <-
3DL2*001Ref   AAG GTC AAC AGA ACA TTC CAG GCA GAC TTT CCT CTG GGC CCT GCC ACC CAC GGA GGG ACC TAC AGA TGC TTC GGC TCT TTC CGT GCC
2DL1*001      --- --- --- G-- --- --- --- --T --- --- --- --- --- --- --- --- --- --- --- --- --- --- --- --- --- --- --- -A- -A-
2DL1*002      --- --- --- G-- --- --- --- --T --- --- --- --- --- --- --- --- --- --- --- --- --- --- --- --- --- --- --- -A- -A-
2DL1*00301    --- --- --- G-- --- --- --- --T --- --- --- --- --- --- --- --- --- --- --- --- --- --- --- --- --- --- --- -A- -A-
2DL1*00302    --- --- --- G-- --- --- --- --T --- --- --- --- --- --- --- --- --- --- --- --- --- --- --- --- --- --- --- -A- -A-
              Igl 2DS1aR                      <- Cook KIR 2DL1uhr 3', Norman   Igl 2DS1bR
2DL1*004      --- --- --- G-- --- --- --- --C A-- --- --- --- --- --- --- --- --T --- --- --- --- --- --- --- --- --- --- --- -A-
2DL1*005      --- --- --- G-- --- --- --- --T --- --- --- --- --- --- --- --- --- --- --- --- --- --- --- --- --- --- --- -A- -A-
                 <-3' cap2DL2.D2.S
consensus     AAG GTC AAC GGA ACA TTC CAG GCC GAC TTT CCT CTG GGC CCT GCC ACC CAC GGA GGG ACC TAC AGA TGC TTC GGC TCT TTC CGT GAC
                                                          Igl 2DS5n
3DL2*001Ref   AAG GTC AAC AGA ACA TTC CAG GCA GAC TTT CCT CTG GGC CCT GCC ACC CAC GGA GGG ACC TAC AGA TGC TTC GGC TCT TTC CGT GCC
2DL2*001      --- --- --- G-- --- --- --- --C --- --- --- --- --- --- --- --- --- --- --A --- --- --- --- --- --- --- --- --- -A-
2DL2*002      --- --- --- G-- --- --- --- --C --- --- --- --- --- --- --- --- --- --- --A --- --- --- --- --- --- --- --- --- -A-
2DL2*003      --- --- --- G-- --- --- --- --C --- --- --- --- --- --- --- --- --- --- --A --- --- --- --- --- --- --- --- --- -A-
2DL2*004      --- --- --- G-- --- --- --- --C --- --- --- --- -A- --- --- --- --- --- --A --G --- --- --- --- --- --- --- --- -A-

2DL3*001      --- --- --- G-- --- --- --- --C --- --- --- --- --- --- --- --- --- --- --A --- --- --- --- --- --- --- --- --- -A-
2DL3*002      --- --- --- G-- --- --- --- --C --- --- --- --- --- --- --- --- --- --- --A --- --- --- --- --- --- --- --- --- -A-
2DL3*003      --- --- --- G-- --- --- --- --C --- --- --- --- --- --- --- --- --- --- --A --- --- --- --- --- --- --- --- --- -A-
2DL3*004      --- --- --- G-- --- --- --- --C --- --- --- --- --- --- --- --- --- --- --A --- --- --- --- --- --- --- --- --- -A-
2DL3*005      --- --- --- G-- --- --- --- --C --- --- --- --- --- --- --- --- --- --- --- --- --- --- --- --- --- --- --- --- -A-
2DL3*006      --- --- --- G-- --- --- --- --C --- --- --- --- --- --- --- --- --- --- --A --- --- --- --- --- --- --- --- --- -A-
                                                                                                  <- GL 2DL4 R939
3DL2*001Ref   AAG GTC AAC AGA ACA TTC CAG GCA GAC TTT CCT CTG GGC CCT GCC ACC CAC GGA GGG ACC TAC AGA TGC TTC GGC TCT TTC CGT GCC
2DL4*00101    -GC A-- --T G-- --- --- --- --C --- --C --- --- --T --- --- --- --- --- -A- --- --- --- --- --- --- --- --- -A- -GA
2DL4*00102    -GC A-- --T G-- --- --- --- --C --- --C --- --- --T --- --- --- --- --- -A- --- --- --- --- --- --- --- --- -A- -GA
2DL4*00201    -GC A-- --T G-- --- --- --- --C --- --C --- --- --T --- --- --- --- --- -A- --- --- --- --- --- --- --- --- -A- -GA
2DL4*00202    -GC A-- --T G-- --- --- --- --C --- --C --- --- --T --- --- --- --- --- -A- --- --- --- --- --- --- --- --- -A- -GA
2DL4*003      -GC A-- --T G-- --- --- --- --C --- --C --- --- --T --- --- --- --- --- -A- --- --- --- --- --- --- --- --- -A- -GA
2DL4*004      -GC A-- --T G-- --- --- --- --C --- --C --- --- --T --- --- --- --- --- -A- --- --- --- --- --- --- --- --- -A- -GA
2DL4*005      -GC A-- --T G-- --- --- --- --C --- --C --- --- --T --- --- --- --- --- -A- --- --- --- --- --- --- --- --- -A- -GA
2DL4*006      -GC A-- --T G-- --- --- --- --C --- --C --- --- --T --- --- --- --- --- -A- --- --- --- --- --- --- --- --- -A- -GA
2DL4*007      -GC A-- --T G-- --- --- --- --C --- --C --- --- --T --- --- --- --- --- -A- --- --- --- --- --- --- --- --- -A- -GA
```

FIG. 1L

```
                                                      Exon 5  |  Exon 6
 280                                  290                     |                    300
  |                                    |                      |                     |
 <-3' cap2DL1.D2.G.no004
TCT CCC TAC GAG TGG TCA AAC TCG AGT GAC CCA CTG CTT GTT TCT GTC ACA G | GA AAC CCT TCA AGT AGT TGG CCT

GL 2DL1 Ra957
CTG CCC TGC GTG TGG TCA AAC TCA AGT GAC CCA CTG CTT GTT TCT GTC ACA G | GA AAC CCT TCA AGT AGT TGG CCT
TCT --A -A- -A- --- --- --G --- --- --- --- --- --- --- --- --- --- - | -- --- --- --- -A- --- --- ---
TCT --A -A- -A- --- --- --G --- --- --- --- --- --- --- --- --- --- - | -- --- --- --- -A- --- --- ---
TCT --A -A- -A- --- --- --G --- --- --- --- --- --- --- --- --- --- - | -- --- --- --- -A- --- --- ---
TCT --A -A- -A- --- --- --G --- --- --- --- --- --- --- --- --- --- - | -- --- --- --- -A- --- --- ---

TCT --A -A- -A- --- --- --G --- --- --- --- --- --- --- --- --- --- - | -- --- --- --- -A- --- --- ---
TCT --A -A- -A- --- --- --G --- --- --- --- --- --- --- --- --- --- - | -- --- --- --- -A- --- --- ---

TCT CCC TAC GAG TGG TCA AAC TCG AGT GAC CCA CTG CTT GTT TCT GTC ACA G | GA AAC CCT TCA AGT AGT TGG CCT
                                           Uhrberg 2DL2-a 5' ->
CTG CCC TGC GTG TGG TCA AAC TCA AGT GAC CCA CTG CTT GTT TCT GTC ACA G | GA AAC CCT TCA AGT AGT TGG CCT
TCT --A -A- -A- --- --- --- --G --- --- --- --- --- --- --- --- -T- - | -- --- --- --- -A- --- --- ---
TCT --A -A- -A- --- --- --- --G --- --- --- --- --- --- --- --- -T- - | -- --- --- --- -A- --- --- ---
TCT --A -A- -A- --- --- --- --G --- --- --- --- --- --- --- --- --- - | -- --- --- --- -A- --- --- ---
TCT --A -A- -A- --- --- --- --G --- --- --- --- --- --- --- --- --- - | -- --- --- --- -A- --- --- ---

TCT --A -A- -A- --- --- --- --G --- --- --- --- --- --- --- --- --- - | -- --- --- --- -A- --- --- ---
TCT --A -A- -A- --- --- --- --G --- --- --- --- --- --- --- --- --- - | -- --- --- --- -A- --- --- -T-
TCT --A -A- -A- --- --- --- --G --- --- --- --- --- --- --- --- --- - | -- --- --- --- -A- --- --- ---
TCT --A -A- -A- --- --- --- --G --- --- --- --- --- --- --- --- --- - | -- --- --- --- -A- --- --- ---
TCT --A -A- -A- --- --- --- --G --- --- --- --- --- --- --- --- --- - | -- --- --- --- -A- --- --- ---
TCT --A -A- -A- --- --- --- --G --- --- --- --- --- --- --- --- --- - | -- --- --- --- -A- --- --- ---
 <- Cook 2DL4 3'
CTG CCC TGC GTG TGG TCA AAC TCA AGT GAC CCA CTG CTT GTT TCT GTC ACA G | GA AAC CCT TCA AGT AGT TGG CCT
TCT --- -A- -AA --- --- G-- G-G --- --- --- --- -C- --- --- --- --- - | -- --- --- --T --- --- --- ---
TCT --- -A- -A- --- --- G-- G-G --- --- --- --- -C- --- --- --- --- - | -- --- --- --T --- --- --- ---
TCT --- -A- -A- --- --- G-- C-G --- --- --- --- -C- --- --- --- --- - | -- --- --- --T --- --- --- ---
TCT --- -A- -A- --- --- G-- C-G --- --- --- --- -C- --- --- --- --- - | -- --- --- --T --- --- --- ---
TCT --- -A- -A- --- --- G-- G-G --- --- --- --- -C- --- --- --- --- - | -- --- --- --T --- --- --- ---
TCT --- -A- -A- --- --- G-- C-G --- --- --- --- -C- --- --- --- --- - | -- --- --- --T --- --- --- ---
TCT --- -A- -A- --- --- G-- C-G --- --- --- --- -C- --- --- --- --- - | -- --- --- --T --- --- --- ---
TCT --- -A- -A- --- --- G-- C-G --- --- --- --- -C- --- --- --- --- - | -- --- --- --T --- --- --- ---
TCT --- -A- -A- --- --- G-- C-G --- --- --- --- -C- --- --- --- --- - | -- --- --- --T --- --- --- ---
```

FIG. 1M

```
                                    Exon 6 | Exon 7
                                310        |                     320
                                 |         |                      |
consensus     TCA CCC ACT GAA CCA AGC TCC AAA ACT G | GT AAC CCC AGA CAC CTG CAT GTT CTG ATT GGG ACC TCA GTG GTC ATC ATC

3DL2*001Ref   TCA CCC ACA GAA CCA AGC TCC AAA TCT G | GT ATC TGC AGA CAC CTG CAT GTT CTG ATT GGG ACC TCA GTG GTC ATC TTC
2DL1*001      --- --- --T --- --- --- --- --- A-C - | -- -A- CC- C-- --- --- --C A-- --- --- --- --- --- --- --- --- A--
2DL1*002      --- --- --T --- --- --- --- --- A-C - | -- -A- CC- C-- --- --- --C A-- --- --- --- --- --- --- --- --- A--
2DL1*00301    --- --- --T --- --- --- --- --- A-G - | -- -A- CC- C-- --- --- --C A-- --- --- --- --- --- --- --- --- A--
2DL1*00302    --- --- --T --- --- --- --- --- A-C - | -- -A- CC- C-- --- --- --C A-- --- --- --- --- --- --- --- --- A--
2DL1*004      --- --- --T --- --- --- --- G-- A-C - | -- -A- CC- C-- --- --- --C A-- --- --- --- --- --- --- --- --- A--
2DL1*005      --- --- --T --- --- --- --- --- A-C - | -- -A- CC- C-- --- --- --C A-- --- --- --- --- --- --- --- --- A--

3DL2*001Ref   TCA CCC ACA GAA CCA AGC TCC AAA TCT G | GT ATC TGC AGA CAC CTG CAT GTT CTG ATT GGG ACC TCA GTG GTC ATC TTC
2DL2*001      --- --- --T --- --- --- --T --- A-C - | -- -A- CC- C-- --- --- --C A-- --- --- --- --- --- --- --- --- A--
2DL2*002      --- --- --T --- --- --- --T --- A-C - | -- -A- CC- C-- --- --- --C A-- --- --- --- --- --- --- --- --- A--
2DL2*003      --- --- --T --- --- --- --T --- A-C - | -- -A- CC- C-- --- --- --C A-- --- --- --- --- --- --- --- --- A--
2DL2*004      --- --- --T --- --- --- --- G-- A-C - | -- -A- CC- C-- --- --- --C A-- --- --- --- --- --- --- --- --- A--

                                                        5' cap2DL3.TC.S.INT->
consensus     TCA CCC ACT GAA CCA AGC TCC AAA ACT G | GT AAC CCC AGA CAC CTG CAT GTT CTG ATT GGG ACC TCA GTG GTC ATC ATC
                  Uhrberg 2DL3-a 5' ->
3DL2*001Ref   TCA CCC ACA GAA CCA AGC TCC AAA TCT G | GT ATC TGC AGA CAC CTG CAT GTT CTG ATT GGG ACC TCA GTG GTC ATC TTC
2DL3*001      --- --- --T --- --- --- --- G-- A-C - | -- -A- CC- --- --- --- --- --- --- --- --- --- --- --- --- --- A--
2DL3*002      --- --- --T --- --- --- --- G-- A-C - | -- -A- CC- --- --- --- --- --- --- --- --- --- --- --- --- --- A--
2DL3*003      --- --- --T --- --- --- --- G-- A-C - | -- -A- CC- --- --- --- --- --- --- --- --- --- --- --- --- --- A--
2DL3*004      --- --- --T --- --- --- --- G-- A-C - | -- -A- CC- -T- --- --- --- --- --- --- --- --- --- --- --- --- A--
2DL3*005      --- --- --T --- --- --- --- G-- A-C - | -- -A- CC- --- --- --- --- --- --- --- --- --- --- --- --- --- A--
2DL3*006      --- --- --T --- --- --- --- G-- A-C - | -- -A- CC- --- --- --- --- --- --- --- --- --- --- --- --- --- A--
```

FIG. 1Q

```
                                                        420                                     430
                                                         |                                       |
consensus    CCA AAT GCT GAG CCC AGA TCC AAA GTT GTC TCC TGC CCA TGA GCA CCA CAG TCA GGC CTT GAG GGG ATC TTC TAG

3DL2*001Ref  CCA AAT GCT GAG CCC AGA TCC AAA GTT GTC TCC TGC CCA CGA GCA CCA CAG TCA GGT CTT GAG GGG GTT TTC TAG
2DL1*001     --- --- --- --- T-- --- --- --- --- --- --- --- --- T-- *** *** *** *** *** *** *** *** *** *** ***
2DL1*002     --- --- --- --- T-- --- --- --- --- --- --- --- --- T-- *** *** *** *** *** *** *** *** *** *** ***
2DL1*00301   --- --- --- --- T-- --- --- --- --- --- --- --- --- T-- *** *** *** *** *** *** *** *** *** *** ***
2DL1*00302   --- --- --- --- T-- --- --- --- --- --- --- --- --- T-- *** *** *** *** *** *** *** *** *** *** ***
2DL1*004     --- --- --- --- T-- --- --- --- --- --- --- --- --- T-- *** *** *** *** *** *** *** *** *** *** ***
2DL1*005     --- --- --- --- T-- --- --- --- --- --- --- --- --- T-- *** *** *** *** *** *** *** *** *** *** ***

             <- Uhrberg 2DL2-a 3'
3DL2*001Ref  CCA AAT GCT GAG CCC AGA TCC AAA GTT GTC TCC TGC CCA CGA GCA CCA CAG TCA GGT CTT GAG GGG GTT TTC TAG
2DL2*001     --- --- --- --- T-- --- --- --- --- --- --- --- --- T-- *** *** *** *** *** *** *** *** *** *** ***
2DL2*002     --- --- --- --- T-- --- --- --- --- --- --- --- --- T-- *** *** *** *** *** *** *** *** *** *** ***
2DL2*003     --- --- --- --- T-- --- --- --- --- --- --- --- --- T-- *** *** *** *** *** *** *** *** *** *** ***
2DL2*004     --- -G- --- --- T-- --- --- --- --- --- --- --- --- T-- *** *** *** *** *** *** *** *** *** *** ***
                                           <- Cook 2DL3-a 3'
                                            <- GL 2DL3 Rt1375
                         NK2DL3/1350  <- Uhrberg 2DL3-a+b 3'
3DL2*001Ref  CCA AAT GCT GAG CCC AGA TCC AAA GTT GTC TCC TGC CCA CGA GCA CCA CAG TCA GGT CTT GAG GGG GTT TTC TAG
2DL3*001     --- --- --- --- --- T-- --- --- --- --- --- --- --- T-- *** *** *** *** *** *** *** *** *** *** ***
2DL3*002     --- --- --- --- --- T-- --- --- --- --- --- --- --- T-- *** *** *** *** *** *** *** *** *** *** ***
2DL3*003     --- --- --- --- --- T-- --- --- --- --- --- --- --- T-- *** *** *** *** *** *** *** *** *** *** ***
2DL3*004     --- --- --- --- --- T-- --- --- --- --- --- --- --- T-- *** *** *** *** *** *** *** *** *** *** ***
2DL3*005     --- --- --- --- --- T-- --- --- --- --- --- --- --- T-- *** *** *** *** *** *** *** *** *** *** ***
2DL3*006     --- --- --- --- --- T-- --- --- --- --- --- --- --- T-- *** *** *** *** *** *** *** *** *** *** ***
```

FIG. 2A

```
consensus      ATG TCG CTC ATG GTC GTC AGC ATG GCG TGT GTT G | GG TTC TTC TTG CTG CAG GGG GCC TGG CCA CAC GAG G |
                                                                           GL  2DL5sub Fa125 ->
3DL2*001Ref    ATG TCG CTC ACG GTC GTC AGC ATG GCG TGC GTT G | GG TTC TTC TTG CTG CAG GGG GCC TGG CCA CTC ATG G |
3DL2*001Ref    ATG TCG CTC ACG GTC GTC AGC ATG GCG TGC GTT G | GG TTC TTC TTG CTG CAG GGG GCC TGG CCA CTC ATG G |
2DL5A*001      --- --- --- -T- --- A-- --- --- --- --T --- - | -- --- --- --- --- --- --- --- --- A-- -AT GA- - |
2DL5B*002      --- --- --- -T- --- --- --- --- --- --T --- - | -- --- --- --- --- --- --- --- --- A-- -AT GA- - |
2DL5B*003      --- --- --- -T- --- --- --- --- --- --T --- - | -- --- --- --- --- --- --- --- --- --- -AT GA- - |
2DL5B*004      --- --- --- -T- --- --- --- --- --- -** *** * | -- --- --- --- --- --- --- --- --- A-- -AT GA- - |
2DL5(2DLXa)    --- --- --- -T- --- A-- --- --- --- --T --- - | -- --- --- --- --- --- --- --- --- A-- -AT GA- - |
2DL5(2DLXb)    --- --- --- -T- --- A-- --- --- --- --T --- - | -- --- --- --- --- --- --- --- --- A-- -AT GA- - |

2DS1*001       --- --- --- --- --- --- --- --- --- --T --- - | -- --- --- --- --- --- --- --- --- --- -AT GA- - |
2DS1*002       --- --- --- --- --- --- --- --- --- --T --- - | -- --- --- --- --- --- --- --- --- --- -AT GA- - |
2DS1*003       --- --- --- -T- --- --- --- --- --- --T --- - | -- --- --- --- --- --- --- --- --- --- -AT GA- - |
2DS1*004       *** *** *** *** *** *** *** *** *** *** *** * | ** *** *-- --- --- --- --- --- --- --- -AT GA- - |

2DS2*001       --- --- --- -T- --- --- --- --- --- --T --- - | -- --- --- --- --- --- --- --- --- --- -AT GA- - |
2DS2*002       --- --- --- -T- --- --- --- --- --- --T --- - | -- --- --- --- --- --- --- --- G-- --- -AT GA- - |
2DS2*003       --- --- --- -T- --- --- --- --- --- --T --- - | -- --- --- --- --- --- --- --- --- --- -AT GA- - |
2DS2*004       *** *** *** *** *** *** *** *** *** *** *** * | ** *** *-- --- --- --- --- --- --- --- -AT GA- - |
2DS2*005       --- --- --- -T- --- --- --- --- --- --T --- - | -- --- --- --- --- --- --- --- --- --- -AT GA- - |

2DS3*00101     --- --- --- -T- --- A-- --- --- --A --T --- - | -- --- --- -G- --- --- --- --- --- --- -AT GA- - |
2DS3*00102     --- --- --- -T- --- A-- --- --- --A --T --- - | -- --- --- -G- --- --- --- --- --- --- -AT GA- - |
2DS3*00103     --- --- --- -T- --- A-- --- --- --A --T --- - | -- --- --- -G- --- --- --- --- --- --- -AT GA- - |

consensus      ATG TCG CTC ATG GTC GTC AGC ATG GCG TGT GTT G | GG TTC TTC TTG CTG CAG GGG GCC TGG CCA CAC GAG G |
```

FIG. 2C

```
                                        40                                           50
                                        |                                            |
                                                                          5' cap2DL5sub2->
               <-3' cap2DL5sub1                                           5' cap2DL5sub3->
consensus      AGG TTT AAC AAT TTC ATG CTA TAC AAA GAA GAC AGA ATC CAC GTT CCC ATC TTC CAT GGC AGA ATA TTC CAG GAG
                   Ig3 2DL5
3DL2*001Ref    GGG TTT AAC AAT TTC ATG CTG TAC AAA GAA GAC AGA AGC CAC GTT CCC ATC TTC CAC GGC AGA ATA TTC CAG GAG
2DL5A*001      --- --- -C- -TC --- -GT --- --- --- --- --T G-G GTG -CT --C --T GAG C-- T-- AA- -A- --- --- TG- A--
2DL5B*002      --- --- -C- -TC --- -GT --- --- --- --- --T G-G GTG -CT --C --T GAG C-- T-- AA- -A- --- --- TG- A--
2DL5B*003      --- --- -C- -TC --- -GT --- --- --- --- --T G-G GTG -CT --C --T GAG C-- T-- AA- -A- --- --- TG- A--
2DL5B*004      --- --- -C- -TC --- -GT --- --- --- --- --T G-G GTG -CT --C --T GAG C-- T-- AA- -A- --- --- TG- A--
2DL5(2DLXa)    --- --- -C- -TC --- -GT --- --- --- --- --T G-G GTG -CT --C --T GAG C-- T-- AA- -A- --- --- TG- A--
2DL5(2DLXb)    --- --- -C- -TC --- -GT --- --- --- --- --T G-G GTG -CT --C --T GAG C-- T-- AA- -A- --- --- TG- A--

2DS1*001       *** *** *** *** *** *** *** *** *** *** *** *** *** *** *** *** *** *** *** *** *** *** *** *** ***
2DS1*002       --- --- --- --C --- -GT --- --A --G --- --T G-G GTG -CT --C --T GAG C-- T-- AA- -T- --- --- TG- A-C
2DS1*003       *** *** *** *** *** *** *** *** *** *** *** *** *** *** *** *** *** *** *** *** *** *** *** *** ***
2DS1*004       *** *** *** *** *** *** *** *** *** *** *** *** *** *** *** *** *** *** *** *** *** *** *** *** ***

2DS2*001       --- --- --- --C --- -GT --- --- --G --- -GT G-G GTG -CT --C --T GAG C-- T-- AA- --- --- --- TG- A-C
2DS2*002       *** *** *** *** *** *** *** *** *** *** *** *** *** *** *** *** *** *** *** *** *** *** *** *** ***
2DS2*003       *** *** *** *** *** *** *** *** *** *** *** *** *** *** *** *** *** *** *** *** *** *** *** *** ***
2DS2*004       *** *** *** *** *** *** *** *** *** *** *** *** *** *** *** *** *** *** *** *** *** *** *** *** ***
2DS2*005       *** *** *** *** *** *** *** *** *** *** *** *** *** *** *** *** *** *** *** *** *** *** *** *** ***

2DS3*00101     *** *** *** *** *** *** *** *** *** *** *** *** *** *** *** *** *** *** *** *** *** *** *** *** ***
2DS3*00102     *** *** *** *** *** *** *** *** *** *** *** *** *** *** *** *** *** *** *** *** *** *** *** *** ***
2DS3*00103     --- --- --- --C --- -GT --- --- --G --T --T G-G GTG -CT --C --T GAA CA- T-- AA- --- --- --- TG- A-A

consensus      AGG TTT AAC AAT TTC ATG CTA TAC AAA GAA GAC AGA ATC CAC GTT CCC ATC TTC CAT GGC AGA ATA TTC CAG GAG
```

FIG. 2E

```
                      <-3' cap2DL5sub2              <-3' cap2DL5sub3 (originates in intron)
consensus         CCC AGC AAC CCC GTG GTG ATC ATG GTC ACA G | GA ATC CAC AGA AAA CCT TCC CTC CTG GCC CAC CCA GGT
                                 2DL5sub3->
3DL2*001Ref       CCC AGC AAC CCC CTG GTG ATC ATG GTC ACA G | GA AAC CAC AGA AAA CCT TCC CTC CTG GCC CAC CCA GGG
                GL 2DL5sub Fg410 + Fcon410 ->   <- GL 2DL5sub Rg410 (originates in intron)
3DL2*001Ref       CCC AGC AAC CCC CTG GTG ATC ATG GTC ACA G | GA AAC CAC AGA AAA CCT TCC CTC CTG GCC CAC CCA GGG
2DL5A*001         --- --- --- --- --- --- --- G-- --- --- - | .. ... ... ... ... ... ... ... ... ... ... ... ...
2DL5B*002         --- --- --- --- --- --- --- G-- --- --- - | .. ... ... ... ... ... ... ... ... ... ... ... ...
2DL5B*003         --- --- --- --- --- --- --- --- --- --- - | .. ... ... ... ... ... ... ... ... ... ... ... ...
2DL5B*004         --- --- --- --- --- --- --- G-- --- --- - | .. ... ... ... ... ... ... ... ... ... ... ... ...
2DL5(2DLXa)       --- --- --- --- --- --- --- G-- --- --- - | .. ... ... ... ... ... ... ... ... ... ... ... ...
2DL5(2DLXb)       --- --- --- --- --- --- --- G-- --- --- - | .. ... ... ... ... ... ... ... ... ... ... ... ...

2DS1*001          *** *** *** *** *** *** *** *** *** *** * | -- GT- --- --- --- --- --- --- --- --- --- --- --T
2DS1*002          --- --- --- --- --- -A- --- -C- --- --- - | -- GT- --- --- --- --- --- --- --- --- --- --- --T
2DS1*003          *** *** *** *** *** *** *** *** *** *** * | -- GT- --- --- --- --- --- --- --- --- --- --- --T
2DS1*004          *** *** *** *** *** *** *** *** *** *** * | -- GT- --- --- --- --- --- --- --- --- --- --- --T

consensus         CCC AGC AAC CCC GTG GTG ATC ATG GTC ACA G | GA ATC CAC AGA AAA CCT TCC CTC CTG GCC CAC CCA GGT


3DL2*001Ref       CCC AGC AAC CCC CTG GTG ATC ATG GTC ACA G | GA AAC CAC AGA AAA CCT TCC CTC CTG GCC CAC CCA GGG
2DS2*001          --- --- --- --- --- --- --- G-- --- -T- - | -- GT- --- --- --- --- --- --- --- --- --- --- --T
2DS2*002          *** *** *** *** *** *** *** *** *** *** * | -- GT- --- --- --- --- --- --- --- --- --- --- --T
2DS2*003          *** *** *** *** *** *** *** *** *** *** * | -- GT- --- --- --- --- --- --- --- --- --- --- --T
2DS2*004          *** *** *** *** *** *** *** *** *** *** * | -- GT- --- --- --- --- --- --- --- --- --- --- --T
2DS2*005          *** *** *** *** *** *** *** *** *** *** * | -- GT- --- --- --- --- --- --- --- --- --- --- --T

consensus         CCC AGC AAC CCC GTG GTG ATC ATG GTC ACA G | GA ATC CAC AGA AAA CCT TCC CTC CTG GCC CAC CCA GGT

2DS3*00101        *** *** *** *** *** *** *** *** *** *** * | -- TT- -G- --- --- --- --- --- --- --- --- --- --T
2DS3*00102        *** *** *** *** *** *** *** *** *** *** * | -- TT- -G- --- --- --- --- --- --- --- --- --- --T
2DS3*00103        --- --- --- --- --- C-- --- --- --- --- - | -- TT- -G- --- --- --- --- --- --- --- --- --- --T
```

FIG. 2G

```
2DL5A*001       ... ... ... ... ... ... ... ... ... ... ... ... ... ... ... ... ... ... ... ... ... ... ... ... ... ...
2DL5B*002       ... ... ... ... ... ... ... ... ... ... ... ... ... ... ... ... ... ... ... ... ... ... ... ... ... ...
2DL5B*003       ... ... ... ... ... ... ... ... ... ... ... ... ... ... ... ... ... ... ... ... ... ... ... ... ... ...
2DL5B*004       ... ... ... ... ... ... ... ... ... ... ... ... ... ... ... ... ... ... ... ... ... ... ... ... ... ...
2DL5(2DLXa)     ... ... ... ... ... ... ... ... ... ... ... ... ... ... ... ... ... ... ... ... ... ... ... ... ... ...
2DL5(2DLXb)     ... ... ... ... ... ... ... ... ... ... ... ... ... ... ... ... ... ... ... ... ... ... ... ... ... ...
                                                                                    GL 2DS1 Fr621 ->
                                                                        Cook 2DS1-a 5' -> Uhrberg 2DS1 5' ->
3DL2*001Ref     GAC CCC TCA CGC CTC GTT GGA CAG ATC CAT GAT GGG GTC TCC AAG GCC AAC TTC TCC ATC GGT CCC TTG ATG CCT GTC
                                                                                            Ig2 2DS1 Agg
2DS1*001        --- A-T -TG --- --- A-- --- G-A CA- --- --- --- --- --- --- --- --- --- --- --- A-- -G- A-- -G- -AA -A-
2DS1*002        --- A-T -TG --- --- A-- --- G-A CA- --- --- --- --- --- --- --- --- --- --- --- A-- -G- A-- -A- -AA -A-
2DS1*003        --- A-T -TG --- --- A-- --- G-A CA- --C --- --- --- --- --- --- --- --- --- --- A-- -G- A-- -A- -AA -A-
2DS1*004        --- A-T -TG --- --- A-- --- G-A CA- --- --- --- --- --- --- --- --- --- --- --- A-- -G- A-- -A- -AA -A-
                                                                                            Ig2 2DS1 Aga2
                                                                <-3' Cap 2DS2.D1.G
consensus       GAC ACT TTG CGC CTC ATT GGA GAG CAC CAT GAT GGG GTC TCC AAG GCC AAC TTC TCC ATC GGT CCC ATG ATG CAT GAC
                    <-2DS2.D1.G
3DL2*001Ref     GAC CCC TCA CGC CTC GTT GGA CAG ATC CAT GAT GGG GTC TCC AAG GCC AAC TTC TCC ATC GGT CCC TTG ATG CCT GTC
2DS2*001        --- A-T -TG -A- --- A-- --- G-- CA- --- --- --- --- --- --- --- --- --- --- --- --- --- A-- --- -AA -A-
2DS2*002        --- A-T -TG -A- --- A-- --- G-- CA- --- --- --- --- --- --- --- --- --- --- --- --- --- A-- --- -AA -A-
2DS2*003        --- A-T -TG -A- --- A-- --- G-- CA- --- --- --- --- --- --- --- --- --- --- --- --- --- A-- --- -AA -A-
2DS2*004        --- A-T -TG -A- --- A-- --- G-- CA- --- --- --- --- --- --- --- --- --- --- --- --- --- A-- --- -AA -A-
2DS2*005        --- A-T -TG -A- --- A-- --- G-- CA- --- --- --- --- --- --- --- --- --- --- --- --- --- A-- --- -AA -A-
              Ig2 2DS2                                                 5' cap2DS3.D1.G->
consensus       GAC ACT TTG CGC CTC ATT GGA GAG CAC CAT GAT GGG GTC TCC AAG GCC AAC TTC TCC ATC GGT CCC ATG ATG CAT GAC


3DL2*001Ref     GAC CCC TCA CGC CTC GTT GGA CAG ATC CAT GAT GGG GTC TCC AAG GCC AAC TTC TCC ATC GGT CCC TTG ATG CCT GTC
2DS3*00101      --- A-T -TG --- --- A-- --- G-- CA- AT- --- --- --- --- --- --- --- --- --- --- --- -G- A-- -G- -AA -A-
2DS3*00102      --- A-T -TG --- --- A-- --- G-- CA- AT- --- --- --- --- --- --- --- --- --- --- --- -G- A-- -G- -AA -A-
2DS3*00103      --- A-T -TG --- --- A-- --- G-- CA- AT- --- --- --- --- --- --- --- --- --- --- --- -G- A-- -G- -AA -A-
```

FIG. 2I

```
                                                  <- GL 2DL5 Ra739
3DL2*001Ref     ATC ACA G | GT CTA TAT GAG AAA CCT TCT CTC TCA GCC CAG CCG GGC CCC ACG GTT CAG GCA GGA GAG AAC GTG ACC TTG TCC
2DL5A*001       ... ... . | -- --- -T- -G- --- --- --A --- --- --- --- --- --- --- --- --- -GC A-- --- --- --- --- --- --- ---
2DL5B*002       ... ... . | -- --- -T- -G- --- --- --A --- --- --- --- --- --- --- --- --- -GC A-- --- --- --- --- --- --- ---
2DL5B*003       ... ... . | -- --- -T- -G- --- --- --A --- --- --- --- --- --- --- --- --- -GC A-- --- --- --- --- --- --- ---
2DL5B*004       ... ... . | -- --- -T- -G- --- --- --A --- --- --- --- --- --- --- --- --- -GC A-- --- --- --- --- --- --- ---
2DL5(2DLXa)     ... ... . | -- --- -T- -G- --- --- --A --- --- --- --- --- --- --- --- --- -GC A-- --- --- --- --- --- --- ---
2DL5(2DLXb)     ... ... . | -- --- -T- -G- --- --- --A --- --- --- --- --- --- --- --- --- -GC A-- --- --- --- --- G-- --- ---
                                                                                         5' cap2DS1.D2.G->
consensus       ATC ACA G | GT CTA TAT GAG AAA CCT TCT CTC TCA GCC CAG CCG GGC CCC ACG GTT CAG GCA GGA GAG AGC GTG ACC TTG TCC
2DS1*001        --- -T- - | -- --- --- --- --- --- --- --- --- --- --- --- --- --- --- --- -T- --- --- --- --T --- --- --- ---
2DS1*002        --- -T- - | -- --- --- --- --- --- --- --- --- --- --- --- --- --- --- --- -T- --- --- --- --T --- --- --- ---
2DS1*003        --- -T- - | -- --- --- --- --- --- --- --- --- --- --- --- --- --- --- --- -T- --- --- --- --T --- --- --- ---
2DS1*004        --- -T- - | -- --- --- --- --- --- --- --- --- --- --- --- --- --- --- --- -T- --- --- --- --T --- --- --- ---
                             5' cap2DS2.D2.G->                                                            <-3' cap2DS2.D2.G
consensus       ATC ACA G | GT CTA TAT GAG AAA CCT TCT CTC TCA GCC CAG CCG GGC CCC ACG GTT CAG GCA GGA GAG AGC GTG ACC TTG TCC
                                                                                    <- GL 2DS2 Rt767, Cook 2DS2-a 3'
                                                                                    <- Uhrberg 2DS2 3'
                                                                   Cook 2DS2-b 5' -> Igl 2DS2   <-2DS2.D2.G
3DL2*001Ref     ATC ACA G | GT CTA TAT GAG AAA CCT TCT CTC TCA GCC CAG CCG GGC CCC ACG GTT CAG GCA GGA GAG AAC GTG ACC TTG TCC
3DL2*001Ref     ATC ACA G | GT CTA TAT GAG AAA CCT TCT CTC TCA GCC CAG CCG GGC CCC ACG GTT CAG GCA GGA GAG AAC GTG ACC TTG TCC
2DS2*001        --- --- - | -- --- --- --- --- --- --- --- --- --- --- --- --- --- --- --- TT- --- --- --- -G- --- --- --- ---
2DS2*002        --- --- - | -- --- --- --- --- --- --- --- --- --- --- --- --- --- --- --- TT- --- --- --- -G- --- --- --- ---
2DS2*003        --- --- - | -- --- --- --- --- --- --- --- --- --- --- --- --- --- --- --- TT- --- --- --- -G- --- --- --- ---
2DS2*004        --- --- - | -- --- --- --- --- --- --- --- --- --- --- --- --- --- --- --- TT- --- --- --- -G- --- --- --- ---
2DS2*005        --- --- - | -- --- --- --- --- --- --- --- --- --- --- --- --- --- --- --- TT- --- --- --- -G- --- --- --- ---
        <-3' cap2DS3.D1.G
consensus       ATC ACA G | GT CTA TAT GAG AAA CCT TCT CTC TCA GCC CAG CCG GGC CCC ACG GTT CAG GCA GGA GAG AGC GTG ACC TTG TCC
3DL2*001Ref     ATC ACA G | GT CTA TAT GAG AAA CCT TCT CTC TCA GCC CAG CCG GGC CCC ACG GTT CAG GCA GGA GAG AAC GTG ACC TTG TCC
2DS3*00101      --- --- - | -- --- --- --- --- --- --- --- --- --- --- --- --- --- --- --- -T- --- --- --- -G- --- --- --- ---
2DS3*00102      --- --- - | -- --- --- --- --- --- --- --- --- --- --- --- --- --- --- --- -T- --- --- --- -G- --- --- --- ---
2DS3*00103      --- --- - | -- --- --- --- --- --- --- --- --- --- --- --- --- --- --- --- -T- --- --- --- -G- --- --- --- ---
```

FIG. 2K

```
                                                                                              <- GL 2DL5sub Rc939
consensus      AAG GTC AAC GGA ACA TTC CAG GCC GAC TTT CCT CTG GGC CCT GCC ACC CAC GGA GGG ACC TAC AGA TGC TTC GGC TCT TTC CGT GAC TCT
                                                  5' cap2DL5.D2.G->          5' cap2DL5sub4->              <- GL 2DL5sub Rcon947
consensus      AAG GTC AAC GGA ACA TTC CAG GCC GAC TTT CCT CTG GGC CCT GCC ACC CAC GGA GGG ACC TAC AGA TGC TTC GGC TCT TTC CGT GAC TCT
                                             <- Cook 2DL5 3'                     2DL5.D2.G->            Igl 2DL5   <-2DL5sub4
3DL2*001Ref    AAG GTC AAC AGA ACA TTC CAG GCA GAC TTT CCT CTG GGC CCT GCC ACC CAC GGA GGG ACC TAC AGA TGC TTC GGC TCT TTC CGT GCC CTG
2DL5A*001      -GC --- --T G-- --- --- --- --T --- --- --- --- --- --- --- --- --- --- --- --- --- -C- --- --- --- --- C-- -A- -A- TCA
2DL5B*002      -GC --- G-T G-- --- --- --- --T --- --- --- --- --- --- --- --- --- --- --- --- --- -C- --- --- A-- --- C-- -A- -A- TCA
2DL5B*003      -GC --- --T G-- --- --- --- --T --- --- --- --- --- --- --- --- --- --- --- --- --- -C- --- --- --- --- C-- -A- -A- TCA
2DL5B*004      -GC --- --T G-- --- --- --- --T --- --- --- --- --- --- --- --- --- --- --- --- --- -C- --- --- --- --- C-- -A- -A- TC*
2DL5(2DLXa)    -GC --- G-T G-- --- --- --- --T --- --- --- --- --- --- --- --- --- --- --- --- --- -C- --- --- A-- --- C-- -A- -A- TCA
2DL5(2DLXb)    -GC --- G-T G-- --- --- --- --T --- --- --- --- --- --- --- --- --- --- --- --- --- -C- --- --- A-- --- C-- -A- -A- TCA

consensus      AAG GTC AAC GGA ACA TTC CAG GCC GAC TTT CCT CTG GGC CCT GCC ACC CAC GGA GGG ACC TAC AGA TGC TTC GGC TCT TTC CGT GAC TCT
                                                <- GL 2DS1 Ra899
               Igl 2DS1aR                        <- Uhrberg 2DS1 3'           Igl 2DS1bR <-2DS1.D2.G
3DL2*001Ref    AAG GTC AAC AGA ACA TTC CAG GCA GAC TTT CCT CTG GGC CCT GCC ACC CAC GGA GGG ACC TAC AGA TGC TTC GGC TCT TTC CGT GCC CTG
2DS1*001       --- --- --- G-- --- --- --- --C A-- --- --- --- --- --- --- --- --T --- --- --- --- --- --- --- --- --- --- --- -A- TCT
2DS1*002       --- --- --- G-- --- --- --- --C A-- --- --- --- --- --- --- --- --T --- --- --- --- --- --- --- --- --- --- --- -A- TCT
2DS1*003       --- --- --- G-- --- --- --- --C A-- --- --- --- --- --- --- --- --T --- --- --- --- --- --- --- --- --- --- --- -A- TCT
2DS1*004       --- --- --- G-- --- --- --- --C A-- --- --- --- --- --- --- --- --T --- --- --- --- --- --- --- --- --- --- --- -A- TCT

2DS2*001       --- --- --- G-- --- --- --- --C --- --- --- --- --- --- --- --- --- --- --A --- --- --- --- --- --- --- --- --- -A- TCT
2DS2*002       --- --- --- G-- --- --- --- --C --- --- --- --- --- --- --- --- --- --- --A --- --- --- --- --- --- --- --- --- -A- TCT
2DS2*003       --- --- --- G-- --- --- --- --C --- --- --- --- --- --- --- --- --- --- --A --- --- --- --- --- --- --- --- --- -A- TCT
2DS2*004       --- --- --- G-- --- --- --- --C --- --- --- --- --- --- --- --- --- --- --A --- --- --- --- --- --- --- --- --- -A- TCT
2DS2*005       --- --- --- G-- --- --- --- --C --- --- --- --- --- --- --- --- --- --- --A --- --- --- --- --- --- --- --- --- -A- TCT
                    5' cap2DS3.D2.S->                                                         <-3' cap2DS3.D2.S
consensus      AAG GTC AAC GGA ACA TTC CAG GCC GAC TTT CCT CTG GGC CCT GCC ACC CAC GGA GGG ACC TAC AGA TGC TTC GGC TCT TTC CGT GAC TCT
                                                                            Ig8 2DS3  <-2DS3.D2.S  <- Uhrberg 2DS3 3' , <- GL 2DS3
3DL2*001Ref    AAG GTC AAC AGA ACA TTC CAG GCA GAC TTT CCT CTG GGC CCT GCC ACC CAC GGA GGG ACC TAC AGA TGC TTC GGC TCT TTC CGT GCC CTG
3DL2*001Ref    AAG GTC AAC AGA ACA TTC CAG GCA GAC TTT CCT CTG GGC CCT GCC ACC CAC GGA GGG ACC TAC AGA TGC TTC GGC TCT TTC CGT GCC CTG
2DS3*00101     --- --- --- G-- --- --- --- --C --- --- --- --- --- --- --- --- --A --- --A --- --- --- --- --- --- --- --- -A- -A- TCT
2DS3*00102     --- --- --- G-- --- --- --- --C --- --- --- --- --- --- --- --- --A --- --A --- --- --- --- --- --- --- --- -A- -A- TCT
2DS3*00103     --- --- --- G-- --- --- --- --C --- --- --- --- --- --- --- --- --A --- --A --- --- --- --- --- --- --- --- -A- -A- TCT
```

FIG. 2L

```
CCC TAC GAG TGG TCA AAC TCG AGT GAC CCA CTG CTT GTT TCT GTC ACA G | GA AAC CCT TCA AGT AGT TGG CCT
                                <-3' cap2DL5.D2.G
CCC TAC GAG TGG TCA AAC TCG AGT GAC CCA CTG CTT GTT TCT GTC ACA G | GA AAC CCT TCA AGT AGT TGG CCT
                                  <-3' cap2DL5sub4
CCC TGC GTG TGG TCA AAC TCA AGT GAC CCA CTG CTT GTT TCT GTC ACA G | GA AAC CCT TCA AGT AGT TGG CCT
--- -AT -A- --- --- G-- C-G --- --- --- --- --- --- --- --- --- - | -- --- T-- --- --- --- -CA T--
--- -AT -A- --- --- G-- C-G --- --- --- --- --- --- --- --- --- - | -- --- T-- --- --- --- -CA T--
--- -AT -A- --- --- G-- C-G --- --- --- --- --- --- --- --- --- - | -- --- T-- --- --- --- -CA T--
*** *** *** *** *** *** *** *** *** *** *** *** *** *** *** *** * | ** *** *** *** *** *** *** ***
--- -AT -A- --- --- G-- C-G --- --- --- --- --- --- --- --- --- - | -- --- T-- --- --- --- -CA T--
--- -AT -A- --- --- G-- C-G --- --- --- --- --- --- --- --- --- - | -- --- T-- --- --- --- -CA T--
                            <-3' cap2DS1.D2.G
CCC TAC GAG TGG TCA AAC TCG AGT GAC CCA CTG CTT GTT TCT GTC ACA G | GA AAC CCT TCA AGT AGT TGG CCT

                                     <- Cook 2DS1-b 3'
CCC TGC GTG TGG TCA AAC TCA AGT GAC CCA CTG CTT GTT TCT GTC ACA G | GA AAC CCT TCA AGT AGT TGG CCT
--A -A- -A- --- --- --G --- --- --- --- --- --- --- --- --- --- - | -- --- --- --- -A- --- --- ---
--A -A- -A- --- --- --G --- --- --- --- --- --- --- --- --- --- - | -- --- --- --- -A- --- --- ---
--A -A- -A- --- --- --G --- --- --- --- --- --- --- --- --- --- - | -- --- --- --- -A- --- --- ---
--A -A- -A- --- --- --G --- --- --- --- --- --- --- --- --- --- - | -- --- --- --- -A- --- --- ---
                              <- Cook 2DS2-b 3'
--- -AT -A- --- --- --- --G --- --- --- --- --- --- --- --- --- - | -- --- --- --- -A- --- --- ---
--- -AT -A- --- --- --- --G --- --- --- --- --- --- --- --- --- - | -- --- --- --- -A- --- --- ---
--- -AT -A- --- --- --- --G --- --- --- --- --- --- --- --- --- - | -- --- --- --- -A- --- --- ---
--- -AT -A- --- --- --- --G --- --- --- --- --- --- --- --- --- - | -- --- --- --- -A- --- --- ---
--- -AT -A- --- --- --- --G --- --- --- --- --- --- --- --- --- - | -- --- --- --- -A- --- --- ---

CCC TAC GAG TGG TCA AAC TCG AGT GAC CCA CTG CTT GTT TCT GTC ACA G | GA AAC CCT TCA AGT AGT TGG CCT
Ra925, <- Cook 2DS3-a 3'          <- Cook 2DS3-b 3'
CCC TGC GTG TGG TCA AAC TCA AGT GAC CCA CTG CTT GTT TCT GTC ACA G | GA AAC CCT TCA AGT AGT TGG CCT
CCC TGC GTG TGG TCA AAC TCA AGT GAC CCA CTG CTT GTT TCT GTC ACA G | GA AAC CCT TCA AGT AGT TGG CCT
--- -A- -A- --- --- --G --- --- --- --- --- --- --- --- --- --- - | -- --- --- --- -A- --- --- ---
--- -A- -A- --- --- --G --- --- --- --- --- --- --- --- --- --- - | -- --- --- --- -A- --- --- ---
--- -A- -A- --- --- --G --- --- --- --- --- --- --- --- --- --- - | -- --- --- --- -A- --- --- ---
```

FIG. 2M

```
                                                                                  <- Uhrberg 2DL4 3'
3DL2*001Ref     TCA CCC ACA GAA CCA AGC TCC AAA TCT G | GT ATC TGC AGA CAC CTG CAT GTT CTG ATT GGG ACC TCA GTG GTC ATC
2DL4*00101      --- --- --T --- --- --- -T- --- A-- - | -- --- GC- --- --- --- --- -C- G-- --- A-- TA- --- --- -C- ---
2DL4*00102      --- --- --T --- --- --- -T- --- A-- - | -- --- GC- --- --- --- --- -C- G-- --- A-- TA- --- --- -C- ---
2DL4*00201      --- --- --T --- --- --- -T- --- A-- - | -- --- GC- --- --- --- --- -C- G-- --- A-- TA- --- --- -C- ---
2DL4*00202      --- --- --T --- --- --- -T- --- A-- - | -- --- GC- --- --- --- --- -C- G-- --- A-- TA- --- --- -C- ---
2DL4*003        --- --- --- --- --- --- -T- --- A-- - | -- --- GC- --- --- --- --- -C- G-- --- A-- TA- --- --- -C- ---
2DL4*004        --- --- --- --- --- --- -T- --- A-- - | -- --- GC- --- --- --- --- -C- G-- --- A-- TA- --- --- -C- ---
2DL4*005        --- --- --T --- --- --- -T- --- A-- - | -- --- GC- --- --- --- --- -C- G-- --- A-- TA- --- --- -C- ---
2DL4*006        --- --- --- --- --- --- -T- --- A-- - | -- --- GC- --- --- --- --- -C- G-- --- A-- TA- --- --- -C- ---
2DL4*007        --- --- --T --- --- --- -T- --- A-- - | -- --- GC- --- --- --- --- -C- G-- --- A-- TA- --- --- -C- ---

consensus       TCA CCC ACT GAA CCA AGC TCC AAA ACT G | GT AAC CCC AGA CAC CTG CAT GTT CTG ATT GGG ACC TCA GTG GTC ATC
3DL2*001Ref     TCA CCC ACA GAA CCA AGC TCC AAA TCT G | GT ATC TGC AGA CAC CTG CAT GTT CTG ATT GGG ACC TCA GTG GTC ATC

2DL5A*001       --- --- --T --- --- --- --- --- A-- - | -- --- C-- --- --- --- --C A-- --- --- --- --- --- --- -CT ---
2DL5B*002       --- --- --T --- --- --- --- --- A-- - | -- --- C-- --- --- --- --C A-- --- --- --- --- --- --- -CT ---
2DL5B*003       --- --- --T --- --- --- --- --- A-- - | -- --- C-- --- --- --- --C A-- --- --- --- --- --- --- -CT ---
2DL5B*004       *** *** *** *** *** *** *** *** *** * | ** *** *** *** *** *** *** *** *** *** *** *** *** *** *** ***
2DL5(2DLXa)     --- --- --T --- --- --- --- --- A-- - | -- --- C-- --- --- --- --C A-- --- --- --- --- --- --- -CT ---
2DL5(2DLXb)     --- --- --T --- --- --- --- --- A-- - | -- --- C-- --- --- --- --C A-- --- --- --- --- --- --- -CT ---

2DS1*001        --- --- --T --- --- --- --- G-- A-C - | -- -A- CC- --- --- --A --- --- --- --- --- --- --- --- --- -AA
2DS1*002        --- --- --T --- --- --- --- G-- A-C - | -- -A- CC- --- --- --A --- --- --- --- --- --- --- --- --- -AA
2DS1*003        --- --- --T --- --- --- --- G-- A-C - | -- -A- CC- --- --- --A --- --- --- --- --- --- --- --- --- -AA
2DS1*004        --- --- --T --- --- --- --- --- A-C - | -- -A- CC- --- --- --A --- --- --- --- --- --- --- --- --- -AA

2DS2*001        --- --- --T --- --- --- --- --- A-C - | -- -A- CC- --- --- --- --- --- --- --- --- --- --- --- --- -AA
2DS2*002        --- --- --T --- --- --- --- --- A-C - | -- -A- CC- --- --- --- --- --- --- --- --- --- --- --- --- -AA
2DS2*003        --- --- --T --- --- --- --- --- A-C - | -- -A- -C- --- T-- --- --C -C- --- --- --- --- --- --- --- ---
2DS2*004        --- --- --T --- --- --- --- G-- A-C - | -- -A- CC- --- --- --- --C --- --- --- --- --- --- --- --- -AA
2DS2*005        --- --- --T --- --- --- --- --- A-C - | -- -A- CC- --- --- --A --C --- --- --- --- --- --- --- --- -AA

2DS3*00101      --- --- --T --- --- --- --- --- A-C - | -- -A- CC- --- --- --A --C --- --- --- --- --- --- --- --- -AA
2DS3*00102      --- --- --T --- --- --- --- --- A-C - | -- -A- CC- --- --- --A --C --- --- --- --- --- --- --- --- -AA
2DS3*00103      --- --- --T --- --- --- --- --- A-C - | -- -A- CC- --- --- --A --C --- --- --- --- --- --- --- --- -AA

consensus       TCA CCC ACT GAA CCA AGC TCC AAA ACT G | GT AAC CCC AGA CAC CTG CAT GTT CTG ATT GGG ACC TCA GTG GTC ATC
```

FIG. 2O

```
                                                                                      5' cap2DL5.TC.G ->
consensus      GCA GGG AAC AGA ACA GTG AAC AGC GAG | GAC TCT GAT GAA CAA GAC CCT CAG GAG GTG ACA TAC GCA CAG TTG GAT

3DL2*001Ref    GCG GGG GAC AGA ACA GTG AAT AGG CAG | GAC TCT GAT GAA CAA GAC CCT CAG GAG GTG ACG TAC GCA CAG TTG GAT
2DL5A*001      --C --- --- --- --- --- --C --- G-- | --- --- --- --T --- --- --- --- --- --- --A --T --- --- --- ---
2DL5B*002      --C --- --- --- --- --- --C --- G-- | --- --- --- --T --- --- --- --- --- --- --A --T --- --- --- ---
2DL5B*003      --C --- --- --- --- --- --C --- G-- | --- --- --- --T --- --- --- --- --- --- --A --T --- --- --- ---
2DL5B*004      *** *** *** *** *** *** *** *** *** | *** *** *** *** *** *** *** *** *** *** *** *** *** *** *** ***
2DL5(2DLXa)    --C --- --- --- --- --- --C --- G-- | --- --- --- --T --- --- --- --- --- --- --A --T --- --- --- ---
2DL5(2DLXb)    --C --- --- --- --- --- --C --- G-- | --- --- --- --T --- --- --- --- --- --- --A --T --- --- --- ---

2DS1*001       --A --- A-- --- --- --- --C --C G-- | --T --- --- --- --- --- -A- --- --- --- T-A --- --- T-A *** ***
2DS1*002       --A --- A-- --- --- --- --C --C G-- | --T --- --- --- --- --- -A- --- --- --- T-A --- --- T-A *** ***
2DS1*003       --A --- A-- --- --- --- --C --C G-- | --T --- --- --- --- --- -A- --- --- --- T-A --- --- T-A *** ***
2DS1*004       --A --- A-- --- --- --- --C --C G-- | --T --- --- --- --- --- -A- --- --- --- T-A --- --- T-A *** ***

2DS2*001       --A --- A-- --- --- --- --C --C G-- | --T --- --- --- --- --- -A- --- --- --- T-A --- --- T-A *** ***
2DS2*002       --A --- A-- --- --- --- --C --C G-- | --T --- --- --- --- --- -A- --- --- --- T-A --- --- T-A *** ***
2DS2*003       --A --- A-- --- --- --- --C --C G-- | --T --- --- --- --- --- -A- --- --- --- T-A --- --- T-A *** ***
2DS2*004       --A --- A-- --- --- --- --C --C G-- | --T --- --- --- --- --- -A- --- --- --- T-A --- --- T-A *** ***
2DS2*005       --- --- A-- --- --- --- --C --- G-- | --T --- --- --- --G --- -A- --- --- --- T-A --- --- T-A *** ***

2DS3*00101     --- --- A-- --- --- --- --C --- G-- | --T --- --C --- --G --- -A- --- --- --- T-A --- --- T-A *** ***
2DS3*00102     --- --- A-- --- --G --- --C --- G-- | --T --- --- --- --G --- -A- --- --- --- T-A --- --- T-A *** ***
2DS3*00103     --- --- A-- --- --- --- --C --- G-- | --T --- --- --- --G --- -A- --- --- --- T-A --- --- T-A *** ***

consensus      GCA GGG AAC AGA ACA GTG AAC AGC GAG | GAC TCT GAT GAA CAA GAC CCT CAG GAG GTG ACA TAC GCA CAG TTG GAT
```

FIG. 2P

```
5' cap2DL5sub5->                             <-3' cap2DL5.TC.G                            <-3' cap2DL5sub5
CAC TGC GTT TTC ACA CAG AGA AAA ATC ACT CGC CCT TCT CAG AGG CCC AAG ACA CCC CCA ACA GAT ACC AGC GTG TAC ACG GAA CTT
      2DL5.TC.G->                                2DL5sub5->
CAC TGC GTT TTC ATA CAG AGA AAA ATC AGT CGC CCT TCT CAG AGG CCC AAG ACA CCC CTA ACA GAT ACC AGC GTG TAC ACG GAA CTT
--- --- --- --- -C- --- -C- --- --- -C- TC- --- --- --- --- --- --- --- --T -C- --- --- --- -C- A-- --- -T- --- ---
--- --- --- --- -C- --- -C- --- --- -C- TC- --- --- --- --- --- --- --- --T -C- --- --- --- -C- A-- --- -T- --- ---
--- --- --- --- -C- --- -C- --- --- -C- TC- --- --- --- --- --- --- --- --T -C- --- --- --- -C- A-- --- -T- --- ---
*** *** *** *** *** *** *** *** *** *** *** *** *** *** *** *** *** *** *** *** *** *** *** *** *** *** *** *** ***
--- --- --- --- -C- --- -C- --- --- -C- TC- --- --- --- --- --- --- G-- --T -C- --- --- --- -C- A-- --- -T- --- ---
--- --- --- --- -C- --- -C- --- --- -C- TC- --- --- --- --- --- --- G-- --T -C- --- --- --- -C- A-- --- -T- --- ---

*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***

*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***

*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***

CAC TGC GTT TTC ACA CAG AGA AAA ATC ACT CGC CCT TCT CAG AGG CCC AAG ACA CCC CCA ACA GAT ACC AGC GTG TAC ACG GAA CTT
```

FIG. 2Q

```
                                                    420                                     430
                                                     |                                       |
consensus       CCA AAT GCT GAG CCC AGA TCC AAA GTT GTC TCC TGC CCA TGA GCA CCA CAG TCA GGC CTT GAG GGG ATC TTC TAG

3DL2*001Ref     CCA AAT GCT GAG CCC AGA TCC AAA GTT GTC TCC TGC CCA CGA GCA CCA CAG TCA GGT CTT GAG GGG GTT TTC TAG

2DL4*00101      --- --- --- --- --- --- G-. ... --- --- --- --- --- T-- --- --- --- --- --C --- --T --- A-C --- ---
2DL4*00102      --- --- --- --- --- --- G-. ... --- A-- --- --- --- T-- --- --- --- --- --C --- --T --- A-C --- ---
2DL4*00201      --- --- --- --- --- --- G-. ... --- --- --- --- --- T-- --- --- --- --- --C --- --T --- A-C --- ---
2DL4*00202      --- --- --- --- --- --- G-. ... --- --- --- --- --- T-- --- --- --- --- --C --- --T --- A-C --- ---
2DL4*003        --- --- --- --- --- --- G-. ... --- A-- --- --- G-- T-- --- --- --- --- --C --- --T --- A-C --- ---
2DL4*004        --- --- --- --- --- --- G-. ... --- --- --- --- G-- T-- --- --- --- --- --C --- --T --- A-C --- ---
2DL4*005        --- --- --- --- --- --- G-. ... --- --- --- --- --- T-- --- --- --- --- --C --- --T --- A-C --- ---
2DL4*006        --- --- --- --- --- --- G-. ... --- --- --- --- --- T-- --- --- --- --- --C --- --T --- A-C --- ---
2DL4*007        --- --- --- --- --- --T G-. ... --- --- --- --- --- T-- --- --- --- --- --C --- --T --- A-C --- ---

2DL5A*001       --- --- --- A-- --A --- --. ... A-- --- --- --- --- TA- --- --- --- --- --C --- --- --- A-C --- ---
2DL5B*002       --- --- --- A-- --A --- --. ... A-- --- --- --- --- TA- --- --- --- --- --C --- --- --- A-C --- ---
2DL5B*003       --- --- --- A-- --A --- --. ... A-- --- --- --- --- TA- --- --- --- --- --C --- --- --- A-C --- ---
2DL5B*004       *** *** *** *** *** *** *** *** *** *** *** *** *** *** *** *** *** *** *** *** *** *** *** *** ***
2DL5(2DLXa)     --- --- --- A-- --A --- --. ... A-- --- --- --- --- TA- --- --- --- --- --C --- --- --- A-C --- ---
2DL5(2DLXb)     --- --- --- A-- --A --- --. ... A-- --- --- --- --- TA- --- --- --- --- --C --- --- --- A-C --- ---

2DS1*001        *** *** *** *** *** *** *** *** *** *** *** *** *** *** *** *** *** *** *** *** *** *** *** *** ***
2DS1*002        *** *** *** *** *** *** *** *** *** *** *** *** *** *** *** *** *** *** *** *** *** *** *** *** ***
2DS1*003        *** *** *** *** *** *** *** *** *** *** *** *** *** *** *** *** *** *** *** *** *** *** *** *** ***
2DS1*004        *** *** *** *** *** *** *** *** *** *** *** *** *** *** *** *** *** *** *** *** *** *** *** *** ***

2DS2*001        *** *** *** *** *** *** *** *** *** *** *** *** *** *** *** *** *** *** *** *** *** *** *** *** ***
2DS2*002        *** *** *** *** *** *** *** *** *** *** *** *** *** *** *** *** *** *** *** *** *** *** *** *** ***
2DS2*003        *** *** *** *** *** *** *** *** *** *** *** *** *** *** *** *** *** *** *** *** *** *** *** *** ***
2DS2*004        *** *** *** *** *** *** *** *** *** *** *** *** *** *** *** *** *** *** *** *** *** *** *** *** ***
2DS2*005        *** *** *** *** *** *** *** *** *** *** *** *** *** *** *** *** *** *** *** *** *** *** *** *** ***

2DS3*00101      *** *** *** *** *** *** *** *** *** *** *** *** *** *** *** *** *** *** *** *** *** *** *** *** ***
2DS3*00102      *** *** *** *** *** *** *** *** *** *** *** *** *** *** *** *** *** *** *** *** *** *** *** *** ***
2DS3*00103      *** *** *** *** *** *** *** *** *** *** *** *** *** *** *** *** *** *** *** *** *** *** *** *** ***

consensus       CCA AAT GCT GAG CCC AGA TCC AAA GTT GTC TCC TGC CCA TGA GCA CCA CAG TCA GGC CTT GAG GGG ATC TTC TAG
```

```
                 440                                                   450
                  |                                                     |

               |                                                  |
GGA GAC AAC AGC CCT GTC TCA AAC CCA GCT TGC CAG CTC TAA TGT ACC AGC AGC TGG AAT CTG A
--- --- --- --- --- --- --- --- --- --- --- --- --- --- --- --- --- --- --- --- --- -
--- --- --- --- --- --- --- --- --- --- --- --- --- --- --- --- --- --- --- --- --- -
--- --- --- --- --- --- --- --- --- --- --- --- --- --- --- --- --- --- --- --- --- -
--- --- --- --- --- --- --- --- --- --- --- --- --- CC- --- --- --- --- --- --- --- -
--- --- --- --- --- --- --- --- --- --- --- --- --- CC- --- --- --- --- --- --- --- -
--- --- --- --- --- --- --- --- --- --- --- --- --- --- --- --- --- --- --- --- --- -
--- --- --- --- --- --- --- --- --- --- --- --- --- --- --- --- --- --- --- --- --- -
--- --- --- --- --- --- --- --- --- --- --- --- -** *** *** *** *** *** *** *** *** *

--- --- --- --- --- --- --- --A --G -G- --- T-- --- CC- --- --- --- --- --- --- --- -
--- --- --- --- --- --- --- --A --G -G- --- T-- --- CC- --- --- --- --- --- --- --- -
--- --- --- --- --- --- --- --A --G -G- --- T-- --- CC- --- --- --- --- --- --- --- -
*** *** *** *** *** *** *** *** *** *** *** *** *** *** *** *** *** *** *** *** *** *
--- --- --- --- --- --- --- --A --G -G- --- T-- --- CC- --- --- --- --- --- --- --- -
--- --- --- --- --- --- --- --A --G -G- --- T-- --- CC- --- --- --- --- --- --- --- -
```

```
               |   -20                                          |-10                                                       |          |
               |    |                                           | |                                                        |          |
consensus      ATG TCG CTC ATG GTC GTC AGC ATG GCG TGT GTT G | GG TTC TTC TTG CTG CAG GGG GCC TGG CCA CAC GAG G |

2DS4*00101     --- --- --- -T- --- A-- -T- --- --- --T --- - | -- --- --- --- --- --- --- --- --- --- -AG GA- - |
2DS4*00102     --- --- --- -T- --- A-- -T- --- --- --T --- - | -- --- --- --- --- --- --- --- --- --- -AG GA- - |
2DS4*002       --- --- --- -T- --- A-- -T- --- --- --T --- - | -- --- --- --- --- --- --- --- --- --- -AG GA- - |
2DS4*003       *** *** *** *** *** *** **- --- --- --T --- - | -- --- --- --- --- --- --- --- --- --- -AG GA- - |

2DS5*001       --- -T- --- -T- --- A-- --- --- --- --T --- - | C- --- --- --- --- --- --- --- --- --- -AT GA- - |
2DS5*002       --- --- --- -T- --- A-- --- --- --- --T --- - | C- --- --- --- --- --- --- --- --- --- -AT GA- - |
2DS5*003       *** *** *** *** *** *-- --- --- --- --T --- - | C- --- --- --- --- --- --- --- --- --- -AT GA- - |

3DL1*00101     --- --- --- -T- --- --- --- --- --- --T --- - | -- --G --- --- G-C --- A-- --- G-T --- -A- --- - |
3DL1*00102     *** *** *** *** *** *** *** *** *** *** *** * | ** *** *** *** *** *** *** *** *** *** *** *** * |
3DL1*002       --- -T- --- -T- --- --- --- --- --- --T --- - | -- --- --- --- G-C --- A-- --- G-T --- -A- G-- - |
3DL1*003       --- -T- --- -T- --- --- --- --- --- --T --- - | -- --- --- --- G-C --- A-- --- G-T --- -A- G-- - |
3DL1*00401     *** *** *** *** *** *** *** *** *** *** *** * | ** *** *** *** *** *** *** *** *** *** *** *** * |
3DL1*00402     *** *** *** *** *** *** *** *** *** *** *** * | ** *** *** *** *** *** *** *** *** *** *** *** * |
3DL1*005       *** *** *** *** *** *** *** *** *** *** *** * | ** *** *** *** *** *** *** *** *** *** *** *** * |
3DL1*006       *** *** *** *** *** *** *** *** *** *** *** * | ** *** *** *** *** *** *** *** *** *** *** *** * |
3DL1*007       --- -T- --- -T- --- --- --- --- --- --T --- - | -- --- --- --- G-C --- A-- --- G-T --- -A- G-- - |
3DL1*008       --- -T- --- -T- --- --- --- --- --- --T --- - | -- --- --- --- G-C --- A-- --- G-T --- -A- G-- - |
3DL1*009       *** *** *** *** *** *** *** *** *** *** *** * | ** *** *** *** *** *** A-- --- G-T --- -A- --- - |

3DL2*001Ref    ATG TCG CTC ACG GTC GTC AGC ATG GCG TGC GTT G | GG TTC TTC TTG CTG CAG GGG GCC TGG CCA CTC ATG G |
3DS1*010       --- --- --- -T- --- --- --- --- --- --T --- - | -- --G --- --- G-C --- A-- --- G-T --- -A- --- - |
3DS1*011       --- --- --- -T- --- --- --- --- --- --T --- - | -- --G --- --- G-C --- A-- --- G-T --- -A- --- - |
3DS1*012       --- --- --- -T- --- --- --- --- --- --T --- - | -- --G --- --- G-C --- A-- --- G-T --- -A- --- - |
3DS1*013       --- -T- --- -T- --- --- --- --- --- --T --- - | -- --G --- --- G-C --- A-- --- G-T --- -A- --- - |
3DS1*014       *** *** *** *** *** *** *** *** *** *** *** * | ** *** *** *** *** *** A-- --- G-T --- -A- --- - |
```

FIG. 3C

```
                                           40                                         50
                                           |                                          |
consensus      AGG TTT AAC AAT TTC ATG CTA TAC AAA GAA GAC AGA ATC CAC GTT CCC ATC TTC CAT GGC AGA ATA TTC CAG GAG

2DS4*00101     --- --- --- --C --- -GT --- --- --G --T --T G-G GTG -CT --C --T GAG C-G T-- AA- --- --- --- TG- A-A
2DS4*00102     *** *** *** *** *** *** *** *** *** *** *** *** *** *** *** *** *** *** *** *** *** *** *** *** ***
2DS4*002       --- --- --- --C --- -GT --- --- --G --T --T G-G GTG -CT --C --T GAG C-- T-- AA- --- --- --- TG- A-A
2DS4*003       *** *** *** *** *** *** *** *** *** *** *** *** *** *** *** *** *** *** *** *** *** *** *** *** ***

2DS5*001       *** *** *** *** *** *** *** *** *** *** *** *** *** *** *** *** *** *** *** *** *** *** *** *** ***
2DS5*002       *** *** *** *** *** *** *** *** *** *** *** *** *** *** *** *** *** *** *** *** *** *** *** *** ***
2DS5*003       *** *** *** *** *** *** *** *** *** *** *** *** *** *** *** *** *** *** *** *** *** *** *** *** ***

                                                               P70-3                  P70-4
3DL2*001Ref    GGG TTT AAC AAT TTC ATG CTG TAC AAA GAA GAC AGA AGC CAC GTT CCC ATC TTC CAC GGC AGA ATA TTC CAG GAG
3DL1*00101     A-- --- --- --- --- --- --A --- --- --- --- --- -T- --- A-- --- --- --- --T --- --- --- --- --- ---
3DL1*00102     A-- --- --- --- --- --- --A --- --- --- --- --- -T- --- A-- --- --- --- --T --- --- --- --- --- ---
3DL1*002       A-- --- --- --- --- --- --A --- --- --- --- --- -T- --- --- --- --- --- --T --- --- T-- --- --- ---
3DL1*003       A-- --- --- --- --- --- --A --- --- --- --- --- -T- --- --- --- --- --- --T --- --- T-- --- --- ---
3DL1*00401     A-- --- --- --- --- --- --A --- --- --- --- G-- -T- --- A-- --- --- --- --T --- --- --- --- --- ---
3DL1*00402     A-- --- --- --- --- --- --A --- --- --- --- G-- -T- --- A-- --- --- --- --T --- --- --- --- --- ---
3DL1*005       A-- --- --- --- --- --- --A --- --- --- --- --- -T- --- A-- --- --- --- --T --- --- --- --- --- ---
3DL1*006       A-- --- --- --- --- --- --A --- --- --- --- --- -T- --- --- --- --- --- --T --- --- T-- --- --- ---
3DL1*007       A-- --- --- --- --- --- --A --- --- --- --- --- -T- --- --- --- --- --- --T --- --- T-- --- --- ---
3DL1*008       A-- --- --- --- --- --- --A --- --- --- --- --- -T- --- --- --- --- --- --T --- --- T-- --- --- ---
3DL1*009       A-- --- --- --- --- --- --A --- --- --- --- --- -T- --- --- --- --- --- --T --- --- --- --- --- ---
                                   5' cap3DS1.D0.S?
consensus      AGG TTT AAC AAT TTC ATG CTA TAC AAA GAA GAC AGA ATC CAC GTT CCC ATC TTC CAT GGC AGA ATA TTC CAG GAG
                                                                                      Cook 3DS1-a 5- ->
                                                                                        GL Fg299 ->
                                                                                      Uhrberg 3DS1-b 5' ->
3DL2*001Ref    GGG TTT AAC AAT TTC ATG CTG TAC AAA GAA GAC AGA AGC CAC GTT CCC ATC TTC CAC GGC AGA ATA TTC CAG GAG
3DS1*010       A-- --- --- --- --- --- --A --- --- --- --- --- -T- --- --- --- --- --- --T --- --- --- --- --- ---
3DS1*011       A-- --- --- --- --- --- --A --- --- --- --- --- -T- --- --- --- --- --- --T --- --- --- --- --- ---
3DS1*012       A-- --- --- --- --- --- --A --- --- --- --- --- -T- --- --- --- --- --- --T --- --- --- --- --- ---
3DS1*013       A-- --- --- --- --- --- --A --- --- --- --- --- -T- --- --- --- --- --- --T --- --- --- --- --- ---
3DS1*014       A-- --- --- --- --- --- --A --- --- --- --- --- -T- --- --- --- --- --- --T --- --- --- --- --- ---
```

FIG. 3D 60 70 80

AGC TTC AAC ATG AGC CCT GTG ACC ACA GCA CAT GCA GGG AAC TAC ACA TGT CGG GGT TCA CAC CCA CAC TCC CCC ACT GGG TGG TCG GCA

--- C-T T-- --- --- --- --- --- --G T-- --- --- --- --- --T --- --C --- --- --- -A- A-- --- --- -C- -G- --- --- --- ---
* * * * * * * * * * * * * * * * * * * * * * * * * * * * * *
--- C-T T-- --- --- --- --- --- --G T-- --C A-- --- --- --T --- --C --- --- --- -A- A-- --- --- -C- -G- --- G-- --- ---
* * * * * * * * * * * * * * * * * * * * * * * * * * * * * *

* * * * * * * * * * * * * * * * * * * * * * * * * * * * * *
* * * * * * * * * * * * * * * * * * * * * * * * * * * * * *
* * * * * * * * * * * * * * * * * * * * * * * * * * * * * *

AGC TTC ATC ATG GGC CCT GTG ACC CCA GCA CAT GCA GGG ACC TAC AGA TGT CGG GGT TCA CGC CCA CAC TCC CTC ACT GGG TGG TCG GCA
--- --- -A- --- A-- --- --- --- A-- --- --- --- --- -A- --- -C- --- --- --- --- -A- --- --- --- -C- --- --- --- --- ---
--- --- -A- --- A-- --- --- --- A-- --- --- --- --- -A- --- -C- --- --- --- --- -A- --- --- --- -C- --- --- --- --- ---
--- --- -A- --- A-- --- --- --- A-- --- --- --- --- -A- --- -C- --- --- --- --- -A- --- --- --- -C- --- --- --- --- ---
--- --- -A- --- A-- --- --- --- A-- --- --- --- --- -A- --- -C- --- --- --- --- -A- --- --- --- -C- --- --- --- --- ---
--- --- -A- --- A-- --- --- --- A-- --- --- --- --- -A- --- -C- --- --- --- --- -A- --- --- --- -C- --- --- --- -T- ---
--- --- -A- --- A-- --- --- --- A-- --- --- --- --- -A- --- -C- --- --- --- --- -A- --- --- --- -C- --- --- --- -T- ---
--- --- -A- --- A-- --- --- --- A-- --- --- --- --- -A- --- -C- --- --- --- --- -A- --- --- --- -C- --- --- --- --- ---
--- --- -A- --- A-- --- --- --- A-- --- --- --- --- -A- --- -C- --- --- --- --- -A- --- --- --- -C- --- --- --- --- ---
--- --- -A- --- A-- --- --- --- A-- --- --- --- --- -A- --- -C- --- --- --- --- -A- --- --- --- -C- --- --- --- --- ---
--- --- -A- --- A-- --- --- --- A-- --- --- --- --- -A- --- -C- --- --- --- --- -A- --- --- --- -C- --- --- --- --- ---
G-- --- -A- --- A-- --- --- --- A-- --- --- --- --- -A- --- -C- --- --- --- --- -A- --- --- --- -C- --- --- --- --- ---

<-3' cap3DS1.D0.S

AGC TTC AAC ATG AGC CCT GTG ACC ACA GCA CAT GCA GGG AAC TAC ACA TGT CGG GGT TCA CAC CCA CAC TCC CCC ACT GGG TGG TCG GCA

<-3DS1.D0.S Uhrberg 3DS1-a 5' ->

AGC TTC ATC ATG GGC CCT GTG ACC CCA GCA CAT GCA GGG ACC TAC AGA TGT CGG GGT TCA CGC CCA CAC TCC CTC ACT GGG TGG TCG GCA
G-- --- -A- --- A-- --- --- --- A-- --- --- --- --- -A- --- -C- --- --- --- --- -A- --- --- --- -C- --- --- --- --- ---
G-- --- -A- --- A-- --- --- --- A-- --- --- --- --- -A- --- -C- --- --- --- --- -A- --- --- --- -C- --- --- --- --- ---
G-- --- -A- --- A-- --- --- --- A-- --- --- --- --- -A- --- -C- --- --- --- --- -A- --- --- --- -C- --- --- --- --- ---
G-- --- -A- --- A-- --- --- --- A-- --- --- --- --- -A- --- -C- --- --- --- --- -A- --- --- --- -C- --- --- --- --- ---
G-- --- -A- --- A-- --- --- --- A-- --- --- --- --- -A- --- -C- --- --- --- --- -A- --- --- --- -C- --- --- --- --- ---

FIG. 3E

```
                 90                                     |    100                                              110
                  |                                     |     |                                                |
consensus     CCC AGC AAC CCC GTG GTG ATC ATG GTC ACA G | GA ATC CAC AGA AAA CCT TCC CTC CTG GCC CAC CCA GGT CCC
                                                                                            Cook 2DS4-a 5' ->
                                                                                             GL 2DS4 Fa549 ->
                                                                        Cook 2DS4-b 5' ->   Uhrberg 2DS4 5' ->
3DL2*001Ref   CCC AGC AAC CCC CTG GTG ATC ATG GTC ACA G | GA AAC CAC AGA AAA CCT TCC CTC CTG GCC CAC CCA GGG CCC
2DS4*00101    --- --- --- --- --- --- --- --- --- --- - | -- GT- --- --- --- --- --- T-- --- --- -T- --- --T -A-
2DS4*00102    *** *** *** *** *** *** *** *** *** *** * | -- GT- --- --- --- --- --- T-- --- --- -T- --- --T -A-
2DS4*002      --- --- --- --- --- --- --- G-- --- --- - | -- GT- --- --- --- --- --- T-- --- --- -T- --- --T -A-
2DS4*003      *** *** *** *** *** *** *** *** *** *** * | -- GT- --- --- --- --- --- T-- --- --- -T- --- --T -A-

3DL2*001Ref   CCC AGC AAC CCC CTG GTG ATC ATG GTC ACA G | GA AAC CAC AGA AAA CCT TCC CTC CTG GCC CAC CCA GGG CCC
2DS5*001      *** *** *** *** *** *** *** *** *** *** * | -- TT- -G- --- --- --- --- --- --- --- --- --- --T ---
2DS5*002      *** *** *** *** *** *** *** *** *** *** * | -- TT- -G- --- --- --- --- --- --- --- --- --- --T ---
2DS5*003      *** *** *** *** *** *** *** *** *** *** * | -- TT- -G- --- --- --- --- --- --- --- --- --- --T ---

3DL1*00101    --- --- --- --- G-- --- --- --- --- --- - | -- --- --- --- --- --- --- --- --- --- --- --- --T ---
3DL1*00102    --- --- --- --- G-- --- --- --- --- --- - | -- --- --- --- --- --- --- --- --- --- --- --- --T ---
3DL1*002      --- --- --- --- G-- --- --- --- --- --- - | -- --- --- --- --- --- --- --- --- --- --- --- --T ---
3DL1*003      --- --- --- --- G-- --- --- --- --- --- - | -- --- --- --- --- --- --- --- --- --- --- --- --T ---
3DL1*00401    --- --- --- --- G-- --- --- --- --- --- - | -- --- --- --- --- --- --- --- --- --- --- --- --T ---
3DL1*00402    --- --- --- --- G-- --- --- --- --- --- - | -- --- --- --- --- --- --- --- --- --- --- --- --T ---
3DL1*005      --- --- --- --- G-- --- --- --- --- --- - | -- --- --- --- --- --- --- --- --- --- --- --- --T ---
3DL1*006      --- --- --- --- G-- --- --- --- --- --- - | -- --- --- --- --- --- --- --- --- --- --- --- --T ---
3DL1*007      --- --- --- --- G-- --- --- --- --- --- - | -- --- --- --- --- --- --- --- --- --- --- --- --T ---
3DL1*008      --- --- --- --- G-- --- --- --- --- --- - | -- --- --- --- --- --- --- --- --- --- --- --- --T ---
3DL1*009      --- --- --- --- A-- --- --- --- --- --- - | -- --- --- --- --- --- --- --- --- --- --- --- --T ---

           Uhrberg 3DS1-a 5' ->
3DL2*001Ref   CCC AGC AAC CCC CTG GTG ATC ATG GTC ACA G | GA AAC CAC AGA AAA CCT TCC CTC CTG GCC CAC CCA GGG CCC
3DS1*010      --- --- --- --- A-- --- --- --- --- --- - | -- --- --- --- --- --- --- --- --- --- --- --- --T ---
3DS1*011      --- --- --- --- A-- --- --- --- --- --- - | -- --- --- --- --- --- --- --- --- --- --- --- --T ---
3DS1*012      --- --- --- --- A-- --- --- --- --- --- - | -- --- --- --- --- --- --- --- --- --- --- --- --T ---
3DS1*013      --- --- --- --- A-- --- --- --- --- --- - | -- --- --- --- --- --- --- --- --- --- --- --- --T ---
3DS1*014      --- --- --- --- A-- --- --- --- --- --- - | -- --- --- --- --- --- --- --- --- --- --- --- --T ---
```

FIG. 3I

```
                  Exon 4  |  Exon 5
                          |      200                                          210
                          |       |                                            |
                                    5' cap2DS4del.G->                               5' cap2DS4del.sub->
consensus         ATC ACA G | GT CTA TAT GAG AAA CCT TCT CTC TCA GCC CAG CCG GGC CCC ACG GTT CAG GCA GGA GAG AGC GTG

3DL2*001Ref       ATC ACA G | GT CTA TAT GAG AAA CCT TCT CTC TCA GCC CAG CCG GGC CCC ACG GTT CAG GCA GGA GAG AAC GTG

2DS4*00101        --- -T- - | -- --- --- --- --- --- --- --- --- --- --- --- --- --- --- --- --- --- --- --- --T ---
2DS4*00102        --- -T- - | -- --- --- --- --- --- --- --- --- --- --- --- --- --- --- --- --- --- --- --- --T ---
2DS4*002          --- -T- - | -- --- --- --- --- --- --- --- --- --- --- --- --- --- --- --- --- --- --- --- --T ---
2DS4*003          --- -T- - | -- --- --- --- --- --- --- --- --- --- --- --- --- --- --- --- --- --- --- --- --T ---

3DL2*001Ref       ATC ACA G | GT CTA TAT GAG AAA CCT TCT CTC TCA GCC CAG CCG GGC CCC ACG GTT CAG GCA GGA GAG AAC GTG
2DS5*001          --- --- - | -- --- --- --- --- --- --- --- C-- --- --- --- --- --- --- --- -T- --- --- --- -G- ---
2DS5*002          --- --- - | -- --- --- --- --- --- --- --- --- --- --- --- --- --- --- --- -T- --- --- --- -G- ---
2DS5*003          --- --- - | -- --- --- --- --- --- --- --- --- --- --- --- --- --- --- --- -T- --- --- --- --T ---
                                 <- Cook 3DL1-a 3'
                                 <- GL 3DL1 Rc723
            Uhrberg 3DL1-a 5' -> <- Uhrberg 3DL1-b 3'
3DL2*001Ref       ATC ACA G | GT CTA TAT GAG AAA CCT TCT CTC TCA GCC CAG CCG GGC CCC ACG GTT CAG GCA GGA GAG AAC GTG
3DL1*00101        G-- --- - | -- -C- --- --- --- --- --- --- --- --- --- --- --- --- -A- --- --- --- --- --- -G- ---
3DL1*00102        G-- --G - | -- -C- --- --- --- --- --- --- --- --- --- --- --- --- -A- --- --- --- --- --- -G- ---
3DL1*002          G-- --- - | -- -C- --- --- --- --- --- --- --- --- --- --- --- --- -A- --- --- --- --- --- -G- ---
3DL1*003          G-- --- - | -- -C- --- --- --- --- --- --- --- --- --- --- --- --- -A- --- --- --- --- --- -G- ---
3DL1*00401        G-- --- - | -- -C- --- --- --- --- --- --- --- --- --- --- --- --- -A- --- --- --- --- --- -G- ---
3DL1*00402        G-- --- - | -- -C- --- --- --- --- --- --- --- --- --- --- --- --- -A- --- --- --- --- --- -G- ---
3DL1*005          G-- --- - | -- -C- --- --- --- --- --- --- --- --- --- --- --- --- -A- --- --- --- --- --- -G- ---
3DL1*006          G-- --- - | -- -C- --- --- --- --- --- --- --- --- --- --- --- --- -A- --- --- --- --- --- -G- ---
3DL1*007          G-- --- - | -- -C- --- --- --- --- --- --- --- --- --- --- --- --- -A- --- --- --- --- --- -G- ---
3DL1*008          G-- --- - | -- -C- --- --- --- --- --- --- --- --- --- --- --- --- -A- --- --- --- --- --- -G- ---
3DL1*009          G-- --- - | -- -C- --- --- --- --- --- --- --- --- --- --- --- --- -A- --- --- --- --- --- -G- ---

3DS1*010          G-- --- - | -- --- --- --- --- --- --- --- --- --- --- --- --- --- -A- --- --- --- --- --- -G- ---
3DS1*011          G-- --- - | -- --- --- --- --- --- --- --- --- C-G --- --- --- --- -A- --- --- --- --- --- -G- ---
3DS1*012          G-- --- - | -- --- --- --- --- --- --- --- --- --- --- --- --- --- -A- --- --- --- --- --- -G- ---
3DS1*013          G-- --- - | -- --- --- --- --- --- --- --- --- --- --- --- --- --- -A- --- --- --- --- --- -G- ---
3DS1*014          G-- --- - | -- --- --- --- --- --- --- --- --- --- --- --- --- --- -A- --- --- --- --- --- -G- ---
```

```
                250                                        260                                        270
                 |                                          |                                          |
                     5' cap2DS4.D2.S->
consensus       AAG GTC AAC GGA ACA TTC CAG GCC GAC TTT CCT CTG GGC CCT GCC ACC CAC GGA GGG ACC TAC AGA TGC TTC GGC TCT TTC CGT
                   <- GL 2DS4 Rg876, <- Cook 2DS4a 3'                                                             2DS4.D2.S->
3DL2*001Ref     AAG GTC AAC AGA ACA TTC CAG GCA GAC TTT CCT CTG GGC CCT GCC ACC CAC GGA GGG ACC TAC AGA TGC TTC GGC TCT TTC CGT
2DS4*00101      -GC A-- --- G-- --- --- --- --C --- --- --- --- --- --- --- --- --- --- --- --- --- --- --- --- --- --- --- ---
2DS4*00102      -GC A-- --- G-- --- --- --- --C --- --- --- --- --- --- --- --- --- --- --- --- --- --- --- --- --- --- --- ---
2DS4*002        -GC A-- C-- G-- --- --- --- --C --- --- --- --- --- --- --- --- --- --- --- --- --- --- --- --- --- --- --- ---
2DS4*003        -GC A-- --- G-- --- --- --- --C --- --- --- --- --- --- --- --- --- --- --- --- --- --- --- --- --- --- --- ---
                                                                                                    <-3' cap2DS5.D2.G
consensus       AAG GTC AAC GGA ACA TTC CAG GCC GAC TTT CCT CTG GGC CCT GCC ACC CAC GGA GGG ACC TAC AGA TGC TTC GGC TCT TTC CGT
                                                                                                      <-  GL 2DS5 R939
3DL2*001Ref     AAG GTC AAC AGA ACA TTC CAG GCA GAC TTT CCT CTG GGC CCT GCC ACC CAC GGA GGG ACC TAC AGA TGC TTC GGC TCT TTC CGT
                                                                  <- Norman 2DS5 3'
                                                     Igl 2DS5n  <-2DS5.D2.G        <- Uhrberg 2DS5 3', <- Cook 2DS5-b 3'
3DL2*001Ref     AAG GTC AAC AGA ACA TTC CAG GCA GAC TTT CCT CTG GGC CCT GCC ACC CAC GGA GGG ACC TAC AGA TGC TTC GGC TCT TTC CGT
2DS5*001        --- --- --- --- --- --- --- --C --- -C- --- --- --- --- -A- --- --- --- --- G-- --- --- --- --- --- --- --- ---
2DS5*002        --- --- --- --- --- --- --- --C --- --- --- --- --- --- -A- --- --- --- --- --- --- --- --- --- --- --- --- ---
2DS5*003        --- --- --- G-- --- --- --- --C --- --- --- --- --- --- -A- --- --- --- --- --- --- --- --- --- --- --- --- ---

3DL1*00101      --- --- --- --- --- --- --- --- --T --C --- --- --- --- --- --- --- --- --- --- --- --- --- --- --- --- --- ---
3DL1*00102      --- --- --- --- --- --- --- --- --T --C --- --- --- --- --- --- --- --- --- --- --- --- --- --- --- --- --- ---
3DL1*002        --- --- --- --- --- --- --- --- --T --C --- --- --- --- --- --- --- --- --- --- --- --- --- --- --- --- --- ---
3DL1*003        --- --- --- --- --- --- --- --- --T --C --- --- --- --- --- --- --- --- --- --- --- --- --- --- --- --- --- ---
3DL1*00401      --- --- --- --- --- --- --- --- --T --C --- --- --- --- --- --- --- --- --- --- --- --- --- --T --- --- --- ---
3DL1*00402      --- --- --- --- --- --- --- --- --T --C --- --- --- --- --- --- --- --- --- --- --- --- --- --T --- --- --- ---
3DL1*005        --- --- --- --- --- --- --- --- --T --C --- --- --- --- --- --- --- --- --- --- --- --- --- --T --- --- --- ---
3DL1*006        --- --- --- --- --- --- --- --- --T --C --- --- --- --- --- --- --- --- --- --- --- --- --- --- --- --- --- T--
3DL1*007        --- --- --- --- --- --- --- --- --T --C --- --- --- --- --- --- --- --- --- --- --- --- --- --- --- --- --- ---
3DL1*008        --- --- --- --- --- --- --- --- --T --C --- --- --- --- --- --- --- --- --- --- --- --- --- --- --- --- --- ---
3DL1*009        --- --- --- --- --- --- --- --- --T --C --- --- --- --- --- --- --- --- --- --- --- --- --- --- --- --- --- ---

3DS1*010        --- --- --- --- --- --- --- --- --T --C --- --- --- --- --- --- --- --- --- --- --- --- --- --- --- --- --- ---
3DS1*011        --- --- --- --- --- --- --- --- --T --C --- --- --- --- --- --- --- --- --- --- --- --- --- --- --- --- --- ---
3DS1*012        --- --- --- --- --- --- --- --- --T --C --- --- --- --- --- --- --- --- --- --- --- --- --- --- --- --- --- ---
3DS1*013        --- --- --- --- --- --- --- --- --T --C --- --- --- --- --- --- --- --- --- --- --- --- --- --- --- --- --- ---
3DS1*014        --- --- --- --- --- --- --- --- --T --C --- --- --- --- --- --- --- --- --- --- --- --- --- --- --- --- --- ---
```

```
                                                              Exon 5 | Exon 6
       280                                 290                       |              300
        |                                   |                        |               |
      <-3' cap2DS4del.sub                <-3' cap2DS4.D2.S
GAC TCT CCC TAC GAG TGG TCA AAC TCG AGT GAC CCA CTG CTT GTT TCT GTC ACA G | GA AAC CCT TCA AGT AGT TGG CCT
 Ig1 2DS4  <- Cook 2DS4-b 3'
GCC GTG CCC TGC GTG TGG TCA AAC TCA AGT GAC CCA CTG CTT GTT TCT GTC ACA G | GA AAC CCT TCA AGT AGT TGG CCT
-A- GCT --- -A- -A- --- --- --- --G --- --T --- --- --- --- --C --- --- - | -- --- --- --- -A- --- --- ---
-A- GCT --- -A- -A- --- --- --- --G --- --T --- --- --- --- --C --- --- - | -- --- --- --- -A- --- --- ---
-A- GCT --- -A- -A- --- --- --- --G --- --T --- --- --- --- --C --- --- - | -- --- --- --- -A- --- --- ---
-A- GCT --- -A- -A- --- --- --- --G --- --T --- --- --- --- --C --- --- - | -- --- --- --- -A- --- --- ---

GAC TCT CCC TAC GAG TGG TCA AAC TCG AGT GAC CCA CTG CTT GTT TCT GTC ACA G | GA AAC CCT TCA AGT AGT TGG CCT

GCC CTG CCC TGC GTG TGG TCA AAC TCA AGT GAC CCA CTG CTT GTT TCT GTC ACA G | GA AAC CCT TCA AGT AGT TGG CCT


GCC CTG CCC TGC GTG TGG TCA AAC TCA AGT GAC CCA CTG CTT GTT TCT GTC ACA G | GA AAC CCT TCA AGT AGT TGG CCT
-A- TCT --A -A- -A- --- --- --G --- --- --- --- --- --- --- --- --- --- - | -- --- T-- --- -A- --- --- ---
-A- TCT --A -A- -A- --- --- --G --- --- --- --- --- --- --- --- --- --- - | -- --- T-- --- -A- --- --- ---
-A- TCT --A -A- -A- --- --- --G --- --- --- --- --- --- --- --- --- --- - | -- --- T-- --- -A- --- --- ---

CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- -T- --- G-- C-G --- --- --- --- --- --- --- --- --- - | -- --- --- --- --- --- --- ---
CA- TCT --- -A- -A- -T- --- G-- C-G --- --- --- --- --- --- --- --- --- - | -- --- --- --- --- --- --- ---
CA- TCT --- -A- -A- -T- --- G-- C-G --- --- --- --- --- --- --- --- --- - | -- --- --- --- --- --- --- ---
CA- TCT --- -A- -A- -T- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---

CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
CA- TCT --- -A- -A- --- --- G-- C-G --- --- --- --- --- --- --- --- --- - | -- --- --- --- --- --- --- ---
```

FIG. 3M

```
                                         310           |                  320
                                          |            |                   |
consensus    TCA CCC ACT GAA CCA AGC TCC AAA ACT G | GT AAC CCC AGA CAC CTG CAT GTT CTG ATT GGG ACC TCA GTG GTC ATC

2DS4*00101   --- --- --T --- --- --- --- --- A-C - | -- -A- CC- --- --- --A --- --- --- --- --- --- --- --- --- -AA
2DS4*00102   --- --- --T --- --- --- --- --- A-C - | -- -A- CC- --- --- --A --- --- --- --- --- --- --- --- --- -AA
2DS4*002     --- --- --T --- --- --- --- --- A-C - | -- -A- CC- --- --- --A --- --- --- --- --- --- --- --- --- -AA
2DS4*003     --- --- --T --- --- --- --- --- A-C - | -- -A- CC- --- --- --A --- --- --- --- --- --- --- --- --- -AA

2DS5*001     --- --- --T --- --- --- --- G-- A-C - | -- -A- CC- --- --- --A --C --- --- --- --- --- --- --- --- -AA
2DS5*002     --- --- --T --- --- --- --- G-- A-C - | -- -A- CC- --- --- --A --C --- --- --- --- --- --- --- --- -AA
2DS5*003     --- --- --T --- --- --- --- G-- A-C - | -- -A- CC- --- --- --A --C --- --- --- --- --- --- --- --- -AA

3DL2*001Ref  TCA CCC ACA GAA CCA AGC TCC AAA TCT G | GT ATC TGC AGA CAC CTG CAT GTT CTG ATT GGG ACC TCA GTG GTC ATC

3DL1*00101   --- --- --- --- --- --- --- --- --- - | -- -A- CC- --- --- --- --C A-- --- --- --- --- --- --- --- ---
3DL1*00102   --- --- --- --- --- --- --- --- --- - | -- -A- CC- --- --- --- --C A-- --- --- --- --- --- --- --- ---
3DL1*002     --- --- --- --- --- --- --- --- --- - | -- -A- CC- --- --- --- --C A-- --- --- --- --- --- --- --- ---
3DL1*003     --- --- --- --- --- --- --- --- -G- - | -- -A- CC- --- --- --- --C A-- --- --- --- --- --- --- --- ---
3DL1*00401   --- --- --- --- --- --- --- --- --- - | -- -A- CC- --- --- --- --- --- --C --- --- --- --- --- --- ---
3DL1*00402   --- --- --- --- --- --- --- --- --- - | -- -A- CC- --- --- --- --- --- --C --- --- --- --- --- --- ---
3DL1*005     --- --- --- --- --- --- --- --- --- - | -- -A- CC- --- --- --- --C A-- --- --- --- --- --- --- --- ---
3DL1*006     --- --- --- --- --- --- --- --- --- - | -- -A- CC- --- --- --- --C A-- --- --- --- --- --- --- --- ---
3DL1*007     --- --- --- --- --- --- --- --- --- - | -- -A- CC- --- --- --- --C --- --- --- --- --- --- --- --- ---
3DL1*008     --- --- --- --- --- --- --- --- --- - | -- -A- CC- --- --- --- --C A-- --- --- --- --- --- --- --- ---
3DL1*009     --- --- --- --- --- --- --- --- --- - | -- -A- CC- --- --- --- --C A-- --- --- --- --- --- --- --- ---

                                   5' cap3DS1.TC.S.INT->(intronic)
consensus    TCA CCC ACT GAA CCA AGC TCC AAA ACT G-|-GT AAC CCC AGA CAC CTG CAT GTT CTG ATT GGG ACC TCA GTG GTC ATC
                                                            <-3DS1..TC.S.INT
3DL2*001Ref  TCA CCC ACA GAA CCA AGC TCC AAA TCT G | GT ATC TGC AGA CAC CTG CAT GTT CTG ATT GGG ACC TCA GTG GTC ATC

3DS1*010     --- --- --- --- --- --- --- --- --- - | -- -A- CT- --- --- --- --C A-- --- --- --- --- --- --- --- -AA
3DS1*011     --- --- --- --- --- --- --- --- --- - | -- -A- CT- --- --- --- --C A-- --- --- --- --- --- --- --- -AA
3DS1*012     --- --- --- --- --- --- --- --- --- - | -- -A- CT- --- --- --- --C A-- --- --- --- --- --- --- --- -AA
3DS1*013     --- --- --- --- --- --- --- --- --- - | -- -A- CT- --- --- --- --C A-- --- --- --- --- --- --- --- -AA
3DS1*014     --- --- --- --- --- --- --- --- --- - | -- -A- CT- --- --- --- --C A-- --- --- --- --- --- --- --- -AA
```

FIG. 3N

```
330                                          340                                   350
|                                            |                               |     |
ATC CTC TTC ATC CTC CTC CTC TTC TTT CTC CTT CAT CGC TGG TGC TCC AAC AAA AAA A | .AT GCT GCT GTA ATG GAC CAA GAG CCT

A-- -CT --- -C- A-- --- --- --- --- --- --- C-- --- --- --- --- G-- --- --A - | .-- --- --- --- --- --- --- --- ---
A-- -CT --- -C- A-- --- --- --- --- --- --- C-- --- --- --- --- G-- --- --A - | .-- --- --- --- --- --- --- --- ---
A-- -CT --- -C- A-- --- --- --- --- --- --- C-- --- --- --- --- G-- --- --A - | .-- --- --- --- --- --- --- --- ---
A-- -CT --- -C- A-- --- --- --- --- --- --- C-- --- --- --- --- G-- --- --A - | .-- --- --- --- --- --- --- --- ---

C-- -CT --- -C- A-- --- --- --- --- --- --- C-- --- --- --- --- --- --- --A - | .-- --A T-- --- --- --- --- -G- ---
C-- -CT --- -C- A-- --- --- --- --- --- --- C-- --- --- --- --- --- --- --A - | .-- --A T-- --- --- --- --- -G- ---
C-- -CT --- -C- A-- --- --- --- --- --- --- C-- --- --- --- --- --- --- --A - | .-- --A T-- --- --- --- --- -G- ---

TTC CTC TTC ATC CTC CTC CTC TTC TTT CTC CTT TAT CGC TGG TGC TCC AAC AAA AAG A | .AT GCT GCT GTA ATG GAC CAA GAG CCT

A-- --- --- --- --- --- --- --- --- --- --- C-- -T- --- --- --- --- --- --A - | .-- --- --- --- --- --- --- --- ---
A-- --- --- --- --- --- --- --- --- --- --- C-- -T- --- --- --- --- --- --A - | .-- --- --- --- --- --- --G --- ---
A-- --- --- --- --- --- --- --- --- --- --- C-- -T- --- --- --- --- --- --A - | .-- --- --- --- --- --- --- --- ---
A-- --- --- --- --- --- --- --- --- --- --- C-- -T- --- --- --- --- --- --A - | .-- --- --- --- --- --- --- --- ---
A-- --- --- --- --- --- --- --- --- --- --- C-- -T- --- -A- --- --- --- --A - | .-- --- --- --- --- --- --- --- ---
A-- --- --- --- --- --- --- --- --- --- --- C-- -T- --- -A- --- --- --- --A - | .-- --- --- --- --- --- --- --- ---
A-- --- --- --- --- --- --- --- --- --- --- C-- -T- --- --- --- --- --- --A - | .-- --- --- --- --- --- --- --- ---
A-- --- --- --- --- --- --- --- --- --- --- C-- -T- --- --- --- --- --- --A - | .-- --- --- --- --- --- --- --- ---
A-- --- --- --- --- --- --- --- --- --- --- C-- -T- --- --- --- --- --- --A - | .-- --- --- --- --- --- --- --- ---
A-- --- --- --- --- --- --- --- --- --- --- C-- -T- --- --- --- --- --- --A - | .-- --- --- --- --- --- --- --- ---
A-- --- --- --- --- --- --- --- --- --- --- C-- -T- --- --- --- --- --- --A - | .-- --- --- --- --- --- --- --- ---

                <-3' cap3DS1.TC.S.INT
ATC CTC TTC ATC CTC CTC CTC TTC TTT CTC CTT CAT CGC TGG TGC TCC AAC AAA AAA A | .AT GCT GCT GTA ATG GAC CAA GAG CCT

TTC CTC TTC ATC CTC CTC CTC TTC TTT CTC CTT TAT CGC TGG TGC TCC AAC AAA AAG A | .AT GCT GCT GTA ATG GAC CAA GAG CCT

A-- -CT --- -C- A-- --- --- --- --- --- --- C-- --- --- --- --- --- --- --A - | .-- --- --- --- --- --- --- --- ---
A-- -CT --- -C- A-- --- --- --- --- --- --- C-- --- --- --- --- --- --- --A - | A-- --- --- --- --- --- --- --- ---
A-- -CT --- -C- A-- --- --- --- --- --- --- C-- --- --- --- --- --- --- --A - | A-- --- --- --- --- --- --- --- ---
A-- -CT --- -C- A-- --- --- --- --- --- --- C-- --- --- --- --- --- --- --A - | A-- --- --- --- --- --- --- --- ---
A-- -CT --- -C- A-- --- --- --- --- --- --- C-- --- --- --- --- --- --- --A - | .-- --- --- --- --- --- --- --- ---
```

FIG. 3O

```
                                                         Exon 8 | Exon 9
                 360                                            |              370                                   380
                  |                                             |               |                                     |
consensus    GCA GGG AAC AGA ACA GTG AAC AGC GAG | GAC TCT GAT GAA CAA GAC CCT CAG GAG GTG ACA TAC GCA CAG TTG GAT

2DS4*00101   --A --- A-- --- --- --- --C --C G-- | --T --- --- --- --- --- -A- --- --- --- T-A --- --- T-A *** ***
2DS4*00102   --A --- A-- --- --- --- --C --C G-- | --T --- --- --- --- --- -A- --- --- --- T-A --- --- T-A *** ***
2DS4*002     --A --- A-- --- --- --- --C --C G-- | --T --- --- --- --- --- -A- --- --- --- T-A --- --- T-A *** ***
2DS4*003     --A --- A-- --- --- --- --C --C G-- | --T --- --- --- --- --- -A- --- --- --- T-A --- --- T-A *** ***

2DS5*001     --- --- A-- --- --- --- --C --- G-- | --T --- --- --- --G --- -A- --- --- --- T-A --- --- T-A *** ***
2DS5*002     --- --- A-- --- --- --- --C --- G-- | --T --- --- --- --G --- -A- --- --- --- T-A --- --- T-A *** ***
2DS5*003     --- --- A-- --- --- --- --C --- G-- | --T --- --- --- --G --- -A- --- --- --- T-A --- --- T-A *** ***

consensus    GCA GGG AAC AGA ACA GTG AAC AGC GAG | GAC TCT GAT GAA CAA GAC CCT CAG GAG GTG ACA TAC GCA CAG TTG GAT
                                NK6                      Cook 3DL1-b 5' ->          <- Uhrberg 3DL1-a 3'
3DL2*001Ref  GCG GGG GAC AGA ACA GTG AAT AGG CAG | GAC TCT GAT GAA CAA GAC CCT CAG GAG GTG ACG TAC GCA CAG TTG GAT
3DL1*00101   --A --- A-- --- --- -CC --C --C G-- | --- --- --- --- --- --- --- G-- --- --- --A --- --- --- --- ---
3DL1*00102   --A --- A-- --- --- -CC --C --C G-- | --- --- --- --- --- --- --- G-- --- --- --A --- --- --- --- ---
3DL1*002     --A --- A-- --- --- -CC --C --C G-- | --- --- --- --- --- --- --- G-- --- --- --A --- --- --- --- ---
3DL1*003     --A --- A-- --- --- -CC --C --C G-- | --- --- --- --- --- --- --- G-- --- --- --A --- --- --- --- ---
3DL1*00401   --A --- A-- --- --- -CC --C --C G-- | --T --- --- --- --- --- --- --- --- --- --A --- --- --- --- ---
3DL1*00402   --A --- A-- --- --- -CC --C --C G-- | --- --- --- --- --- --- --- --- --- --- --A --- --- --- --- ---
3DL1*005     --A --- A-- --- --- -CC --C --C G-- | --- --- --- --- --- --- --- G-- --- --- --A --- --- --- --- ---
3DL1*006     --A --- A-- --- --- -CC --C --C G-- | --- --- --- --- --- --- --- G-- --- --- --A --- --- --- --- ---
3DL1*007     --A --- A-- --- --- -CC --C --C G-- | --- --- --- --- --- --- --- --- --- --- --A --T --- --- --- ---
3DL1*008     --A --- A-- --- --- -CC --C --C G-- | --- --- --- --- --- --- --- G-- --- --- --A --- --- --- --- ---
3DL1*009     --A --- A-- --- --- -CC --C --C G-- | --- --- --- --- --- --- --- G-- --- --- --A --- --- --- --- ---

                            NK8
3DL2*001Ref  GCG GGG GAC AGA ACA GTG AAT AGG CAG | GAC TCT GAT GAA CAA GAC CCT CAG GAG GTG ACG TAC GCA CAG TTG GAT
3DS1*010     --A --- A-- --- -,, --- --C --C G-- | --T --- --* *** *** *** *** *** *** *** *** *** *** *** *** ***
3DS1*011     --A --- A-- --- -,, --- -** *** *** | *** *** *** *** *** *** *** *** *** *** *** *** *** *** *** ***
3DS1*012     --A --- A-- --- -,, --- -** *** *** | *** *** *** *** *** *** *** *** *** *** *** *** *** *** *** ***
3DS1*013     --A --- A-- --- -,, --- -** *** *** | *** *** *** *** *** *** *** *** *** *** *** *** *** *** *** ***
3DS1*014     --A --- A-- --- -,, --- --C --C G-- | --T --- --* *** *** *** *** *** *** *** *** *** *** *** *** ***
                                                            5' cap3DL2.TC.G->
consensus    GCA GGG AAC AGA ACA GTG AAC AGC GAG | GAC TCT GAT GAA CAA GAC CCT CAG GAG GTG ACA TAC GCA CAG TTG GAT
```

FIG. 3P

```
                                    390                                     400                                     410
                                     |                                       |                                       |
CAC TGC GTT TTC ACA CAG AGA AAA ATC ACT CGC CCT TCT CAG AGG CCC AAG ACA CCC CCA ACA GAT ACC AGC GTG TAC ACG GAA CTT

*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***

*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
            5' cap3DL1.TC.S->
CAC TGC GTT TTC ACA CAG AGA AAA ATC ACT CGC CCT TCT CAG AGG CCC AAG ACA CCC CCA ACA GAT ACC AGC GTG TAC ACG GAA CTT
                                                                        3DL1.TC.S->       <- Cook 3DL1-b 3'
CAC TGC GTT TTC ATA CAG AGA AAA ATC AGT CGC CCT TCT CAG AGG CCC AAG ACA CCC CTA ACA GAT ACC AGC GTG TAC ACG GAA CTT
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---
--- --- --- --- -C- --- --- --- --- -C- --- --- --- --- --- --- --- --- --- -CT --- --- --- -T- T-- --- --- --- ---

CAC TGC GTT TTC ATA CAG AGA AAA ATC AGT CGC CCT TCT CAG AGG CCC AAG ACA CCC CTA ACA GAT ACC AGC GTG TAC ACG GAA CTT
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
                                                                                <-3' cap3DL2.TC.G
CAC TGC GTT TTC ACA CAG AGA AAA ATC ACT CGC CCT TCT CAG AGG CCC AAG ACA CCC CCA ACA GAT ACC AGC GTG TAC ACG GAA CTT
```

FIG. 3Q

```
                                                      420                             430
                                                       |                               |
consensus    CCA AAT GCT GAG CCC AGA TCC AAA GTT GTC TCC TGC CCA TGA GCA CCA CAG TCA GGC CTT GAG GGG ATC TTC TAG

2DS4*00101   *** *** *** *** *** *** *** *** *** *** *** *** *** *** *** *** *** *** *** *** *** *** *** *** ***
2DS4*00102   *** *** *** *** *** *** *** *** *** *** *** *** *** *** *** *** *** *** *** *** *** *** *** *** ***
2DS4*002     *** *** *** *** *** *** *** *** *** *** *** *** *** *** *** *** *** *** *** *** *** *** *** *** ***
2DS4*003     *** *** *** *** *** *** *** *** *** *** *** *** *** *** *** *** *** *** *** *** *** *** *** *** ***

2DS5*001     *** *** *** *** *** *** *** *** *** *** *** *** *** *** *** *** *** *** *** *** *** *** *** *** ***
2DS5*002     *** *** *** *** *** *** *** *** *** *** *** *** *** *** *** *** *** *** *** *** *** *** *** *** ***
2DS5*003     *** *** *** *** *** *** *** *** *** *** *** *** *** *** *** *** *** *** *** *** *** *** *** *** ***
                                       <-3' cap3DL1.TC.S
consensus    CCA AAT GCT GAG CCC AGA TCC AAA GTT GTC TCC TGC CCA TGA GCA CCA CAG TCA GGC CTT GAG GGG ATC TTC TAG

3DL1*00101   --- --- --- A-- --- --- --- --- --- --- --- --- --- T-- *** *** *** *** *** *** *** *** *** *** ***
3DL1*00102   --- --- --- A-- --- --- --- --- --- --- --- --- --- T-- *** *** *** *** *** *** *** *** *** *** ***
3DL1*002     --- --- --- A-- --- --- --- --- --- --- --- --- --- T-- *** *** *** *** *** *** *** *** *** *** ***
3DL1*003     --- --- --- A-- --- --- --- --- --- --- --- --- --- T-- *** *** *** *** *** *** *** *** *** *** ***
3DL1*00401   --- --- --- A-- --- --- --- --- --- --- --- --- --- T-- *** *** *** *** *** *** *** *** *** *** ***
3DL1*00402   --- --- --- A-- --- --- --- --- --- --- --- --- --- T-- *** *** *** *** *** *** *** *** *** *** ***
3DL1*005     --- --- --- A-- --- --- --- --- --- --- --- --- --- T-- *** *** *** *** *** *** *** *** *** *** ***
3DL1*006     --- --- --- A-- --- --- --- --- --- --- --- --- --- T-- *** *** *** *** *** *** *** *** *** *** ***
3DL1*007     --- --- --- A-- --- --- --- --- --- --- --- --- --- T-- *** *** *** *** *** *** *** *** *** *** ***
3DL1*008     --- --- --- A-- --- --- --- --- --- --- --- --- --- T-- *** *** *** *** *** *** *** *** *** *** ***
3DL1*009     --- --- --- A-- --- --- --- --- --- --- --- --- --- T-- *** *** *** *** *** *** *** *** *** *** ***
```

FIG. 4A

```
consensus       ATG TCG CTC ATG GTC GTC AGC ATG GCG TGT GTT G | GG TTC TTC TTG CTG CAG GGG GCC TGG CCA CAC GAG G |
3DL2*001Ref     ATG TCG CTC ACG GTC GTC AGC ATG GCG TGC GTT G | GG TTC TTC TTG CTG CAG GGG GCC TGG CCA CTC ATG G |
3DL2*001        --- --- --- --- --- --- --- --- --- --- --- - | -- --- --- --- --- --- --- --- --- --- --- --- - |
3DL2*002        --- --- --- --T --- --- --- --- --- --- --- - | -- --- --- --- --- --- --- --- --- --- --- --- - |
3DL2*003        --- --- --- --- --- --- --- --- --- --- --- - | -- --- --- --- --- --- --- --- --- --- --- --- - |
3DL2*004        --- --- --- --- --- --- --- --- --- --- --- - | -- --- --- --- --- --- --- --- --- --- --- --- - |
3DL2*005        --- --- --- --- --- --- --- --- --- --- --- - | -- --- --- --- --- --- --- --- --- --- --- --- - |
3DL2*006        *** *** *** *** *** *** *** *** *** *** *** * | ** *** *** *** *** *** *** *** *** *** *** *** * |
3DL2*007        *** *** *** *** *** *** *** *** *** *** *** * | ** *** *** *** *** *** *** *** *** *** *** *** * |
3DL2*008        --- --- --- --T --- --- --- --- --- --- --- - | -- --- --- --- --- --- --- --- --- --- --- --- - |
3DL2*009        --- --- --- --- --- --- --- --- --- --- --- - | -- --- --- --- --- --- --- --- --- --- --- --- - |
3DL2*010        *** *** *** *** *** *** *** *** *** *** *** * | ** *** *** *** *** *** *** *** *** *** *** *** - |
3DL2*011        *** *** *** *** *** *** *** *** *** *** *** * | ** *** *** *** *** *** *** *** *** *** *** *** - |
3DL2*012        *** *** *** *** *** *** *** *** *** *** *** * | ** *** *** *** *** *** *** *** *** *** *** *** - |

3DL2*001Ref     ATG TCG CTC ACG GTC GTC AGC ATG GCG TGC GTT G | GG TTC TTC TTG CTG CAG GGG GCC TGG CCA CTC ATG G |
3DL3*001        --- --- --- -T- --- --- --- --- --- --T --- - | -- --- --- --- --- G-- --- C-- --- --- -AT G-- - |
3DL3*00201      --- --- --- -T- --- --- --- --- --- --T --- - | -- --- --- --- --- G-- --- C-- --- --- -AT G-- - |
3DL3*00202      *** *** *** *** *** *** *** *** *** *** *** * | -- --- --- --- --- G-- --- C-- --- --- -AT G-- - |
3DL3*003        --- --- --- -T- --- --- --- --- --- --T --- - | -- --- --- --- --- G-- --- C-- --- --- -AT G-- - |
3DL3*004        --- --- --- -T- --- --- --- --- --- --T --- - | -- --- --- --- --- G-- --- C-- --- --- -AT G-- - |

                  GL 3DP1 Fcon80 ->                               GL 3DP1 Fcon113 ->
3DL2*001Ref     ATG TCG CTC ACG GTC GTC AGC ATG GCG TGC GTT G | GG TTC TTC TTG CTG CAG GGG GCC TGG CCA CTC ATG G |
3DP1*001        *** *** *** *** *** *** *** *** *** *** *** * | -- --- --- --- --- --- --- --- --- A-- -AT GA- - |
3DP1*002        --- --- --- -T- --- --- --- --- --- --T --- - | -- --- --- --- --- --- --- --- --- --- -AT GA- - |
3DP1*00301      --- --- --- -T- --- --- --- --- --- --T --- - | .. ... ... ... ... ... ... ... ... ... ... ... . |
3DP1*00302      --- --- --- -T- --- --- --- --- --- --T --- - | .. ... ... ... ... ... ... ... ... ... ... ... . |

2DP1*001        *** *** *** *** *** *** *** *** *** *** *** * | -- --- --- --- --- --- --- --- --- --- -AT GA- - |
2DP1*002        --- --- --- --- --- --- --- --- --- --T --- - | -- --- --- --- --- --- --- --- --- --- -AT GA- - |

consensus       ATG TCG CTC ATG GTC GTC AGC ATG GCG TGT GTT G | GG TTC TTC TTG CTG CAG GGG GCC TGG CCA CAC GAG G |
```

FIG. 4C

```
                                                                  Ig3 3DL2
3DL2*001Ref  GGG TTT AAC AAT TTC ATG CTG TAC AAA GAA GAC AGA AGC CAC GTT CCC ATC TTC CAC GGC AGA ATA TTC CAG GAG
3DL2*001     --- --- --- --- --- --- --- --- --- --- --- --- --- --- --- --- --- --- --- --- --- --- --- --- ---
3DL2*002     --- --- --- --- --- --- --- --- --- --- --- --- --- --- --- --- --- --- --- --- --- --- --- --- ---
3DL2*003     --- --- --- --- --- --- --- --- --- --- --- --- --- --- --- --- --- --- --- --- --- --- --- --- ---
3DL2*004     --- --- --- --- --- --- --- --- --- --- --- --- --- --- --- --- --- --- --- --- --- --- --- --- ---
3DL2*005     --- --- --- --- --- --- --- --- --- --- --- --- --- --- --- --- --- --- --- --- --- --- --- --- ---
3DL2*006     --- --- --- --- --- --- --- --- --- --- --- --- --- --- --- --- --- --- --- --- --- --- --- --- ---
3DL2*007     --- --- --- --- --- --- --- --- --- --- --- --- --- --- --- --- --- --- --- --- --- --- --- --- ---
3DL2*008     --- --- --- --- --- --- --- --- --- --- --- --- --- --- --- --- --- --- --- --- --- --- --- --- ---
3DL2*009     --- --- --- --- --- --- --- --- --- --- --- --- --- --- --- --- --- --- --- --- --- --- --- --- ---
3DL2*010     --- --- --- --- --- --- --- --- --- --- --- --- --- --- --- --- --- --- --- --- --- --- --- --- ---
3DL2*011     --- --- --- --- --- --- --- --- --- --- --- --- --- --- --- --- --- --- --- --- --- --- --- --- ---
3DL2*012     --- --- --- --- --- --- --- --- --- --- --- --- --- --- --- --- --- --- --- --- --- --- --- --- ---

3DL3*001     --- --- --- G-A --- -GT --- -C- --- --- --- G-G -TG -CT --C --T GAG C-- T-- AA- --- --- --- -G- A-C
3DL3*00201   --- --- --- G-A --- -GT --- -C- --- --- --- G-G -TG -CT --C --T GAG C-- T-- AA- --- --- --- -G- A-C
3DL3*00202   --- --- --T G-A --- -GT --- -C- --- --- --- G-G -TG -CT --C --T GAG C-- T-- AA- --- --- --- -G- A-C
3DL3*003     --- --- --- G-A --- -GT --- -C- --- --- --- G-G -TG -CT --C --T GAG C-- T-- AA- --- --- --- -G- A-C
3DL3*004     --- --- --- G-A --- -GT --- -C- --- --- --- G-G -TG -CT --C --T GAG C-- T-- AA- --- --- --- -G- A-C

consensus    AGG TTT AAC AAT TTC ATG CTA TAC AAA GAA GAC AGA ATC CAC GTT CCC ATC TTC CAT GGC AGA ATA TTC CAG GAG

3DL2*001Ref  GGG TTT AAC AAT TTC ATG CTG TAC AAA GAA GAC AGA AGC CAC GTT CCC ATC TTC CAC GGC AGA ATA TTC CAG GAG
3DP1*001     --- --- --- G-A --- -GT --- -C- --- --- --- G-G -TG -CT --C --T GAG C-- T-- AA- --- G-- --- -GA A-C
3DP1*002     --- --- --- G-A --- -GT --- -C- --- --- --- G-G -TG -CT --C --T GAG C-- T-- AA- --- G-- --- -GA A-C
3DP1*00301   --- --- --- G-A --- -GT --- -C- --- --- --- G-G -TG -CT --C --T GAG C-- T-- AA- --- G-- --- -GA A-C
3DP1*00302   --- --- --- G-A --- -GT --- -C- --- --- --- G-G -TG -CT --C --T GAG C-- T-- AA- --- G-- --- -GA A-C

                 5' cap2DP1.D0.G->
consensus    AGG TTT AAC AAT TTC ATG CTA TAC AAA GAA GAC AGA ATC CAC GTT CCC ATC TTC CAT GGC AGA ATA TTC CAG GAG
                                                                        <-2DP1.D0.G
3DL2*001Ref  GGG TTT AAC AAT TTC ATG CTG TAC AAA GAA GAC AGA AGC CAC GTT CCC ATC TTC CAC GGC AGA ATA TTC CAG GAG
2DP1*001     --- --- --- --C --- -GT --- --A --G --- --T G-G GTG -CT -GC A-T GAG C-- T-- AA- --- --- --- TG- A--
2DP1*002     --- --- --- --C --- -GT --- --A --G --- --T G-G GTG -CT -GC A-T GAG C-- T-- AA- --- --- --- TG- A--
```

FIG. 4D

```
AGC TTC ATC ATG GGC CCT GTG ACC CCA GCA CAT GCA GGG ACC TAC AGA TGT CGG GGT TCA CGC CCA CAC TCC CTC ACT GGG TGG TCG GCA
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- A--
--- --- --- --- --- --- --- --- --- --- --- --- --- --- --- --- --- --- --- --- --- --- --- --- --- --- --- --- --- A--
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---

--- --T C-- --- --- --- --- --- --- --- --- --- --- --- --- --- --- T-C A-- --- -A- --- --- --- -C- --- --- --- --- ---
--- --T C-- --- --- --- --- --- --- --- --- --- --- --- --- --- --- T-C A-- --- -A- --- --- --- -C- --- --- --- --- ---
--- --T C-- --- --- --- --- --- --- --- --- --- --- --- --- --- --- T-C A-- --- -A- --- --- --- -C- --- --- --- --- ---
--- --T C-- --- --- --- --- --- --- --- --- --- --- --- --- --- --- T-C A-- --- -A- --- --- --- -C- --- --- --- --- ---
--- --T C-- --- --- --- --- --- --- --- --- --- --- --- --- --- --- T-C A-- --- -A- --- --- --- -C- --- --- --- --- ---
```

AGC TTC AAC ATG AGC CCT GTG ACC ACA GCA CAT GCA GGG AAC TAC ACA TGT CGG GGT TCA CAC CCA CAC TCC CCC ACT GGG TGG TCG GCA

```
                                                                                                <- GL 3DP1 Rt369
AGC TTC ATC ATG GGC CCT GTG ACC CCA GCA CAT GCA GGG ACC TAC AGA TGT CGG GGT TCA CGC CCA CAC TCC CTC ACT GGG TGG TCG GCA
-C- G-T T-- --A --- --- --- --- --- --- --- --- --- --- --- --- --- --- --- --- -A- --- --- -T- --- --- --- --- --A ---
-C- G-T T-- --A --- --- --- --- --- --- --- --- --- --- --- --- --- --- --- --- -A- --- --- -T- --- --- --- --- --A ---
-C- G-T T-- --A --- --- --- --- --- --- --- --- --- --- --- --- --- --- --- --- -A- --- --- -T- --- --- --- --- --A ---
-C- G-T T-- --A --- --- --- --- --- --- --- --- --- --- --- --- --- --- --- --- -A- --- --- -T- --- --- --- --- --A ---
```

<-3' cap2DP1.D0.G

AGC TTC AAC ATG <u>AGC CCT GTG ACC ACA GCA CAT</u> GCA GGG AAC TAC ACA TGT CGG GGT TCA CAC CCA CAC TCC CCC ACT GGG TGG TCG GCA

```
AGC TTC ATC ATG GGC CCT GTG ACC CCA GCA CAT GCA GGG ACC TAC AGA TGT CGG GGT TCA CGC CCA CAC TCC CTC ACT GGG TGG TCG GCA
--- C-T T-- --- --- --- --- --- --- --- --C A-- --- --G --- --- --- --- --- --- -A- --- --- --- -C- -G- --- --- --- ---
--- C-T T-- --- --- --- --- --- --- --- --C A-- --- --G --- --- --- --- --- --- -A- --- --- -A- -C- -G- --- --- --- ---
```

FIG. 4E

```
consensus      CCC AGC AAC CCC GTG GTG ATC ATG GTC ACA G | GA ATC CAC AGA AAA CCT TCC CTC CTG GCC CAC CCA GGT CCC

3DL2*001Ref    CCC AGC AAC CCC CTG GTG ATC ATG GTC ACA G | GA AAC CAC AGA AAA CCT TCC CTC CTG GCC CAC CCA GGG CCC

3DL2*001       --- --- --- --- --- --- --- --- --- --- - | -- --- --- --- --- --- --- --- --- --- --- --- --- ---
3DL2*002       --- --- --- --- --- --- --- --- --- --- - | -- --- --- --- --- --- --- --- --- --- --- --- --- ---
3DL2*003       --- --- --- --- G-- --- --- --- --- --- - | -- --- --- --- --- --- --- --- --- --- --- --- --- ---
3DL2*004       --- --- --- --- G-- --- --- --- --- --- - | -- --- --- --- --- --- --- --- --- --- --- --- --- ---
3DL2*005       --- --- --- --- G-- --- --- --- --- --- - | -- --- --- --- --- --- --- --- --- --- --- --- --- ---
3DL2*006       --- --- --- --- --- --- --- --- --- --- - | -- --- --- --- --- --- --- --- --- --- --- --- --- ---
3DL2*007       --- --- --- --- --- --- --- --- --- --- - | -- --- --- --- --- --- --- --- --- --- --- --- --- ---
3DL2*008       --- --- --- --- --- --- --- --- --- --- - | -- --- --- --- --- --- --- --- --- --- --- --- --- A--
3DL2*009       --- --- --- --- --- --- --- --- --- --- - | -- --- --- --- --- --- --- --- --- --- --- --- --- ---
3DL2*010       --- --- --- --- --- --- --- --- --- --- - | -- --- --- --- --- --- --- --- --- --- --- --- --- ---
3DL2*011       --- --- --- --- G-- --- --- --- --- --- - | -- --- --- --- --- --- --- --- --- --- --- --- --- ---
3DL2*012       --- --- --- --- --- --- --- --- --- --- - | -- --- --- --- --- --- --- --- --- --- --- --- --- ---

consensus      CCC AGC AAC CCC GTG GTG ATC ATG GTC ACA G | GA ATC CAC AGA AAA CCT TCC CTC CTG GCC CAC CCA GGT CCC

3DL3*001       --- --- --- --T G-- --- --- --- --- --- - | -- GT- --- --- --- --- --- --- --- --- --- --- --T ---
3DL3*00201     --- --- --- --T G-- --- --- --- --- --- - | -- GT- --- --- --- --- --- --- --- --- --- --- --T ---
3DL3*00202     --- --- --- --T G-- --- --- --- --- --- - | -- GT- --- --- --- --- --- --- --- --- --- --- --T ---
3DL3*003       --- --- --- --T G-- --- --- --- --- --- - | -- GT- --- --- --- --- --- --- --- --- --- --- --T ---
3DL3*004       --- --- --- --T G-- --- --- --- --- --G - | -- GT- --- --- --- --- --- --- --- --- --- --- --T ---

3DP1*001       --- --- --- --- --- --- --- --- --- --- - | -- GT- --- --- --- --- --- --- --- --- --- --- --T ---
3DP1*002       --- --- --- --- --- --- --- --- --- --- - | -- GT- --- --- --- --- --- --- --- --- --- --- --T ---
3DP1*00301     --- --- --- --- --- --- --- --- --- --- - | -- GT- --- --- --- --- --- --- --- --- --- --- --T ---
3DP1*00302     --- --- --- --- --- --- --- --- --- --- - | -- GT- --- --- --- --- --- --- --- --- --- --- --T ---

2DP1*001       --- --- --- --- --- --- --- --- -C- --- - | -- GT- --- --- --- --- --- --- --- --- --- --- --T ---
2DP1*002       --- --- --- A-- --- --- --- --- -C- --- - | -- GT- --- --- --- --- --- --- --- --- --- --- --T ---

consensus      CCC AGC AAC CCC GTG GTG ATC ATG GTC ACA G | GA ATC CAC AGA AAA CCT TCC CTC CTG GCC CAC CCA GGT CCC
```

FIG. 4F

```
CTG GTG AAA TCA GAA GAG ACA GTC ATC CTG CAA TGT TGG TCA GAT GTC ATG TTT GAG CAC TTC CTT CTG CAC AGA GAG GGG ATG TCT AAG

CTG CTG AAA TCA GGA GAG ACA GTC ATC CTG CAA TGT TGG TCA GAT GTC ATG TTT GAG CAC TTC TTT CTG CAC AGA GAG GGG ATC TCT GAG

--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --T --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --T --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
--- --- --- --- --- --- --- --- --- --- --- --- --- --- --- --- --- --- --- --- --- --- --- --- --- --- --- --- --- ---
                                                                                                5' cap3DL3.D1.G->
CTG GTG AAA TCA GAA GAG ACA GTC ATC CTG CAA TGT TGG TCA GAT GTC ATG TTT GAG CAC TTC CTT CTG CAC AGA GAG GGG ATG TCT AAG

--- G-- --- --G --- --- --G --- --- --- --- --- --- --- --- --- -G- --- --- -G- --- C-- --- --- --- --- --- --- A-- ---
--- G-- --- --G --- --- --G --- --- --- --- --- --- --- --- --- -G- --- --- -G- --- C-- --- --- --- --- --- --- A-- ---
--- G-- --- --- --- --- --G --- --- --- --- --- --- --- --- --- -G- --- --- -G- --- C-- --- --- --- --- --- --- A-- ---
--- G-- --- --G --- --- --G --- --- --- --- --- --- --- --- --- -G- --- --- -G- --- C-- --- --- --- --- --- --- A-- ---
--- G-- --- --G --- --- --G --- --- --- --- --- --- --- --- --- -G- --- --- -G- --- C-- --- --- --- --- --- --- A-- ---

--- G-- --- --- -A- --- --- --- --- --- --- --- --- --- --- --- --- --- --- --- --- C-- --- --- --- --- --- -AG -T- A-T
--- G-- --- --- -A- --- --- --- --- --- --- --- --- --- --- --- --- --- --- --- --- C-- --- --- --- --- --- -AG -T- A-T
--- G-- --- --- -A- --- --- --- --- --- --- --- --- --- --- --- --- --- --- --- --- C-- --- --- --- --- --- -AG -T- A-T
--- G-- --- --- -A- --- --- --- --- --- --- --- --- --- --- --- --- --- --- --- --- C-- --- --- --- --- --- -AG -T- A-T

--- G-- --- --- -A- --- --- --- --- --- --- --- --- --- --- --- -G- --- --- --- --- C-- --- --- --- --- --- -CA -T- A-C
--- G-- --- --- -A- --- --- --- --- --- --- --- --- --- --- --- -G- --- C-- --- --- C-- --- --- --- --A --- -AG -T- A-C

CTG GTG AAA TCA GAA GAG ACA GTC ATC CTG CAA TGT TGG TCA GAT GTC ATG TTT GAG CAC TTC CTT CTG CAC AGA GAG GGG ATG TCT AAG
```

FIG. 4G

5' cap3DL2.D1.G->
consensus GAC ACT TTG CGC CTC ATT GGA GAG CAC CAT GAT GGG GTC TCC AAG GCC AAC TTC TCC ATC GGT CCC ATG ATG CAT GAC
GL 3DL2 Ft627 ->
Cook 3DL2-a 5' -> Uhrberg 3DL2 5' ->
3DL2*001Ref GAC CCC TCA CGC CTC GTT GGA CAG ATC CAT GAT GGG GTC TCC AAG GCC AAC TTC TCC ATC GGT CCC TTG ATG CCT GTC
3DL2*001 --- --- --- --- --- --- --- --- --- --- --- --- --- --- --- --- --- --- --- --- --- --- --- --- --- ---
3DL2*002 --- --- --- --- --- --- --- --- --- --- --- --- --- --- --- --- --- --- --- --- --- --- --- --- --- ---
3DL2*003 --- --- --- --- --- --- --- --- --- --- --- --- --- --- --- --- --- --- --- --- --- --- --- --- --- ---
3DL2*004 --- --- --- -A- --- --- --- --- --- --- --- --- --- --- --- --- --- --- --- --- --- --- --- --- --- ---
3DL2*005 --- --- --- -A- --- --- --- --- --- --- --- --- --- --- --- --- --- --- --- --- --- --- --- --- --- ---
3DL2*006 --- --- --- --- --- --- --- --- --- --- --- --- --- --- --- --- --- --- --- --- --- --- --- --- --- ---
3DL2*007 --- --- --- --- --- --- --- --- --- --- --- --- --- --- --- --- --- --- --- --- --- --- --- --- --- ---
3DL2*008 --- --- --- --- --- --- --- --- --- --- --- --- --- --- --- --- --- --- --- --- --- --- --- --- --- ---
3DL2*009 --- --- --- --- --- --- --- --- --- --- --- --- --- --- --- --- --- --- --- --- --- --- --- --- --- ---
3DL2*010 --- --- --- --- --- --- --- --- --- --- --- --- --- --- --- --- --- --- --- --- --- --- --- --- --- ---
3DL2*011 --- --- --- --- --- --- --- --- --- --- --- --- --- --- --- --- --- --- --- --- --- --- --- --- --- ---
3DL2*012 --- --- --- -A- --- --- --- --- --- --- --- --- --- --- --- --- --- --- --- --- --- --- --- --- --- ---

5' cap3DL3.D1.G-> <-3' cap3DL3.D1.G
consensus GAC ACT TTG CGC CTC ATT GGA GAG CAC CAT GAT GGG GTC TCC AAG GCC AAC TTC TCC ATC GGT CCC ATG ATG CAT GAC
Ig2 3DL3 <-3DL3.D1.G
3DL2*001Ref GAC CCC TCA CGC CTC GTT GGA CAG ATC CAT GAT GGG GTC TCC AAG GCC AAC TTC TCC ATC GGT CCC TTG ATG CCT GTC
3DL3*001 --- --- -TG --- --- A-- --- --- C-- --C --- -C- -GT --- C-- -T- --- -AT --- --G --- --- A-- -CA --- -C-
3DL3*00201 --- --- -TG --- --- --- --- --- C-- --C --- -C- -GT --- C-- -T- --- -AT --- --G --- --- A-- -CA --- -C-
3DL3*00202 --- --- -TG --- --- --- --- --- C-- --C --- -C- -GT --- C-- -T- --- -AT --- --G --- --- A-- -CA --- -C-
3DL3*003 --- --- -TG --- --- A-- --- --- C-- --C --- -C- -GT --- C-- -T- --- -AT --- --G --- --- A-- -CA --- -C-
3DL3*004 --- --- -TG --- --- --- --- --- C-- --C --- -C- -GT --- C-- -T- --- -AT --- --G --- --- A-- -CA --- -C-

3DP1*001 --- A-T -TG --- --- AC- --- G-- C-- --- --- --- --- --- --- --- --- --- --- --- --- -G- A-- -C- -AA -A-
3DP1*002 --- A-T -TG --- --- AC- --- G-- C-- --- --- --- --- --- --- --- --- --- --- --- --- -G- A-- -C- -AA -A-
3DP1*00301 --- A-T -TG --- --- AC- --- G-- C-- --- --- --- --- --- --- --- --- --- --- --- --- -G- A-- -C- -AA -A-
3DP1*00302 --- A-T -TG --- --- AC- --- G-- C-- --- --- --- --- --- --- --- --- --- --- --- --- -G- A-- -C- -AA -A-

3DL2*001Ref GAC CCC TCA CGC CTC GTT GGA CAG ATC CAT GAT GGG GTC TCC AAG GCC AAC TTC TCC ATC GGT CCC TTG ATG CCT GTC
2DP1*001 --- A-T -TG -A- --- AC- --- G-- CA- --- --- --- --- --- --- --- --- --- --- --- --- --- A-- --- GAA -A-
2DP1*002 --- A-T -TG -A- --- AC- --- G-- CA- --- --- --- --T --- --- --- --- --- --- --- --- --- A-- --- GAA -A-

FIG. 4I

```
3DL2*001Ref  ATC ACA G | GT CTA TAT GAG AAA CCT TCT CTC TCA GCC CAG CCG GGC CCC ACG GTT CAG GCA GGA GAG AAC GTG ACC TTG TCC TGT AGC TCC TGG AGC TCC
3DL2*001     --- --- - | -- --- --- --- --- --- --- --- --- --- --- --- --- --- --- --- --- --- --- --- --- --- --- --- --- --- --- --- --- ---
3DL2*002     --- --- - | -- --- --- --- --- --- --- --- --- --- --- --- --- --- --- --- --- --- --- --- --- --- --- --- --- --- --- --- --- ---
3DL2*003     --- --- - | -- --- --- --- --- --- --- --- --- --- --- --- --- --- --- --- --- --- --- --- --- --- --- --- --- --- --- --- --- ---
3DL2*004     --- --- - | -- --- --- --- --- --- --- --- --- C-G --- --- --- --- --- --- --- --- --- --- --- --- --- --- --- --- --- --- --- ---
3DL2*005     --- --- - | -- --- --- --- --- --- --- --- --- --- --- --- --- --- --- --- --- --- --- --- --- --- --- --- --- --- --- --- --- ---
3DL2*006     --- --- - | -- --- --- --- --- --- --- --- --- --- --- --- --- --- --- --- --- --- --- --- --- --- --- --- --- --- --- --- --- ---
3DL2*007     --- --- - | -- --- --- --- --- --- --- --- --- --- --- --- --- --- --- --- --- --- --- --- --- --- --- --- --- --- --- --- --- ---
3DL2*008     --- --- - | -- --- --- --- --- --- --- --- --- --- --- --- --- --- --- --- --- --- --- --- --- --- --- --- --- --- --- --- --- ---
3DL2*009     --- --- - | -- --- --- --- --- --- --- --- --- --- --- --- --- --- --- --- --- --- --- --- --- --- --- --- --- --- --- --- --- ---
3DL2*010     --- --- - | -- --- --- --- --- --- --- --- --- --- --- --- --- --- --- --- --- --- --- --- --- --- --- --- --- --- --- --- --- ---
3DL2*011     --- --- - | -- --- --- --- --- --- --- --- --- --- --- --- --- --- --- --- --- --- --- --- --- --- --- --- --- --- --- --- --- ---
3DL2*012     --- --- - | -- --- --- --- --- --- --- --- --- --- --- --- --- --- --- --- --- --- --- --- --- --- --- --- --- --- --- --- --- ---

                                                                                                   5' cap3DL3.D2.G->
consensus    ATC ACA G | GT CTA TAT GAG AAA CCT TCT CTC TCA GCC CAG CCG GGC CCC ACG GTT CAG GCA GGA GAG AGC GTG ACC TTG TCC TGC AGC TCC CGG AGC TCC

3DL2*001Ref  ATC ACA G | GT CTA TAT GAG AAA CCT TCT CTC TCA GCC CAG CCG GGC CCC ACG GTT CAG GCA GGA GAG AAC GTG ACC TTG TCC TGT AGC TCC TGG AGC TCC

3DL3*001     G-- GT- - | -- --- --- -G- --- --- --- --- --- --- --- --- --- --- --- --- --- --- --- --- --T --- --- --- --- --C --- --- C-- --- -TG
3DL3*00201   G-- GT- - | -- --- --- -G- --- --- --- --- --- --- --- --- --- --- --- --- --- --- --- --- --T --- --- --- --- --C --- --- C-- --- -TG
3DL3*00202   G-- GT- - | -- --- --- -G- --- --- --- --- --- --- --- --- --- --- --- --- --- --- --- --- --T --- --- --- --- --C --- --- C-- --- -TG
3DL3*003     G-- GT- - | -- --- --- -G- --- --- --- --- --- --- --- --- --- --- --- --- --- --- --- --- --T --- --- --- --- --C --- --- C-- --- -TG
3DL3*004     G-- GT- - | -- --- --- -G- --- --- --- --- --- --- --- --- --- --- --- --- --- --- --- --- --T --- --- --- --- --C --- --- C-- --- -TG

                          5' cap3DP1.D2.G2->                                                           <-3' cap3DP1.D2.G2
consensus    ATC ACA G | GT CTA TAT GAG AAA CCT TCT CTC TCA GCC CAG CCG GGC CCC ACG GTT CAG GCA GGA GAG AGC GTG ACC TTG TCC TGC AGC TCC CGG AGC TCC
                                                     3DP1.D2.G2->
3DL2*001Ref  ATC ACA G | GT CTA TAT GAG AAA CCT TCT CTC TCA GCC CAG CCG GGC CCC ACG GTT CAG GCA GGA GAG AAC GTG ACC TTG TCC TGT AGC TCC TGG AGC TCC

3DP1*001     --T --- - | -- --- -G- -G- --- --- --- --- --- --- --- C-- --- -T- --- A-- --- --- --- -G- --- --- --- --- --C --- --- C-- --- ---
3DP1*002     --T --- - | -- --- -G- -G- --- --- --- --- --- --- --- C-- --- -T- --- A-- --- --- --- -G- --- --- --- --- --C --- --- C-- --- ---
3DP1*00301   --T --- - | -- --- -G- -G- --- --- --- --- --- --- --- C-- --- -T- --- A-- --- --- --- -G- --- --- --- --- --C --- --- C-- --- ---
3DP1*00302   --T --- - | -- --- -G- -G- --- --- --- --- --- --- --- C-- --- -T- --- A-- --- --- --- -G- --- --- --- --- --C --- --- C-- --- ---

2DP1*001     --- --- - | -- --- --- --- --- --- --- --- --- --- --- --- --- --- --- -T- --- --- --- -G- --- --- --- --- --C --- --- C-- --- ---
2DP1*002     --- --- - | -- --- --- --- --- --- --- --- --- --- --- --- --- --- --- -T- --- --- --- -G- --- --- --- --- --C --- --- C-- --- ---
```

```
                                                Cook 3DL2-b 5' ->
TAT GAC ATC TAC CAT CTG TCC AGG GAA GGG GAG GCC CAT GAA CGT AGG CTC CGT GCA GTG CCC
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- -C- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---
--- --- --- --- --- --- --- --- --- --- --- --- --- --- --- --- --- --- --- --- ---

                                                <-3' cap3DL3.D2.G
TAT GAC ATG TAC CAT CTA TCC AGG GAG GGG GAG GCC CAT GAA CGT AGG CTC CCT GCA GTG CCC
    <-3DL3.D2.G
TAT GAC ATC TAC CAT CTG TCC AGG GAA GGG GAG GCC CAT GAA CGT AGG CTC CGT GCA GTG CCC

-T- --- --T --- --- --A --- --- --G -CA --- --- GG- --- -T- --- --- AC- --G --- -TG
-T- --- --T --- --- --A --- --- --G -CA --- --- GG- --- -T- --- --- AC- --G --- -TG
-T- --- --T --- --- --A --- --- --G -C- --- --- GG- --- -T- --- --- AC- --- --- -TG
-T- --- --T --- --- --A --- --- --G -CA --- --- GG- --- -T- --- --- AC- --G --- -TG
-T- --- --T --- --- --A --- --- --G -CA --- --- GG- --- -T- --- --- AC- --G --- -TG

TAT GAC ATG TAC CAT CTA TCC AGG GAG GGG GAG GCC CAT GAA CGT AGG CTC CCT GCA GTG CCC

TAT GAC ATC TAC CAT CTG TCC AGG GAA GGG GAG GCC CAT GAA CGT AGG CTC CGT GCA GTG CCC

--- --- --- --- --- --A --A --- --G --- --- --T --- --- -T- --- T-- -C- --- --- ---
--- --- --- --- --- --A --A --- --C --- --- --T --- --- -T- --- T-- -C- --- --- ---
--- --- --- --- --- --A --A --- --G --- --- --T --- --- -T- --- T-- -C- --- --- ---
--- --- --- --- --- --A --A --- --G --- --- --T --- --- -T- --- T-- -C- --- --- ---

--- --- --G --- --- --A --- -C- --G --- --- --- --- --- --- --- T-- TC- --- -G- A--
--- --- --G --- --- --A --- --- --G --- --- --- --- --- --- --- T-- TC- --- -G- ---
```

```
3DL2*001Ref   AAG GTC AAC AGA ACA TTC CAG GCA GAC TTT CCT CTG GGC CCT GCC ACC CAC GGA GGG ACC TAC AGA TGC TTC GGC TCT TTC CGT
3DL2*001      --- --- --- --- --- --- --- --- --- --- --- --- --- --- --- --- --- --- --- --- --- --- --- --- --- --- --- ---
3DL2*002      --- --- --- --- --- --- --- --- --- --- --- --- --- --- --- --- --- --- --- --- --- --- --- --- --- --- --- ---
3DL2*003      --- --- --- --- --- --- --- --- --- --- --- --- --- --- --- --- --- --- --- --- --- --- --- --- --- --- --- ---
3DL2*004      --- --- --- --- --- --- --- --- --- --- --- --- --- --- --- --- --- --- --- --- --- --- --- --- --- --- --- ---
3DL2*005      --- --- --- --- --- --- --- --- --- --- --- --- --- --- --- --- --- --- --- --- --- --- --- --- --- --- --- ---
3DL2*006      --- --- --- --- --- --- --- --- --- --- --- --- --- --- --- --- --- --- --- --- --- --- --- --- --- --- --- ---
3DL2*007      --- --- --- --- --- --- --- --- --- --- --- --- --- --- --- --- --- --- --- --- --- --- --- --- --- --- --- ---
3DL2*008      --- --- --- --- --- --- --- --- --- --- --- --- --- --- --- --- --- --- --- --- --- --- --- --- --- --- --- ---
3DL2*009      --- --- --- --- --- --- --- --- --- --- --- --- --- --- --- --- --- --- --- --- --- --- --- --- --- --- --- -A-
3DL2*010      --- --- --- --- --- --- --- --- --- --- --- --- --- --- --- --- --- --- --- --- --- --- --- --- --- --- --- ---
3DL2*011      --- --- --- --- --- --- --- --- --- --- --- --- --- --- --- --- --- --- --- --- --- --- --- --- --- --- --- ---
3DL2*012      --- --- --- --- --- --- --- --- --- --- --- --- --- --- --- --- --- --- --- --- --- --- --- --- --- --- --- ---

3DL3*001      -G- --- --T G-- --- --- --- --C A-- --C --- --- --- --- -TG --- --- --- --- -A- --- --- --- --- --- --- --- ---
3DL3*00201    -G- --- --T G-- --- --- --- --C A-- --C --- --- --- --- -TG --- --- --- --- -A- --- --- --- --- --- --- --- ---
3DL3*00202    -G- --- --T G-- --- --- --- --C A-- --C --- --- --- --- -TG --- --- --- --- -A- --- --- --- --- --- --- --- -**
3DL3*003      -G- --- --T G-- --- --- --- --C A-- --C --- --- --- --- -TG --- --- --- --- -A- --- --- --- --- --- --- --- ---
3DL3*004      -G- --- --T G-- --- --- --- --C A-- --C --- --- --- --- -TG --- --- --- --- -A- --- --- --- --- --- --- --- ---

3DL2*001Ref   AAG GTC AAC AGA ACA TTC CAG GCA GAC TTT CCT CTG GGC CCT GCC ACC CAC GGA GGG ACC TAC AGA TGC TTC GGC TCT TTC CGT
3DP1*001      --- --- --T G-- --C --- --- --C A-- --- --- --- --- --- --- --- --- --- --- --- --- --- --- --- --- --- --- -**
3DP1*002      --- --- --T G-- --C --- --- --C A-- --- --- --- --- --- --- --- --- --- --- --- --- --- --- --- --- --- --- ---
3DP1*00301    --- --- --T G-- --C --- --- --C A-- --- --- --- --- --- --- --- --- --- --- --- --- --- --- --- --- --- --- -**
3DP1*00302    --- --- --T G-- --C --- --- --C A-- --- --- --- --- --- --- --- --- --- --- --- --- --- --- --- --- --- --- ---

                                                                                               <- GL 2DP1 R939
3DL2*001Ref   AAG GTC AAC AGA ACA TTC CAG GCA GAC TTT CCT CTG GGC CCT GCC ACC CAC GGA GGG ACC TAC AGA TGC TTC GGC TCT TTC CGT
2DP1*001      --- --- --- G-- --- --- --- --T --- --- --- --- --- --- --- --- --- --- --A --- --- --- --- --- --- --- --- -**
2DP1*002      --- --- --- G-- --- --- --- --T --- --- --- --- --- --- --- --- --- --- --A --- --- --- --- --- --- --- --- ---
```

FIG. 4M

```
3DL2*001Ref   TCA CCC ACA GAA CCA AGC TCC AAA TCT G | GT ATC TGC AGA CAC CTG CAT GTT CTG ATT GGG ACC TCA GTG GTC ATC

3DL2*001      --- --- --- --- --- --- --- --- --- - | -- --- --- --- --- --- --- --- --- --- --- --- --- --- --- ---
3DL2*002      --- --- --- --- --- --- --- --- --- - | -- --- --- --- --- --- --- --- --- --- --- --- --- --- --- ---
3DL2*003      --- --- --- --- --- --- --- --- --- - | -- --- --- --- --- --- --- --- --- --- --- --- --- --- --- ---
3DL2*004      --- --- --- --- --- --- --- --- --- - | -- --- --- --- --- --- --- --- --- --- --- --- --- --- --- ---
3DL2*005      --- --- --- --- --- --- --- --- --- - | -- --- --- --- --- --- --- --- --- --- --- --- --- --- --- ---
3DL2*006      --- --- --- --- --- --- --- --- --- - | -- --- --- --- --- --- --- --- --- --- --- --- --- --- --- ---
3DL2*007      --- --- --- --- --- --- --- --- --- - | -- --- --- --- --- --- --- --- --- --- --- --- --- --- --- ---
3DL2*008      --- --- --- --- --- --- --- --- --- - | -- --- --- --- --- --- --- --- --- --- --- --- --- --- --- ---
3DL2*009      --- --- --- --- --- --- --- --- --- - | -- --- --- --- --- --- --- --- --- --- --- --- --- --- --- ---
3DL2*010      --- --- --- --- --- --- --- --- --- - | -- --- --- --- --- --- --- --- --- --- --- --- --- --- --- ---
3DL2*011      --- --- --- --- --- --- --- --- --- - | -- --- --- --- --- --- --- --- --- --- --- --- --- --- --- ---
3DL2*012      --- --- --- --- --- --- --- --- --- - | -- --- --- --- --- --- --- --- --- --- --- --- --- --- --- ---

3DL3*001      ... ... ... ... ... ... ... ... ... . | -- -A- -C- --- A-- --- --C --- --- --- --- --- --- --- --- ---
3DL3*00201    ... ... ... ... ... ... ... ... ... . | -- -A- -C- --- --- --- --C --- --- --- --- --- --- --- --- ---
3DL3*00202    *** *** *** *** *** *** *** *** *** * | ** *** *** *** *** *** *** *** *** *** *** *** *** *** *** ***
3DL3*003      ... ... ... ... ... ... ... ... ... . | -- -A- -C- --- T-- --- --C -C- --- --- --- --- --- --- --- ---
3DL3*004      ... ... ... ... ... ... ... ... ... . | -- -A- -C- --- T-- --- --C -C- --- --- --- --- --- --- --- ---

3DP1*001      *** *** *** *** *** *** *** *** *** * | ** *** *** *** *** *** *** *** *** *** *** *** *** *** *** ***
3DP1*002      *** *** *** *** *** *** *** *** *** * | ** *** *** *** *** *** *** *** *** *** *** *** *** *** *** ***
3DP1*00301    *** *** *** *** *** *** *** *** *** * | ** *** *** *** *** *** *** *** *** *** *** *** *** *** *** ***
3DP1*00302    *** *** *** *** *** *** *** *** *** * | ** *** *** *** *** *** *** *** *** *** *** *** *** *** *** ***

2DP1*001      *** *** *** *** *** *** *** *** *** * | ** *** *** *** *** *** *** *** *** *** *** *** *** *** *** ***
2DP1*002      --- --- --T --- --- --- --- --- A-C - | -- -A- CCA --- --- --- --C --- --- --- --- --- --- --- --- ---

consensus     TCA CCC ACT GAA CCA AGC TCC AAA ACT G | GT AAC CCC AGA CAC CTG CAT GTT CTG ATT GGG ACC TCA GTG GTC ATC
```

FIG. 4O

```
3DL2*001Ref   GCG GGG GAC AGA ACA GTG AAT AGG CAG | GAC TCT GAT GAA CAA GAC CCT CAG GAG GTG ACG TAC GCA CAG TTG GAT
                  NK7
3DL2*001      --- --- --- --- --- --- --- --- --- | --- --- --- --- --- --- --- --- --- --- --- --- --- --- --- ---
3DL2*002      --- --- --- --- --- --- --- --- --- | --- --- --- --- --- --- --- --- --- --- --- --- --- --- --- ---
3DL2*003      --- --- --- --- --- --- --- --- --- | --- --- --- --- --- --- --- --- --- --- --- --- --- --- --- ---
3DL2*004      --- --- --- --- --- --- --- --- --- | --- --- --- --- --- --- --- --- --- --- --- --- --- --- --- ---
3DL2*005      --- --- --- --- --- --- --- --- --- | --- --- --- --- --- --- --- --- --- --- --- --- --- --- --- ---
3DL2*006      --- --- --- --- --- --- --- --- --- | --- --- --- --- --- --- --- --- --- --- --- --- --- --- --- ---
3DL2*007      --- --- --- --- --- --- --- --- --- | --- --- --- --- --- --- --- --- --- --- -T- --- --- --- --- ---
3DL2*008      --- --- --- --- --- --- --- --- --- | --- --- --- --- --- --- --- --- --- --- --- --- --- --- --- ---
3DL2*009      --- --- --- --- --- --- --- --- --- | --- --- --- --- --- --- --- --- --- --- --- --- --- --- --- ---
3DL2*010      --- --- --- --- --- --- --- --- --- | --- --- --- --- --- --- --- --- --- --- -T- --- --- --- --- ---
3DL2*011      --- --- --- --- --- --- --- --- --- | --- --- --- --- --- --- --- --- --- --- -T- --- --- --- --- ---
3DL2*012      --- --- --- --- --- --- --- --- --- | --- --- --- --- --- --- --- --- --- --- --- --- --- --- --- ---

3DL3*001      --A --- A-- --- --- --- --C --- G-- | --- --- --- --- --- --- --- --- --- --- --A --- --- --- --- A--
3DL3*00201    --A --- A-- --- --- --- --C --- G-- | --- --- --- --- --- --- --- --- --- --- --A --- --- --- --- A--
3DL3*00202    *** *** *** *** *** *** *** *** *** | *** *** *** *** *** *** *** *** *** *** *** *** *** *** *** ***
3DL3*003      --A --- A-- --- --- --- --C --- G-- | --- --- --- --- --- --- --- --- --- --- --A --- --- --- --- A--
3DL3*004      --A --- A-- --- --- --- --C --- G-- | --- --- --- --- --- --- --- --- --- --- --A --- --- --- --- A--

3DP1*001      *** *** *** *** *** *** *** *** *** | *** *** *** *** *** *** *** *** *** *** *** *** *** *** *** ***
3DP1*002      *** *** *** *** *** *** *** *** *** | *** *** *** *** *** *** *** *** *** *** *** *** *** *** *** ***
3DP1*00301    *** *** *** *** *** *** *** *** *** | *** *** *** *** *** *** *** *** *** *** *** *** *** *** *** ***
3DP1*00302    *** *** *** *** *** *** *** *** *** | *** *** *** *** *** *** *** *** *** *** *** *** *** *** *** ***

2DP1*001      *** *** *** *** *** *** *** *** *** | *** *** *** *** *** *** *** *** *** *** *** *** *** *** *** ***
2DP1*002      --A --- A-- --- --- -C- --- --C G-- | --- --- --- --- --- --- --- --- --- --- --A --- -T- --- --- ---

consensus     GCA GGG AAC AGA ACA GTG AAC AGC GAG | GAC TCT GAT GAA CAA GAC CCT CAG GAG GTG ACA TAC GCA CAG TTG GAT
```

FIG. 4P

```
                                           <-3DL2.TC.G
CAC TGC GTT TTC ATA CAG AGA AAA ATC AGT CGC CCT TCT CAG AGG CCC AAG ACA CCC CTA ACA GAT ACC AGC GTG TAC ACG GAA CTT

--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- -C- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---
--- --- --- --- --- --- --- --- --- -≡- --- --- --- --- --- --- --- --- --- --- --- --- --- --- --- --- --- --- ---

--- --- --- --- -C- --- --- --- --- -C- --- --- --- --- --- --- --- --- --- -C- --- --- --- --- --- --A *** *** ***
--- --- --- --- -C- --- --- --- --- -C- --- --- --- --- --- --- --- --- --- -C- --- --- --- --- --- --A *** *** ***
*** *** *** *** *** *** *** *** *** *** *** *** *** *** *** *** *** *** *** *** *** *** *** *** *** *** *** *** ***
--- --- --- --- -C- --- --- --- --- -C- --- --- --- --- --- --- --- --- --- -C- --- --- --- --- --- --A *** *** ***
--- --- --- --- -C- --- --- --- --- -C- --- --- --- --- --- --- --- --- --- -C- --- --- --- --- --- --A *** *** ***

*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***
*** *** *** *** *** *** *** *** *** *** *** *** *** *** *** *** *** *** *** *** *** *** *** *** *** *** *** *** ***

*** *** *** *** *** *** *** *** *** *** *** *** *** *** *** *** *** *** *** *** *** *** *** *** *** *** *** *** ***
--- --- --- --- -C- --- --- --- --- -C- --- --- --- --- --- --- --- --- --- -C- --- --- --- --A --- --- --- --- ---

CAC TGC GTT TTC ACA CAG AGA AAA ATC ACT CGC CCT TCT CAG AGG CCC AAG ACA CCC CCA ACA GAT ACC AGC GTG TAC ACG GAA CTT
```

FIG. 4Q

```
                                                                420                                    430
                                                                 |                                      |
consensus     CCA AAT GCT GAG CCC AGA TCC AAA GTT GTC TCC TGC CCA TGA GCA CCA CAG TCA GGC CTT GAG GGG ATC TTC TAG

3DS1*010      *** *** *** *** *** *** *** *** *** *** *** *** *** *** *** *** *** *** *** *** *** *** *** *** ***
3DS1*011      *** *** *** *** *** *** *** *** *** *** *** *** *** *** *** *** *** *** *** *** *** *** *** *** ***
3DS1*012      *** *** *** *** *** *** *** *** *** *** *** *** *** *** *** *** *** *** *** *** *** *** *** *** ***
3DS1*013      *** *** *** *** *** *** *** *** *** *** *** *** *** *** *** *** *** *** *** *** *** *** *** *** ***
3DS1*014      *** *** *** *** *** *** *** *** *** *** *** *** *** *** *** *** *** *** *** *** *** *** *** *** ***

3DL2*001      --- --- --- --- --- --- --- --- --- --- --- --- --- --- --- --- --- --- --- --- --- --- --- --- ---
3DL2*002      --- --- --- --- --- --- --- --- --- --- --- --- --- --- --- --- --- --- --- --- --- --- --- --- ---
3DL2*003      --- --- --- --- --- --- --- --- --- --- --- --- --- --- --- --- --- --- --- --- --- --- --- --- ---
3DL2*004      --- --- --- --- --- --- --- --- --- --- --- --- --- --- --- --- --- --- --- --- --- --- --- --- ---
3DL2*005      --- --- --- --- --- --- --- --- --- --- --- --- --- --- --- --- --- --- --- --- --- --- --- --- ---
3DL2*006      --- --- --- --- --- --- --- --- --- --- --- --- --- --- --- --- --- --- --- --- --- --- --- --- ---
3DL2*007      --- --- --- --- --- --- --- --- --- --- --- --- --- --- --- --- --- --- --- --- --- --- --- --- ---
3DL2*008      --- --- --- --- --- --- --- --- --- --- --- --- --- --- --- --- --- --- --- --- --- --- --- --- ---
3DL2*009      --- --- --- --- --- --- --- --- --- --- --- --- --- --- --- --- --- --- --- --- --- --- --- --- ---
3DL2*010      --- --- --- --- --- --- --- --- --- --- --- --- --- --- --- --- --- --- --- --- --- --- --- --- ---
3DL2*011      --- --- --- --- --- --- --- --- --- --- --- --- --- --- --- --- --- --- --- --- --- --- --- --- ---
3DL2*012      --- --- --- --- --- --- --- --- --- --- --- --- --- --- --- --- --- --- --- --- --- --- --- --- ---

3DL3*001      *** *** *** *** *** *** *** *** *** *** *** *** *** *** *** *** *** *** *** *** *** *** *** *** ***
3DL3*00201    *** *** *** *** *** *** *** *** *** *** *** *** *** *** *** *** *** *** *** *** *** *** *** *** ***
3DL3*00202    *** *** *** *** *** *** *** *** *** *** *** *** *** *** *** *** *** *** *** *** *** *** *** *** ***
3DL3*003      *** *** *** *** *** *** *** *** *** *** *** *** *** *** *** *** *** *** *** *** *** *** *** *** ***
3DL3*004      *** *** *** *** *** *** *** *** *** *** *** *** *** *** *** *** *** *** *** *** *** *** *** *** ***

3DP1*001      *** *** *** *** *** *** *** *** *** *** *** *** *** *** *** *** *** *** *** *** *** *** *** *** ***
3DP1*002-     *** *** *** *** *** *** *** *** *** *** *** *** *** *** *** *** *** *** *** *** *** *** *** *** ***
3DP1*00301    *** *** *** *** *** *** *** *** *** *** *** *** *** *** *** *** *** *** *** *** *** *** *** *** ***
3DP1*00302    *** *** *** *** *** *** *** *** *** *** *** *** *** *** *** *** *** *** *** *** *** *** *** *** ***

2DP1*001      *** *** *** *** *** *** *** *** *** *** *** *** *** *** *** *** *** *** *** *** *** *** *** *** ***
2DP1*002      --- --- --- --- T-- --- --- --- --- --- --- --- --- T-- *** *** *** *** *** *** *** *** *** *** ***

consensus     CCA AAT GCT GAG CCC AGA TCC AAA GTT GTC TCC TGC CCA TGA GCA CCA CAG TCA GGC CTT GAG GGG ATC TTC TAG
```

FIG. 12

EXON 3

```
             135            150            165            180            195
2DL5A*001     GT GGT CAG GAC AAG CCC TTG CTG TCT GCC TGG CCC AGC GCT GTG GTG CCT CGA GGA GGA CAT GTG ACT CTT CTG
2DL5A*005     GT GGA CAG GAC AAG CCC TTG CTG TCT GCC TGG CCC AGC GCT GTG GTG CCT CGA GGA GGA CAT GTG ACT CTT CTG
2DL5B*002     GT GGA CAG GAC AAG CCC TTG CTG TCT GCC TGG CCC AGC GCT GTG GTG CCT CGA GGA GGA CAT GTG ACT CTT CTG
2DL5B*003     GT GGT CAG GAC AAG CCC TTG CTG TCT GCC TGG CCC AGC GCT GTG GTG CCT CGA GGA GGA CAT GTG ACT CTT CTG
2DL5B*004     GT GGT CAG GAC AAG CCC TTG CTG TCT GCC TGG CCC AGC ACT GTG GTG CCT CGA GGA GGA CAT GTG ACT CTT CTG
2DL5B*006     GT GGT CAG GAC AAG CCC TTG CTG TCT GCC TGG CCC AGC GCT GTG GTG CCT CGA GGA GGA CAT GTG ACT CTT CTG
2DL5B*007     GT GGT CAG GAC AAG CCC TTG CTG TCT GCC TGG CCC AGC GCT GTG GTG CCT CGA GGA GGA CAT GTG ACT CTT CTG
OLGA          GT GGT CAG GAC AAG CCC TTG CTG TCT GCC TGG CCC AGC GCT GTG GTG CCT CGA GGA GGA CAT GTG ACT CTT CTG
             210            225            240            255            270
2DL5A*001    TGT CGC TCT CGT CTT GGG TTT ACC ATC TTC AGT CTG TAC AAA GAA GAT GGG GTG CCT GTC CCT GAG CTC TAC AAC
2DL5A*005    TGT CGC TCT CGT CTT GGG TTT ACC ATC TTC AGT CTG TAC AAA GAA GAT GGG GTG CCT GTC CCT GAG CTC TAC AAC
2DL5B*002    TGT CGC TCT CGT CTT GGG TTT ACC ATC TTC AGT CTG TAC AAA GAA GAT GGG GTG CCT GTC CCT GAG CTC TAC AAC
2DL5B*003    TGT CGC TCT CGT CTT GGG TTT ACC ATC TTC AGT CTG TAC AAA GAA GAT GGG GTG CCT GTC CCT GAG CTC TAC AAC
2DL5B*004    TGT CGC TCT CGT CTT GGG TTT ACC ATC TTC AGT CTG TAC AAA GAA GAT GGG GTG CCT GTC CCT GAG CTC TAC AAC
2DL5B*006    TGT CGC TCT CGT CTT GGG TTT ACC ATC TTC AGT CTG TAC AAA GAA GAT GGG GTG CCT GTC CCT GAG CTC TAC AAC
2DL5B*007    TGT CGC TCT CGT CTT GGG TTT ACC ATC TTC AGT CTG TAC AAA GAA GAT GGG GTG CCT GTC CCT GAG CTC TAC AAC
OLGA         TGT CGC TCT CGT CTT GGG TTT ACC ATC TTC AGT CTG TAC AAA GAA GAT GGG GTG CCT GTC CCT GAG CTC TAC AAC
             285            300            315            330            345
2DL5A*001    AAA ATA TTC TGG AAG AGC ATC CTC ATG GGC CCT GTG ACC CCT GCA CAC GCA GGG ACC TAC AGA TGT CGG GGT TCA
2DL5A*005    AAA ATA TTC TGG AAG AGC ATC CTC ATG GGC CCT GTG ACC CCT GCA CAC GCA GGG ACC TAC AGA TGT CGG GGT TCA
2DL5B*002    AAA ATA TTC TGG AAG AGC ATC CTC ATG GGC CCT GTG ACC CCT GCA CAC GCA GGG ACC TAC AGA TGT CGG GGT TCA
2DL5B*003    AAA ATA TTC TGG AAG AGC ATC CTC ATG GGC CCT GTG ACC CCT GCA CAC GCA GGG ACC TAC AGA TGT CGG GGT TCA
2DL5B*004    AAA ATA TTC TGG AAG AGC ATC CTC ATG GGC CCT GTG ACC CCT GCA CAC GCA GGG ACC TAC AGA TGT CGG GGT TCA
2DL5B*006    AAA ATA TTC TGG AAG AGC ATC CTC ATG GGC CCT GTG ACC CCT GCA CAC GCA GGG ACC TAC AGA TGT CGG GGT TCA
2DL5B*007    AAA ATA TTC TGG AAG AGC ATC CTC ATG GGC CCT GTG ACC CCT GCA CAC GCA GGG ACC TAC AGA TGT CGG GGT TCA
OLGA         AAA ATA TTC TGG AAG AGC ATC CTC ATG GGC CCT GTG ACC CCT GCA CAC GCA GGG ACC TAC AGA TGT CGG GGT TCA
             360            375            390            405
2DL5A*001    CAC CCA CGC TCC CCC ATT GAG TGG TCA GCA CCC AGC AAC CCC CTG GTG ATC GTG GTC ACA G
2DL5A*005    CAC CCG CGC TCC CCC ATT GAG TGG TCG GCA CCC AGC AAC CCC CTG GTG ATC GTG GTC ACA G
2DL5B*002    CAC CCG CGC TCC CCC ATT GAG TGG TCG GCA CCC AGC AAC CCC CTG GTG ATC GTG GTC ACA G
2DL5B*003    CAC CCA CGC TCC CCC ATT GAG TGG TCA GCA CCC AGC AAC CCC CTG GTG ATC ATG GTC ACA G
2DL5B*004    CAC CCA CGC TCC CCC ATT GAG TGG TCA GCA CCC AGC AAC CCC CTG GTG ATC GTG GTC ACA G
2DL5B*006    CAC CCA CGC TCC CCC ATT GAG TGG TCA GCA CCC AGC AAC CCC CTG GTG ATC GTG GTC ACA G
2DL5B*007    CAC CCA CGC TCC CCC ATT GAG TGG TCA GCA CCC AGC AAC CCC CTG GTG ATC ATG GTC ACA G
OLGA         CAC CCA CGC TCC CCC ATT GAG TGG TCG GCA CCC AGC AAC CCC CTG GTG ATC GTG GTC ACA G
```

FIG. 13

```
EXON 5
                420                 435                 450                 465                 480
2DL5A*001        GT CTA TTT GGG AAA CCT TCA CTC TCA GCC CAG CCG GGC CCC ACG GTT CGC ACA GGA GAG AAC GTG ACC TTG TCC
2DL5A*005        GT CTA TTT GGG AAA CCT TCA CTC TCA GCC CAG CCG GGC CCC ACG GTT CGC ACA GGA GAG AAC GTG ACC TTG TCC
2DL5B*002        GT CTA TTT GGG AAA CCT TCA CTC TCA GCC CAG CCG GGC CCC ACG GTT CGC ACA GGA GAG AAC GTG ACC TTG TCC
2DL5B*003        GT CTA TTT GGG AAA CCT TCA CTC TCA GCC CAG CCG GGC CCC ACG GTT CGC ACA GGA GAG AAC GTG ACC TTG TCC
2DL5B*004        GT CTA TTT GGG AAA CCT TCA CTC TCA GCC CAG CCG GGC CCC ACG GTT CGC ACA GGA GAG AAC GTG ACC TTG TCC
2DL5B*006        GT CTA TTT GGG AAA CCT TCA CTC TCA GCC CAG CCG GGC CCC ACG GTT CGC ACA GGA GAG AAC GTG ACC TTG TCC
2DL5B*007        GT CTA TTT GGG AAA CCT TCA CTC TCA GCC CAG CCG GGC CCC ACG GTT CGC ACA GGA GAG AAC GTG ACC TTG TCC
OLGA             GT CTA TTT GGG AAA CCT TCA CTC TCA GCC CAG CCG GGC CCC ACG GTT CGC ACA GGA GAG AAC GTG ACC TTG TCC
                495                 510                 525                 540                 555
2DL5A*001       TGC AGC TCC AGG AGC TCA TTT GAC ATG TAC CAT CTA TCC AGG GAG GGG AGG GCC CAT GAA CCT AGG CTC CCT GCA
2DL5A*005       TGC AGC TCC AGG AGC TCA TTT GAC ATG TAC CAT CTA TCC AGG GAG GGG AGG GCC CAT GAA CCT AGG CTC CCT GCA
2DL5B*002       TGC AGC TCC AGG AGC TCA TTT GAC ATG TAC CAT CTA TCC AGG GAG GGG AGG GCC CAT GAA CCT AGG CTC CCT GCA
2DL5B*003       TGC AGC TCC AGG AGC TCA TTT GAC ATG TAC CAT CTA TCC AGG GAG GGG AGG GCC CAT GAA CCT AGG CTC CCT GCA
2DL5B*004       TGC AGC TCC AGG AGC TCA TTT GAC ATG TAC CAT CTA TCC AGG GAG GGG AGG GCC CAT GAA CCT AGG CTC CCT GCA
2DL5B*006       TGC AGC TCC AGG AGC TCA TTT GAC ATG TAC CAT CTA TCC AGG GAG GGG AGG GCC CAT GAA CCT AGG CTC CCT GCA
2DL5B*007       TGC AGC TCC AGG AGC TCA TTT GAC ATG TAC CAT CTA TCC AGG GAG GGG AGG GCC CAT GAA CCT AGG CTC CCT GCA
OLGA            TGC AGC TCC AGG AGC TCA TTT GAC ATG TAC CAT CTA TCC AGG GAG GGG AGG GCC CAT GAA CCT AGG CTC CCT GCA
                570                 585                 600                 615                 630
2DL5A*001       GTG CCC AGC GTC AAT GGA ACA TTC CAG GCT GAC TTT CCT CTG GGC CCT GCC ACC CAC GGA GGG ACC TAC ACA TGC
2DL5A*005       GTG CCC AGC GTC GAT GGA ACA TTC CAG GCT GAC TTT CCT CTG GGC CCT GCC ACC CAC GGA GGG ACC TAC ACA TGC
2DL5B*002       GTG CCC AGC GTC GAT GGA ACA TTC CAG GCT GAC TTT CCT CTG GGC CCT GCC ACC CAC GGA GGG ACC TAC ACA TGC
2DL5B*003       GTG CCC AGC GTC AAT GGA ACA TTC CAG GCT GAC TTT CCT CTG GGC CCT GCC ACC CAC GGA GGG ACC TAC ACA TGC
2DL5B*004       GTG CCC AGC GTC AAT GGA ACA TTC CAG GCT GAC TTT CCT CTG GGC CCT GCC ACC CAC GGA GGG ACC TAC ACA TGC
2DL5B*006       GTG CCC AGC GTC AAT GGA ACA TTC CAG GCT GAC TTT CCT CTG GGC CCT GCC ACC CAC GGA GGG ACC TAC ACA TGC
2DL5B*007       GTG CCC AGC GTC AAT GGA ACA TTC CAG GCT GAC TTT CCT CTG GGC CCT GCC ACC CAC GGA GGG ACC TAC ACA TGC
OLGA            GTG CCC AGC GTC AAT GGA ACA TTC CAG GCT GAC TTT CCT CTG GGC CCT GCC ACC CAC GGA GGG ACC TAC ACA TGC
                645                 660                 675                 690                 705
2DL5A*001       TTC GGC TCT CTC CAT GAC TCA CCC TAT GAG TGG TCA GAC CCG AGT GAC CCA CTG CTT GTT TCT GTC ACA G
2DL5A*005       TTC AGC TCT CTC CAT GAC TCA CCC TAT GAG TGG TCA GAC CCG AGT GAC CCA CTG CTT GTT TCT GTC ACA G
2DL5B*002       TTC AGC TCT CTC CAT GAC TCA CCC TAT GAG TGG TCA GAC CCG AGT GAC CCA CTG CTT GTT TCT GTC ACA G
2DL5B*003       TTC GGC TCT CTC CAT GAC TCA CCC TAT GAG TGG TCA GAC CCG AGT GAC CCA CTG CTT GTT TCT GTC ACA G
2DL5B*004       TTC GGC TCT CTC CAT GAC TCA CCC TAT GAG TGG TCA GAC CCG AGT GAC CCA CTG CTT GTT TCT GTC ACA G
2DL5B*006       TTC GGC TCT CTC CAT GAC TCA CCC TAT GAG TGG TCA GAC CCG AGT GAC CCA CTG CTT GTT TCT GTC ACA G
2DL5B*007       TTC GGC TCT CTC CAT GAC TCA CCC TAT GAG TGG TCA GAC CCG AGT GAC CCA CTG CTT GTT TCT GTC ACA G
OLGA            TTC GGC TCT CTC CAT GAC TCA CCC TAT GAG TGG TCA GAC CCG AGT GAC CCA CTG CTT GTT TCT GTC ACA G
```

| SSP Rxn | Result |
| --- | --- |
| F1+R1 | Neg |
| F1+R2 | Pos |
| F2+R1 | Neg |
| F2+R2 | Neg |

METHODS AND COMPOSITIONS FOR KIR GENOTYPING

CROSS-REFERENCE

This application claims the benefit of U.S. Provisional Application No. 60/722,673 filed Sep. 29, 2005, which application is incorporated herein by reference.

GOVERNMENT RIGHTS

This invention was made with government support under grant nos. 1 R21 AI 65254-01Ai, 1P01 CA 111412, and 1 UOI AI067068-01 awarded by the National Institute of Allergy and Infectious Diseases, and the National Institutes of Health. The United States Government has certain rights in this invention.

BACKGROUND OF THE INVENTION

The killer cell immunoglobulin-like receptors (KIR) are a family of receptors that are expressed on natural killer (NK) cells and some T cells. Known KIR ligands are class I HLA-C and HLA-B (Bw4), which interact with KIR inhibitory or stimulatory receptors to regulate the immunological response, thereby regulating cell execution by NK cells and other cytotoxic cells. A total of 17 KIR loci have been identified, including 15 expressed genes and 2 pseudogenes, with between 2 and 12 alleles seen at each of the polymorphic KIR loci. Diversity in terms of both number and combination of KIR genes exists among individuals, as well as extensive allele polymorphism, all of which affect the strength and breadth of the immune response.

Traditional KIR genotyping methods utilize PCR and sequence-specific priming (SSP) (Dupont et al., Tissue Antigens, 49(6):557-63 (1997); Selvakumar et al., Tissue Antigens, 49(6):564-73 (1997); Uhrberg et al., Immunity, 7(6): 753-63 (1997); Shilling et al., Blood, 101(9):3730-3740 (2003); Shilling et al., J Immunol, 168(5):2307-15 (2002)). The SSP assay requires that genomic DNA be amplified using a collection of primers in separate reactions in order to define the various loci or alleles to be detected by fragment lengths using gel electrophoresis. However, there are drawbacks to utilizing the SSP method for higher-throughput analysis of KIR loci in populations. In particular, the KIR SSP amplifications require many different annealing and extension time conditions, which are machine and technologist time intensive, and not conducive to high-throughput analysis. Another significant limitation of the SSP method is that it requires a large quantity of high quality DNA (>5 μg). Furthermore, the SSP method poses the problem of sample amplification failure, which could be due to either general PCR failure or a sequence variant, neither of which can be distinguished utilizing this method. Accordingly, amplification failure could result in erroneous KIR genotyping results.

An alternative KIR genotyping assay uses sequence-specific oligonucleotide probes (SSOP) developed for locus-specific resolution of 14 KIR genes. The SSOP assay requires a small quantity of genomic DNA (50-100 ng) amplified at four KIR domains. PCR products are then denatured and vacuum blotted onto replicate 96-sample nylon membranes. Replicate membranes are hybridized to 39 sequence-specific probes, washed under stringent conditions to remove unbound probe, and developed using non-radioactive detection methods. KIR probe hybridization patterns are then decoded using a computer program. Although generally more efficient than SSP methods, genotyping analysis by SSOP assays is still cumbersome.

Accordingly, there remains a need in the art for a method for performing efficient and reproducible high-throughput genotyping of the KIR locus. The present invention addresses this need.

RELEVANT LITERATURE

U.S. Pat. Nos. 6,723,564, 6,111,251, 6,104,028, 6,558,902, 6,706,530, 6,423,966, 5,777,324, 6,569,385, 6,500,621, 6,300,076, and 6,258,538; Uhrberg et al., Immunity 7:753-763 (1997); Gomez-Lozano et al., Tissue Antigens 59:184-193 (2002); Cook et al., Hum. Immunology 64:567-571 (2003); Crum et al., Tissue Antigens 56:313-326 (2000); Middleton et al., Transplant immunology 10:147-164 (2002); Ross et al., Nature Biotech., 16:1347-1351 (1998); Fei et al., Rapid Comm. Mass. Spec., 14:950-959 (2000); Fei et al., NAR 26(11):2827-2828 (1998); Amexis et al., PNAS 98(21) 12097-12102 (2001); Li et al., Electrophoresis 20:1258-1265 (1999); Buetow et al., PNAS 98(2) 581-584 (2001); Storm et al., Methods in Mol. Biol., 212:241-262 (2003); Parham, Immunology Lett. 92:11-13 (2004); and MassARRAY™ Homogenous Mass EXTEND™ (hME) Assay, Sequenom®, Application Notes, Bulletin #1021.

SUMMARY OF THE INVENTION

The present invention provides methods for single nucleotide polymorphism (SNP)-based killer cell immunoglobulin-like receptor (KIR) gene cluster genotyping using the matrix-assisted laser desorption/ionization time-of-flight (MALDI-TOF) mass spectrometer. In general, the methods involve amplifying a plurality of target sequences of a plurality of KIR genes, and detecting the presence or absence of a plurality of single SNPs of the plurality of KIR genes by MALDI-TOF mass spectrometry. The invention also features compositions, including arrays of capture primers and optionally extension primers on a substrate surface, and kits, for use in the methods of the invention.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 11A and FIG. 11C show spectral data and cluster plots for the single nucleotide call T (3DL1) and G (3DS1), respectively. FIG. 11B shows data for the double nucleotide call T/G (3DL1 and 3DS1 both present). For all panels, the lowest mass peak (6447.2 Da) represents the unextended primer. Pausing peak mass is estimated by Sequenom Designer software and is based on the likelihood of incorporation of a given dNTP. Cluster plots (bottom panels) illustrate the intensity of the high mass product (T) peak vs. intensity of the low mass product (G) peak for a given sample. Assays optimized for both specificity and accuracy show tight, distinct clusters for both single nucleotide and double nucleotide calls.

FIG. 12 is an alignment for exon 3 of the seven known alleles of 2DL5 from the IPD-KIR database (available on the world wide web at ebi.ac.uk/ipd/kir). The sequence of OLGA was determined by sequencing both strands of the exon. The SNPs in the area are highlighted in bold and underline typeface. The T, G, A, G, G pattern of nucleotides for the 5 SNPs in exon 3 is unique to OLGA. The table includes the following sequences: 2DL5A*001 (SEQ ID NO:98), DL5A*005 (SEQ ID NO:99), 2DL5B*002 (SEQ ID NO:100), 2DL5B*003 (SEQ ID NO:101), 2DL5B*004 (SEQ ID NO:102), 2DL5B*006 (SEQ ID NO:103), 2DL5B*007 (SEQ ID NO:104), and 0LGA (SEQ ID NO:105).

FIG. 13 is an alignment for exon 5 of the seven known alleles of 2DL5 from the IPD-KIR database (available on the world wide web at ebi.ac.uk/ipd/kir). The SNPs in the area are highlighted in bold and underline typeface. The sequence of OLGA was determined by sequencing both strands of the exon. The table includes the following sequences: 2DL5A*001 (SEQ ID NO:106), DL5A*005 (SEQ ID NO:107), 2DL5B*002 (SEQ ID NO:108), 2DL5B*003 (SEQ ID NO:109), 2DL5B*004 (SEQ ID NO:110), 2DL5B*006 (SEQ ID NO:111), 2DL5B*007 (SEQ ID NO:112), and 0LGA (SEQ ID NO:113).

DEFINITIONS

Figure 1B:
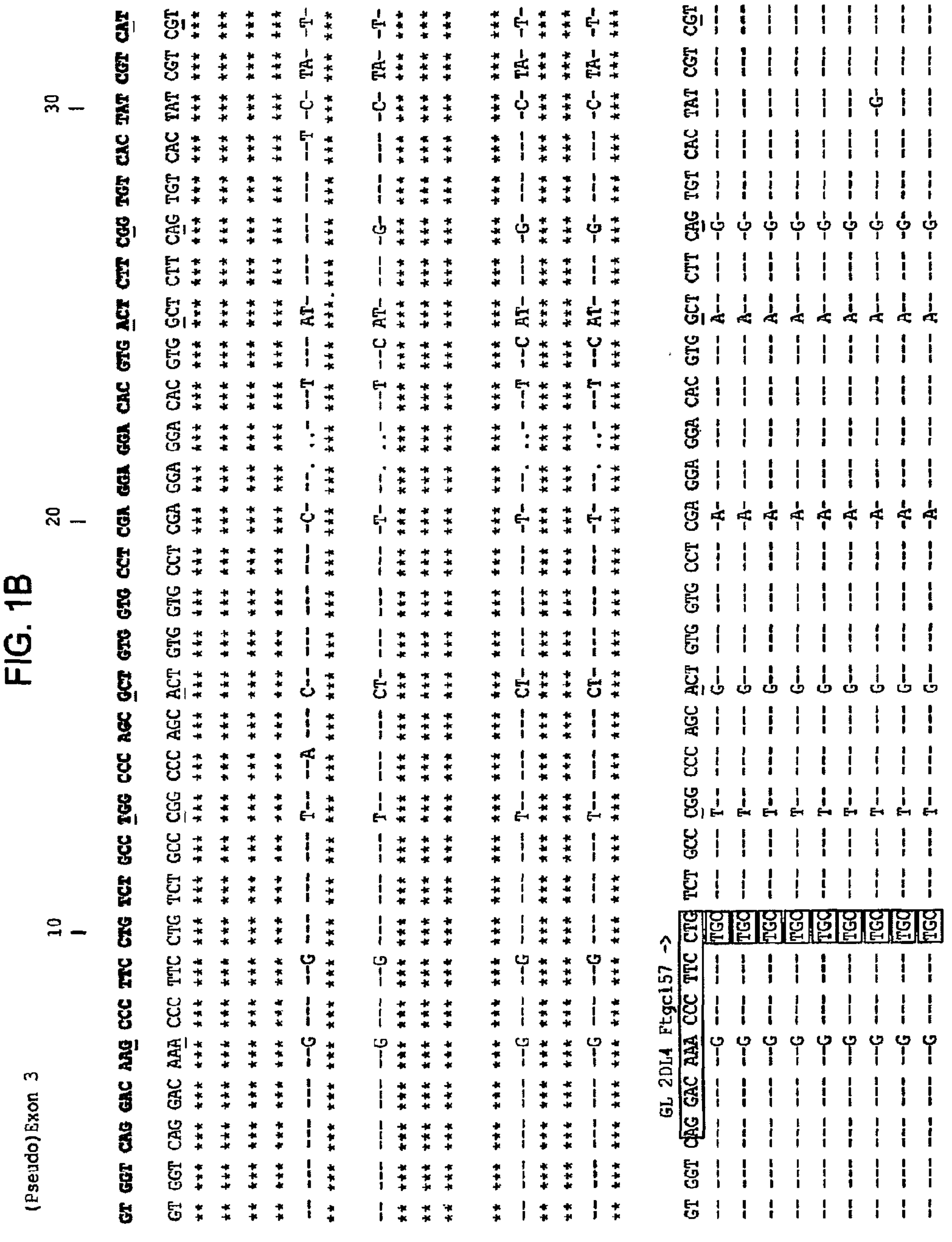
FIG. 1-FIG. 4 are an alignment of the 17 KIR genes and alleles that can be reconfigured to recreate the entire alignment.
FIGS. 1A-1R show the top row of the alignment from left (FIG. 1A) to right (FIG. 1R.)
Figure 1D:
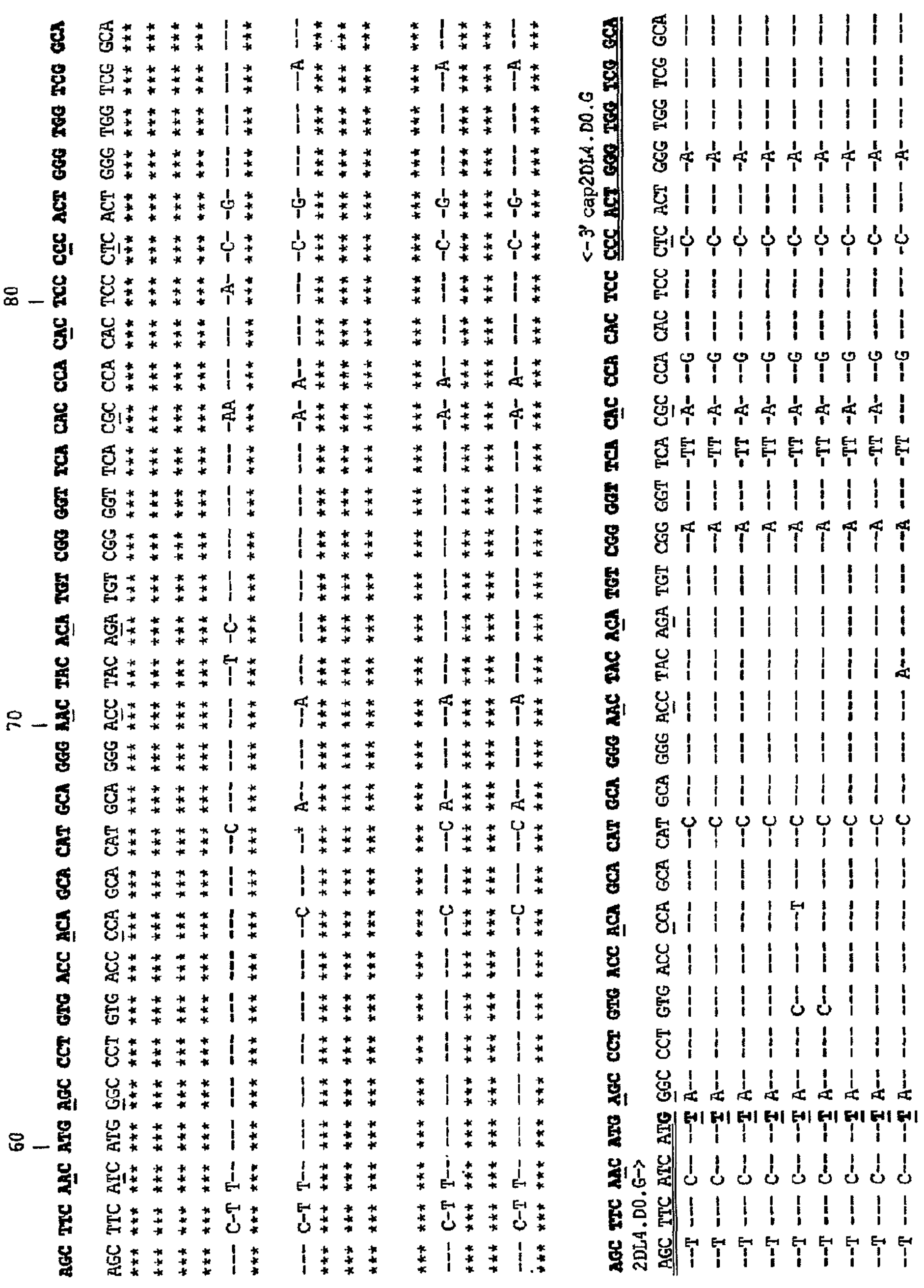
Figure 1F:
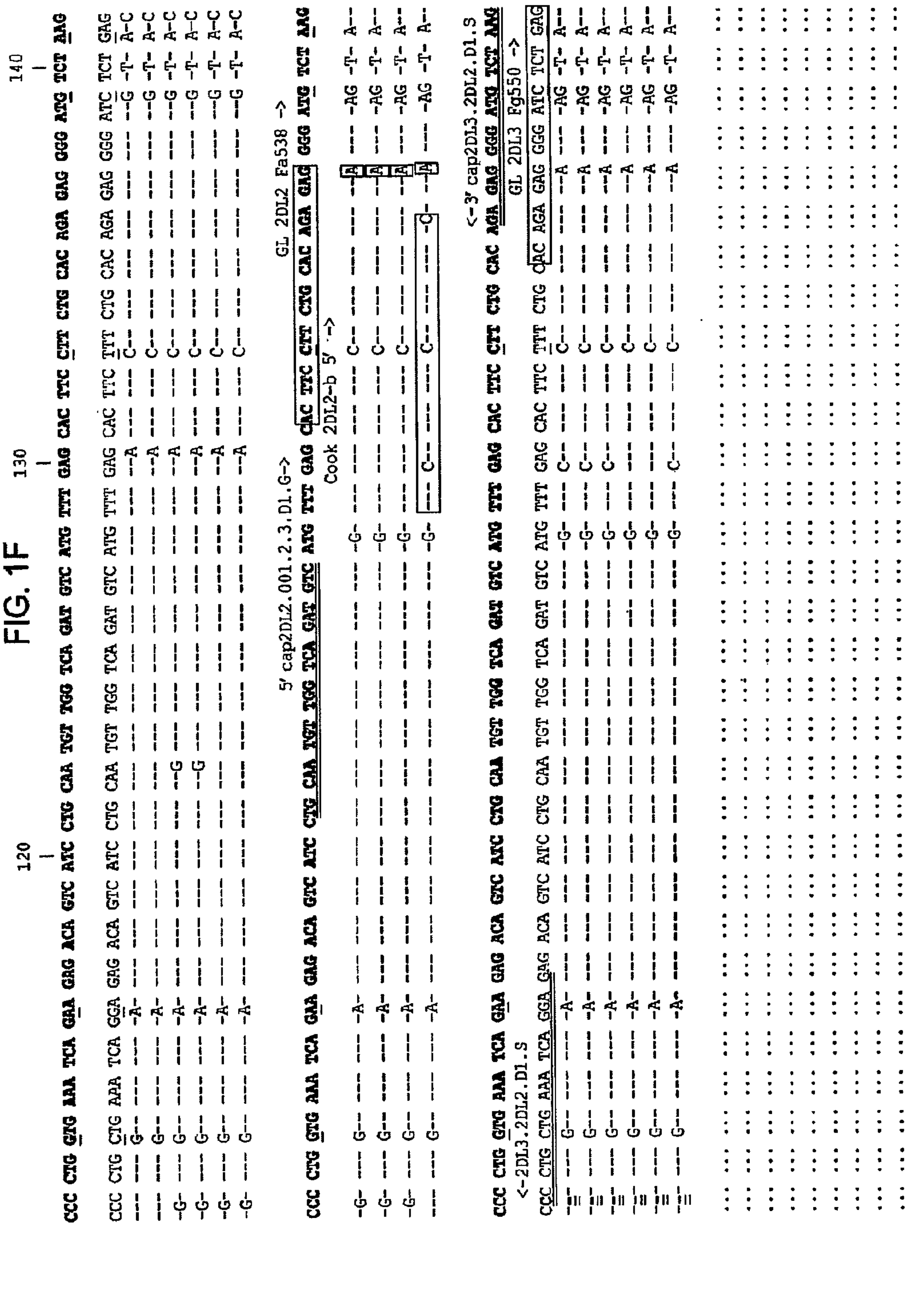
Figure 1G:
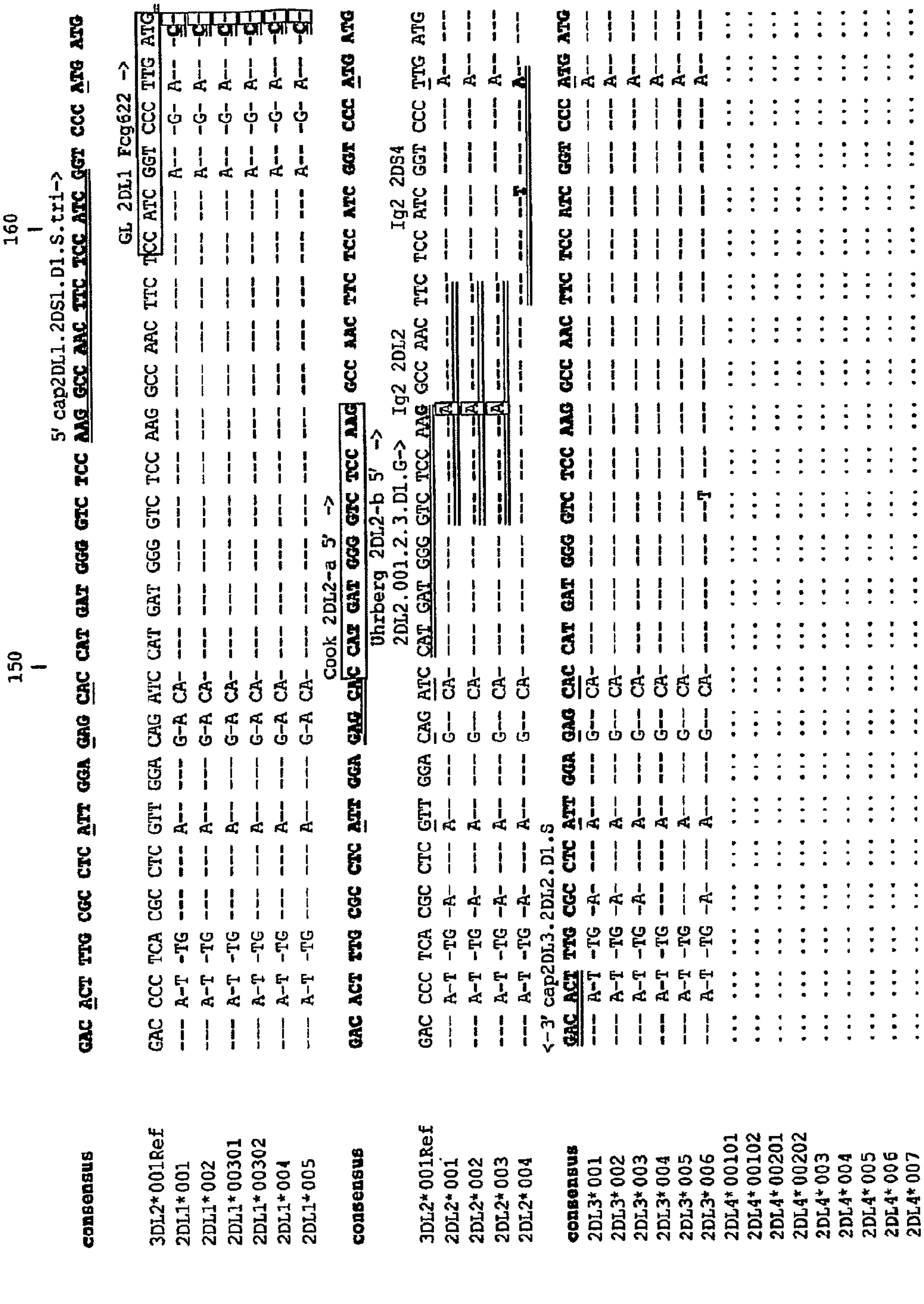
Figure 1J:
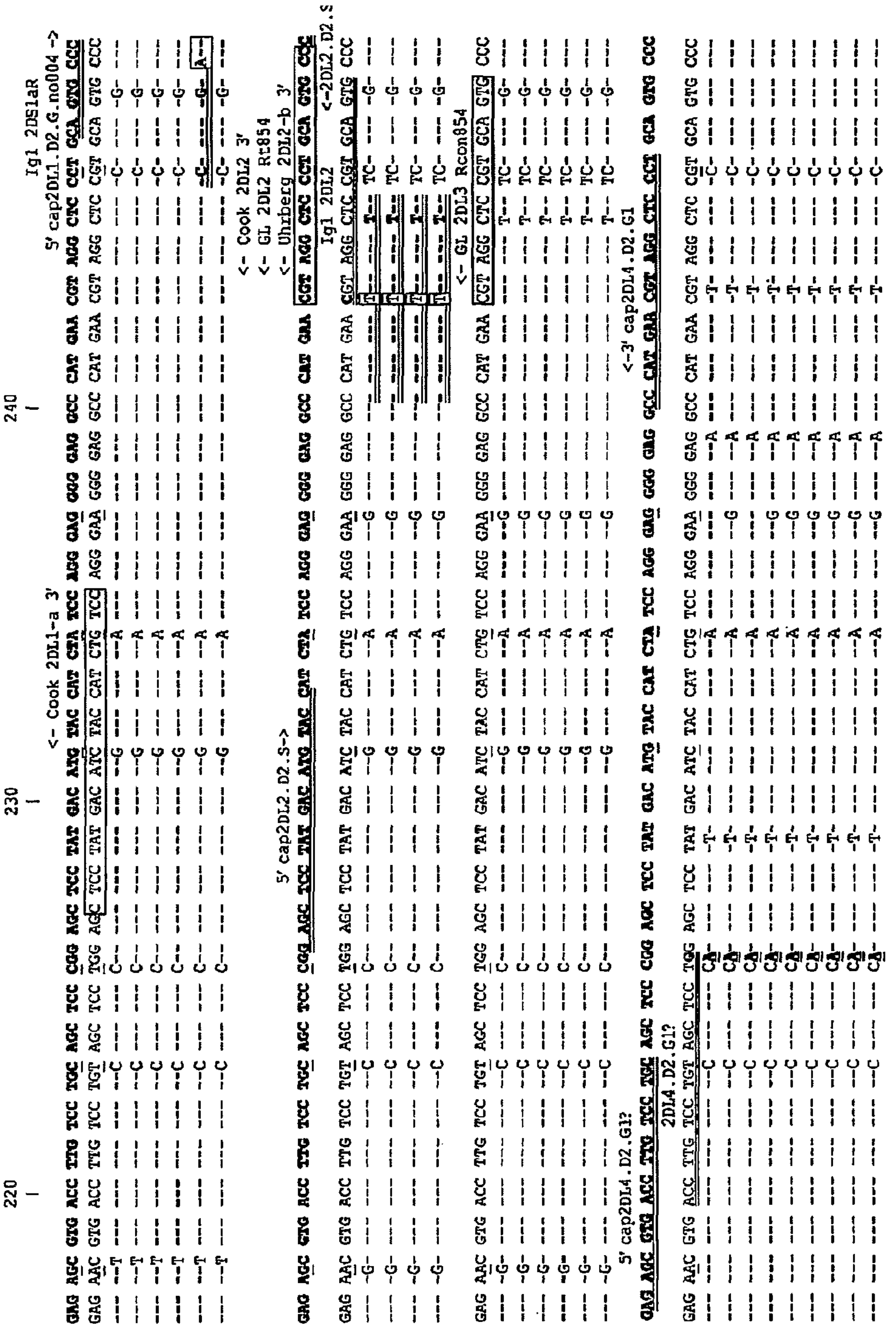
Figure 1N:
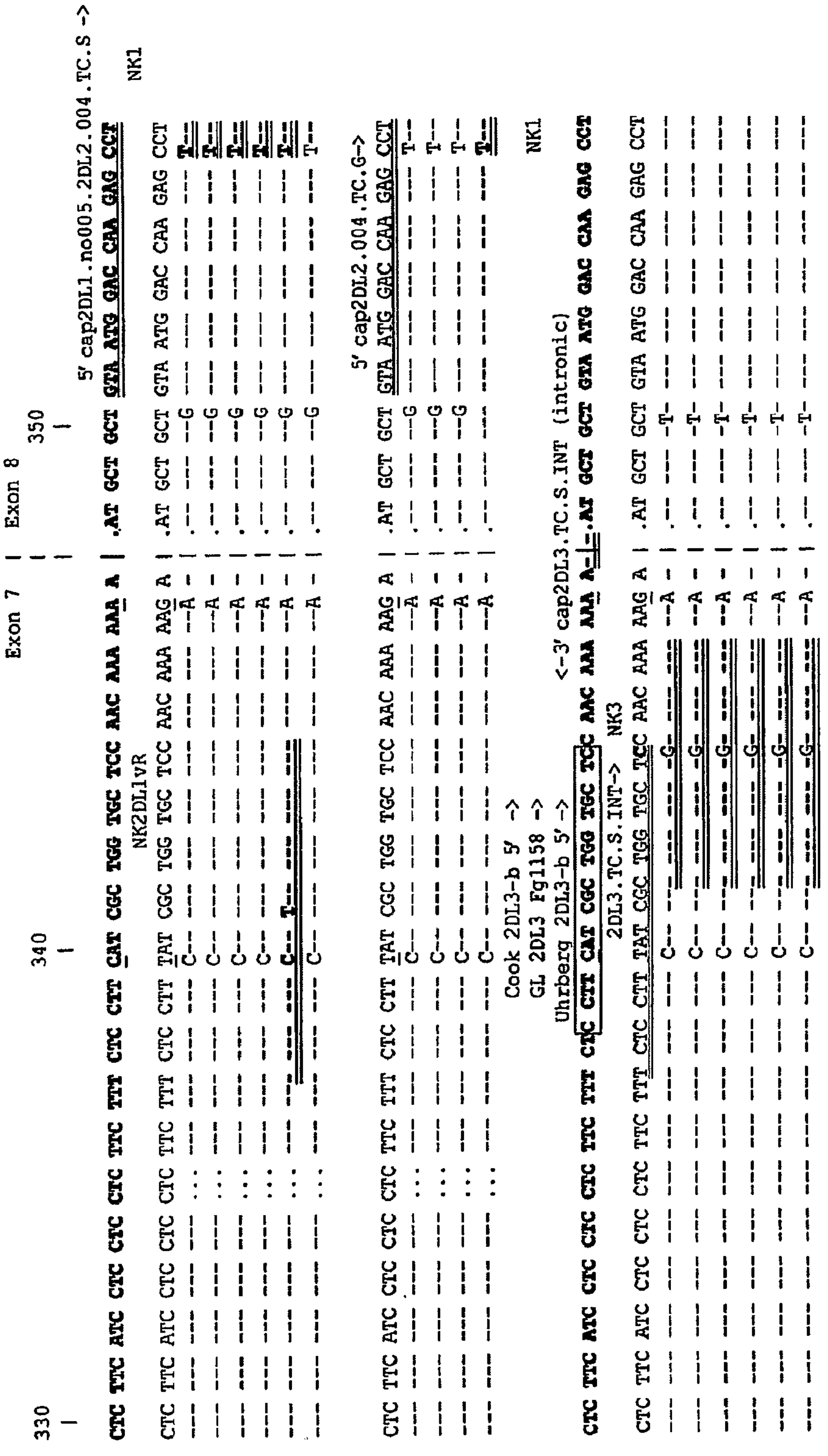

Unless otherwise defined, all technical and scientific terms used herein have the same meaning as commonly understood by one of ordinary skill in the art to which this invention belongs. Still, certain elements are defined for the sake of clarity and ease of reference.

The terms "polynucleotide," "oligonucleotide," "nucleic acid" and "nucleic acid molecule" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

Unless specifically indicated otherwise, there is no intended distinction in length between the terms "polynucleotide," "oligonucleotide," "nucleic acid" and "nucleic acid molecule" and these terms will be used interchangeably. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

Throughout the specification, abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (A or T (U)); S=C or G; W=A or T (U); M=A or C; K=G or T (U); V=A, C or G; and N=any nucleotide (A, T (U), C, or G). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides.

The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement.

Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

The term "polymorphism" as used herein refers to the occurrence of two or more genetically determined alternative sequences or alleles in a population. A polymorphic marker or site is the locus at which divergence occurs. Preferred markers have at least two alleles, each occurring at a frequency of greater than 1%, and more preferably greater than 10% or 20% of a selected population, and can be present at a frequency greater than 30% to 50% or more in selected portions of the population. A polymorphic locus may be as small as one base pair. Polymorphic markers include restriction fragment length polymorphisms, VNTR's, hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. Polymorphisms refer to sequence differences between a reference form and a selected allele, and encompasses single or multiple nucleotide differences which can result from nucleotide insertion(s), deletion(s), substitution(s) and/or a combination thereof. The allelic form occurring most frequently in a selected population is sometimes referred to as the wild-type form. Diploid organisms may be homozygous or heterozygous for allelic forms. A diallelic polymorphism has two forms. A triallelic polymorphism has three forms. The term "polymorphism" as used herein refers to any detectable polymorphic site in DNA or RNA that is detectable using the present methods. The term as used herein encompasses, for example, polymorphisms associated with a disease state (i.e. mutations), "silent" polymorphisms (i.e. associated with a wild-type phenotype or in a non-coding region), and polymorphisms associated with a predisposition and/or response to treatment (i.e. a polymorphism in an allele of a gene).

The term "single nucleotide polymorphism" and "SNP" as used interchangeably herein refers to a polymorphic site occupied by a single nucleotide (i.e. single base), which is the site of variation between allelic sequences. In general, SNPs are DNA sequence variations that occur when a single nucleotide (A, T, C or G) in the genomic sequence is altered. For example a SNP might change the DNA sequence AAGGCTAA (SEQ ID NO:114) to ATGGCTAA (SEQ ID NO:115). SNPs can occur in both coding (gene) and noncoding regions of the genome. The site is usually preceded by and followed by highly conserved sequences of the allele (e.g., sequences that vary in less than 1/100 or 1/1000 members of the population).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele. Hybridizations are usually performed under stringent conditions, for example, at a salt concentration of no more than 1M and a temperature of at least 25° C. For example, conditions of 5×SSPE (750 mM NaCl, 50 mM NaPhosphate, 5 mM EDTA, pH 7.4) and a temperature of 25°-30° C. are suitable for allele-specific probe hybridizations.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which the recited material is unaccompanied by at least some of the material with which it is normally associated in its natural state, preferably constituting at least about 90%, more preferably at least about 95% by weight of the total compound in a given sample. For example, the term "isolated" with respect to a polynucleotide generally refers to a nucleic acid molecule devoid, in whole or part, of sequences normally associated with it in nature; or a sequence, as it exists in nature, but having heterologous sequences in association therewith; or a molecule disassociated from the chromosome.

A polynucleotide "derived from" or "specific for" a designated sequence, such as a target sequence of a target nucleic acid, refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from" or "specific for" a designated sequence include polynucleotides that are in a sense or an antisense orientations relative to the original polynucleotide.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%, at least about 85%, preferably at least about 90%, and most preferably at least about 95% or at least about 98% sequence similarity over a defined length of the molecules. As used herein, substantially homologous also refers to sequences showing complete Identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as LASERGENE™ from DNASTAR™, Inc., and ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet on a website sponsored by the National Center for Biotechnology Information (NCBI) and the National Library of Medicine (see the world wide website of ncbi.nlm.gov/cgi-bin/BLAST).

"Recombinant" as used herein to describe a nucleic acid molecule refers to a polynucleotide of genomic, cDNA, mammalian, bacterial, viral, semisynthetic, synthetic or other origin which, by virtue of its origin, manipulation, or both is not associated with all or a portion of the polynucleotide with which it is associated in nature. The term "recombinant" as used with respect to a protein or polypeptide means a polypeptide produced by expression of a recombinant polynucleotide.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for or facilitate the transcription and translation of a coding sequence in a host cell.

A "DNA-dependent DNA polymerase" is an enzyme that synthesizes a complementary DNA copy from a DNA template. Examples include DNA polymerase I from *E. coli* and bacteriophage T7 DNA polymerase. All known DNA-dependent DNA polymerases require a complementary primer to initiate synthesis. Under suitable conditions, a DNA-dependent DNA polymerase may synthesize a complementary DNA copy from an RNA template.

As used herein, the term "target nucleic acid region" or "target nucleic acid" or "target molecules" refers to a nucleic acid molecule with a "target sequence" to be detected (e.g., by amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" refers to the particular nucleotide sequence of the target nucleic acid to be detected (e.g., through amplification) . The target sequence may include a probe-hybridizing region contained within the target molecule with which a probe will form a stable hybrid under desired conditions. The "target sequence" may also include the complexing sequences to which the oligonucleotide primers complex and can be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are usually are in the range of between 8 to 100 nucleotides in length, such as 8 to 75, 10 to 74, 12 to 72, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. The typical probe is in the range of between 10-50 nucleotides long, such as 15-45, 18-40, 20-30, 21-28, 22-25 and so on, and any length between the stated ranges.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid primers and the corresponding nucleic acid targets that are present in the sample.

As used herein, the term "binding pair" refers to first and second molecules that specifically bind to each other, such as complementary polynucleotide pairs capable of forming nucleic acid duplexes. "Specific binding" of the first member of the binding pair to the second member of the binding pair in a sample is evidenced by the binding of the first member to the second member, or vice versa, with greater affinity and specificity than to other components in the sample. The binding between the members of the binding pair is typically noncovalent.

By "selectively bind" is meant that the molecule binds preferentially to the target of interest or binds with greater affinity to the target than to other molecules. For example, a DNA molecule will bind to a substantially complementary sequence and not to unrelated sequences.

The "melting temperature" or "Tm" of double-stranded DNA is defined as the temperature at which half of the helical structure of DNA is lost due to heating or other dissociation of the hydrogen bonding between base pairs, for example, by acid or alkali treatment, or the like. The $T_m$ of a DNA molecule depends on its length and on its base composition. DNA molecules rich in GC base pairs have a higher $T_m$ than those having an abundance of AT base pairs. Separated complementary strands of DNA spontaneously reassociate or anneal to form duplex DNA when the temperature is lowered below the $T_m$. The highest rate of nucleic acid hybridization occurs approximately 25° C. below the $T_m$. The $T_m$ may be estimated using the following relationship: $T_m$=69.3+0.41 (GC) % (Marmur et al. (1962) J. Mol. Biol. 5:109-118).

As used herein, a "biological sample" refers to a sample of tissue or fluid isolated from a subject, which in the context of the invention generally refers to samples suspected of containing nucleic acid, which samples, after optional processing, can be analyzed in an in vitro assay. Typical samples of interest include, but are not necessarily limited to, biological fluids, including urine, saliva, amniotic fluid, mouth wash, blood products, such as blood, plasma, serum, blood cells, and the like, as well as solid materials, including tissues, cell pellets, biopsies, and the like.

The term "mixture", as used herein, refers to a combination of elements, e.g., capture primers, that are interspersed and not in any particular order. A mixture is homogenous and not spatially separable into its different constituents. Examples of mixtures of elements include a number of different elements that are dissolved in the same aqueous solution, or a number of different elements attached to a solid support at random or in no particular order in which the different elements are not especially distinct. In other words, a mixture is not addressable. To be specific, an array of capture primers, as is commonly known in the art and described below, is not a mixture of capture primers because the species of capture primers are spatially distinct and the array is addressable.

An "array," includes any two-dimensional or substantially two-dimensional (as well as a three-dimensional) arrangement of spatially addressable regions (i.e., "features") containing agents, such as capture primers or extension primers, and the like. The agents may be adsorbed, physisorbed, chemisorbed, or covalently attached to the arrays at any point or points along the nucleic acid chain. In some embodiments, the agents are not bound to the array, but are present in a solution that is deposited into or on features of the array.

Any given substrate may carry one, two, four or more arrays disposed on a surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 $cm^2$ or even less than 10 $cm^2$, e.g., less than about 5 $cm^2$, including less than about 1 $cm^2$, less than about 1 $mm^2$, e.g., 100 $\mu m^2$, or even smaller. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features are of the same or different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids. Such inter-feature areas typically will be present where the arrays are formed by processes involving drop deposition of reagents. It will be appreciated though, that the inter-feature areas, when present, could be of various sizes and configurations. The term "array" encompasses the term "microarray" and refers to any one-dimensional, two-dimensional or substantially two-dimensional (as well as a three-dimensional) arrangement of spatially addressable regions, usually bearing biopolymeric capture agents, e.g., polypeptides, nucleic acids, and the like.

An array is "addressable" when it has multiple regions of different moieties (e.g., different capture agent) such that a region (i.e., a "feature" or "spot" of the array) at a particular predetermined location (i.e., an "address") on the array will detect a particular sequence. Array features are typically, but need not be, separated by intervening spaces.

An "array layout" refers to one or more characteristics of the features, such as feature positioning on the substrate, one or more feature dimensions, and an indication of a moiety at a given location.

The term "MALDI mass spectrometer" refers to a mass spectrometer which uses a laser as a means to desorb, volatize, and ionize an analyte. Matrix-assisted laser desorption-ionization (MALDI-TOF) time-of-flight (TOF) mass spectrometer.

A "MALDI sample plate" is a device that, when positionally engaged in an interrogatable relationship to a laser desorption ionization source of a MALDI mass spectrometer, can be used to deliver ions derived from an analyte on the plate to the mass spectrometer. In other words, the term "MALDI sample plate" refers to a device that is removably insertable into a MALDI mass spectrometer and contains a substrate having a surface for presenting analytes for detection by the mass spectrometer. As will be described in greater detail below, a MALDI sample plate may contain a plurality of features, i.e., discrete, addressable regions, each containing a different analyte for ionization by the laser of the MALDI mass spectrometer.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Precision" refers to the ability of an assay to reproducibly generate the same or comparable result for a given sample.

"Accuracy" refers to the ability of an assay to correctly detect a target molecule in a blinded panel containing both positive and negative specimens.

By "remote location," it is meant a location other than the location at which the mass spectrometer is present and primer extension occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The present invention provides methods for single nucleotide polymorphism (SNP)-based killer cell immunoglobulin-like receptor (KIR) gene cluster genotyping using the matrix-assisted laser desorption/ionization time-of-flight (MALDI-TOF) mass spectrometer. In general, the methods involve amplifying a plurality of target sequences of a plurality of KIR genes, and detecting the presence or absence of a plurality of single SNPs of the plurality of KIR genes by MALDI-TOF mass spectrometry. The invention also features compositions, including arrays of capture primers and optionally extension primers on a substrate surface, and kits, for use in the methods of the invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the gene" includes reference to one or more genes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The invention will now be described in more detail.

Methods

The present invention provides methods for SNP-based KIR gene cluster genotyping using the MALDI-TOF mass spectrometer. In general, the methods involve amplifying a plurality of target sequences of a plurality of KIR genes using capture primer pairs, and detecting the presence or absence of a plurality of single SNPs of the plurality of KIR genes by MALDI-TOF mass spectrometry. A total of 17 KIR loci have been identified, including 15 expressed genes and 2 pseudogenes, with between 2 and 12 alleles seen at each of the polymorphic KIR loci.

Figure 5:
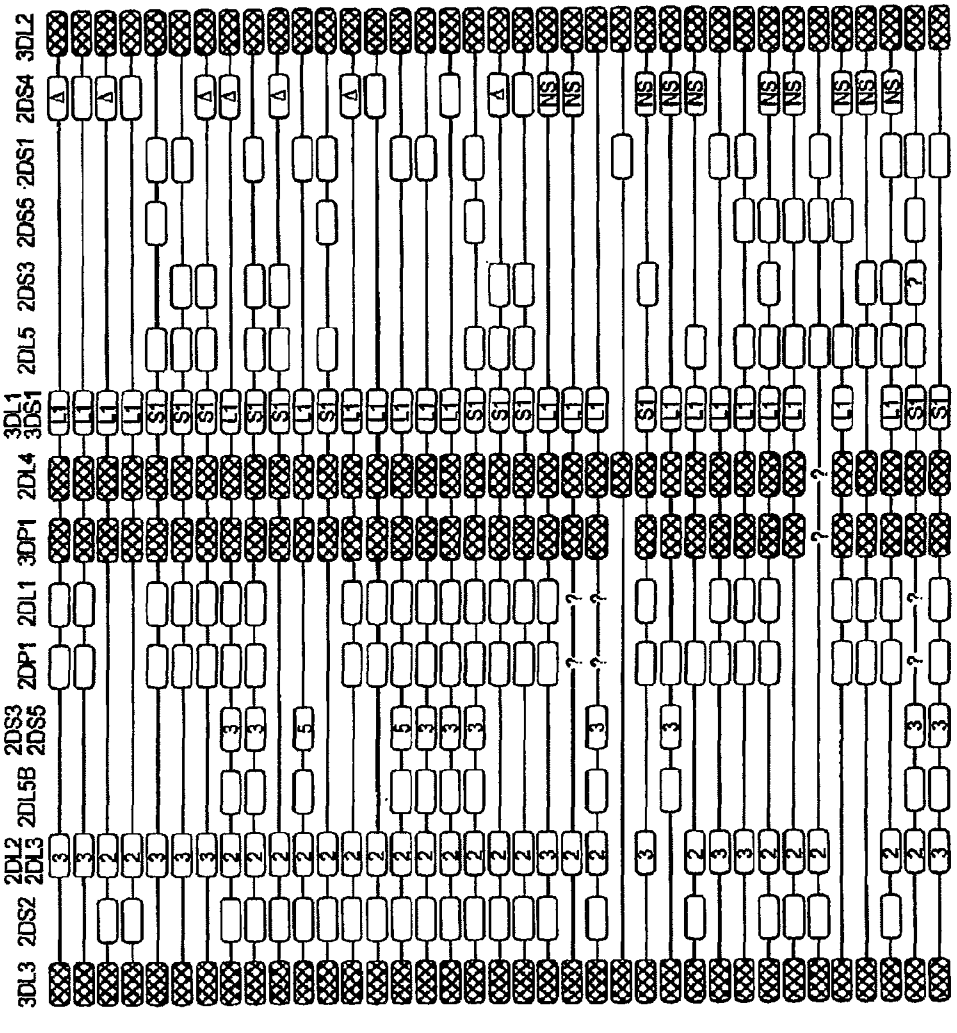
FIG. 5 is a schematic representation of exemplary KIR haplotypes based on gene content. The anchor KIR genes are represented by shaded boxes and the variable KIR genes are represented by the open boxes.

In general, the method includes detecting an expected nucleotide in at least one anchor KIR gene and a SNP of a queried gene. As used herein, "anchor KIR gene" or "framework KIR gene" refers to a common KIR gene that is present in all individuals in a defined population. Such anchor KIR genes, also referred to as "common KIR genes", or "control KIR genes", include, for example 3DL3, 3DP1, 2DL4 and 3DL2. As used herein a "queried KIR gene" refers to any KIR gene that is analyzed according to the subject methods. Due to the amplification and detection of the presence of a SNP of one anchor KIR gene in conjunction with a SNP of a queried gene, a positive signal will be present for every reaction, regardless of whether or not the SNP of the queries gene is positive. In the context of the KIR gene cluster, an individual may have a certain combination of genes that includes at least the anchor KIR genes, as well as a combination of the other KIR genes (FIG. 5). If the subject assay is performed to determine the presence or absence of a particular SNP of a queried KIR gene, without also assaying for the presence of a SNP of a anchor KIR gene, it would be impossible to determine conclusively whether a negative result is indicative of the absence of the SNP or whether the assay was not properly performed. Therefore only a negative result for a SNP for a queried KIR gene in conjunction with a positive result for the presence of a SNP of an anchor KIR gene is indicative of the absence of the SNP of the queried KIR gene.

The 17 KIR genes include 2DL1, 2DL2, 2DL3, 2DL4, 2DL5A, 2DL5B, 2DS1, 2DS2, 2DS3, 2DS4, 2DS5, 3DL1, 3DL2, 3DL3, 3DS1, 2DP1 and 3DP1. The 38 SNPs of the KIR genes include 2DS3.D1.G, 2DL2.D2.S, 3DL3.D1.G, 3DL3.D2.G, 2DL4.DO.G, 3DL2.TC.G, 3DS1.3DL1.D1.S, 2DL5.D2.G, 2DL5.TC.G, 2DS4.D1.G, 2DL1.D2.G.no004, 2DL4.TC.G, 2DL2.004.TC.G, 2DS2.D1.G, 3DL1.TC.S, 2DS5.D2.G, 2DL1.no005, 2DL3.2DL2.D1.S, 3DS1.DO.S, 3DL2.D1.G, 2DS3.D2.S, 3DS1.TC.S.INT, 3DP1.D2.G2, 2DL5sub5, 2DL5sub4, 2DL5sub1, 2DS5.D1.G, 2DP1.D0.G, 2DS2.D2.G, 2DL1.2DS1.D1.S.tri, 2DL5sub3, 2DL5sub2, 2DS4del.sub, 2DS4.D2.S, 2DL3.TC.S.INT, 2DL2.001.2.3.D1.G, 2DS1.D2.G, and 2DL5sub6. An alignment of the 17 KIR genes, alleles, and the positioning of the SNPs is provided in FIGS. 1-4.

Both inhibitory and activating KIRs are found on natural killer (NK) cells and a small percentage of cytotoxic T-cells, where the KIRs are important in regulating cell execution and cytokine response. The diversity in terms of both the number and combination of KIR genes among individuals, as well as extensive allelic polymorphism, affect the strength and breadth of the immune response. The balance between inhibitory and activating KIR and their specific HLA ligands plays an important role in immune related disease, including autoimmune disease, infectious diseases, and cancers. Therefore, the present invention is useful for determining the KIR genotype of an individual and thus the susceptibility of the subject to immune related disease, including autoimmune disease, infectious diseases, and cancers. Furthermore, a determined genotype of an individual is also useful for identifying whether a candidate donor is a suitable transplant donor.

Figure 10:
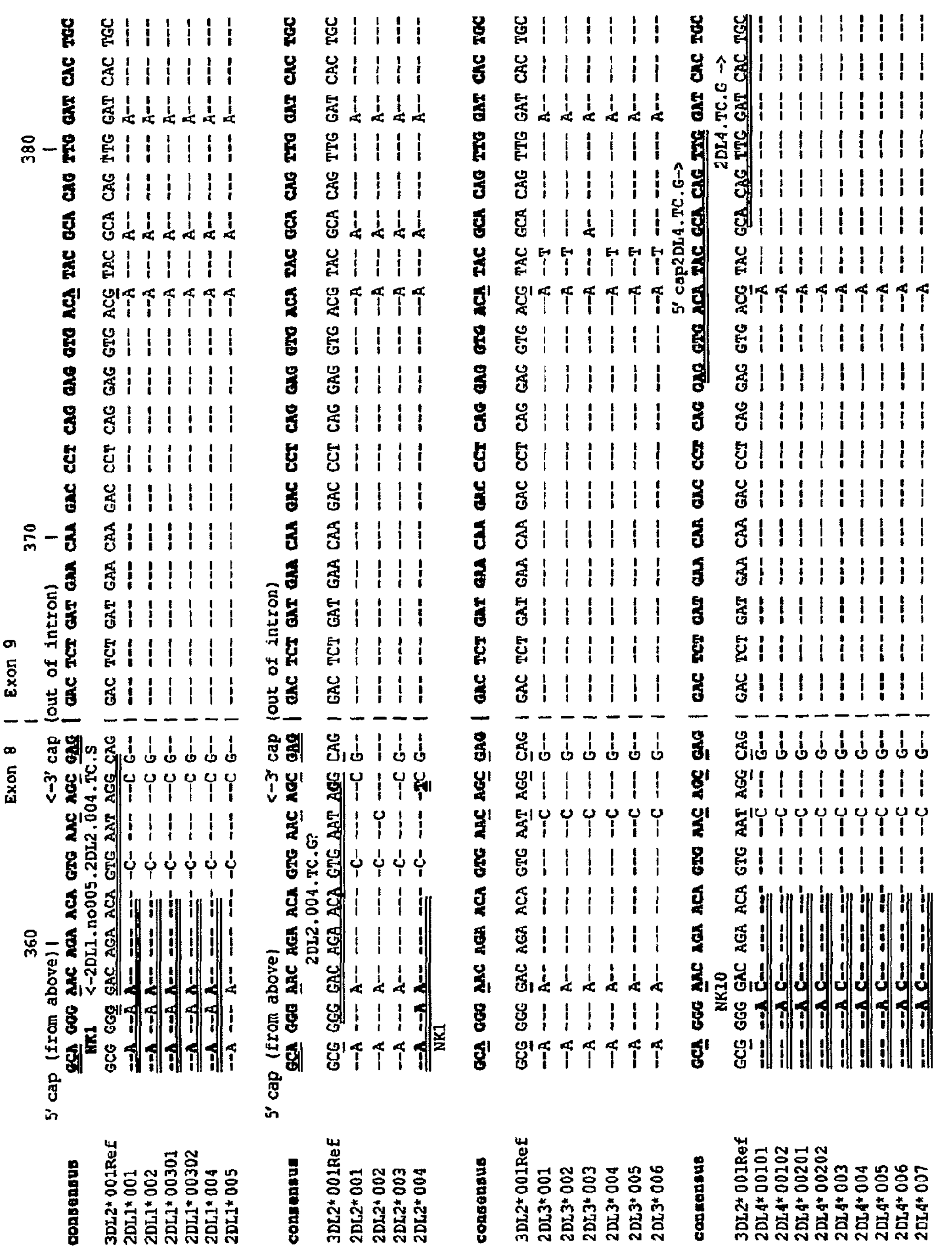
FIG. 10 is a schematic representation of an exemplary hME primer extension reaction. Primers are designed to terminate at the base preceding the base to be queried. After extension and desalting, the reactions are run in the MALDI-TOF MS. The spectrum for each of the reactions can be analyzed. An illustration of the spectra for the extended primers produced by the mixture of dGTP and ddATP/ddCTP/ddTTP used in a hypothetical hME reaction is seen below. P is the unextended primer, A1 is Allele 1, and A2 is Allele 2. Allele 1 is terminated by the addition of a single base, a ddATP. Allele 2 is not terminated by the first base added, a dGTP, but is terminated by the ddATP. The mass difference between the two extension products is the difference between the mass of the primer+ddATP, and the primer+dGTP+ddATP, which is equal to the mass of a single dGTP, or 329.2 Daltons, easily resolvable on the MS.
Figure 1P:
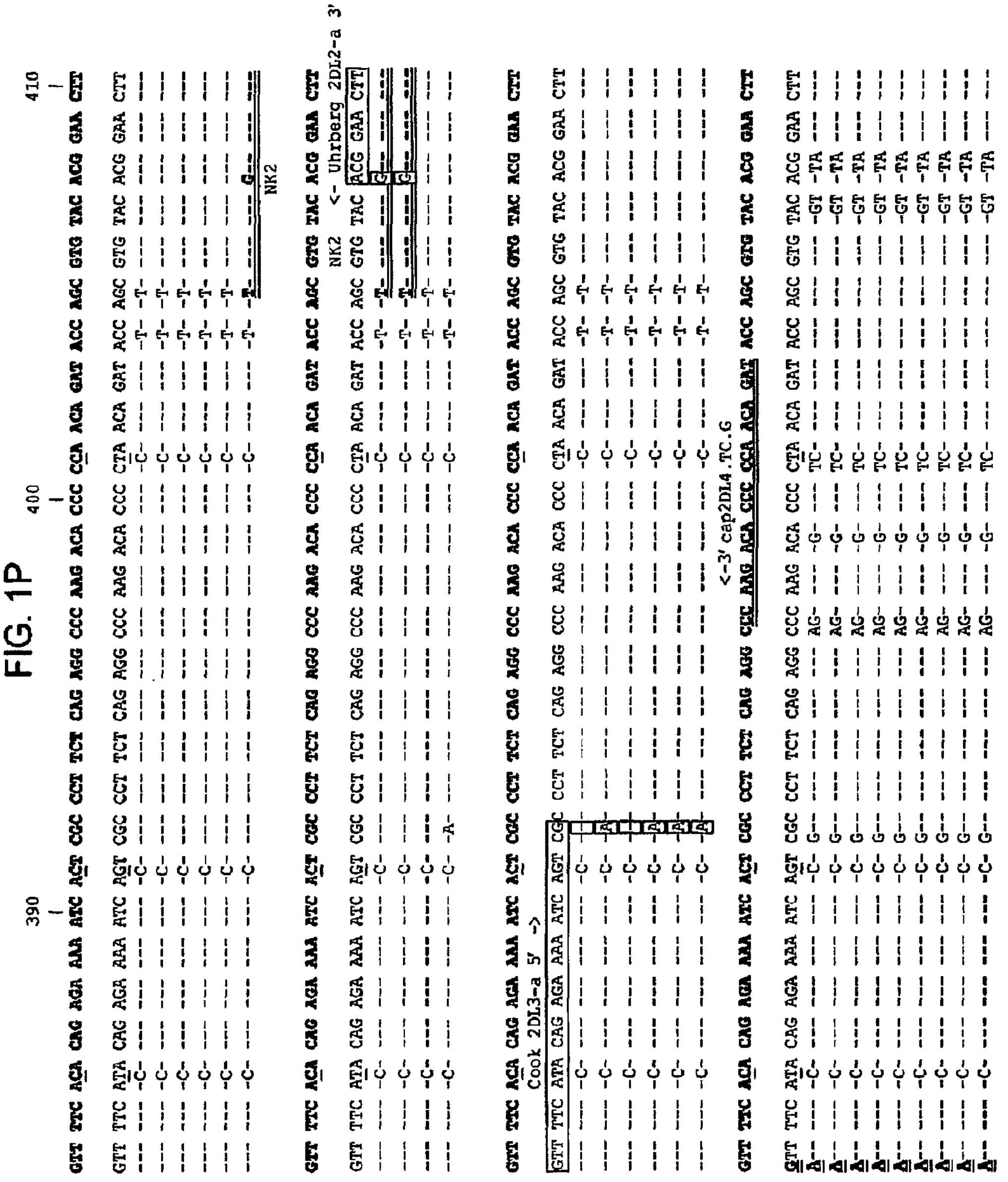
Figure 1R:
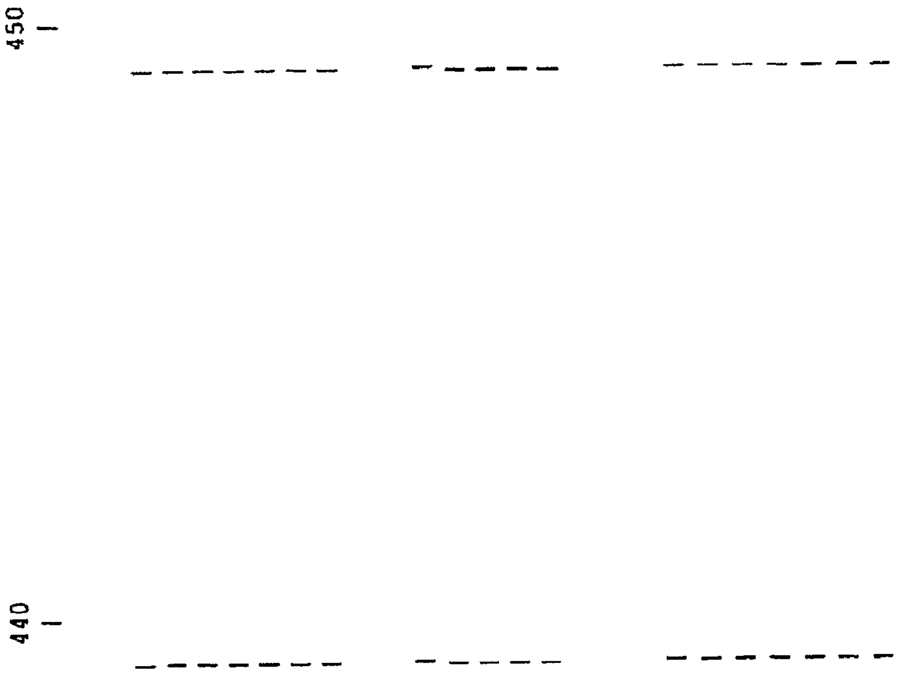
Figure 2B:
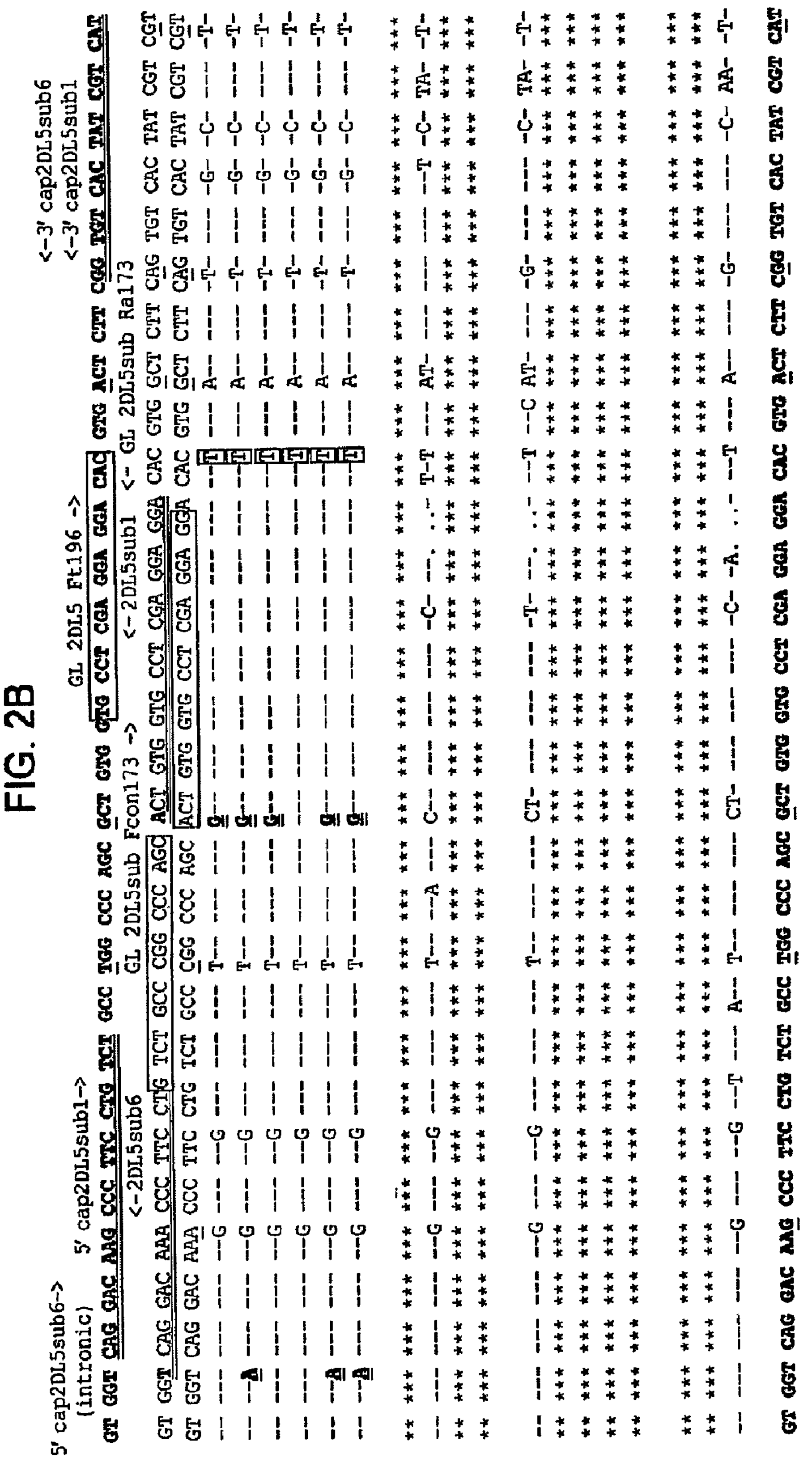
FIGS. 2A-2R show the second row of the alignment just below the first row from left (FIG. 2A) to right (FIG. 2R).
Figure 2D:
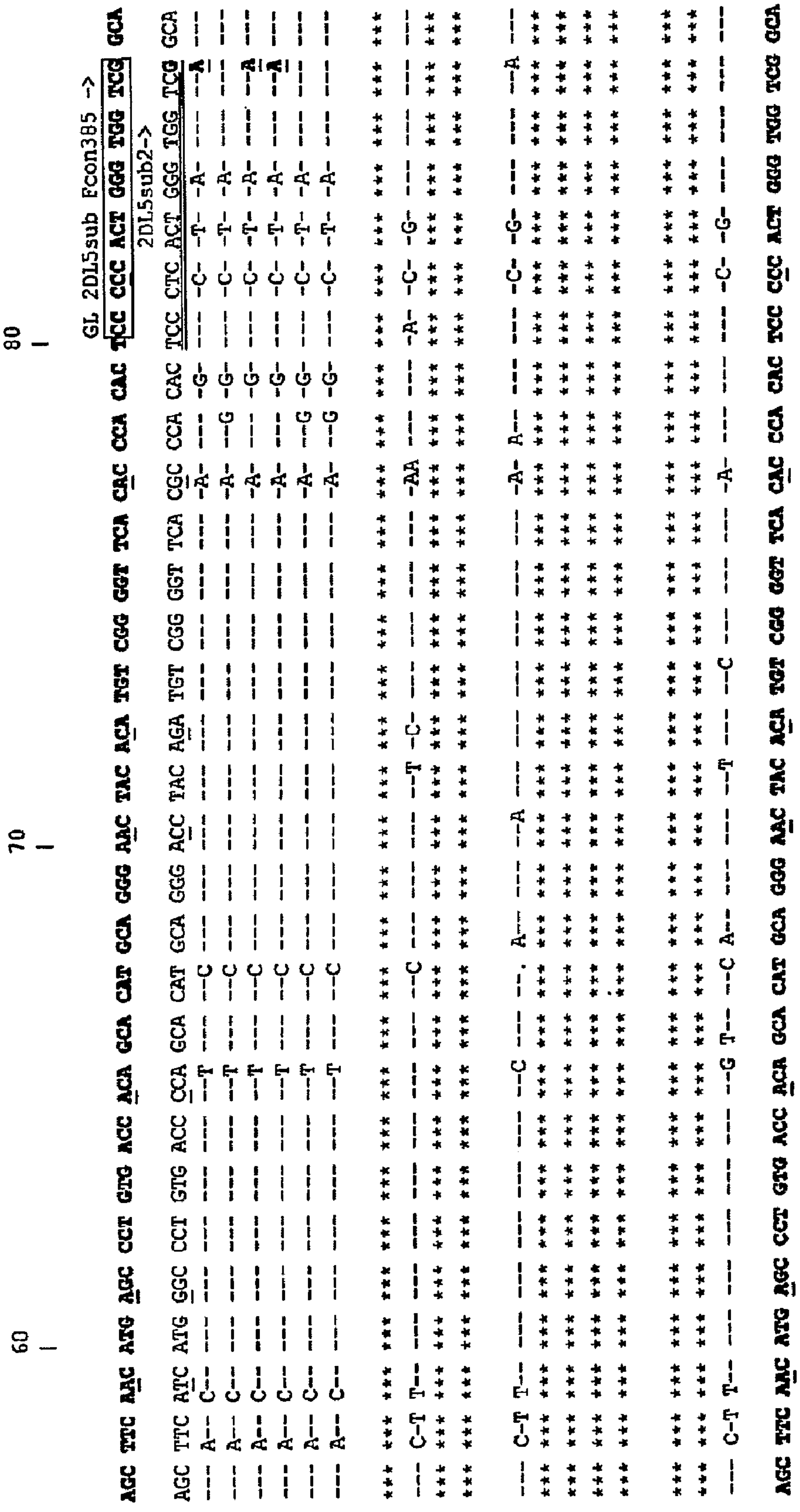
Figure 2F:
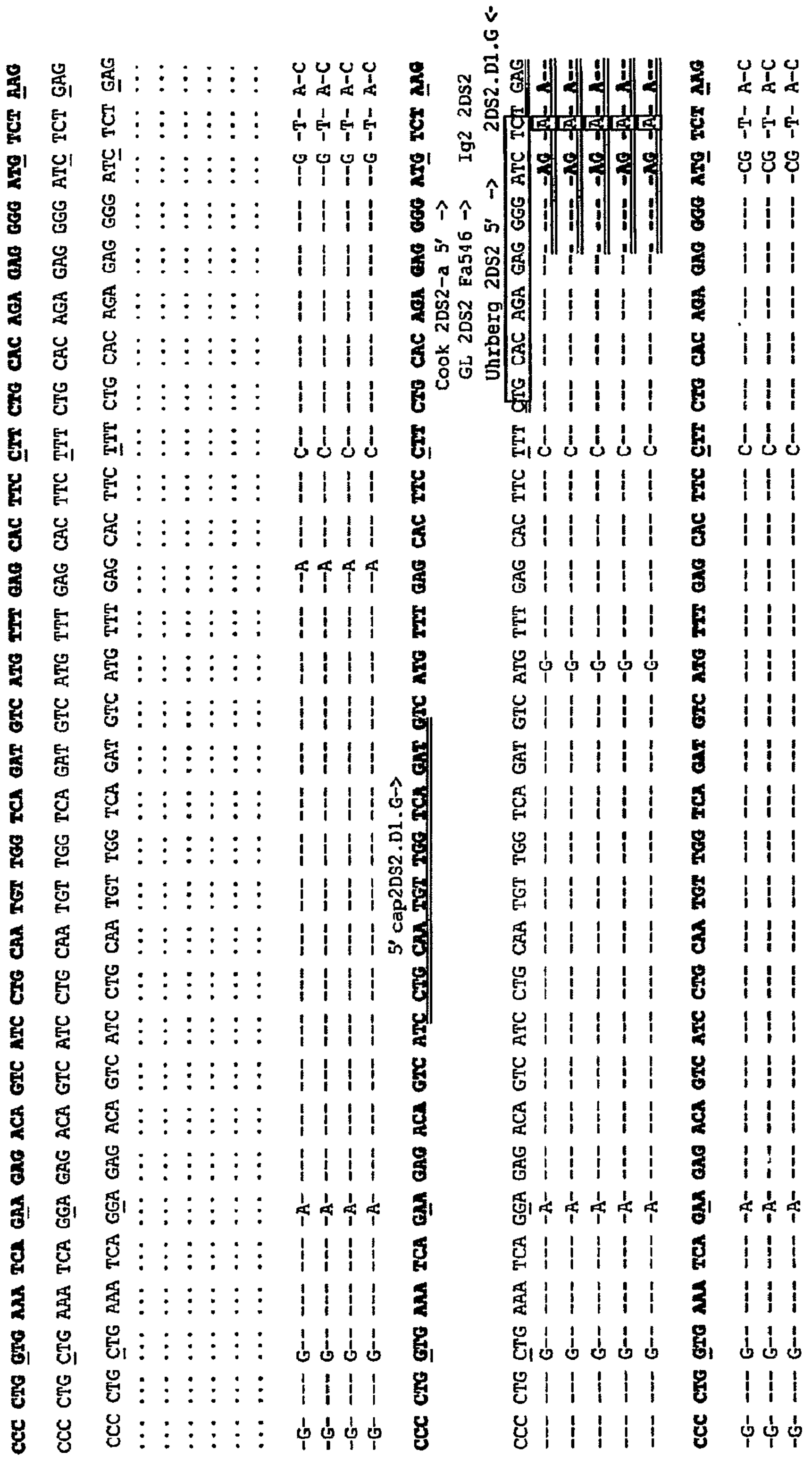
Figure 2H:
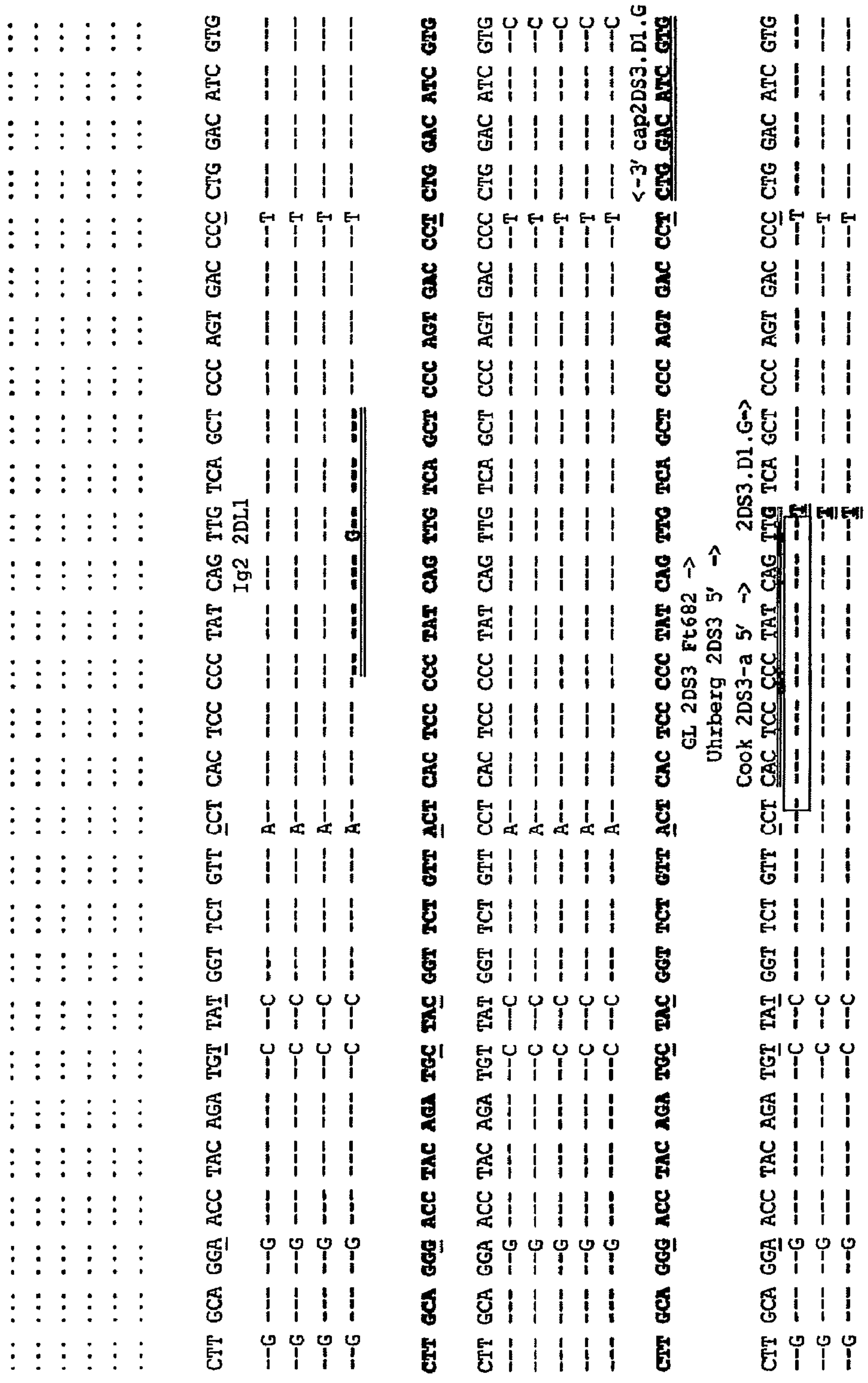
Figure 2J:
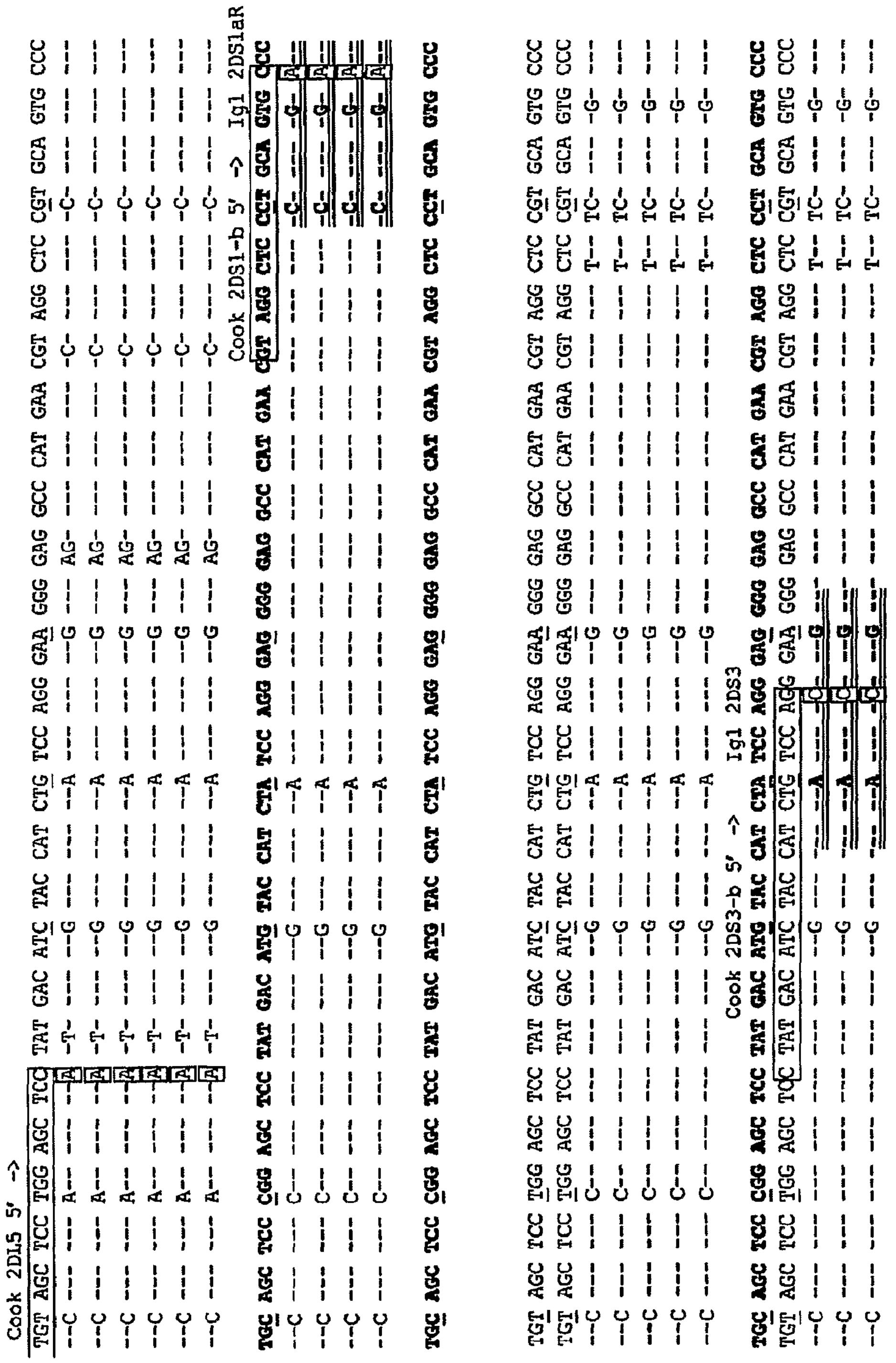
Figure 2N:
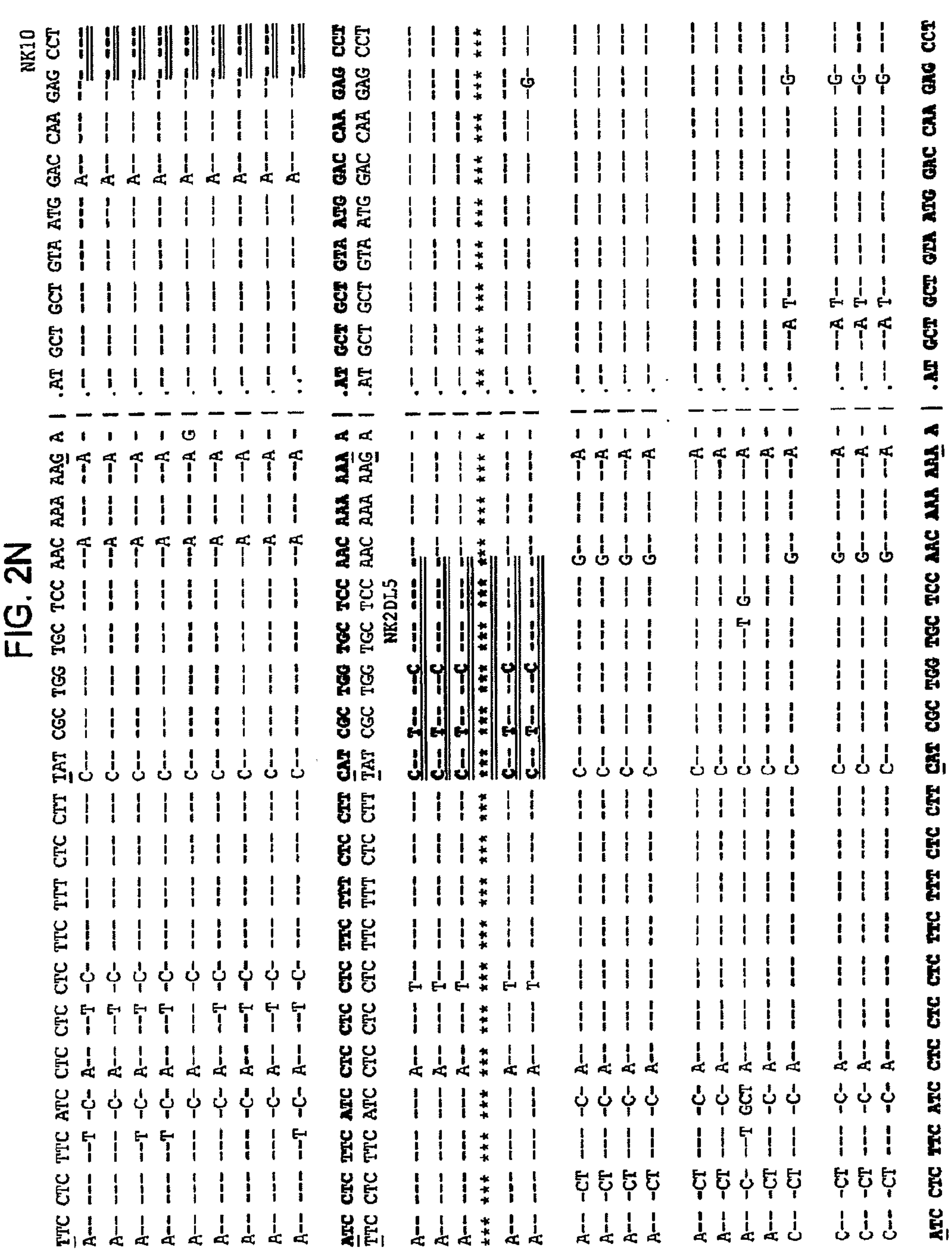
Figure 3B:
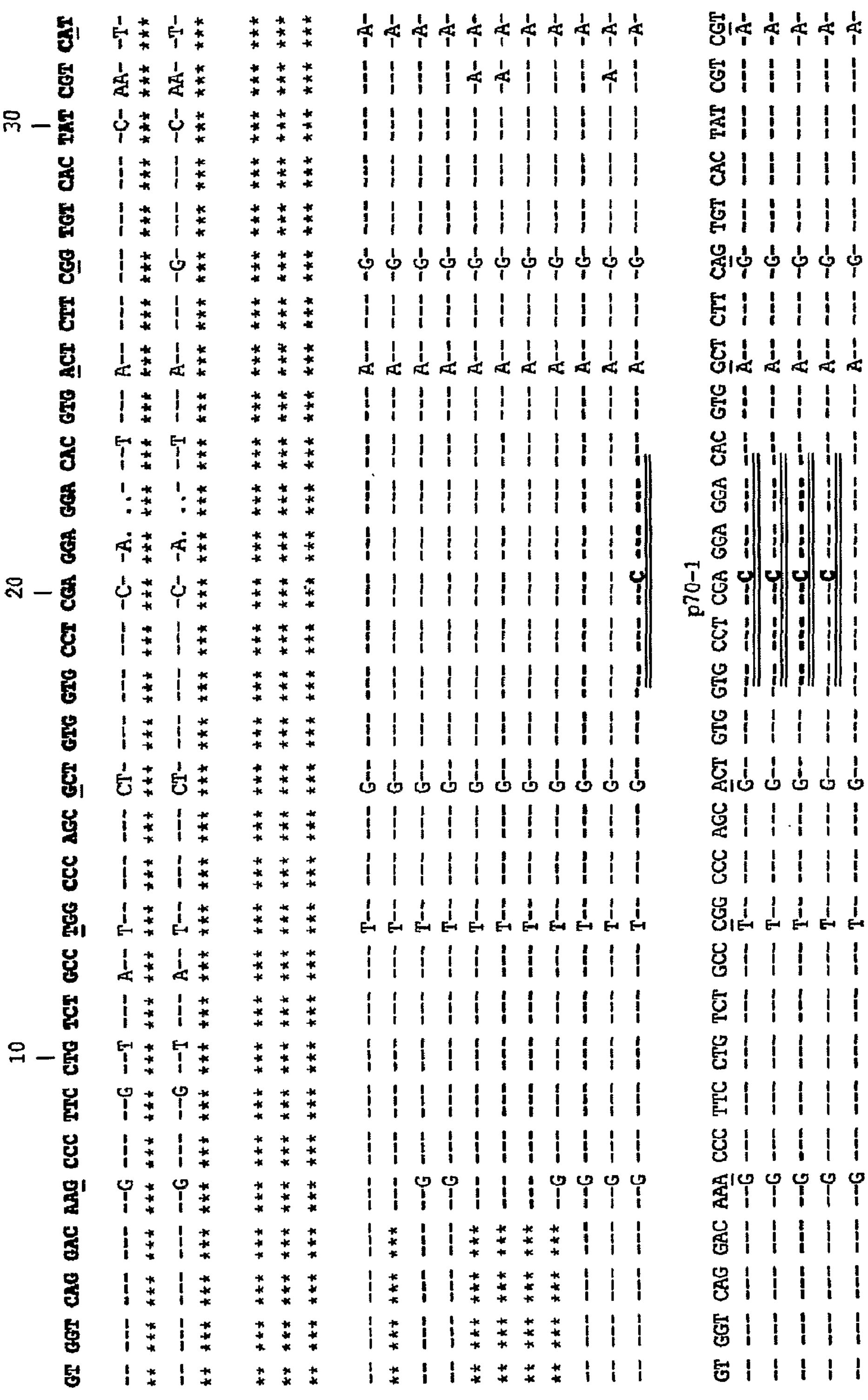
FIGS. 3A-3Q show the third row of the alignment just below the second row from left (FIG. 3A) to right (FIG. 3Q).
Figure 3F:
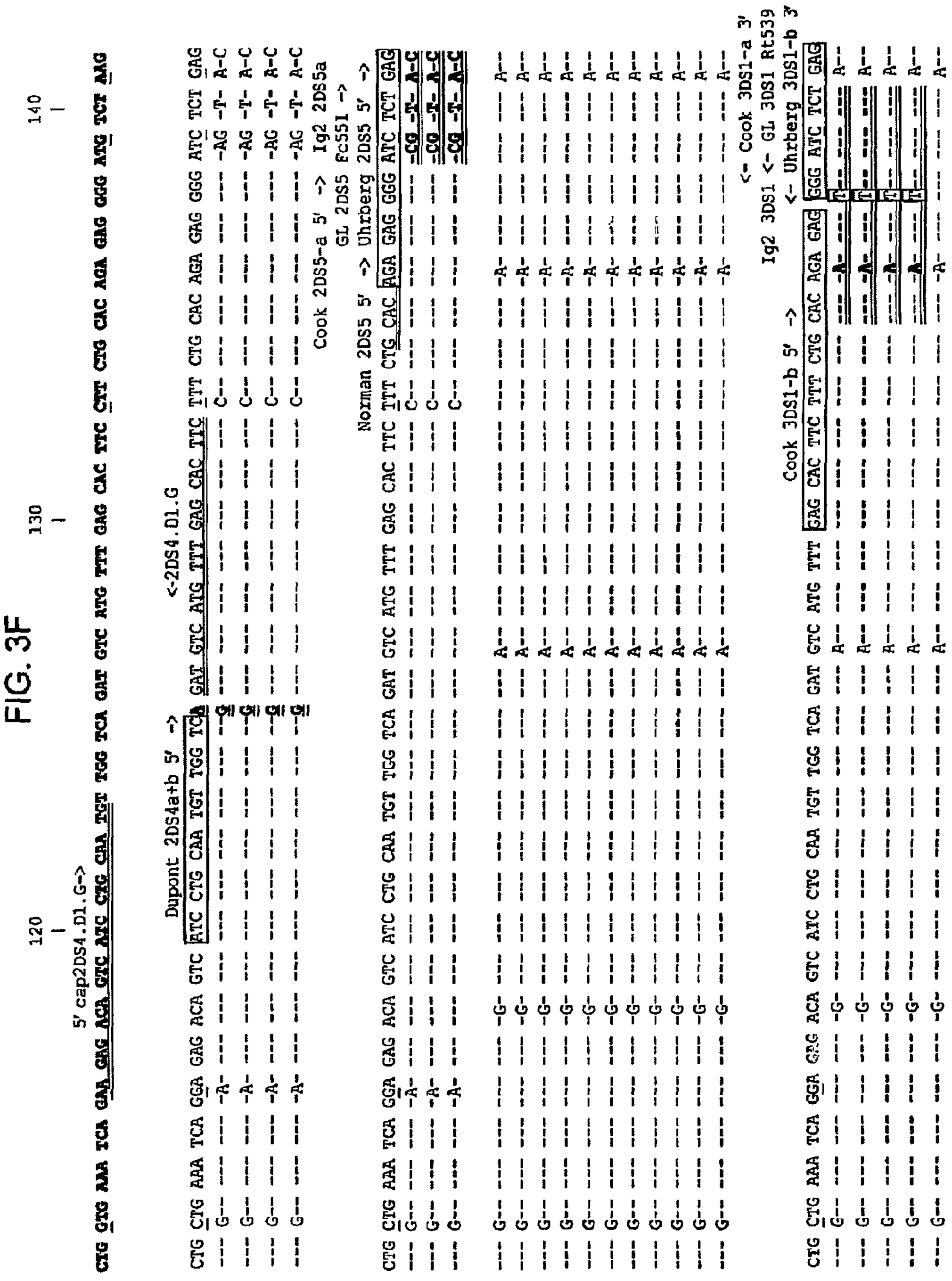
Figure 3G:
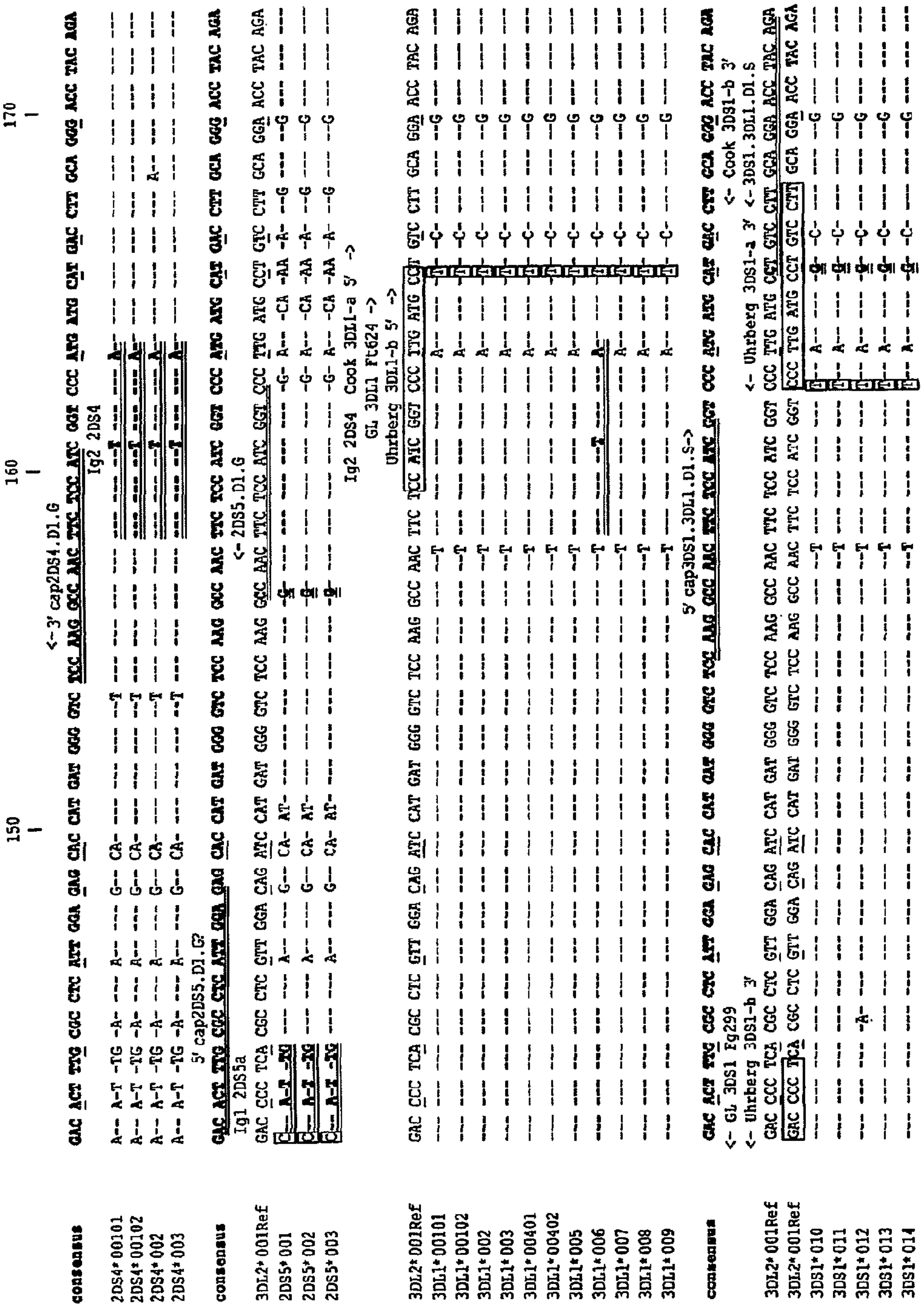
Figure 3H:
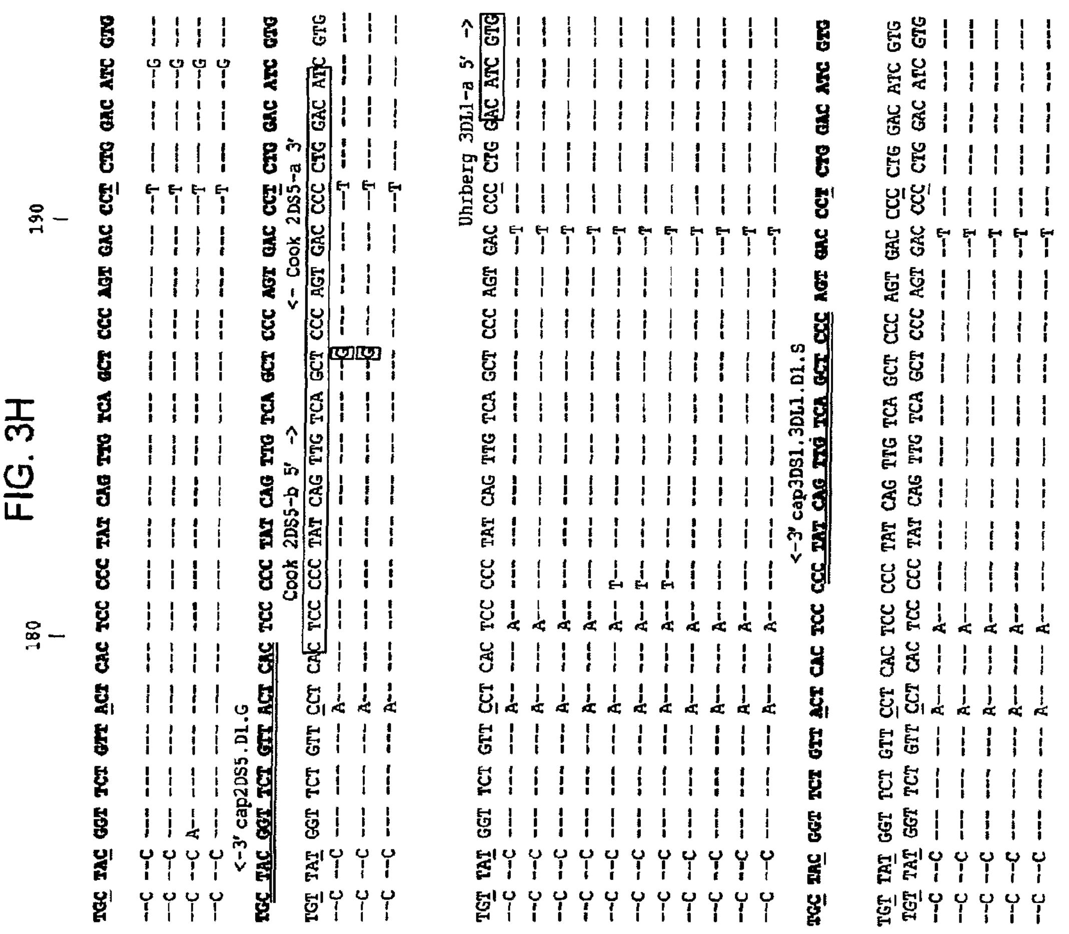
Figure 3J:
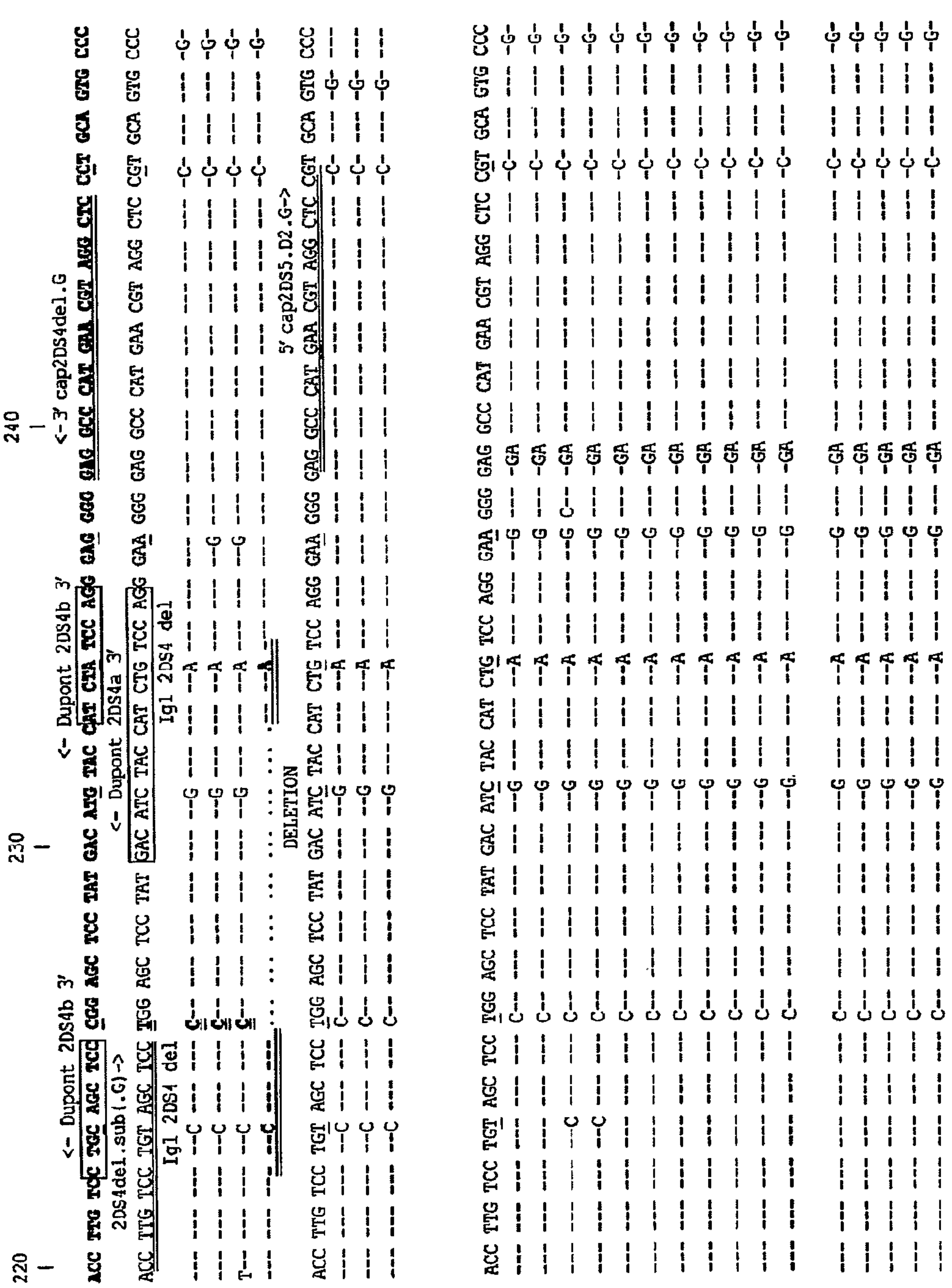
Figure 4B:
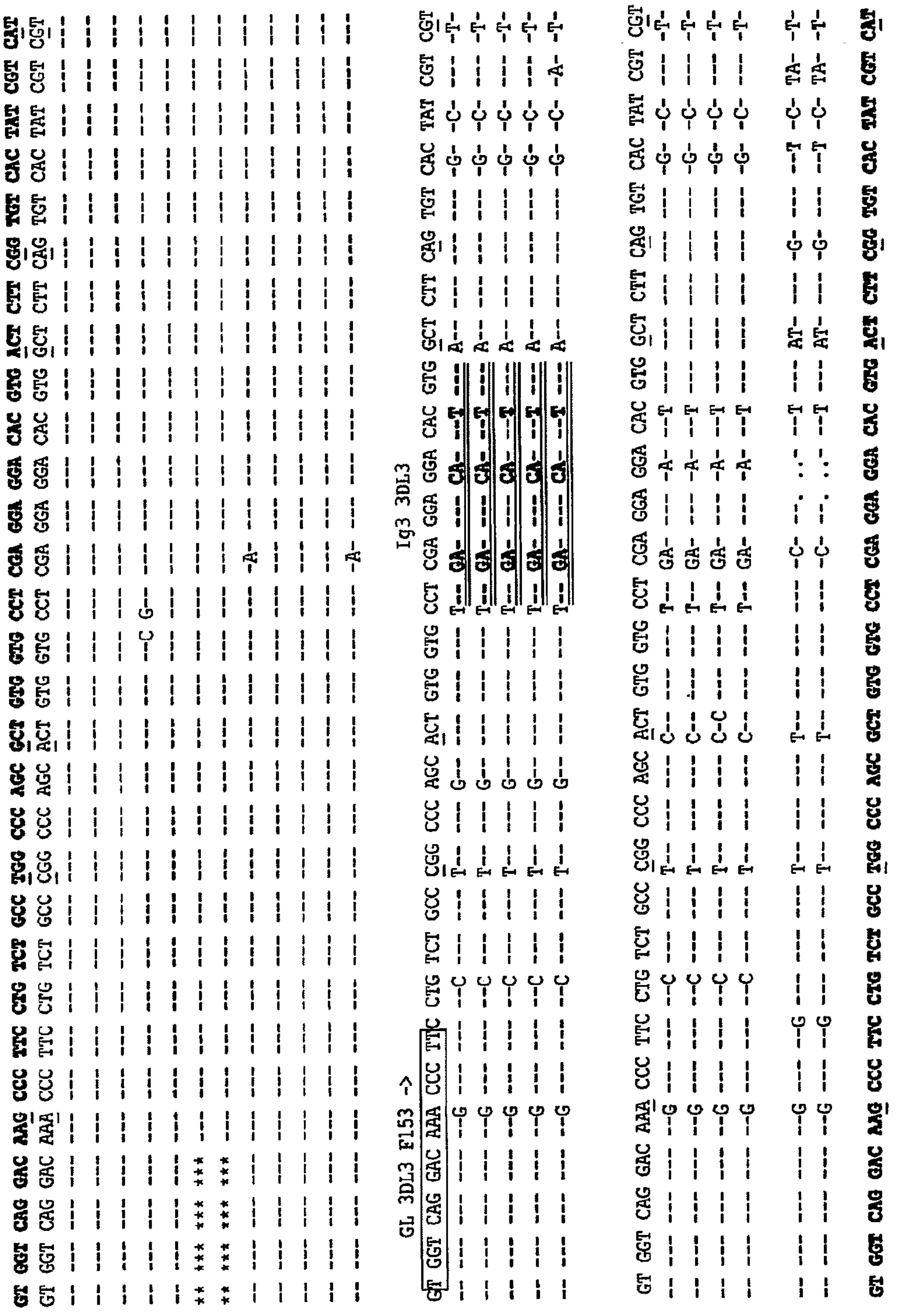
FIGS. 4A-4Q show the forth row of the alignment just below the third row from left (FIG. 4A) to right (FIG. 4Q). A consensus sequence is provided in bold text, with single nucleotide polymorphisms indicated in underlined text within the consensus sequence and throughout the alleles. Exemplary locations of capture primers and extension primers are indicated using double underlined text. Exemplary locations of SSP primers are indicated using a box surrounding the text. Exemplary locations of SSO probes are indicated using bold and double underlined text with the name noted above the sequence. Sequence positions indicated by a dash (-) are the same as the consensus sequence. Sequence positions indicated by a star (*) have not be sequenced and can be any nucleotide. Sequence positions indicated by a period (.) are deletions. The table includes the following sequences: consensus sequence (SEQ ID NO:01), 3DL2*001Ref (SEQ ID NO:02), 2DL1*001 (SEQ ID NO:03), 2DL1*002 (SEQ ID NO:04), 2DL1*00301 (SEQ ID NO:05), 2DL1*00302 (SEQ ID NO:06), 2DL1*004 (SEQ ID NO:07), 2DL1*005 (SEQ ID NO:08), 2DL2*001 (SEQ ID NO:09), 2DL2*002 (SEQ ID NO:10), 2DL2*003 (SEQ ID NO:11), 2DL2*004 (SEQ ID NO:12), 2DL3*001 (SEQ ID NO:13), 2DL3*002 (SEQ ID NO:14), 2DL3*003 (SEQ ID NO:15), 2DL3*004 (SEQ ID NO:16), 2DL3*005 (SEQ ID NO:17), 2DL3*006 (SEQ ID NO:18), 3DL2*001Ref (SEQ ID NO:19), 2DL4*00101 (SEQ ID NO:20), 2DL4*00102 (SEQ ID NO:21), 2DL4*00201 (SEQ ID NO:22), 2DL4*00202 (SEQ ID NO:23), 2DL4*003 (SEQ ID NO:24), 2DL4*004 (SEQ ID NO:25), 2DL4*005 (SEQ ID NO:26), 2DL4*006 (SEQ ID NO:27), 2DL4*007 (SEQ ID NO:28), 3DL2*001Ref (SEQ ID NO:29), 2DL5A*001 (SEQ ID NO:30), 2DL5B*002 (SEQ ID NO:31), 2DL5B*003 (SEQ ID NO:32), 2DL5B*004 (SEQ ID NO:33), 2DL5 (2DLXa) (SEQ ID NO:34), 2DL5 (2DLXb) (SEQ ID NO:35), 2DS1*001 (SEQ ID NO:36), 2DS1*002 (SEQ ID NO:37), 2DS1*003 (SEQ ID NO:38), 2DS1*004 (SEQ ID NO:39), 2DS2*001 (SEQ ID NO:40), 2DS2*002 (SEQ ID NO:41), 2DS2*003 (SEQ ID NO:42), 2DS2*004 (SEQ ID NO:43), 2DS2*005 (SEQ ID NO:44), 2DS3*00101 (SEQ ID NO:45), 2DS3*00102 (SEQ ID NO:46), 2DS3*00103 (SEQ ID NO:47), 2DS4*00101 (SEQ ID NO:48), 2DS4*00102 (SEQ ID NO:49), 2DS4*002 (SEQ ID NO:50), 2DS4*003 (SEQ ID NO:51), 2DS5*001 (SEQ ID NO:52), 2DS5*002 (SEQ ID NO:53), 2DS5*003 (SEQ ID NO:54), 3DL1*00101 (SEQ ID NO:55), 3DL1*00102 (SEQ ID NO:56), 3DL1*002 (SEQ ID NO:57), 3DL1*003 (SEQ ID NO:58), 3DL1*00401 (SEQ ID NO:59), 3DL1*00402 (SEQ ID NO:60), 3DL1*005 (SEQ ID NO:61), 3DL1*006 (SEQ ID NO:62), 3DL1*007 (SEQ ID NO:63), 3DL1*008 (SEQ ID NO:64), 3DL1*009 (SEQ ID NO:65), 3DL2*001Ref (SEQ ID NO:66), 3DS1*010 (SEQ ID NO:67), 3DS1*011 (SEQ ID NO:68), 3DS1*012 (SEQ ID NO:69), 3DS1*013 (SEQ ID NO:70), 3DS1*014 (SEQ ID NO:71), 3DL2*001Ref (SEQ ID NO:72), 3DL2*001 (SEQ ID NO:73), 3DL2*002 (SEQ ID NO:74), 3DL2*003 (SEQ ID NO:75), 3DL2*004 (SEQ ID NO:76), 3DL2*005 (SEQ ID NO:77), 3DL2*006 (SEQ ID NO:78), 3DL2*007 (SEQ ID NO:79), 3DL2*008 (SEQ ID NO:80), 3DL2*009 (SEQ ID NO:81), 3DL2*010 (SEQ ID NO:82), 3DL2*011 (SEQ ID NO:83), 3DL2*012 (SEQ ID NO:84), 3DL2*001Ref (SEQ ID NO:85), 3DL3*001 (SEQ ID NO:86), 3DL3*00201 (SEQ ID NO:87), 3DL3*00202 (SEQ ID NO:88), 3DL3*003 (SEQ ID NO:89), 3DL3*004 (SEQ ID NO:90), 3DL2*001Ref (SEQ ID NO:91), 3DP1*001 (SEQ ID NO:92), 3DP1*002 (SEQ ID NO:93), 3DP1*00301 (SEQ ID NO:94), 3DP1*00302 (SEQ ID NO:95), 2DP1*001 (SEQ ID NO:96), and 2DP1*002 (SEQ ID NO:97).
Figure 4H:
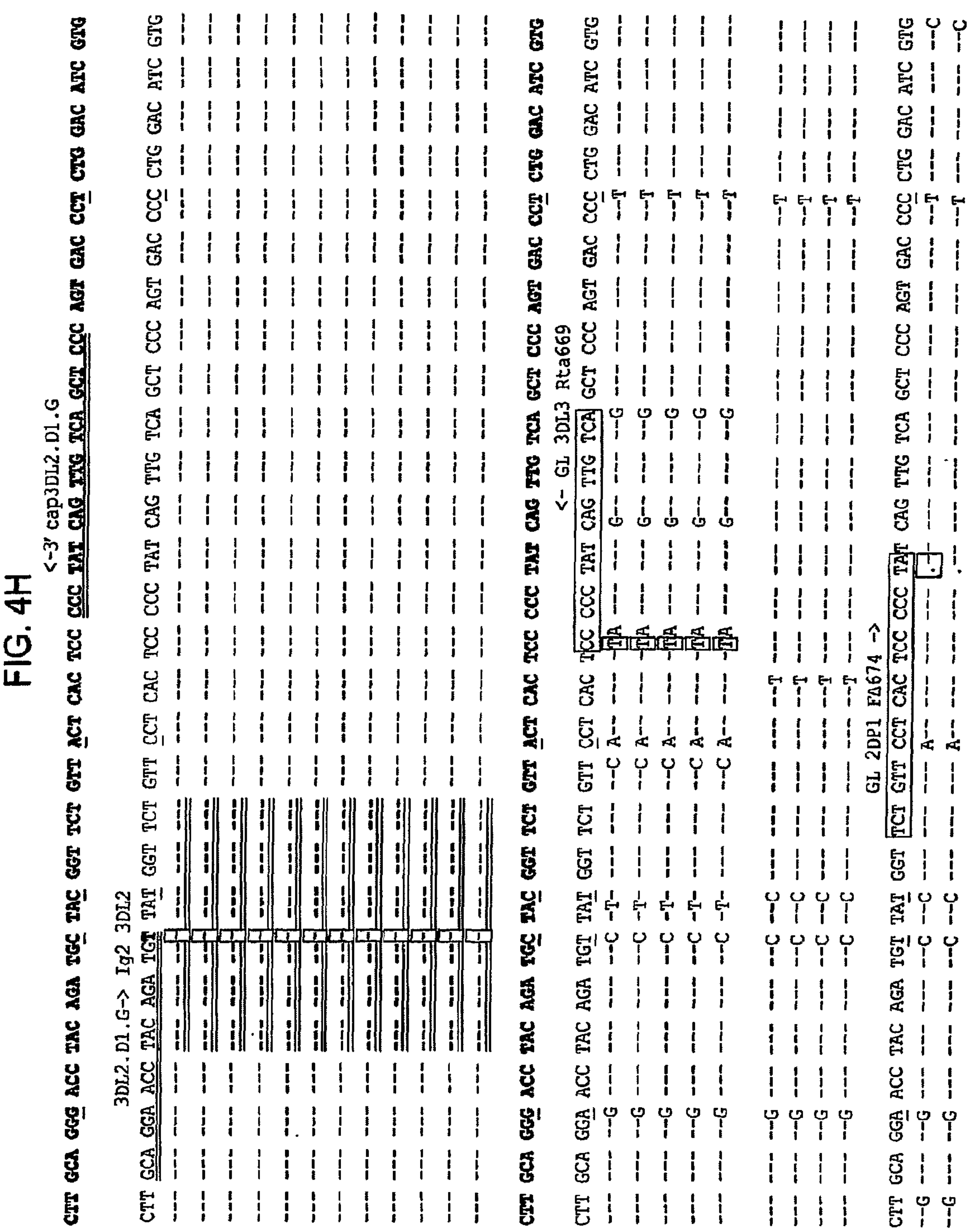
Figure 4L:
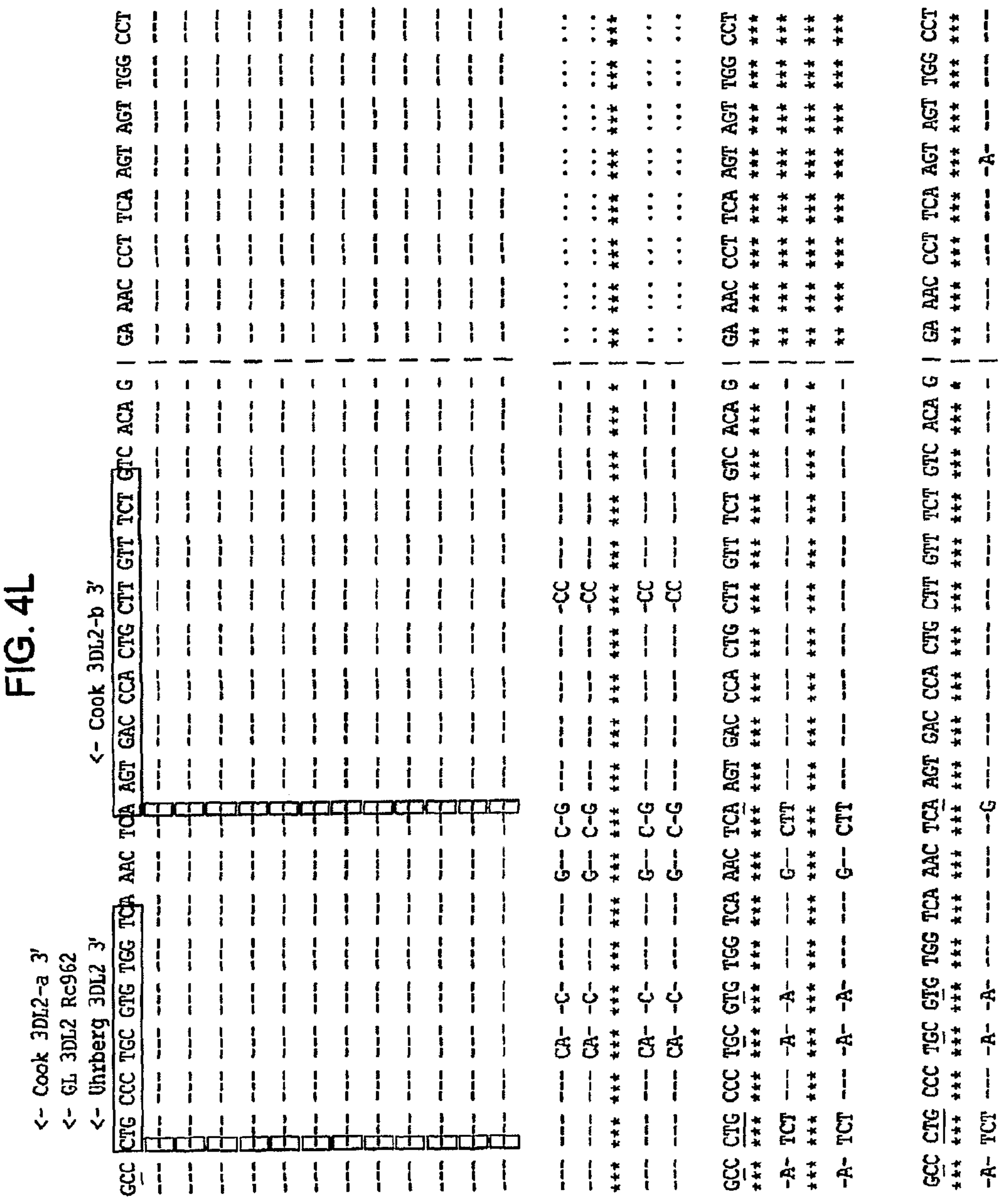
Figure 4N:
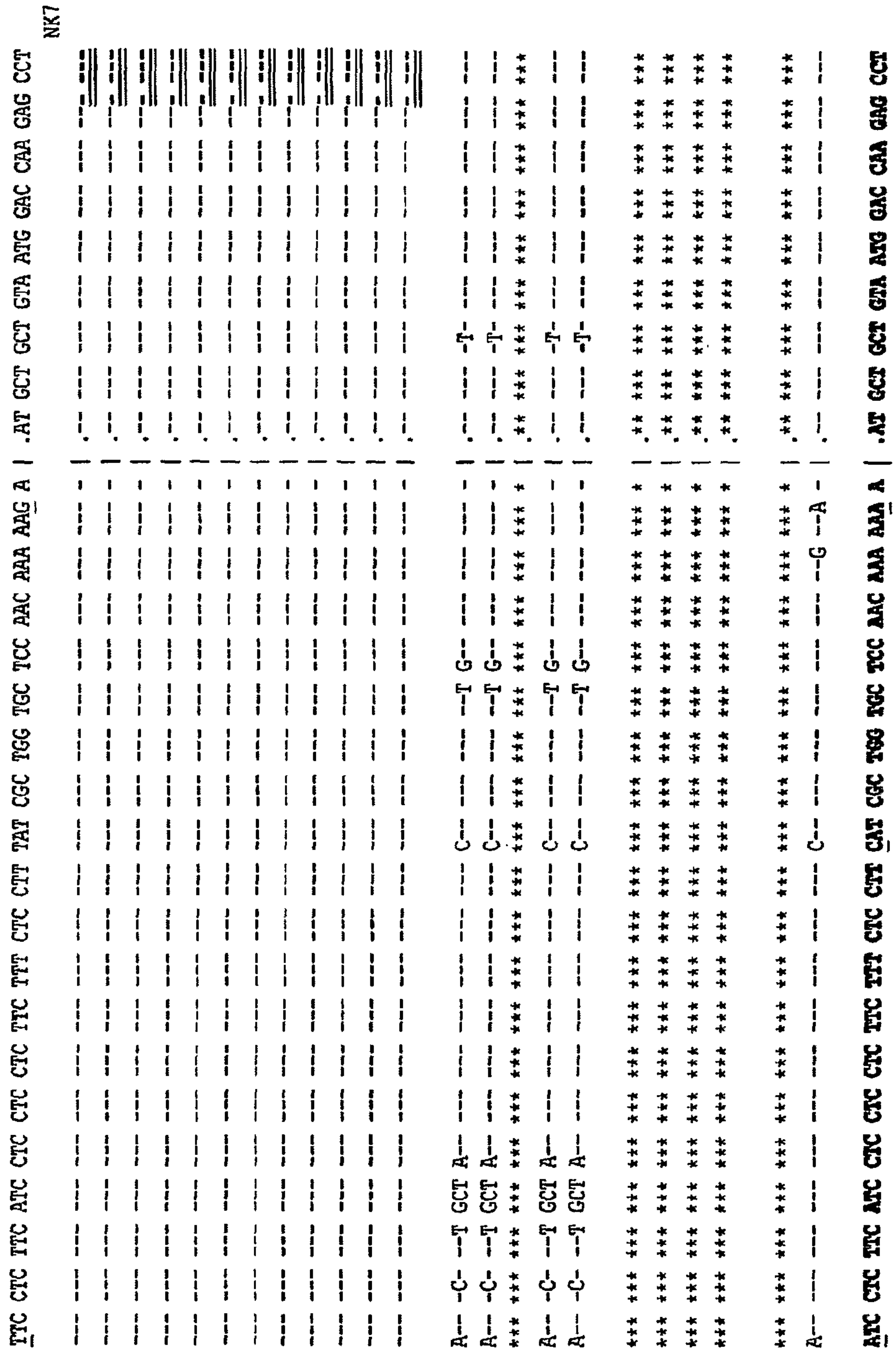
Figure 6:
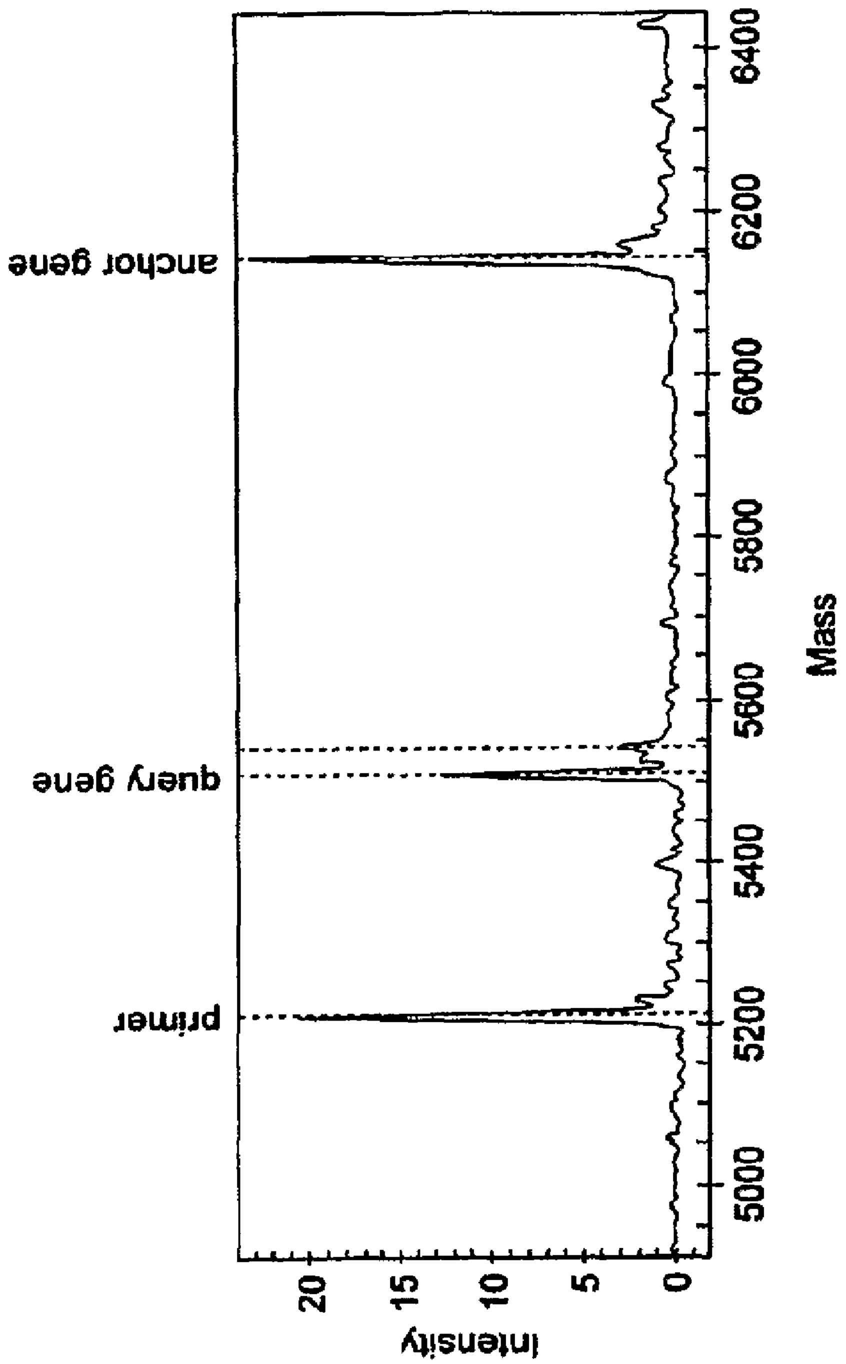
FIG. 6 is an exemplary extension result showing the peak for unextended primer, the peak for the SNP of the query gene and the peak for the SNP of the anchor gene. The peak following the query gene peak is a pausing peak and is background signal resulting from extension using deoxynucleotides and dideoxynucleotides.
Figure 9:
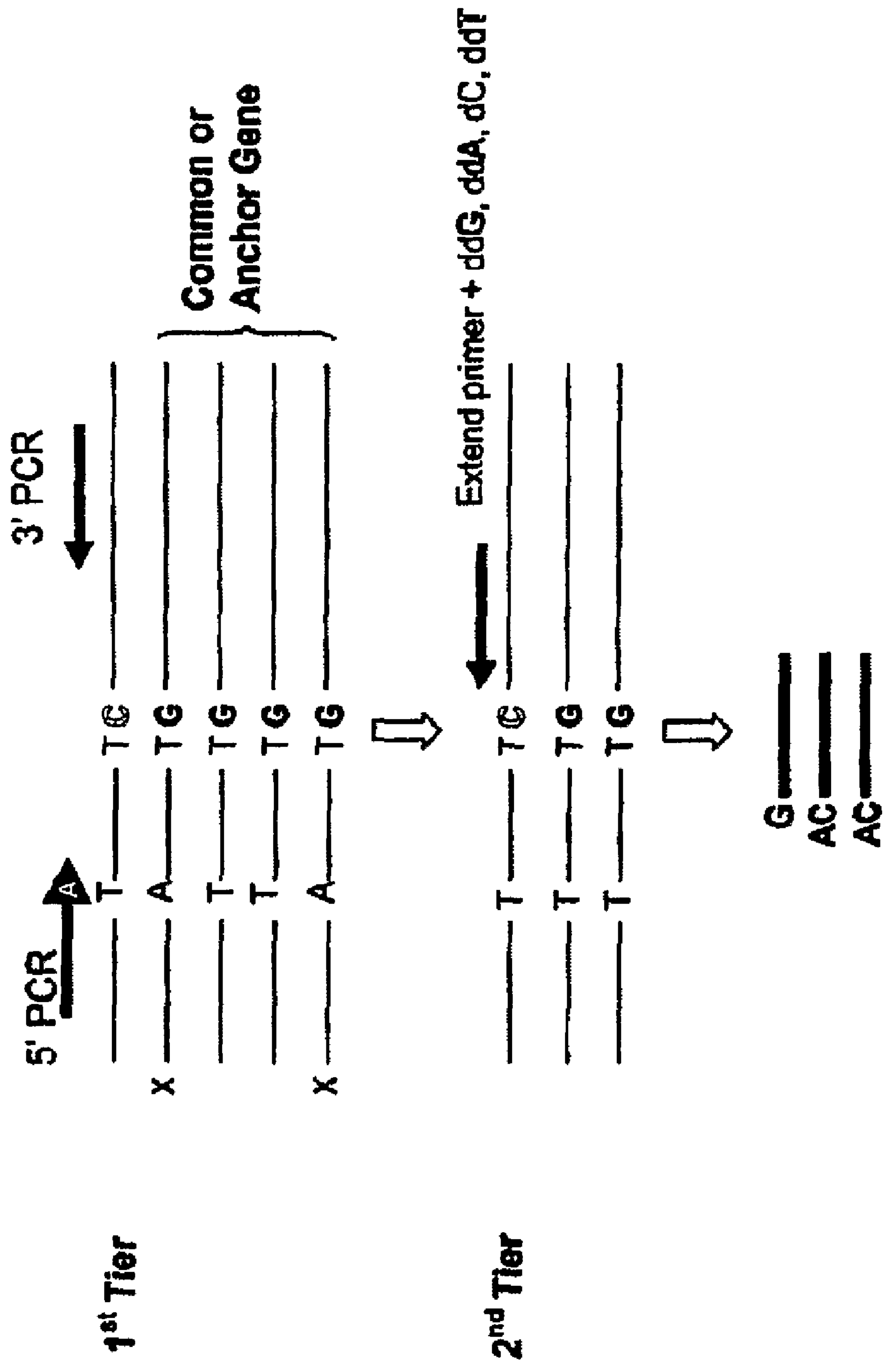
FIG. 9 exemplifies how two tiers of specificity are incorporated into the KIR/MALDI assay. The SEQUENOM™ software allows input of expected extension for each homogenous MassExtend (hME) and accounts for reverse strand results automatically (e.g. in this case C→G and TG→AC). The present assay will flag an unusual SNP pattern if it is other than the expected nucleotides to alert the user of a potential novel allele or anomalous type.
Figure 10:
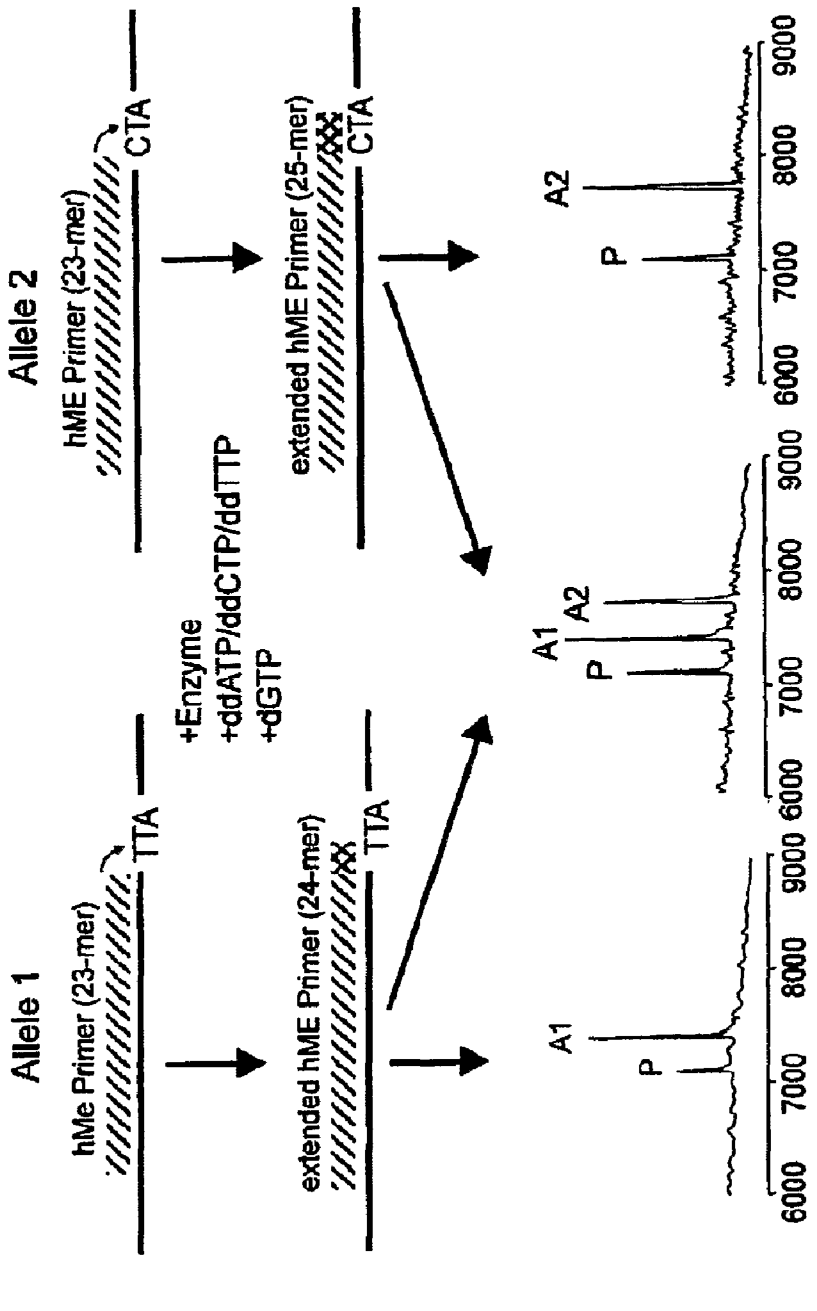

The SNP-based KIR gene cluster genotyping method is based on a primer-extension assay which uses spectrometry to measure the exact mass of an extension primer that is extended by either one or two nucleotides. In representative embodiments, a target sequence surrounding a SNP of interest is first amplified using a pair of capture primers that are complementary to nucleic acid sequences on the 5' side and the 3' side of a SNP. Accordingly, the amplification product includes the desired SNP. The presence or absence of the SNP is then detected by using an extension primer that is complementary to a nucleotide sequence on either the 5' side of a SNP or the 3' side of a SNP. The extension primer will typically be complementary to a nucleotide sequence that is at least one nucleotide away from the SNP (FIGS. 9 and 10). The extension primer is then extended using deoxynucleotides and dideoxynucleotides. If the KIR gene is present and the queried SNP is present, there will be two extension products: one for the queried gene and one for a common or anchor gene control (FIG. 6). Alternatively, if the queried KIR gene is not present, there will be only one extension product for the common or anchor gene control (FIG. 6). If the queried KIR gene is present and the SNP nucleotide is different from expected, the primer will be extended according to the nucleotide make-up of the gene, and the software ("KIR Genotype Caller") will alert the user of the difference; in this ease the spectral data can then be analyzed to determine the exact nature of the unexpected nucleotide extension products.

Figure 7:
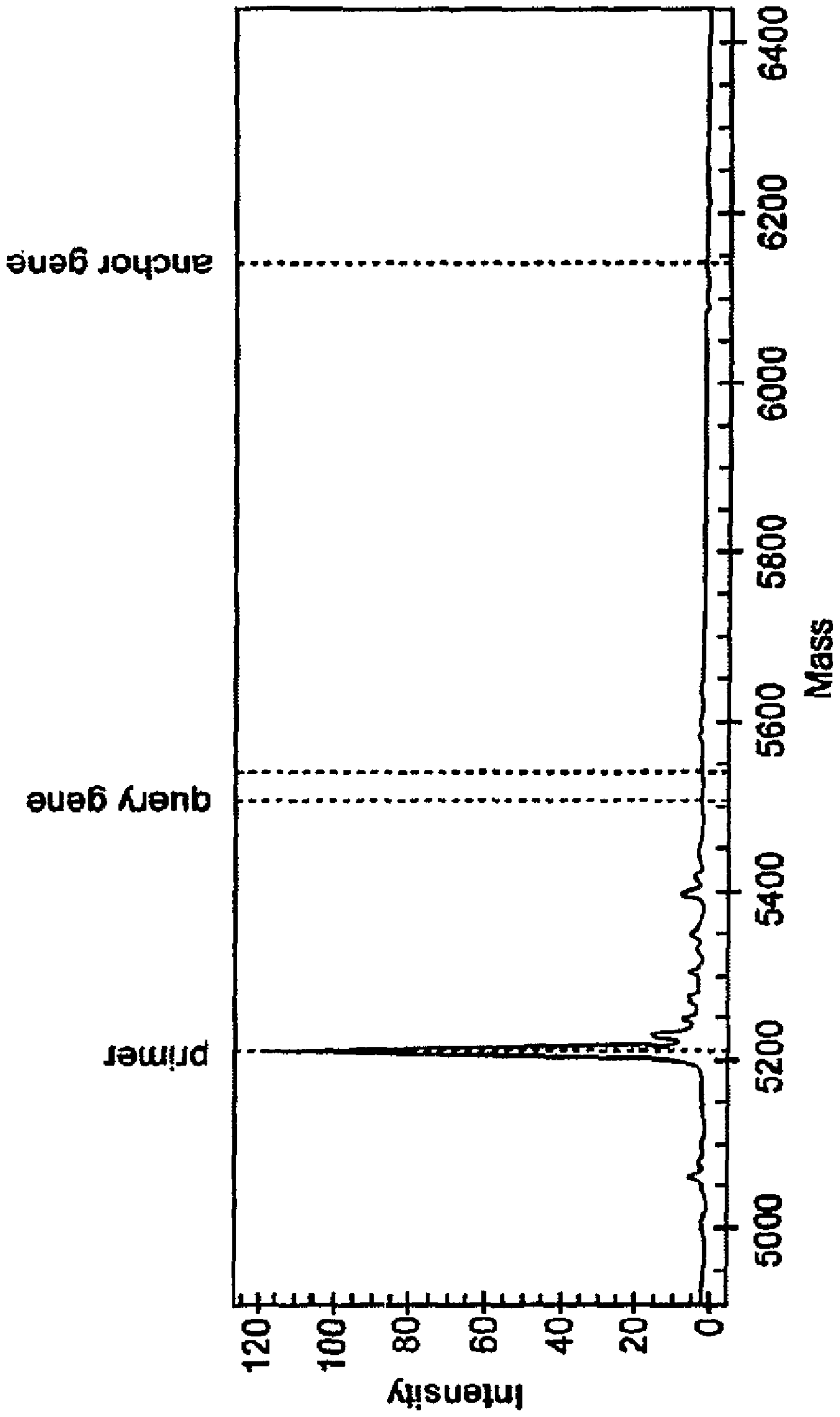
FIG. 7 is an exemplary failed or unsuccessful extension assay showing the peak for unextended primer, absence of a peak for the SNP of the query gene and absence of a peak for the SNP of the anchor gene.
Figure 8:
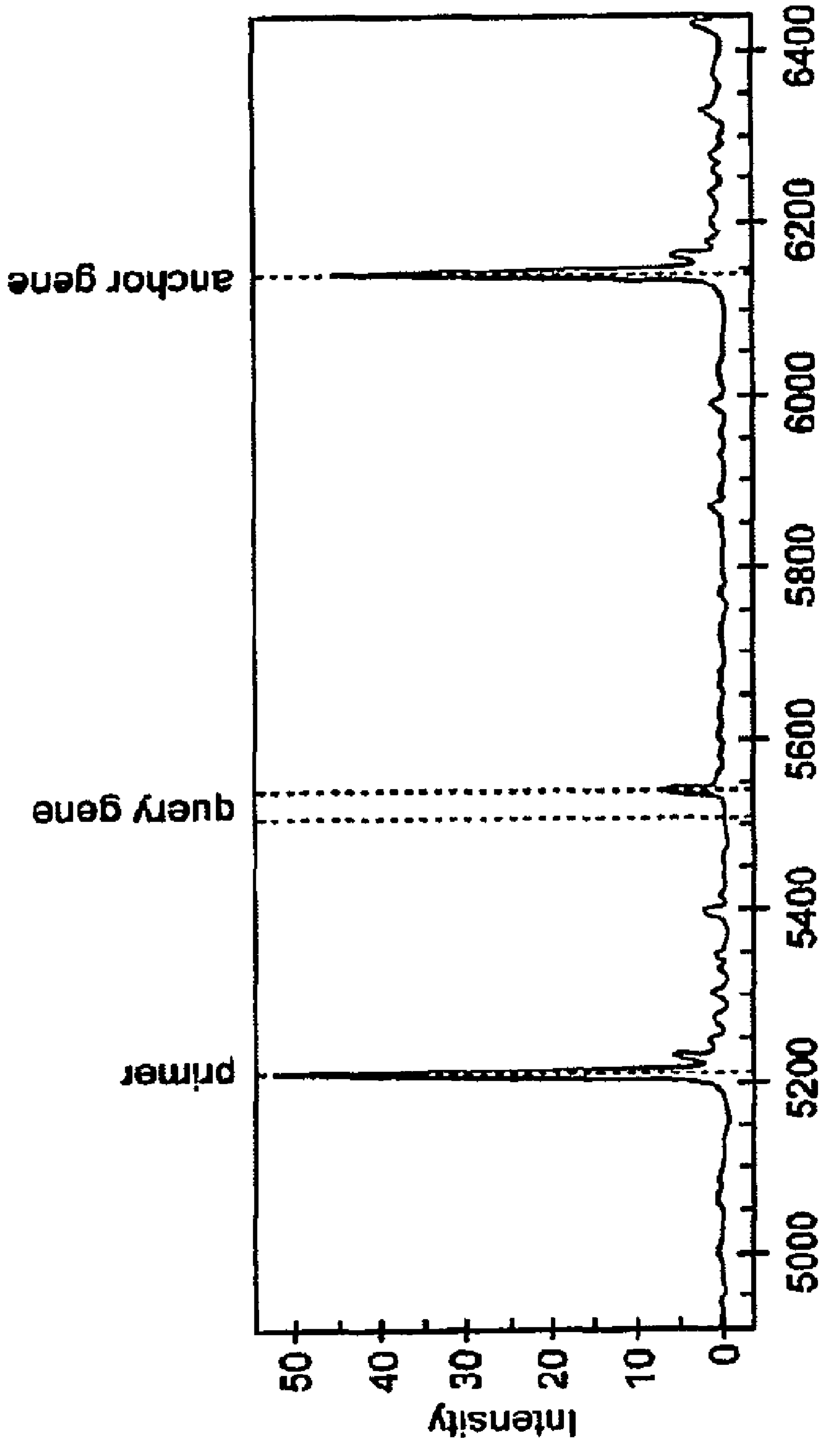
FIG. 8 is an exemplary extension result showing the peak for unextended primer, absence of a peak for the SNP of the query gene and the presence of a peak for the SNP of the anchor gene. The peak following the query gene peak is a pausing peak and is background signal resulting from extension using deoxynucleotides and dideoxynucleotides.

As noted above, not every KIR gene is present in every individual. Of the 17 KIR genes, only the anchor KIR genes (e.g., 3DL3, 3DL2, 2DL4, and 3DP1) are present in every individual. It is these anchor genes that are used for internal quality control of the reactions. Therefore, if the queried KIR gene is not present in the subject, there will be no extension of the queried product, but there will be extension of the anchor gene product, and the reaction is considered negative for the queried gene (FIG. 7). A "negative result" for the presence of a SNP of a KIR gene is distinguishable from an "unsuccessful reaction" in that an unsuccessful reaction is entirely no extension of the extension primer for both the anchor KIR gene control and the variant in question (FIG. 8). The assays are developed to always have extension of the primer for one of the common or anchor genes. Therefore a result showing absolutely no extension of the extension primer indicates that the reaction was unsuccessful. Traditional MALDI-TOF methods of analyzing primer extension products do not employ the use of a control or anchor gene to distinguish between an unsuccessful reaction and a negative reaction, or the absence of the queried gene. Therefore, the detection of at least one anchor KIR gene in the present method provides a positive control to distinguish between an unsuccessful reaction and the absence of the queried KIR gene.

The mass of the extended primer is then analyzed to determine the presence or absence of the SNP using a MALDI-TOF mass spectrometer. The MALDI-TOF mass spectrometer can measure the smallest difference between the four dideoxynucleotides reproducibly. For example, the system can resolve the 9 Da difference between the ddT (288 Da) and the ddA (297 Da) polymorphism. The instrument software resolves mass differences by the signal-to-noise ratio and peak probability statistics. Samples can be resolved at this level within 5 sec, and a 384-well microchip can be analyzed in less than one hour.

In general, the capture primers provide for amplification of target nucleic acid sequences surrounding a target SNP to produce a target nucleic acid amplification product (also referred to as an "amplicon"). 5' primers generally bind to a region to provide for amplification of the target nucleic acid sequence, and preferably bind to a 5' portion of the target sequence, as exemplified in FIGS. 1-4. 3' primers generally bind to a sequence that is complementary to a 3' portion of the nucleic acid sequence generated by extension from the 5' primer or genomic DNA, as exemplified in FIGS. 1-4. In certain embodiments, primers are designed so as to have a sequence complementary to one or more variant nucleotides within a target region sequence and/or to have a 3' end adjacent to a variant nucleotide of a sequence of a target region. Because of the homology between KIR loci, each set of capture primers are designed for their specificity of selection for precise genes and exclusion of others. This is necessary in order to increase the specificity of the subsequent SNP extension primer reactions.

Extension primers are generally designed so as to have a sequence complementary to a nucleotide sequence on either the 5' side of a target SNP or the 3' side of a target SNP. The extension primers will generally be designed to have a sequence complementary to a nucleotide sequence up to 25 nucleotides on either the 5' side or 3' side of a target SNP, including about 22 nucleotides, about 20 nucleotides, about 18 nucleotides, about 16 nucleotides, about 14 nucleotides, about 12 nucleotides, about 10 nucleotides, about 8 nucleotides, about 6 nucleotides, about 4 nucleotides, about 3 nucleotides, about 2 nucleotides, and about 1 nucleotide on either the 5' side or 3' side of a target SNP. The extension primers are designed so as to have a sequence complementary to a sequence flanked by the sequence(s) complementary to a pair of capture primers that were used for amplification of the surrounding sequence.

In certain embodiments, the extension primer is complementary to a nucleotide sequence on the 5' side of a target SNP. In such embodiments, the extension primer will be designed so that the 3' terminal end of the extension primer will be up to 25 nucleotides away from the 5' side of a target SNP, including about 22 nucleotides, about 20 nucleotides, about 18 nucleotides, about 16 nucleotides, about 14 nucleotides, about 12 nucleotides, about 10 nucleotides, about 8 nucleotides, about 6 nucleotides, about 4 nucleotides, about 3 nucleotides, about 2 nucleotides, and about 1 nucleotide on the 5' side of a target SNP. In certain embodiments, the extension primer will be designed so that the 3' terminal end of the extension primer will be about 2 nucleotides away from the 5' side of a target SNP. In other embodiments, the extension primer will be designed so that the 3' terminal end of the extension primer will be about one nucleotide away from the 5' side of a target SNP.

In certain embodiments, the extension primer is complementary to a nucleotide sequence on the 3' side of a target SNP. In such embodiments, the extension primer will be designed so that the 5' terminal end of the extension primer will be up to 25 nucleotides away from the 3' side of a target SNP, including about 22 nucleotides, about 20 nucleotides, about 18 nucleotides, about 16 nucleotides, about 14 nucleotides, about 12 nucleotides, about 10 nucleotides, about 8 nucleotides, about 6 nucleotides, about 4 nucleotides, about 3 nucleotides, about 2 nucleotides, and about 1 nucleotide on the 3' side of a target SNP. In certain embodiments, the extension primer will be designed so that the 5' terminal end of the extension primer will be about 2 nucleotides away from the 3' side of a target SNP. In other embodiments, the extension primer will be designed so that the 5' terminal end of the extension primer will be about one nucleotide away from the 3' side of a target SNP.

Capture primers and extension primers for use in the assays herein are designed based on the sequence disclosed herein and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Typically, the capture primer sequences are in the range of between 10-75 nucleotides in length, such as 10 to 70, 12 to 65, 15 to 60, 20 to 55, 25 to 50, 30 to 45, and the like. More typically, primers are in the range of between 18 to 40, 19 to 39, 20 to 38, 21 to 37, 22 to 36, 23 to 35, 24 to 34, 25 to 33, 26 to 32, 27 to 31, 28 to 30 nucleotides long, and any length between the stated ranges. Capture primers of about 25 to 35 nucleotides in length are of particular interest.

The typical extension primer is in the range of between 10-50 nucleotides long, such as such as 10 to 50, 12 to 45, 15 to 40, 20 to 35, 25 to 30 and the like. More typically, probes are in the range of between 17 to 45, 18 to 40, 19 to 35, 20 to 30, 21 to 29, 22 to 28, 23 to 27, 24-25 nucleotides long, and any length between the stated ranges. Extension primers of about 15 to 25 nucleotides in length are of particular interest.

Exemplary 5' and 3' capture primers suitable for use with the subject invention with the corresponding SNP are provided in Table 1 (5' Capture Primers) (including 5' 10 mer tag) and Table 2 (3' Capture Primers) (including 5' 10 mer tag).

TABLE 1

| SNP | 5' Capture Primer |
|---|---|
| 2DS3.D1.G | ACGTTGGATGCTGTGATCACGATGTCCAG (SEQ ID NO: 116) |
| 2DL2.D2.S | ACGTTGGATGGAGCTCCTATGACATGTACC (SEQ ID NO: 117) |
| 3DL3.D1.G | ACGTTGGATGGATGACTAAGGACCCCTTGC (SEQ ID NO: 118) |
| 3DL3.D2.G | ACGTTGGATGAGAATGTGACCTTGTCCTGC (SEQ ID NO: 119) |
| 2DL4.DO.G | ACGTTGGATGTGCCGACCACTCAGTGGG (SEQ ID NO: 120) |
| 3DL2.TC.G | ACGTTGGATGGATGAACAAGACCCTCAGGAGGTG (SEQ ID NO: 121) |
| 3DS1.3DL1.D1.S | ACGTTGGATGCAAGGCCAATTTCTCCATCG (SEQ ID NO: 122) |
| 2DL5.D2.G | ACGTTGGATGTGACAGAAACAAGCAGTGGG (SEQ ID NO: 123) |
| 2DL5.TC.G | ACGTTGGATGCTTGGGCCTCTGAGAAGGG (SEQ ID NO: 124) |
| 2DS4.D1.G | ACGTTGGATGAGAGACAGTCATCCTGCAATG (SEQ ID NO: 125) |
| 2DL1.D2.G.no004 | ACGTTGGATGGACTTTGACCACTCGTAT (SEQ ID NO: 126) |
| 2DL4.TC.G | ACGTTGGATGATCTGTTGAGGGTCTCTTGC (SE ID NO: 127) |
| 2DL2.004.TC.G | ACGTTGGATGGGCCGAGGAGTACCTACCT (SEQ ID NO: 128) |

TABLE 1-continued

| SNP | 5' Capture Primer |
|---|---|
| 2DS2.D1.G | ACGTTGGATGAGAAGTTGGCCTTGGAGACC (SEQ ID NO: 129) |
| 3DL1.TC.S | ACGTTGGATGATGGGCAGGAGACAACTTTG (SEQ ID NO: 130) |
| 2DS5.D2.G | ACGTTGGATGAGGCCCATGAACGTAGGCTCC (SEQ ID NO: 131) |
| 2DL1.no005.2DL2.004.TC.S | ACGTTGGATGGTAATGGACCAAGAGTCTGC (SEQ ID NO: 132) |
| 2DL3.2DL2.D1.S | ACGTTGGATGGAGTCCACAGAAAACCTTCCCTCC (SEQ ID NO: 133) |
| 3DS1.D0.S | ACGTTGGATGTCATGCTATACAAAGAAGAC (SEQ ID NO: 134) |
| 3DL2.D1.G | ACGTTGGATGGGAGCTGACAACTGATAGGG (SEQ ID NO: 135) |
| 2DS3.D2.S | ACGTTGGATGAGGTCAACGGAACATTCCAGGCCG (SEQ ID NO: 136) |
| 3DS1.TC.S.INT | ACGTTGGATGAACTGCTATGATTAGCTTC (SEQ ID NO: 137) |
| 3DP1.D2.G2 | ACGTTGGATGGAGCTGCAGGACAAGGTCAC (SEQ ID NO: 138) |
| 2DL5sub5 | ACGTTGGATGGATCTTGGCTTAGCATTTGG (SEQ ID NO: 139) |
| 2DL5sub4 | ACGTTGGATGCCACGGAGGGACCTACAC (SEQ ID NO: 140) |
| 2DL5sub1 | ACGTTGGATGAGGACAAGCCCTTGCTGTCT (SEQ ID NO: 141) |
| 2DS5.D1.G | ACGTTGGATGACACTTTGCGCCTCATTGGAG (SEQ ID NO: 142) |
| 2DP1.D0.G | ACGTTGGATGGGGTTTAACAACTTCAGTCTGT (SEQ ID NO: 143) |
| 2DS2.D2.G | ACGTTGGATGGTCTATATGAGAAACCTTC (SEQ ID NO: 144) |
| 2DL1.2DS1.D1.S.tri | ACGTTGGATGAAGGCCAACTTCTCCATCA (SEQ ID NO: 145) |
| 2DL5sub3 | ACGTTGGATGGACATGAGTCCTCTGACCTG (SEQ ID NO: 146) |
| 2DL5sub2 | ACGTTGGATGGACATGAGTCCTCTGACCTG (SEQ ID NO: 147) |

TABLE 1-continued

| SNP | 5' Capture Primer |
|---|---|
| 2DS4del.sub | ACGTTGGATGTTGACCACTCGTAGGGAGC (SEQ ID NO: 148) |
| 2DS4.D2.S | ACGTTGGATGGAGCTCTGTGACGGAAACAA (SEQ ID NO: 149) |
| 2DL3.TC.S.INT | ACGTTGGATGCTGCTTCGTGAGACTTACTT (SEQ ID NO: 150) |
| 2DL2.001.2.3.D1.G | ACGTTGGATGGGAGCTGACAACTGATAGGG (SEQ ID NO: 151) |
| 2DS1.D2.G | ACGTTGGATGACTTGACTTTGACCACTCGT (SEQ ID NO: 152) |
| 2DL5sub6 | ACGTTGGATGTAAGGTGGCGCCTCCTTCTC (SEQ ID NO: 153) |

TABLE 2

| SNP | 3' Capture Primer |
|---|---|
| 2DS3.D1.G | ACGTTGGATGAAGGCCAACTTCTCCATCGG (SEQ ID NO: 154) |
| 2DL2.D2.S | ACGTTGGATGGCCTGGAATGTTCCGTTGACCTTG (SEQ ID NO: 155) |
| 3DL3.D1.G | ACGTTGGATGTCATGGGACCCATGGAATAG (SEQ ID NO: 156) |
| 3DL3.D2.G | ACGTTGGATGCAGTGAGCCTAAGTTCACCG (SEQ ID NO: 157) |
| 2DL4.D0.G | ACGTTGGATGCCCTGAGCTCTACAACAGAA (SEQ ID NO: 158) |
| 3DL2.TC.G | ACGTTGGATGTACACGCTGGTATCTGTT (SEQ ID NO: 159) |
| 3DS1.3DL1.D1.S | ACGTTGGATGGGGAGCTGACAACTGATAGG (SEQ ID NO: 160) |
| 2DL5.D2.G | ACGTTGGATGGACTTTCCTCTGGGCCCTG (SEQ ID NO: 161) |
| 2DL5.TC.G | ACGTTGGATGCAAGACCCTCAGGAGGTGAC (SEQ ID NO: 162) |
| 2DS4.D1.G | ACGTTGGATGATGGAGAAGTTGGCCTTGGA (SEQ ID NO: 163) |
| 2DL1.D2.G.no004 | ACGTTGGATGCAGGGCCCAAGGTCAACG (SEQ ID NO: 164) |

TABLE 2-continued

| SNP | 3' Capture Primer |
|---|---|
| 2DL4.TC.G | ACGTTGGATGAGGTGACATACGCACAGTTG (SEQ ID NO: 165) |
| 2DL2.004.TC.G | ACGTTGGATGGTAATGGACCAAGAGTCTGC (SEQ ID NO: 166) |
| 2DS2.D1.G | ACGTTGGATGCCTGCAATGTTGGTCAGATG (SEQ ID NO: 167) |
| 3DL1.TC.S | ACGTTGGATGCACTGCGTTTTCACACAGAG (SEQ ID NO: 168) |
| 2DS5.D2.G | ACGTTGGATGAAGAGCCGAAGCATCTGTAG (SEQ ID NO: 169) |
| 2DL1.no005.2DL2.004.TC.S | ACGTTGGATGCGGGCCGAGGAGTACCTACCT (SEQ ID NO: 170) |
| 2DL3.2DL2.D1.S | ACGTTGGATGAGTGTCCTTAAACTTCCCTTCTC (SEQ ID NO: 171) |
| 3DS1.DO.S | ACGTTGGATGTGTGTAGTTCCCTGCATGTG (SEQ ID NO: 172) |
| 3DL2.D1.G | ACGTTGGATGCCAAGGCCAACTTCTCCATC (SEQ ID NO: 173) |
| 2DS3.D2.S | ACGTTGGATGAAGAGCCGAAGCATCTGTAG (SEQ ID NO: 174) |
| 3SD1.TC.S.INT | ACGTTGGATGGATGAAGGAGAAAGAAGAGGAGGA (SEQ ID NO: 175) |
| 3DP1.D2.G2 | ACGTTGGATGTGGGAAACCTTCTCTCTCAGCC (SEQ ID NO: 176) |
| 2DL5sub5 | ACGTTGGATGCTGCGTTTTCACACAGAC (SEQ ID NO: 177) |
| 2DL5sub4 | ACGTTGGATGGTGACAGAAACAAGCAGTGG (SEQ ID NO: 178) |
| 2DL5sub1 | ACGTTGGATGCAAGACGAGAGCGACACA (SEQ ID NO: 179) |
| 2DS5.D1.G | ACGTTGGATGGTGAGTAACAGAACCGTAG (SEQ ID NO: 180) |
| 2DP1.D0.G | ACGTTGGATGTGTGCTGGGGTCACAGGGCC (SEQ ID NO: 181) |
| 2DS2.D2.G | ACGTTGGATGGGACAAGGTCACGCTCTCTC (SEQ ID NO: 182) |
| 2DL1.2DS1.D1.S.tri | ACGTTGGATGGTGAGTAACAGAACCGTAGC (SEQ ID NO: 183) |

TABLE 2-continued

| SNP | 3' Capture Primer |
|---|---|
| 2DL5sub3 | ACGTTGGATGCCCTGAGCTCTACAACAA (SEQ ID NO: 184) |
| 2DL5sub2 | ACGTTGGATGCCCTGAGCTCTACAACAA (SEQ ID NO: 185) |
| 2DS4del.sub | ACGTTGGATGCGGTTCAGGCAGGAGAGAAT (SEQ ID NO: 186) |
| 2DS4.D2.S | ACGTTGGATGGCATCAACGGAACATTCCAGGCC (SEQ ID NO: 187) |
| 2DL3.TC.S.INT | ACGTTGGATGGTAACCCCAGACACCTGCATG (SEQ ID NO: 188) |
| 2DL2.001.2.3.D1.G | ACGTTGGATGCCTGCAATGTTGGTCAGATG (SEQ ID NO: 189) |
| 2DS1.D2.G | ACGTTGGATGCCTATGACATGTACCATCTA (SEQ ID NO: 190) |
| 2DL5sub6 | ACGTTGGATGCAAGACGAGAGCGACACA (SEQ ID NO: 191) |

Exemplary extension primers suitable for use with the subject invention with the corresponding SNP are provided in Table 3.

TABLE 3

| SNP_ID | Extend-SNP |
|---|---|
| 2DS3.D1.G | CACTCCCCCTATCAGTT (SEQ ID NO: 192) |
| 2DL2.D2.S | CCCTGCAGAGAACCTAC (SEQ ID NO: 193) |
| 3DL3.D1.0 | AATAGTTGACCTGGGAACCC (SEQ ID NO: 194) |
| 3DL3.D2.G | GGATAGATGGTAAATGTCAAA (SEQ ID NO: 195) |
| 2DL4.DO.G | TGGAACAGTTTCCTCAT (SEQ ID NO: 196) |
| 3DL2.TC.G | GCCTCTGAGAAGGGCGA (SEQ ID NO: 197) |
| 3DS1.3DL1.D1.S | CTGTAGGTCCCTGCAAGGGCA (SEQ ID NO: 198) |
| 2DL5.D2.G | CCACGGAGGGACCTACA (SEQ ID NO: 199) |
| 2DL5.TC.G | CACTGCGTTTTCACACAGA (SEQ ID NO: 200) |
| 2DS4.D1.G | GAAGTGCTCAAACATGACATC (SEQ ID NO: 201) |
| 2DL1.D2.G.no004 | ATGCTTCGGCTCTTTCC (SEQ ID NO: 202) |
| 2DL4.TC.G | CACAGTTGGATCACTGC (SEQ ID NO: 203) |

TABLE 3-continued

| SNP_ID | Extend-SNP |
|---|---|
| 2DL2.004.TC.G | GAAACAGAACAGCGAATA (SEQ ID NO: 204) |
| 2DS2.D1.G | GCACAGAGAGGGGAAGT (SEQ ID NO: 205) |
| 3DL1.TC.S | GAGGCCCAAGACACCCCC (SEQ ID NO: 206) |
| 2DS5.D2.G | CTCCGTGGGTGGCAGGG (SEQ ID NO: 207) |
| 2DL1.no005.2DL2.004.TC.S | CGCTATTCGCTGTTCTGTT (SEQ ID NO: 208) |
| 2DL3.2DL2.D1.S | CTTCTGATTTCACCAGG (SEQ ID NO: 209) |
| 3DS1.DO.S | AGGGCTCATGTTGAAGC (SEQ ID NO: 210) |
| 3DL2.D1.G | CTTGCAGGAACCTACAGATG (SEQ ID NO: 211) |
| 2DS3.D2.S | CATCTGTAGGTTCCTCC (SEQ ID NO: 212) |
| 3951.TC.S.TNT | GAATGTGCAGGTGTCTG (SEQ ID NO: 213) |
| 3DP1.D2.G2 | CTCTCTCAGCCCAGCCG (SEQ ID NO: 214) |
| 2DL5sub5 | CTTCTCAGAGGCCCAAG (SEQ ID NO: 215) |
| 2DL5sub4 | GTGAGTCATGGAGAGAGC (SEQ ID NO: 216) |
| 2DL5sub1 | GTCCTCCTCGAGGCACCACAG (SEQ ID NO: 217) |
| 2DS5.D1.G | GACCGATGGAGAAGTTG (SEQ ID NO: 218) |
| 2DP1.D0.G | ATTCTGTTGTAGAGCTCAG (SEQ ID NO: 219) |
| 2DS2.D2.G | CACGCTCTCTCCTGCCA (SEQ ID NO: 220) |
| 2DL1.2DS1.D1.S.tri | GGTCCCTGCCAGGTCTTGC (SEQ ID NO: 221) |
| 2DL5sub3 | GCAACCCCCTGGTGATC (SEQ ID NO: 222) |
| 2DL5sub2 | CGCTCCCCCATTGAGTGGTC (SEQ ID NO: 223) |
| 2DS4del.sub | CCTTGTCCTGCAGCTCC (SEQ ID NO: 224) |
| 2DS4.D2.S | TCGGCTCTTTCCGTGAC (SEQ ID NO: 225) |
| 2DL3.TC.S.INT | TCTCCTTCATCGCTGGTGCT (SEQ ID NO: 226) |
| 2DL2.001.2.3.D1.G | CATGATGGGGTCTCCAA (SEQ ID NO: 227) |

TABLE 3-continued

| SNP_ID | Extend-SNP |
|---|---|
| 2DS1.D2.G | CAACGGAACATTCCAGGCC (SEQ ID NO: 228) |
| 2DL5sub6 | AGCAAGGGCTTGTCCTG (SEQ ID NO: 229) |

The target nucleic acid sequences can be amplified in any of a variety of methods well known in the art. For example, the pairs of capture primers described above may be used in polymerase chain reaction (PCR)-based techniques to amplify the target nucleic acid sequences. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, preferably by heat, and hybridized with first and second primers which are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from Thermus aquaticus (Taq), available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer.

Sample Preparation

As noted above, the instant invention provides methods for determining the KIR genotype of a subject by detecting the presence or absence of a plurality of SNPs of the plurality of KIR genes by MALDI-TOF mass spectrometry. For assay of genomic DNA virtually any biological sample containing nucleic acid molecules is appropriate for use. Examples of appropriate biological samples for use in the instant invention include: solid materials (e.g. tissue, cell pellets, biopsies) and biological fluids (e.g. urine, blood, saliva, amniotic fluid, mouth wash).

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Rolff, A et al. PCR: Clinical Diagnostics and Research, Springer (1994).

Analysis of Samples with MALDI-TOF Mass Spectrometry

Methods of analyzing nucleic acids using matrix-assisted laser desorption-ionization time-of-flight (MALDI-TOF) mass spectrometry (MS) are well known in the art. A description of the MALDI-TOF system can be found in the literature, such as Tang et al. 1999, Proc Natl Acad Sci USA 96:10016-10020; Jurinke et al. 2002, Methods Mol Biol 187:179-192; Jurinke et al. 2002, Adv Biochem Eng Biotechnol 77:57-74; Storm et al. 2003, Methods Mol Biol 212:241-262; Ross et al. 1998, Nat Biotechnol 16:1347-1351; Buetow et al. 2001, Proc Natl Acad Sci USA 98:581-584; Amexis et al. 2001, Proc Natl Acad Sci USA 98:12097-12102; and Fei et al. 1998, Nucleic Acids Res 26:2827-2828, the disclosures of which are herein incorporated by reference.

Prior to their analysis, extension products are typically mixed with an energy absorbing molecule, i.e., a matrix, as is known in the art. The matrix is typically a small organic, volatile compound with certain properties that facilitate the performance of MALDI. Accordingly, a matrix is selected based on a variety of factors such as the analyte of interest (such as type, size, and the like), etc. Examples of matrices include, but are not limited to, sinapinic acid (SA) and derivatives thereof; cinnamic acid and derivatives thereof such as alpha-cyano-4-hydroxycinnamic acid (HCCA); 2,5-dihydroxybenzoic acid (DHB); 3-hydroxypicolinic acid (HPA); 2',4',6'-trihydroxyacetophenone; and dithranol. The matrix is typically dissolved in a suitable solvent that is selected at least in part so that it is miscible with the analyte solution. For example, in the analysis of peptides/proteins HCCA and SA work best with ACN/0.1% TFA as solvent and in the analysis of oligonucleotides HPA and ACN/$H_2O$ may be employed.

Prior to mass spectrometric analysis, it may be useful to "condition" nucleic acid extension products, for example to decrease the laser energy required for volatilization and/or to minimize fragmentation. Conditioning is preferably performed while a target detection site is immobilized. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule with an alkylating agent such as alkyliodide, iodoacetamide, beta.-iodoethanol, 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides which reduce sensitivity for depuration (fragmentation during MS) such as N7- or N9-deazapurine nucleotides, or RNA building blocks or using oligonucleotide triesters or incorporating phosphorothioate functions which are alkylated or employing oligonucleotide mimetics such as PNA.

Compositions

The invention also provides compositions comprising arrays of capture primer pairs or arrays of extension primers for use with the methods disclosed herein for determining the KIR genotype of a subject using MALDI-TOF mass spectrometry. Such an array generally comprises a plurality of spatially addressable features (e.g., more than about 10, more than about 50, more than about 100, more than 200, features, usually up to about 500 or more features), and these features contain either capture primer pairs or extension primers.

The subject array may be an array of features, each feature corresponding to a "fluid-retaining structure", e.g., a well, wall, hydrophobic barrier, or the like. Such arrays are well known in the art, and include 24-well, 48-well, 96-well, 192-well, 384-well and 1536-well microtiter plates, or multiple thereof. In certain embodiments, the features are delineated by a hydrophobic chemical boundary, and, accordingly, the array substrate may be planar and contain features containing a hydrophobic boundary. Features may be delineated by drawing lines between them with a hydrophobic pen (e.g., a PAP PEN from Newcomer Supply, Middleton, Wis.), for example. Other fluid retaining structures are well known in the art and include physical and chemical barriers. On one embodiment, the fluid retaining structure is formed by a bead of hydrophobic material, e.g., a bead of a viscose silicone material, around a fluid-retaining area. Capture primer pairs or extension primers may be present in the fluid retaining structure, but not necessarily bound to the surface of the array substrate.

Computer-Related Instructions

The invention also provides a variety of computer-related embodiments. Specifically, an automated means, such as a program, designed to synthesize the data from several different assays into a KIR genotype. The genotyping program "KIR Genotype Caller" captures the output data from the SpectroAnalyzer module of the SEQUENOM™ software suite to generate a genotype from the individual SNP assays based on a hierarchical hit table, and simultaneously tag anomalous calls and problematic samples for user inspection. For each run, the KIR Genotype Caller creates a: 1) conflict log—which checked for agreement between replicates of the same assay applied to the same sample in a given data set (duplicate check); 2) a partial match log—which checked for agreement between assays which type for the same gene in different domains, and generated a potential recombinants list; and 3) a control check—which checks the SNP profiles of previously characterized samples against an index of expected results for these samples. Also, the automated means for performing the methods described above may be controlled using computer-readable instructions, i.e., programming. Accordingly, the invention provides computer programming for directing a means, e.g., a liquid handling workstation, to analyze the samples to determine the KIR genotype of a subject using MALDI-TOF mass spectrometry.

With respect to computer readable media, "permanent memory" refers to memory that is permanent. Permanent memory is not erased by termination of the electrical supply to a computer or processor. Computer hard-drive ROM (i.e. ROM not used as virtual memory), CD-ROM, floppy disk and DVD are all examples of permanent memory. Random Access Memory (RAM) is an example of non-permanent memory. A file in permanent memory may be editable and re-writable.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A "processor" references any hardware and/or software combination which will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In most embodiments, the processor will be in operable linkage, i.e., part of or networked to, the aforementioned workstation, and capable of directing its activities.

Kits

Also provided by the subject invention are kits for practicing the subject methods, as described above. The subject kits at least include sets of capture primers and extension primers for detection of a plurality of SNPs of a plurality of KIR genes. As discussed above, the capture primers and optionally extension primers for the detection of a plurality of SNPs of a plurality of KIR genes may be provided as an addressable array on a substrate surface. Other optional components of the kit include: control analytes for spiking into a sample, buffers, including binding, washing and elution buffers, solid supports, such as beads, protein A or G or avidin coated sepharose or agarose, etc., and a MALDI sample plate. The kit may also contain a database, which may be a table, on paper or in electronic media, containing information for the plurality of SNPs of the plurality of KIR genes. In some embodiments, the kits contain programming to allow a robotic system to perform the subject methods, e.g., programming for instructing a robotic pipettor or a contact or inkjet printer to add, mix and remove reagents, as described above. The various components of the kit may be present in separate containers or certain compatible components may be precombined into a single container, as desired.

The subject kits may also include one or more other reagents for preparing or processing an analyte sample for MALDI-TOF. The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps of a MALDI-TOF protocol.

In addition to above-mentioned components, the subject kits typically further include instructions for using the components of the kit to practice the subject methods, i.e., to prepare a MALDI-TOF sample plate and/or assess a sample. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control analyte mixtures, e.g., two or more control samples for use in testing the kit.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following methods and materials were used in the examples described below.

Platform

The SEQUENOM, Inc. (San Diego, Calif.) matrix-assisted laser desorption-ionization time-of-flight (MALDI-TOF) mass spectrometry (MS) based primer extension assay for small nucleotide polymorphism (SNP) detection, referred to as homogenous MASSEXTEND™ (hME) was used in the high-throughput KIR genotyping assay. The instrumentation and related assay design and genotyping software comprise the MASSARRAY™ MALDI-TOF system (Tang et al. 1999, Proc Natl Acad Sci USA 96:10016-10020; Jurinke et al. 2002, Methods Mol Biol 187:179-192; Jurinke et al. 2002, Adv Biochem Eng Biotechnol 77:57-74; Storm et al. 2003, Methods Mol Biol 212:241-262; Ross et al. 1998, Nat Biotechnol 16:1347-1351; Buetow et al. 2001, Proc Natl Acad Sci USA 98:581-584; Amexis et al. 2001, Proc Natl Acad Sci USA 98:12097-12102; and Fei et al. 1998, Nucleic Acids Res 26:2827-2828).

Assay Design

Potentially informative SNPs were identified by inspection in silico of the 17 locus IPD-KIR sequence alignment (available on the world wide web at ebi.ac.uk/ipd/kir), and carefully evaluated for 1) homology in the flanking regions and 2) base composition of extension primer site. Using the Sequenom software (SPECTRODESIGNER™) PCR primers and extension primers were designed to capture the appropriate region of the genome and to query the specified SNP. The Sequenom SPECTRODESIGNER™ software was also used to help define multiplex levels for the assays. Multiplexing was used to increase the number of assays per reaction but needed to be empirically designed and tested to define the final set of primers for the multiplex reactions. Due to the large number of highly homologous genes in the KIR complex, the designer software was carefully manipulated in order to obtain the primer designs necessary to create a working assay. The primers were typically 17-21 bp in length, to capture a ~150-250 bp region surrounding the SNP. The "capture primers" were designed with a 5' 10-mer tag in order to keep them out of the 5K-10K Da window of detection used in the assay; without the 10-mer tag, the capture primers would have similar mass to the extended and unextended hME products and confound the analysis. The 10-mer tag also helps to balance the primers so that they can function well in multiplex reactions, which were identified using the SEQUENOM™ Design software. The primers or termination mixes in a reaction were also empirically manipulated in order to increase the multiplex level or specificity of the reaction. Due to the high degree of homology between the KIR loci some assays could not be multiplexed.

Extension primers that query the chosen SNP were designed to terminate at the base immediately adjacent to the SNP. Due to regions of high homology in the KIR genes, the designer software required extensive manipulation in order to obtain the primer designs necessary to create the specificity needed for a working KIR assay. Both capture primers and extension primers were chosen with an eye towards simultaneous identification of a particular locus (locus-specific assay) and a highly conserved region (positive control assay). Tables 4 and 5 provide the sequences of the 5' capture primers (shown without the 5' 10 mer tag), 3' capture primers (shown without the 5' 10 mer tag), and extension primers used in the assays (Abbreviations: "W"=well e.g. W1=well No. 1; INT=intronic; G=general; S=specific; D0=Domain 0; D1=Domain 1; D2=Domain 2; Trans/Cyt=Transmembrane/Cytoplasmic Domain. The assays are named according to the following convention: "Targeted Locus.Targeted Domain-.Specificity (G or S)").

TABLE 4

| Well No. | SNP assay name | 5' Capture Primer (5' 10 mer tag not shown) | 3' Capture Primer (5' 10 mer tag not shown) | Extend Primer |
|---|---|---|---|---|
| W1 4 plex | 2DS3.D1.G | CTGTGATCACGATGTCCA G (SEQ ID NO: 230) | AAGGCCAACTTCTCCATCG G (SEQ ID NO: 268) | CACTCCCCCTATCAGTT (SEQ ID NO: 192) |
| | 2DL2.D2.S | GAGCTCCTATGACATGTA CC (SEQ ID NO: 231) | GCCTGGAATGTTCCGTTGA CCTTG (SEQ ID NO: 269) | CCCTGCAGAGAACCTAC (SEQ ID NO: 193) |
| | 3DL3.D1.G | GATGACTAAGGACCCCTT GC (SEQ ID NO: 232) | TCATGGGACCCATGGAATA G (SEQ ID NO: 270) | AATAGTTGACCTGGGAA CCC (SEQ ID NO: 194) |
| | 3DL3.D2.G | AGAATGTGACCTTGTCCT GC (SEQ ID NO: 233) | CAGTGAGCCTAAGTTCACC G (SEQ ID NO: 271) | GGATAGATGGTAAATGT CAAA (SEQ ID NO: 195) |
| W2 3 plex | 2DL4.DO.G | TGCCGACCACTCAGTGGG (SEQ ID NO: 234) | CCCTGAGCTCTACAACAGA A (SEQ ID NO: 272) | TGGAACAGTTTCCTCAT (SEQ ID NO: 196) |
| | 3DL2.TC.G | GATGAACAAGACCCTCAG GAGGTG (SEQ ID NO: 235) | TACACGCTGGTATCTGTT (SEQ ID NO: 273) | GCCTCTGAGAAGGGCGA (SEQ ID NO: 197) |
| | 3DS1.3DL1. D1.S | CAAGGCCAATTTCTCCATC G (SEQ ID NO: 236) | GGGAGCTGACAACTGATA GG (SEQ ID NO: 274) | CTGTAGGTCCCTGCAAG GGCA (SEQ ID NO: 198) |
| W3 4 plex | 2DL5.D2.G | TGACAGAAACAAGCAGTG GG (SEQ ID NO: 237) | GACTTTCCTCTGGGCCCTG (SEQ ID NO: 275) | CCACGGAGGGACCTACA (SEQ ID NO: 199) |
| | 2DL5.TC.G | CTTGGGCCTCTGAGAAGG G (SEQ ID NO: 238) | CAAGACCCTCAGGAGGTG AC (SEQ ID NO: 276) | CACTCGCGTTTTCACACAG A (SEQ ID NO: 200) |
| | 2DS4.D1.G | AGAGACAGTCATCCTGCA ATG (SEQ ID NO: 239) | ATGGAGAAGTTGGCCTTGG A (SEQ ID NO: 277) | GAAGTGCTCAAACATGA CATC (SEQ ID NO: 201) |
| | 3DL2.D1.G | GGAGCTGACAACTGATAG GG (SEQ ID NO: 240) | CCAAGGCCAACTTCTCCAT C (SEQ ID NO: 278) | CTTGCAGGAACCTACAG ATG (SEQ ID NO: 211) |

TABLE 4-continued

| Well No. | SNP assay name | 5' Capture Primer (5' 10 mer tag not shown) | 3' Capture Primer (5' 10 mer tag not shown) | Extend Primer |
|---|---|---|---|---|
| W4 3 plex | 2DL1.D2.G. no004 | GACTTTGACCACTCGTAT (SEQ ID NO: 241) | CAGGGCCCAAGGTCAACG (SEQ ID NO: 279) | ATGCTTCGGCTCTTTCC (SEQ ID NO: 202) |
| | 2DL4.TC.G | ATCTGTTGAGGGTCTCTTGC (SEQ ID NO: 242) | AGGTGACATACGCACAGTTG (SEQ ID NO: 280) | CACAGTTGGATCACTGC (SEQ ID NO: 203) |
| | 2DL2.004.TC.G | GGCCGAGGAGTACCTACCT (SEQ ID NO: 243) | GTAATGGACCAAGAGTCTGC (SEQ ID NO: 281) | GAAACAGAACAGCGAATA (SEQ ID NO: 204) |
| W5 2 plex | 2DS2.D1.G | AGAAGTTGGCCTTGGAGACC (SEQ ID NO: 244) | CCTGCAATGTTGGTCAGATG (SEQ ID NO: 282) | GCACAGAGAGGGGAAGT (SEQ ID NO: 205) |
| | 3DL1.TC.S | ATGGGCAGGAGACAACTTTG (SEQ ID NO: 245) | CACTGCGTTTTCACACAGAG (SEQ ID NO: 283) | GAGGCCCAAGACACCCCC (SEQ ID NO: 206) |
| W6 2 plex | 2DS5.D2.G | AGGCCCATGAACGTAGGCTCC (SEQ ID NO: 246) | AAGAGCCGAAGCATCTGTAG (SEQ ID NO: 284) | CTCCGTGGGTGGCAGGG (SEQ ID NO: 207) |
| | 2DL1.no005. 2DL2.004.TC.S | GTAATGGACCAAGAGTCTGC (SEQ ID NO: 247) | CGGGCCGAGGAGTACCTACCT (SEQ ID NO: 285) | CGCTATTCGCTGTTCTGTT (SEQ ID NO: 208) |
| W7 uniplex | 2DL3.2DL2. D1.S | GAGTCCACAGAAAACCTTCCCTCC (SEQ ID NO: 248) | AGTGTCCTTAAACTTCCCTTCTC (SEQ ID NO: 286) | CTTCTGATTTCACCAGG (SEQ ID NO: 209) |

TABLE 5

| Well No. | SNP assay name | 5' Capture Primer (5' 10 mer tag not shown) | 3' Capture Primer (5' 10 mer tag not shown) | Extend |
|---|---|---|---|---|
| W8 2 plex | 2DS3.D2.S | AGGTCAACGGAACATTCCAGGCCG (SEQ ID NO: 249) | AAGAGCCGAAGCATCTGTAG (SEQ ID NO: 287) | CATCTGTAGGTTCCTCC (SEQ ID NO: 212) |
| | 3DS1.TC.G. INT | AACTGCTATGATTAGCTTC (SEQ ID NO: 250) | GATGAAGGAGAAAGAAGAGGAGGA (SEQ ID NO: 288) | GAATGTGCAGGTGTCTG (SEQ ID NO: 213) |
| W9 5 plex | 3DP1.D2.G | GAGCTGCAGGACAAGGTCAC (SEQ ID NO: 251) | TGGGAAACCTTCTCTCTCAGCC (SEQ ID NO: 289) | CTCTCTCAGCCCAGCCG (SEQ ID NO: 214) |
| | 3DS1.D0.S | TCATGCTATACAAAGAAGAC (SEQ ID NO: 252) | TGTGTAGTTCCCTGCATGTG (SEQ ID NO: 290) | AGGGCTCATGTTGAAGC (SEQ ID NO: 210) |
| | 2DL5sub5 | GATCTTGGCTTAGCATTTGG (SEQ ID NO: 253) | CTGCGTTTTCACACAGAC (SEQ ID NO: 291) | CTTCTCAGAGGCCCAAG (SEQ ID NO: 215) |
| | 2DL5sub4 | CCACGGAGGGACCTACAC (SEQ ID NO: 254) | GTGACAGAAACAAGCAGTGG (SEQ ID NO: 292) | GTGAGTCATGGAGAGAGC (SEQ ID NO: 216) |
| | 2DL5sub1 | AGGACAAGCCCTTGCTGTCT (SEQ ID NO: 255) | CAAGACGAGAGCGACACA (SEQ ID NO: 293) | GTCCTCCTCGAGGCACCACAG (SEQ ID NO: 217) |
| W10 2 plex | 2DS5.D1.G | ACACTTTGCGCCTCATTGGAG (SEQ ID NO: 256) | GTGAGTAACAGAACCGTAG (SEQ ID NO: 294) | GACCGATGGAGAAGTTG (SEQ ID NO: 218) |
| | 2DP1.D0.G | GGGTTTAACAACTTCAGTCTGT (SEQ ID NO: 257) | TGTGCTGGGGTCACAGGGCC (SEQ ID NO: 295) | ATTCTGTTGTAGAGCTCAG (SEQ ID NO: 219) |

TABLE 5-continued

| Well No. | SNP assay name | 5' Capture Primer (5' 10 mer tag not shown) | 3' Capture Primer (5' 10 mer tag not shown) | Extend |
|---|---|---|---|---|
| W11 2 plex | 2DS2.D2.G | GTCTATATGAGAAACCTTC (SEQ ID NO: 258) | GGACAAGGTCACGCTCTCTC (SEQ ID NO: 296) | CACGCTCTCTCCTGCCA (SEQ ID NO: 220) |
| | 2DL1.2DS1.D1.S.tri | AAGGCCAACTTCTCCATCA (SEQ ID NO: 259) | GTGAGTAACAGAACCGTAGC (SEQ ID NO: 297) | GGTCCCTGCCAGGTCTTGC (SEQ ID NO: 221) |
| W12 2 plex | 2DL5sub3 | GACATGAGTCCTCTGACCTG (SEQ ID NO: 260) | CCCTGAGCTCTACAACAA (SEQ ID NO: 298) | GCAACCCCCTGGTGATC (SEQ ID NO: 222) |
| | 2DL5sub2 | GACATGAGTCCTCTGACCTG (SEQ ID NO: 261) | CCCTGAGCTCTACAACAA (SEQ ID NO: 299) | CGCTCCCCCATTGAGTGGTC (SEQ ID NO: 223) |
| W13 2 plex | 2DS4del.sub | TTGACCACTCGTAGGGAGC (SEQ ID NO: 262) | CGGTTCAGGCAGGAGAGAAT (SEQ ID NO: 300) | CCTTGTCCTGCAGCTCC (SEQ ID NO: 224) |
| | 2DL5sub6 | TAAGGTGGCGCCTCCTTCTC (SEQ ID NO: 263) | CAAGACGAGAGCGACACA (SEQ ID NO: 301) | AGCAAGGGCTTGTCCTG (SEQ ID NO: 229) |
| W14 2 plex | 2DS4.D2.S | GAGCTCTGTGACGGAAACAA (SEQ ID NO: 264) | GCATCAACGGAACATTCCAGGCC (SEQ ID NO: 302) | TCGGCTCTTTCCGTGAC (SEQ ID NO: 225) |
| | 2DL3.RTC.S.INT | CTGCTTCGTGAGACTTACTT (SEQ ID NO: 265) | GTAACCCCAGACACCTGCATG (SEQ ID NO: 303) | TCTCCTTCATCGCTGGTGCT (SEQ ID NO: 226) |
| W15 uniplex | 2DL2.001.2.3.D1.G | GGAGCTGACAACTGATAGGG (SEQ ID NO: 266) | CCTGCAATGTTGGTCAGATG (SEQ ID NO: 304) | CATGATGGGGTCTCCAA (SEQ ID NO: 227) |
| W16 unioplex | 2DS1.D2.G | ACTTGACTTTGACCACTCGT (SEQ ID NO: 267) | CCTATGACATGTACCATCTA (SEQ ID NO: 305) | CAACGGAACATTCCAGGCC (SEQ ID NO: 228) |

Sample Population

DNA samples for validation of the method consisted of previously typed samples from the International Histocompatibility Working Group (IHWG) DNA repository, previously typed samples from the Parham Laboratory (Stanford University), 60 donor/recipient pairs from the National Marrow Donor Program (NMDP) repository, and 163 samples from the Chicago Multicenter AIDS Cohort Study (MACS). NMDP samples were selected to enrich the ethnic diversity represented in the NMDP repository by a factor of two: as such the ethnic breakdown of the sample group is 66.5% White/Caucasian, 13% Black/African American, 14% Hispanic, and 13% “other” or mixed samples (Asian, Amerindian, or multi-ethnic). All samples were genotyped in-house or previously genotyped by other laboratories using SSOP (Cram et al., *Tissue Antigens* 56:313-326 (2000) and/or SSP methodologies (Uhrberg et al., *Immunity* 7:753-763 (1997); Gomez-Lozano et al., *Tissue Antigens* 59:184-193 (2002)). Data from these previous analyses were used in the validation of the KIR/MALDI method.

DNA Extraction/Quantitation/Normalization

Samples were extracted using Qiagen's 96-well block extraction method (QIAamp 96 DNA Blood Kit) and a Sigma 4-15 centrifuge, or using Genovision's robotic GenoM-6 magnetic bead-based extraction method. The samples were then quantitated using Picogreen (Invitrogen, Carlsbad, Calif.) fluorescence methodology, and normalized to a final concentration of 2 ng/μl. A fraction of the samples yielded concentrations below 2 ng/μl and were therefore typed using lower DNA concentrations.

Primary PCR

Primary amplification (capture of region surrounding the SNP) was performed on an Applied Biosystems GeneAmp PCR System 9700 in a 384 well format in a volume of 5 μl with the following profile: denaturing at 95° C. for 15 minutes, followed by 45 cycles of denaturing at 95° C. for 20 seconds, annealing at 56° C. for 30 seconds, and extension at 72° C. for 1 minute, and a final extension at 72° C. for 3 minutes. Final concentrations of each component were as follows: 1.25× Qiagen HotStar 10×PCR Buffer, 3.5 mM $MgCl_2$, 500 uM dNTPs (each), 100 nM PCR primers, 0.15 U/rxn of Qiagen HotStar Taq, and 2 ng genomic DNA (gDNA).

Shrimp Alkaline Phosphatase (SAP) Quench

SAP cocktail, consisting of nanopure water, 10×hME buffer (SEQUENOM™), and 0.3 units of Shrimp Alkaline Phosphatase per reaction, was distributed using a Beckman Multimek 9600 to the 384-well reaction plates. Plates were then cycled on an Applied Biosystems GeneAmp PCR System 9700 with the following profile: dNTP terminal phosphate cleavage at 37° C. for 20 minutes, followed by heat-deactivation of the SAP enzyme at 85° C. for five minutes, and a 4° C. final hold.

Primer Extension Reactions

The hME cocktails that include nanopure water, deoxy and dideoxy termination mixes, hME primers added at 9 μM, and Thermosequenase enzyme, were then distributed in 2 µl aliquots using the Beckman Multimek 9600. Extension reactions were then cycled on an Applied Biosystems GeneAmp PCR System 9700 according to the following profile: denaturing for two minutes at 94° C., followed by 99 cycles of denaturing at 94° C. for 5 seconds, annealing at 52° C. for 5 seconds, and extension at 72° C. for 5 seconds, and a final hold at 4° C. Final concentrations of each component were as follows: 50 µM each d/ddNTP, about 1 µM each extend primer, and 1.25 U/reaction Thermosequenase enzyme (Amersham).

Following primer extension, 6 mg of SPECTROCLEAN™ ion-exchange resin (SEQUENOM™) and 16 µl of nanopure water were distributed to each reaction using the Beckman Multimek 9600. Plates were sealed with MJ Research Microseal B Adhesive Sealers (#MSB-1001), rotated for approximately twenty minutes and centrifuged at 3000 rpm for five minutes. The reactions, along with a three point calibrant were spotted onto SPECTROCHIP™ 384 chips with a Samsung MASSARRAY™ NanoDispenser at dispense speed 65 mm/second.

MALDI-TOF Analysis and Genotype Calling

Samples were analyzed on the MASSARRAY™ Compact MALDI-TOF MS. The Compact MALDI-TOF MS is capable of processing two 384 format chips in approximately one hour. Data collection was automatic and was viewed in real time with SEQUENOM™'s SpectroACQUIRE software. Following the run, the data was viewed within the TrafficLights module of the MassARRAY Typer software.

Figure 11A:
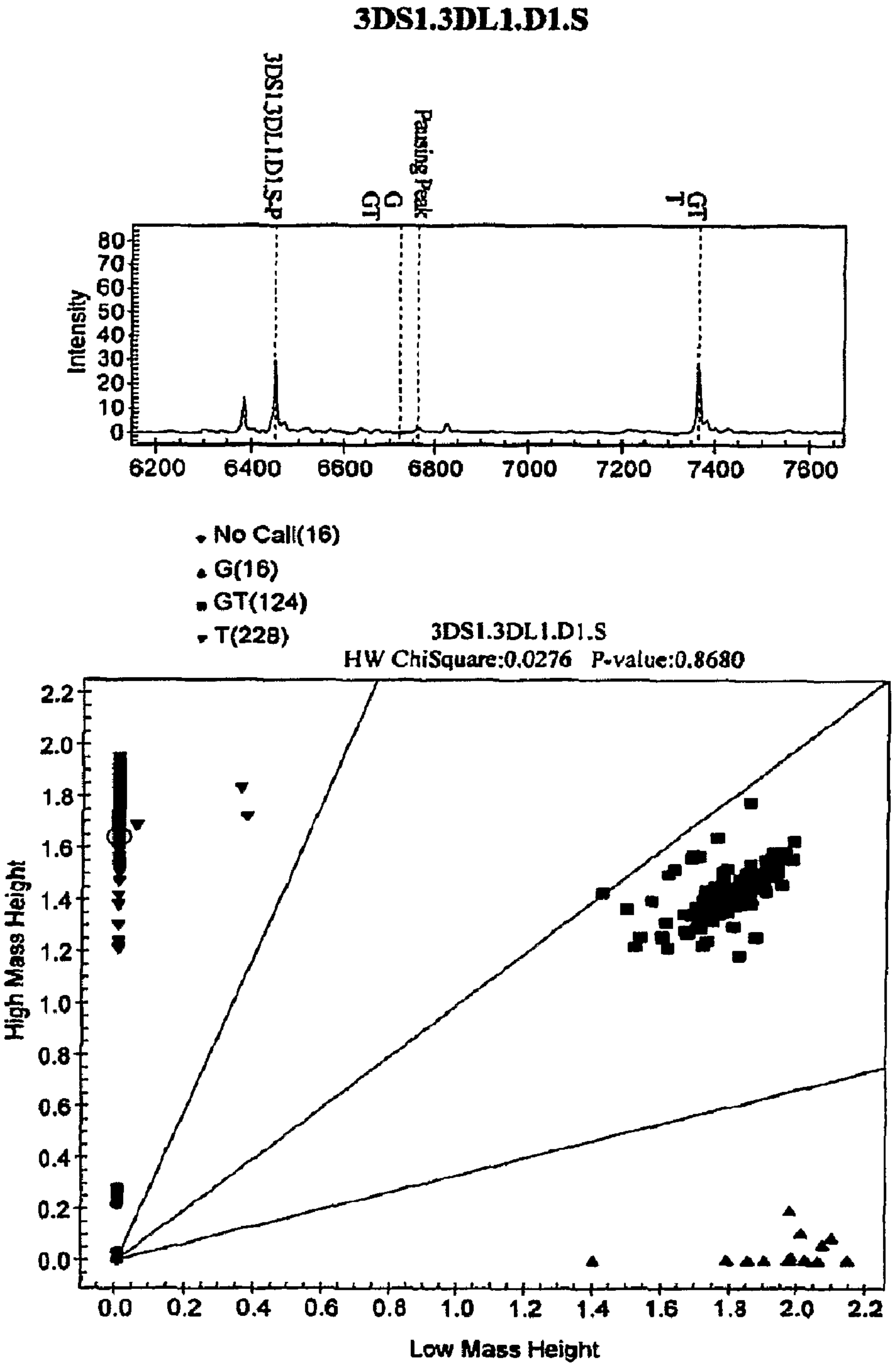
FIG. 11A-11C show spectral data (top panels) and cluster plots (bottom panels) illustrating single nucleotide and double nucleotide calls with the hME 3DS1.3DL1.D1.S which discriminates between 3DS1 and 3DL1.
Figure 11B:
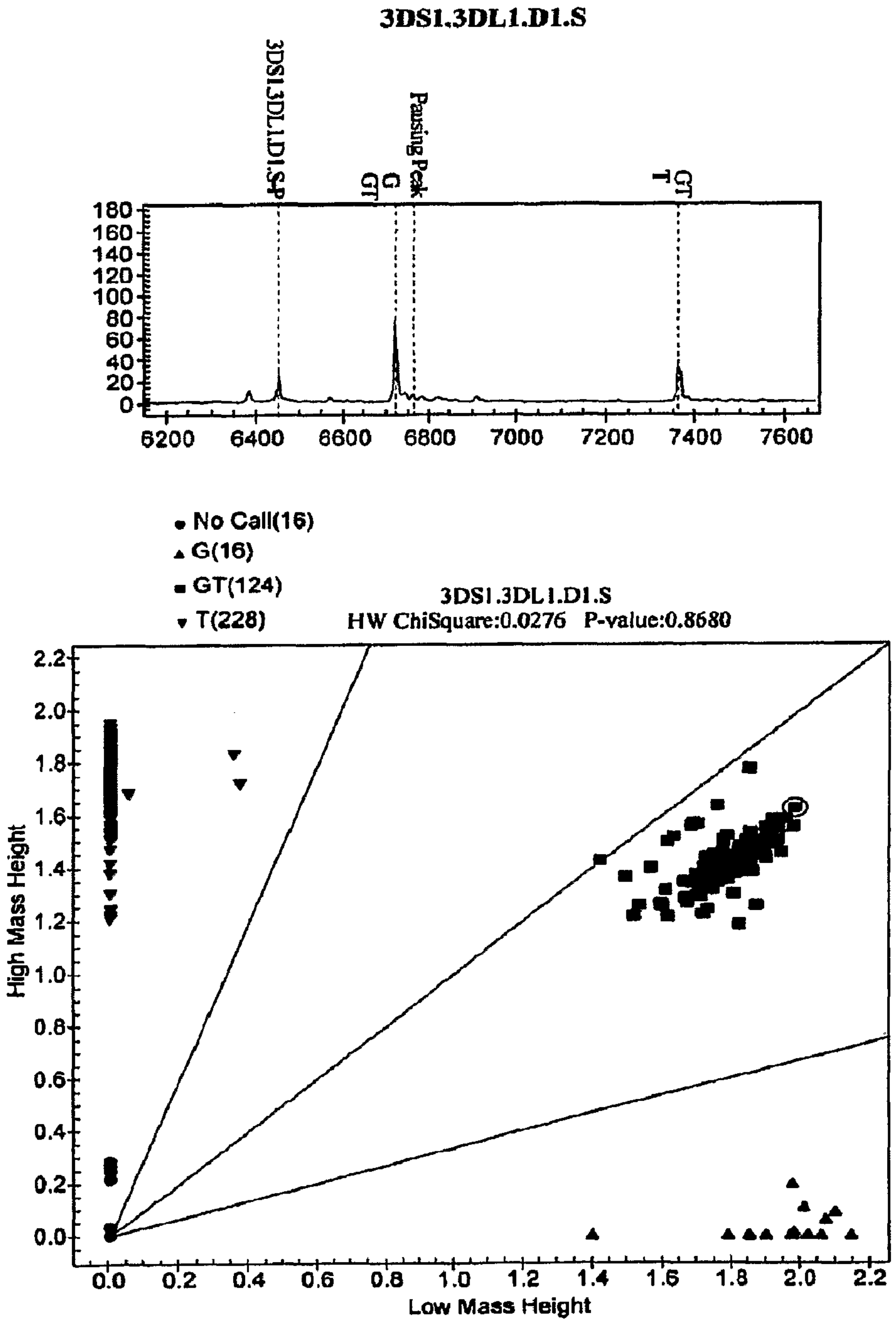
Figure 11C:
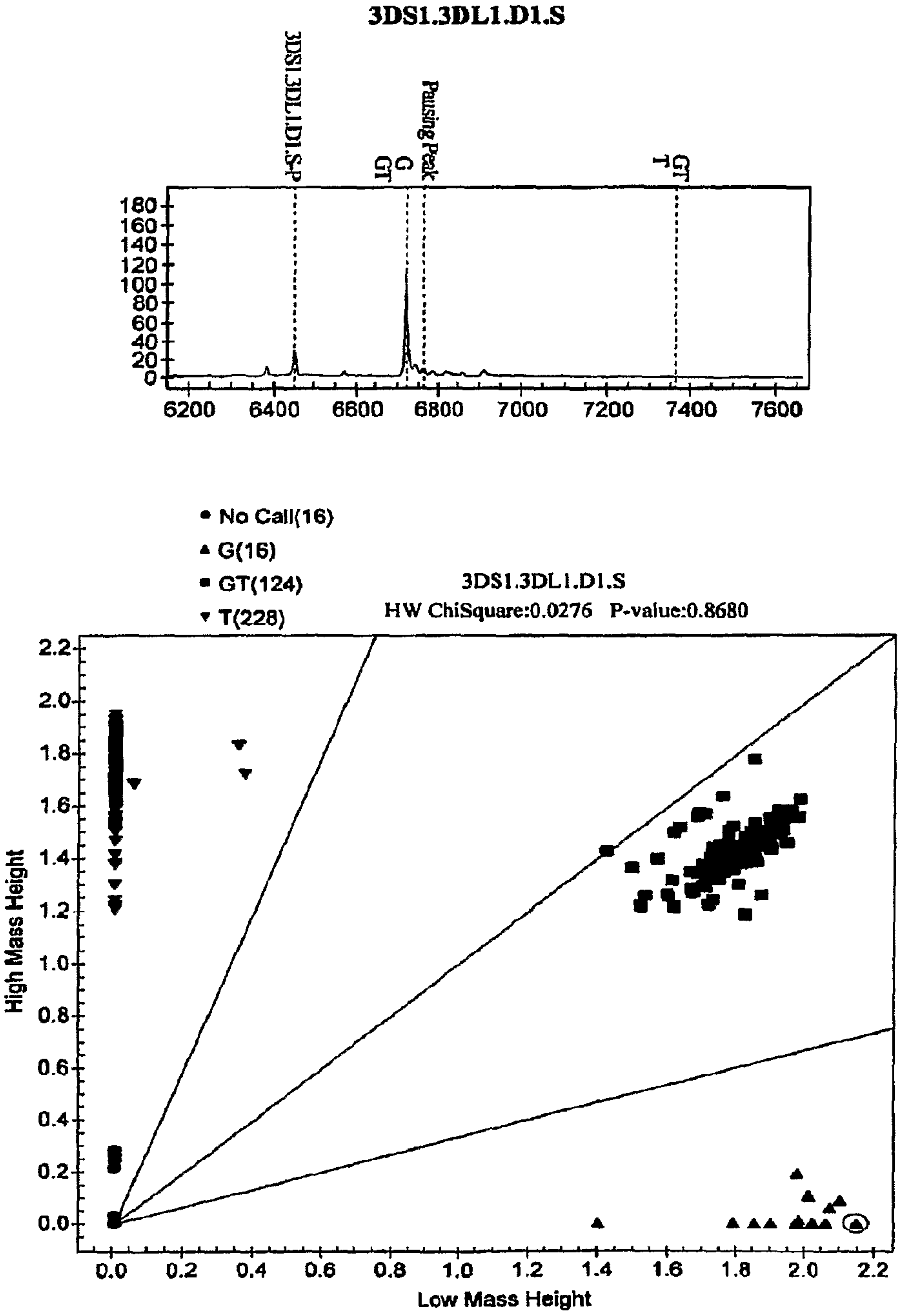
Figure 14:
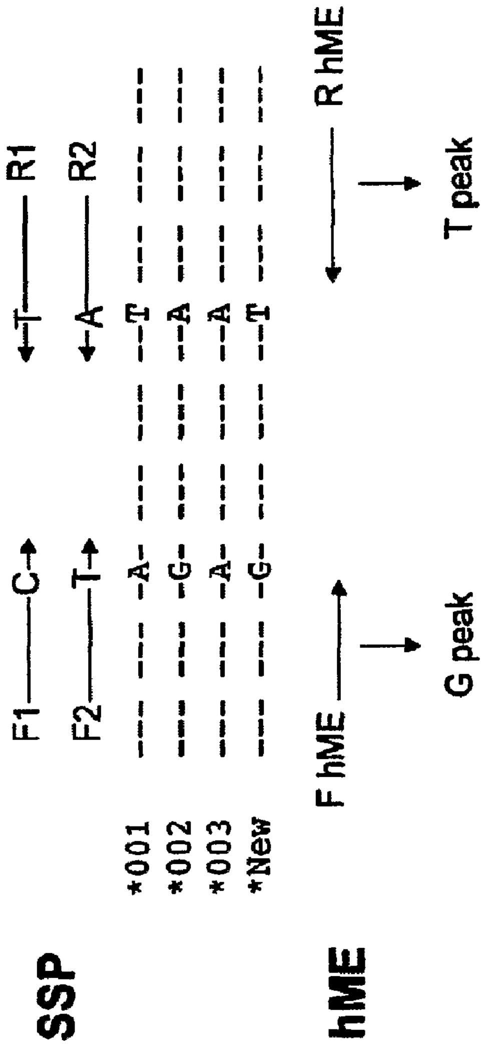
FIG. 14 shows the advantage of using the present methods over other methods. As shown in the figure, four SSP primer reactions would be necessary to characterize a sample homozygous for an allele. However, only two primer extension reactions of the present methods would be needed to achieve the same resolution. While a new allele carrying a C or T nucleotide in the forward SNP position would be undetected by the SSP screen, the primer extension reaction would be able to identify the novel change with one assay.

Spectral data was viewed for each sample, for each of the individual assays (FIG. 11A to FIG. 11C, top panels). Detailed information on peak heights for each assay, and a probability value for each call, based on signal to noise ratios and peak probability statistics were determined. Probability was calculated for three levels of stringency—conservative, moderate and aggressive. Conservative calls resulted in the highest rate of uncalled genotypes, while aggressive calls resulted in the highest error rate, but an error rate that is nonetheless less than 1%. Non-calls resulted from a low probability or bad spectrum. Low probability (LP) calls were initially excluded but can be reviewed by the user and are helpful in understanding and trouble-shooting the reaction. A Cluster Plot software module was used to facilitate a visual assessment of the power of each assay to discriminate between the heterozygous and homozygous states (FIG. 11A to FIG. 11C, bottom panels).

The output data from the SPECTROANALYZER™ module of the SEQUENOM™ software suite was exported to KIR Genotype Caller 1.1 to generate a genotype from the individual assays based on hierarchical SNP hit tables (Tables 6-8), and simultaneously tag anomalous calls and problematic samples for user inspection. The program creates a:

1) conflict log—which checks for agreement between replicates of the same assay applied to the same sample in a given data set (duplicate check), 2) a partial match log—which checks for agreement between assays which type for the same gene in different domains, and generates potential recombinants list, and 3) a control check—which checks the SNP profiles of previously characterized samples in a given run against an index of expected results for these samples.

Table 9 shows the hME hit pattern used to distinguish between 3DL1 and 3D1 as an example of how the "KIR Genotype Caller" program uses the hit patterns from the targeted domains to determine the genotype.

TABLE 6

Expected SNP Locus and Allele-Specific Extension Primers for KIR Genes (variants in bold/underline)

| | D0 | | | D1 | | | |
|---|---|---|---|---|---|---|---|
| | 2DL4. D0.G | 3DS1. D0.S | 2DP1. D0.G | 2DL1.2DS1.D1. S.tri | 2DL2.001.2.3. D1.G | 2DL3.2DL2. D1.S | 2DS2. D1.G |
| 2DL1*001 | | | | **C** | | | |
| 2DL1*002 | | | | **C** | | | |
| 2DL1*003 | | | | **C** | | | |
| 2DL1*004 | | | | **C** | | | |
| 2DL1*005 | | | | **C** | | | |
| 2DL2*001 | | | | | **A** | **G** | T |
| 2DL2*002 | | | | | **A** | **G** | T |
| 2DL2*003 | | | | | **A** | **G** | T |
| 2DL2*004 | | | | | G | **C** | T |
| 2DL3*001 | | | | | G | **C** | T |
| 2DL3*002 | | | | | G | **C** | T |
| 2DL3*003 | | | | | G | **C** | T |
| 2DL3*004 | | | | | G | **C** | T |
| 2DL3*005 | | | | | G | **C** | T |
| 2DL3*006 | | | | | G | **C** | T |
| 2DL4*001 | **T** | | | | | | |
| 2DL4*002 | **T** | | | | | | |
| 2DL4*003 | **T** | | | | | | |
| 2DL4*004 | **T** | | | | | | |
| 2DL4*005 | **T** | | | | | | |
| 2DL4*006 | **T** | | | | | | |
| 2DL4*007 | **T** | | | | | | |
| 2DL5A*001 | | | | | | | |
| 2DL5B*002 | | | | | | | |
| 2DL5B*003 | | | | | | | |
| 2DL5B*004 | | | | | | | |

TABLE 6-continued

Expected SNP Locus and Allele-Specific Extension Primers for KIR Genes
(variants in bold/underline)

| | D1 | | | | | | D2 | |
|---|---|---|---|---|---|---|---|---|
| | 2DS3.D1.G | 2DS4.D1.G | 2DS5.D1.G | 3DL2.D1.G | 3DL3.D1.G | 3DS1.3DL1.D1.S | 2DL1.D2.G.no004 | 2DL2.D2.S |
| 2DL1*001 | | | C | | | | **A** | |
| 2DL1*002 | | | C | | | | **A** | |
| 2DL1*003 | | | C | | | | **A** | |
| 2DL1*004 | | | C | | | | G | |
| 2DL1*005 | | | C | | | | **A** | |
| 2DL2*001 | | | | | | | G | **T** |
| 2DL2*002 | | | | | | | G | **T** |
| 2DL2*003 | | | | | | | G | **T** |
| 2DL2*004 | | | | | | | G | **T** |
| 2DL3*001 | | | | | | | G | C |
| 2DL3*002 | | | | | | | G | C |
| 2DL3*003 | | | | | | | G | C |
| 2DL3*004 | | | | | | | G | C |
| 2DL3*005 | | | | | | | G | C |
| 2DL3*006 | | | | | | | G | C |
| 2DL4*001 | | | | | | | | |
| 2DL4*002 | | | | | | | | |
| 2DL4*003 | | | | | | | | |
| 2DL4*004 | | | | | | | | |
| 2DL4*005 | | | | | | | | |
| 2DL4*006 | | | | | | | | |
| 2DL4*007 | | | | | | | | |
| 2DL5A*001 | | | | | | | | |
| 2DL5B*002 | | | | | | | | |
| 2DL5B*003 | | | | | | | | |
| 2DL5B*004 | | | | | | | | |

| | D2 | | | | | | | |
|---|---|---|---|---|---|---|---|---|
| | 2DL5.D2.G | 2DS1.D2.G | 2DS2.D2.G | 2DS3.D2.S | 2DS4.D2.S | 2DS5.D2.G | 3DL3.D2.G | 3DP1.D2.G |
| 2DL1*001 | G | | C | | | G | | |
| 2DL1*002 | G | | C | | | G | | |
| 2DL1*003 | G | | C | | | G | | |
| 2DL1*004 | G | **T** | C | | | G | | |
| 2DL1*005 | G | | C | | | G | | |
| 2DL2*001 | | C | | C | T | | | |
| 2DL2*002 | | C | | C | T | | | |
| 2DL2*003 | | C | | C | T | | | |
| 2DL2*004 | | C | | C | T | | | |
| 2DL3*001 | | C | C | C | T | | | |
| 2DL3*002 | | C | C | C | T | | | |
| 2DL3*003 | | C | C | C | T | | | |
| 2DL3*004 | | C | C | C | T | | | |
| 2DL3*005 | | C | C | C | T | | | |
| 2DL3*006 | | C | C | C | T | | | |
| 2DL4*001 | | | | | | | | |
| 2DL4*002 | | | | | | | | |
| 2DL4*003 | | | | | | | | |
| 2DL4*004 | | | | | | | | |
| 2DL4*005 | | | | | | | | |
| 2DL4*006 | | | | | | | | |
| 2DL4*007 | | | | | | | | |
| 2DL5A*001 | **C** | | | | | | | |
| 2DL5B*002 | **C** | | | | | | | |
| 2DL5B*003 | **C** | | | | | | | |
| 2DL5B*004 | **C** | | | | | | | |

| | Trans/cytoplasmic | | | | | | |
|---|---|---|---|---|---|---|---|
| | 2DL1.no005.2DL2.004.TC.S | 2DL2.004.TC.G | 2DL3.TC.S.INT | 2DL4.TC.G | 2DL5.TC.G | 3DL1.TC.S | 3DL2.TC.G |
| 2DL1*001 | **A** | G | | | G | A | |
| 2DL1*002 | **A** | G | | | G | A | |
| 2DL1*003 | **A** | G | | | G | A | |
| 2DL1*004 | **A** | G | | | G | A | |
| 2DL1*005 | G | G | | | G | A | |
| 2DL2*001 | G | G | C | | G | A | |
| 2DL2*002 | G | G | C | | G | A | |
| 2DL2*003 | G | G | C | | G | A | |

TABLE 6-continued

Expected SNP Locus and Allele-Specific Extension Primers for KIR Genes
(variants in bold/underline)

| | | | | | | |
|---|---|---|---|---|---|---|
| 2DL2*004 | **A** | **T** | C | | G | A |
| 2DL3*001 | | G | **G** | | G | A |
| 2DL3*002 | | G | **G** | | G | A |
| 2DL3*003 | | G | **G** | | G | A |
| 2DL3*004 | | G | **G** | | G | A |
| 2DL3*005 | | G | **G** | | G | A |
| 2DL3*006 | | G | **G** | | G | A |
| 2DL4*001 | | | | **A** | | |
| 2DL4*002 | | | | **A** | | |
| 2DL4*003 | | | | **A** | | |
| 2DL4*004 | | | | **A** | | |
| 2DL4*005 | | | | **A** | | |
| 2DL4*006 | | | | **A** | | |
| 2DL4*007 | | | | **A** | | |
| 2DL5A*001 | | | | | **C** | |
| 2DL5B*002 | | | | | **C** | |
| 2DL5B*003 | | | | | **C** | |
| 2DL5B*004 | | | | | **C** | |

| | Trans/ | subtyping | | | | | | |
|---|---|---|---|---|---|---|---|---|
| | cytoplasmic 3DS1.TC.G.INT | 2DL5. sub1 | 2DL5. sub2 | 2DL5. sub3 | 2DL5. sub4 | 2DL5. sub5 | 2DL5. sub6 | 2DS4del. sub |
| 2DL1*001 | | | | | | | | |
| 2DL1*002 | | | | | | | | |
| 2DL1*003 | | | | | | | | |
| 2DL1*004 | | | | | | | | |
| 2DL1*005 | | | | | | | | |
| 2DL2*001 | | | | | | | | |
| 2DL2*002 | | | | | | | | |
| 2DL2*003 | | | | | | | | |
| 2DL2*004 | | | | | | | | |
| 2DL3*001 | C | | | | | | | |
| 2DL3*002 | C | | | | | | | |
| 2DL3*003 | C | | | | | | | |
| 2DL3*004 | C | | | | | | | |
| 2DL3*005 | C | | | | | | | |
| 2DL3*006 | C | | | | | | | |
| 2DL4*001 | | | | | | | | |
| 2DL4*002 | | | | | | | | |
| 2DL4*003 | | | | | | | | |
| 2DL4*004 | | | | | | | | |
| 2DL4*005 | | | | | | | | |
| 2DL4*006 | | | | | | | | |
| 2DL4*007 | | | | | | | | |
| 2DL5A*001 | | **G** | **A** | **G** | **G** | **A** | **T** | |
| 2DL5B*002 | | **G** | **G** | **G** | **A** | **A** | **A** | |
| 2DL5B*003 | | **G** | **A** | **A** | **G** | **A** | **T** | |
| 2DL5B*004 | | **A** | **A** | **G** | **G** | **A** | **T** | |

TABLE 7

Expected SNP Locus and Allele-Specific Extension Primers for KIR Genes
(variants in bold/underline)

| | D0 | | | D1 | | | |
|---|---|---|---|---|---|---|---|
| | 2DL4. D0.G | 3DS1. D0.S | 2DP1. D0.G | 2DL1.2DS1.D1. S.tri | 2DL2.001.2.3. D1.G | 2DL3.2DL2. D1.S | 2DS2. D1.G |
| DS1*001 | | | | **G** | G | | |
| DS1*002 | | | | **A** | G | | |
| DS1*003 | | | | **A** | G | | |
| DS1*004 | | | | **A** | G | | |
| DS2*001 | | | | | G | | **A** |
| DS2*002 | | | | | G | | **A** |
| DS2*003 | | | | | G | | **A** |
| DS2*004 | | | | | G | | **A** |
| DS2*005 | | | | | G | | **A** |
| DS3*001 | | | | | | | |
| DS4*001 | | | | | | | |
| DS4*002 | | | | | | | |
| DS4*003 | | | | | | | |

TABLE 7-continued

Expected SNP Locus and Allele-Specific Extension Primers for KIR Genes (variants in bold/underline)

| | |
|---|---|
| DS5*001 | |
| DS5*002 | |
| DS5*003 | |
| DL1*001 | A |
| DL1*002 | A |
| DL1*003 | A |
| DL1*004 | A |
| DL1*005 | A |
| DL1*006 | A |
| DL1*007 | A |
| DL1*008 | A |
| DL1*009 | **G** |

| | D1 | | | | | | D2 | |
|---|---|---|---|---|---|---|---|---|
| | 2DS3. D1.G | 2DS4. D1.G | 2DS5. D1.G | 3DL2. D1.G | 3DL3. D1.G | 3DS1.3DL1. D1.S | 2DL1.D2.G. no004 | 2DL2. D2.S |
| DS1*001 | | | C | | | | | C |
| DS1*002 | | | C | | | | | C |
| DS1*003 | | | C | | | | | C |
| DS1*004 | | | C | | | | | C |
| DS2*001 | | | | | | | | C |
| DS2*002 | | | | | | | | C |
| DS2*003 | | | | | | | | C |
| DS2*004 | | | | | | | | C |
| DS2*005 | | | | | | | | C |
| DS3*001 | **T** | | C | | | | | C |
| DS4*001 | | **G** | | | | | | |
| DS4*002 | | **G** | | | | | | |
| DS4*003 | | **G** | | | | | | |
| DS5*001 | | | **G** | | | | | |
| DS5*002 | | | **G** | | | | | |
| DS5*003 | | | **G** | | | | | |
| DL1*001 | | | | | | **T** | | |
| DL1*002 | | | | | | **T** | | |
| DL1*003 | | | | | | **T** | | |
| DL1*004 | | | | | | **T** | | |
| DL1*005 | | | | | | **T** | | |
| DL1*006 | | | | | | **T** | | |
| DL1*007 | | | | | | **T** | | |
| DL1*008 | | | | | | **T** | | |
| DL1*009 | | | | | | **T** | | |

| | D2 | | | | | | | |
|---|---|---|---|---|---|---|---|---|
| | 2DL5. D2.G | 2DS1.D2.G | 2DS2. D2.G | 2DS3. D2.S | 2DS4. D2.S | 2DS5.D2.G | 3DL3. D2.G | 3DP1. D2.G |
| DS1*001 | | **T** | C | | | | | |
| DS1*002 | | **T** | C | | | | | |
| DS1*003 | | **T** | C | | | | | |
| DS1*004 | | **T** | C | | | | | |
| DS2*001 | | C | **T** | C | | | | |
| DS2*002 | | C | **T** | C | | | | |
| DS2*003 | | C | **T** | C | | | | |
| DS2*004 | | C | **T** | C | | | | |
| DS2*005 | | C | **T** | C | | | | |
| DS3*001 | | | C | **A** | | | | |
| DS4*001 | | | C | | **G** | G | | |
| DS4*002 | | | C | | **G** | G | | |
| DS4*003 | | | C | | **G** | G | | |
| DS5*001 | | | C | | | **A** | | |
| DS5*002 | | | C | | | **A** | | |
| DS5*003 | | | C | | | **A** | | |
| DL1*001 | | | | | | | | |
| DL1*002 | | | | | | | | |
| DL1*003 | | | | | | | | |
| DL1*004 | | | | | | | | |
| DL1*005 | | | | | | | | |
| DL1*006 | | | | | | | | |
| DL1*007 | | | | | | | | |
| DL1*008 | | | | | | | | |
| DL1*009 | | | | | | | | |

TABLE 7-continued

Expected SNP Locus and Allele-Specific Extension Primers for KIR Genes
(variants in bold/underline)

| | Trans/cytoplasmic | | | | | | |
|---|---|---|---|---|---|---|---|
| | 2DL1.no005.2DL2.004.TC.S | 2DL2.004.TC.G | 2DL3.TC.S.INT | 2DL4.TC.G | 2DL5.TC.G | 3DL1.TC.S | 3DL2.TC.G |
| DS1*001 | | | | | | | |
| DS1*002 | | | | | | | |
| DS1*003 | | | | | | | |
| DS1*004 | | | | | | | |
| DS2*001 | | | | | | | |
| DS2*002 | | | | | | | |
| DS2*003 | | | | | | | |
| DS2*004 | | | | | | | |
| DS2*005 | | | | | | | |
| DS3*001 | | | | | | | |
| DS4*001 | | | | | | | |
| DS4*002 | | | | | | | |
| DS4*003 | | | | | | | |
| DS5*001 | | | | | | | |
| DS5*002 | | | | | | | |
| DS5*003 | | | | | | | |
| DL1*001 | | | | | | **T** | |
| DL1*002 | | | | | | **T** | |
| DL1*003 | | | | | | **T** | |
| DL1*004 | | | | | | **T** | |
| DL1*005 | | | | | | **T** | |
| DL1*006 | | | | | | **T** | |
| DL1*007 | | | | | | **T** | |
| DL1*008 | | | | | | **T** | |
| DL1*009 | | | | | | **T** | |

| | Trans/ | subtyping | | | | | | |
|---|---|---|---|---|---|---|---|---|
| | cytoplasmic 3DS1.TC.G.INT | 2DL5.sub1 | 2DL5.sub2 | 2DL5.sub3 | 2DL5.sub4 | 2DL5.sub5 | 2DL5.sub6 | 2DS4del.sub |
| DS1*001 | C | | | | | | | |
| DS1*002 | C | | | | | | | |
| DS1*003 | C | | | | | | | |
| DS1*004 | C | | | | | | | |
| DS2*001 | C | | | | | | | |
| DS2*002 | C | | | | | | | |
| DS2*003 | C | | | | | | | |
| DS2*004 | C | | | | | | | |
| DS2*005 | C | | | | | | | |
| DS3*001 | C | | | | | | | |
| DS4*001 | C | | | | | | | **C** |
| DS4*002 | C | | | | | | | **C** |
| DS4*003 | C | | | | | | | **A** |
| DS5*001 | C | | | | | | | |
| DS5*002 | C | | | | | | | |
| DS5*003 | C | | | | | | | |
| DL1*001 | C | | | | | | | |
| DL1*002 | C | | | | | | | |
| DL1*003 | C | | | | | | | |
| DL1*004 | C | | | | | | | |
| DL1*005 | C | | | | | | | |
| DL1*006 | C | | | | | | | |
| DL1*007 | C | | | | | | | |
| DL1*008 | C | | | | | | | |
| DL1*009 | C | | | | | | | |

TABLE 8

Expected SNP Locus and Allele-Specific Extension Primers for KIR Genes
(variants in bold/underline)

| | D0 | | | D1 | | | |
|---|---|---|---|---|---|---|---|
| | 2DL4.D0.G | 3DS1.D0.S | 2DP1.D0.G | 2DL1.2DS1.D1.S.tri | 2DL2.001.2.3.D1.G | 2DL3.2DL2.D1.S | 2DS2.D1.G |
| 3DS1*010 | | **G** | | | | | |
| 3DS1*011 | | **G** | | | | | |

TABLE 8-continued

Expected SNP Locus and Allele-Specific Extension Primers for KIR Genes (variants in bold/underline)

| | | | |
|---|---|---|---|
| 3DS1*012 | **G** | | |
| 3DS1*013 | **G** | | |
| 3DS1*014 | **G** | | |
| 3DL2*001 | | | G |
| 3DL2*002 | | | G |
| 3DL2*003 | | | G |
| 3DL2*004 | | | G |
| 3DL2*005 | | | G |
| 3DL2*006 | | | G |
| 3DL2*007 | | | G |
| 3DL2*008 | | | G |
| 3DL2*009 | | | G |
| 3DL2*010 | | | G |
| 3DL2*011 | | | G |
| 3DL2*012 | | | G |
| 3DL3*001 | | C | |
| 3DL3*002 | | C | |
| 3DL3*003 | | C | |
| 3DL3*004 | | C | |
| 3DP1*001 | | C | |
| 3DP1*002 | | C | |
| 3DP1*003 | | C | |
| 2DP1*001 | | **A** | |
| 2DP1*002 | | **A** | |

| | D1 | | | | | | D2 | |
|---|---|---|---|---|---|---|---|---|
| | 2DS3.D1.G | 2DS4.D1.G | 2DS5.D1.G | 3DL2.D1.G | 3DL3.D1.G | 3DS1.3DL1.D1.S | 2DL1.D2.G.no004 | 2DL2.D2.S |
| 3DS1*010 | | | | | | **G** | | |
| 3DS1*011 | | | | | | **G** | | |
| 3DS1*012 | | | | | | **G** | | |
| 3DS1*013 | | | | | | **G** | | |
| 3DS1*014 | | | | | | **G** | | |
| 3DL2*001 | G | A | | **T** | | | | |
| 3DL2*002 | G | A | | **T** | | | | |
| 3DL2*003 | G | A | | **T** | | | | |
| 3DL2*004 | G | A | | **T** | | | | |
| 3DL2*005 | G | A | | **T** | | | | |
| 3DL2*006 | G | A | | **T** | | | | |
| 3DL2*007 | G | A | | **T** | | | | |
| 3DL2*008 | G | A | | **T** | | | | |
| 3DL2*009 | G | A | | **T** | | | | |
| 3DL2*010 | G | A | | **T** | | | | |
| 3DL2*011 | G | A | | **T** | | | | |
| 3DL2*012 | G | A | | **T** | | | | |
| 3DL3*001 | | | | | **C** | | | |
| 3DL3*002 | | | | | **C** | | | |
| 3DL3*003 | | | | | **C** | | | |
| 3DL3*004 | | | | | **C** | | | |
| 3DP1*001 | | A | | | | | | |
| 3DP1*002 | | A | | | | | | |
| 3DP1*003 | | A | | | | | | |
| 2DP1*001 | | | | | | | | |
| 2DP1*002 | | | | | | | | |

| | D2 | | | | | | | |
|---|---|---|---|---|---|---|---|---|
| | 2DL5.D2.G | 2DS1.D2.G | 2DS2.D2.G | 2DS3.D2.S | 2DS4.D2.S | 2DS5.D2.G | 3DL3.D2.G | 3DP1.D2.G |
| 3DS1*010 | | | | | | | | |
| 3DS1*011 | | | | | | | | |
| 3DS1*012 | | | | | | | | |
| 3DS1*013 | | | | | | | | |
| 3DS1*014 | | | | | | | | |
| 3DL2*001 | G | | C | | | G | | |
| 3DL2*002 | G | | C | | | G | | |
| 3DL2*003 | G | | C | | | G | | |
| 3DL2*004 | G | | C | | | G | | |
| 3DL2*005 | G | | C | | | G | | |
| 3DL2*006 | G | | C | | | G | | |
| 3DL2*007 | G | | C | | | G | | |
| 3DL2*008 | G | | C | | | G | | |
| 3DL2*009 | G | | C | | | G | | |
| 3DL2*010 | G | | C | | | G | | |

TABLE 8-continued

Expected SNP Locus and Allele-Specific Extension Primers for KIR Genes
(variants in bold/underline)

| | | | | | |
|---|---|---|---|---|---|
| 3DL2*011 | G | C | G | | |
| 3DL2*012 | G | C | G | | |
| 3DL3*001 | | | | **G** | G |
| 3DL3*002 | | | | **G** | G |
| 3DL3*003 | | | | **G** | G |
| 3DL3*004 | | | | **G** | G |
| 3DP1*001 | | | | | **C** |
| 3DP1*002 | | | | | **C** |
| 3DP1*003 | | | | | **C** |
| 2DP1*001 | | | | | G |
| 2DP1*002 | | | | | G |

| | Trans/cytoplasmic | | | | | | |
|---|---|---|---|---|---|---|---|
| | 2DL1.no005.2DL2.004.TC.S | 2DL2.004.TC.G | 2DL3.TC.S.INT | 2DL4.TC.G | 2DL5.TC.G | 3DL1.TC.S | 3DL2.TC.G |
| 3DS1*010 | | | C | | | | |
| 3DS1*011 | | | C | | | | |
| 3DS1*012 | | | C | | | | |
| 3DS1*013 | | | C | | | | |
| 3DS1*014 | | | C | | | | |
| 3DL2*001 | | | | | | | G |
| 3DL2*002 | | | | | | | **G** |
| 3DL2*003 | | | | | | | **G** |
| 3DL2*004 | | | | | | | **G** |
| 3DL2*005 | | | | | | | **G** |
| 3DL2*006 | | | | | | | **G** |
| 3DL2*007 | | | | | | | **G** |
| 3DL2*008 | | | | | | | **G** |
| 3DL2*009 | | | | | | | **G** |
| 3DL2*010 | | | | | | | **G** |
| 3DL2*011 | | | | | | | **G** |
| 3DL2*012 | | | | | | | **G** |
| 3DL3*001 | | | | | G | | C |
| 3DL3*002 | | | | | G | | C |
| 3DL3*003 | | | | | G | | C |
| 3DL3*004 | | | | | G | | C |
| 3DP1*001 | | | | | | | |
| 3DP1*002 | | | | | | | |
| 3DP1*003 | | | | | | | |
| 2DP1*001 | | | | | | | |
| 2DP1*002 | | | | | | | |

| | Trans/ | subtyping | | | | | | |
|---|---|---|---|---|---|---|---|---|
| | cytoplasmic 3DS1.TC.G.INT | 2DL5.sub1 | 2DL5.sub2 | 2DL5.sub3 | 2DL5.sub4 | 2DL5.sub5 | 2DL5.sub6 | 2DS4del.sub |
| 3DS1*010 | **T** | | | | | | | |
| 3DS1*011 | **T** | | | | | | | |
| 3DS1*012 | **T** | | | | | | | |
| 3DS1*013 | **T** | | | | | | | |
| 3DS1*014 | T | | | | | | | |
| 3DL2*001 | | | | | | | | |
| 3DL2*002 | | | | | | | | |
| 3DL2*003 | | | | | | | | |
| 3DL2*004 | | | | | | | | |
| 3DL2*005 | | | | | | | | |
| 3DL2*006 | | | | | | | | |
| 3DL2*007 | | | | | | | | |
| 3DL2*008 | | | | | | | | |
| 3DL2*009 | | | | | | | | |
| 3DL2*010 | | | | | | | | |
| 3DL2*011 | | | | | | | | |
| 3DL2*012 | | | | | | | | |
| 3DL3*001 | | | | | | | | |
| 3DL3*002 | | | | | | | | |
| 3DL3*003 | | | | | | | | |
| 3DL3*004 | | | | | | | | |
| 3DP1*001 | | | | | | | | |
| 3DP1*002 | | | | | | | | |
| 3DP1*003 | | | | | | | | |
| 2DP1*001 | | | | | | | | |
| 2DP1*002 | | | | | | | | |

TABLE 9 hMEs (A) and hit patterns (B) used to distinguish 3DS1 from 3DS1

A. hMEs

| | DOMAIN | | | | |
|---|---|---|---|---|---|
| ALLELE | D0 | D1 | D2 | TRANS/CYT | NO. HITS |
| 3DL1 | | 3DS1.3DL1.D1.S | | 3DL1.TC.S | 2 |
| 3DS1 | 3DS1.D0.S | 3DS1.3DL1.D1.S | | 3DS1.TC.G.INT | 3 |

B. Hit patterns

| | DOMAIN | | | |
|---|---|---|---|---|
| | D0<br>3DS1.D0.S | D1<br>3DS1.3DL1.D1.S | TC<br>3DL1.TC.S | TC<br>3DS1.TC.G.INT |
| 3DL1 | | | | |
| 3DL1*001 | | T | T | |
| 3DL1*002 | | T | T | |
| 3DL1*004 | | T | T | |
| 3DL1*005 | | T | T | |
| 3DL1*006 | | T | T | |
| 3DL1*007 | | T | T | |
| 3DL1*008 | | T | T | |
| 3DL1*009 | G | T | T | |
| 3DS1 | | | | |
| 3DS1*010 | G | G | | T |
| 3DS1*011 | G | G | | T |
| 3DS1*012 | G | G | | T |
| 3DS1*013 | G | G | | T |
| 3DS1*014 | G | G | | T |

Locus-Specific Genotyping Using SSOP

Samples were amplified at KIR domains D0, D1 and D2 and a transmembrane-cytoplasmic region using ~100 ng of genomic DNA per amplification and assayed in an SSOP format with 39 biotinylated probes designed to identify 14 KIR genes, and some alleles (Crum et al., *Tissue Antigens* 56:313-326 (2000)). The specific constellation of 39 SSO probes utilized did not distinguish KIR2DL5 subtypes A and B. Amplified PCR products were denatured and vacuum blotted onto replicate 96-sample nylon membranes. Replicate membranes were hybridized to SSO probes, washed under stringent conditions to remove unbound probe, and developed using non-radioactive detection methods. KIR probe hybridization patterns were then individually decoded.

Cloning and Sequencing of Novel KIR2DL5 Allele

Genomic DNA was extracted from the OLGA B cell line using the Qiagen Genomic-tip 20/G kit. Primers LFcon63 and LRg1769 were used to amplify the entire coding region of KIR2DL5 (Vilches et al., *J Immunol* 164:5797-5804 (2000)). OLGA is known to be homozygous consanguineous for the KIR locus. A total of 100 ng of DNA was amplified in 20 µl reactions containing 0.4 U Phusion DNA Polymerase (New Engand BioLabs, Beverly, Mass.), 1×GC buffer and 10 pmol of each primer. The following conditions were used for long range PCR: initial denaturation at 98° C. for 45 seconds; 35 cycles of 98° C. for 10 seconds, 67° C. for 30 seconds and 72° C. for 5 minutes, followed by a final extension at 72° C. for 8 minutes and a 4° C. hold. The PCR products were electrophoresed in a 0.8% agarose gel and the DNA visualized by crystal violet staining. The 9.3 kb fragment was purified using a SNAP column (Invitrogen, Carlsbad, Calif.). Three-prime (3') A-overhangs were added to the purified fragment using U Taq DNA polymerase (Roche) and dATP and incubation at 72° C. for 20 minutes. The fragment was subsequently inserted into the pCR-XL-TOPO cloning vector (Invitrogen, Carlsbad, Calif.). Plasmids were isolated from individual colonies using the QIAPREP™ Spin miniprep kit and sent to the UC Berkeley DNA Sequencing Facility (Berkeley, Calif.) for sequencing exons 1 through 9. Primers were chosen based on genomic sequence for 2DL5.

Collection and Analysis of KIR Genotype Data Generated by the MALDI-TOF Mass Spectrometer High-throughput SNP analysis with MALDI-TOF mass spectrometry generated a large amount of data quickly. After the data collection, the results are imported into an Oracle database. The database has the run-plate sample listings, genotype probability scores, an assessment of the quality of the score, and links to displays of the raw mass spectrum plot for each sample in each run.

Example 1

Resolution of KIR Genotypes Using SNPs by MALDI-TOF Mass Spectrometry

The Sequenom MALDI-TOF system comprises a primer-extension based assay which uses mass spectrometry to measure the exact mass of a genotyping primer that is extended by one or two nucleotides. The Sequenom MASSARRAY™ system includes the matrix-assisted laser desorption/ionization time-of-flight (MALDI-TOF) mass spectrometer (MS) with assorted robotics. This system is designed for speed and accuracy in high-throughput genomics.

A set of SNPs that distinguish the 17 KIR genes and pseudogenes was identified by in silico inspection of the aligned KIR sequences from the Immuno-Polymorphism Database (IPD) (available on the world wide web at ebi.ac.uk/ipd/kir) (see FIGS. 1-4). The two pseudogenes (2DP1 and 3DP1) were included in the analysis to help identify recombination and to assist with haplotype analysis. Pairs of nucleotide primers were developed to 'capture' these SNPs in ~400 bp PCR amplification products from genomic DNA samples (see Tables 4 and 5).

First, DNA was amplified by PCR using "capture primers" to capture and amplify the nucleic acid region surrounding the SNP. The amplified DNA was then aliquoted using a robotic system. This "capture" PCR product was then hybridized to a primer designed to terminate at the nucleotide position just before the SNP site. The primer was extended using a mixture of deoxynucleotides and dideoxynucleotides. Consequently, the extensions consisted of one or two nucleotides depending upon the allele. The extended product-DNA was spotted onto a 384-well microchip using a nanodispenser and analyzed by the MALDI-TOF mass spectrometer. The instrument can measure the smallest difference between the four dideoxynucleotides reproducibly, resolving the 9 dalton (Da) difference between the ddT (288 Da) and the ddA (297 Da) polymorphism. To enable novel, recombinant alleles to be identified, the hME reactions for each functional KIR gene were designed to be redundant: SNPs in exons encoding two different domains being targeted. The primer-extension products (hMEs) from the hME reactions were analyzed by MALDI-TOF MS, which measures the mass of single and double nucleotide extension products, and uses the mass differences to determine which nucleotides were incorporated.

The instrument software is capable of resolving mass differences by the signal-to-noise ratio and peak probability statistics. Each sample can be resolved within 5 sec and a 384-well microchip can be analyzed in less than 30 minutes. The format is extremely flexible and extension primers can be designed to work in either the forward or reverse direction. Therefore, special labels are not required. Measurements made for duplicate reactions are capable of achieving a greater than 99% accuracy and the mass spectrometer can detect 0.2 femtomole of target DNA sequence in the presence of a $10^4$-fold excess of other DNA sequences. Because small amounts of input DNA are needed, this approach enabled the efficient use of samples with limited amounts of DNA.

The SNPs and expected reaction patterns for the 15 expressed KIR genes, 2 KIR pseudogenes and most common allelic variants are listed in Tables 6-8. The capture primer reactions were designed and titrated to amplify 1-2 ng of genomic DNA segments per multiplex reaction. All primers were BLASTed to verify KIR specificity. Amplicons were determined to be robust by gel electrophoresis, and then analyzed using the 37 multiplexed SNP extension primer reactions on the MALDI. The multiplex level for the combined capture and primer extension reaction varied from 1-4 per well, average of 3.

This method for KIR genotyping provides two levels of specificity (FIG. 9). The capture reaction limits the subsequent analysis to the queried KIR gene (FIG. 9), and also allows for simultaneous analysis of a conserved region in an anchor or framework gene, which provides a positive control for the PCR reaction. In the hME reaction, the choice of SNP and of the extension primer provide the second level of specificity and the potential for distinguishing allelic variants as well as the presence or absence of the targeted gene (FIG. 9). 38 primer sets in 16 multiplexed reactions were used in the assay to distinguish all 15 functional KIR genes and two pseudogenes, as well as certain KIR2DS4 and KIR2DL5 variants. For MALDI-TOF MS analysis the hMEs were distributed on 384-array microchips and analyzed in less than 30 minutes. The data generated was directly deposited into an Oracle database which can be accessed to visualize the spectra and assess the assignments.

Example 2

Concordance Between SNP/MALDI-TOF KIR Gene-Content Typing and Established Methods The KIR genotyping assay was designed to have at least two SNPs per locus and to have SNPs in at least two KIR domains whenever possible in an effort to detect novel alleles or loci created by recombination which are known to occur in this complex. The assays were also designed to detect the expected nucleotide in a framework or common locus and the nucleotide specific for the locus queried, to ensure at least one positive signal for most SNP assays and that no calls are based on a "missing" (negative) result.

To validate the approach, 15 previously characterized IHWG samples from individuals who encompass most of the published variability at the KIR locus (as shown by analysis with established SSOP and/or SSP methods) were tested The set of 38 hME assays proved necessary and sufficient to define the presence or absence of the 15 expressed KIR genes and the two KIR pseudogenes. At this level of resolution there was complete agreement between the results obtained with SNP/MALDI-TOF KIR genotyping and those obtained by SSOP and SSP (Table 10).

Comparative analysis of 233 samples shows excellent agreement between the results obtained by SSP, SSO and MALDI-TOF (Table 11). However, KIR typing by SNP MALDI-TOF has major advantages over the SSP and SSO methods. Mass spectrometric analysis uses smaller DNA samples (<40) ng) and gives much higher throughput and greater accuracy. The use of primer extension PCR also increases precision and accommodates DNA samples of poorer quality. Primer extension's advantage is that the primer which queries a SNP anneals not to the polymorphic position, but terminates to one nucleotide position preceeding the SNP. Consequently, an extension product is made regardless of the nucleotide at the SNP. It is thus possible to determine all the nucleotide(s) present at a given SNP position from one primer extension assay. Consequently, the MALDI-TOF approach can give greater precision with fewer assays than SSP and SSO. This property is illustrated by the new KIR2DL1, 3DL1, 2DS5 and 2DL5 alleles identified during MALDI-TOF analysis of the 233 samples.

TABLE 10

Typing results for 15 samples at 17 loci

| | | 2DL1 | 2DL2 | 2DL3 | 2DL4 | 2DL5 | 2DL5 A&B | 3DL1 | 3DL2 | 3DL3 |
|---|---|---|---|---|---|---|---|---|---|---|
| | | Number of probes/locus | | | | | | | | |
| | | 3 | 4 | 2 | 2 | 2 | 5 | 2 | 2 | 2 |
| BM16 | Exp | + | | + | + | | | + | + | + |
| | Obs | + | | + | + | | | + | + | + |
| PITOUT | Exp | + | + | + | + | | | + | + | + |
| | Obs | + | + | + | + | | | + | + | + |

TABLE 10-continued

Typing results for 15 samples at 17 loci

| | | | | | | | | | | |
|---|---|---|---|---|---|---|---|---|---|---|
| BM92 | Exp | + | + | + | + | + | *** | + | + | + |
| | Obs | + | + | + | + | + | A + B | + | + | + |
| OLGA | Exp | + | | + | + | + | A + B | + | + | + |
| | Obs | + | | + | + | + | NEW*** | + | + | + |
| RML | Exp | + | + | + | + | + | A | + | + | + |
| | Obs | + | + | + | + | + | A | + | + | + |
| HS | Exp | + | | + | + | | | + | + | + |
| | Obs | + | | + | + | | | + | + | + |
| NV | Exp | + | + | | + | + | A + B | + | + | + |
| | Obs | + | + | | + | + | A + B | + | + | + |
| WC | Exp | + | + | + | + | + | *** | + | + | + |
| | Obs | + | + | + | + | + | B | + | + | + |
| WT47 | Exp | + | + | | + | + | A + B | | + | + |
| | Obs | + | + | | + | + | A + B | | + | + |
| RR | Exp | + | + | + | + | + | B | + | + | + |
| | Obs | + | + | + | + | + | B | + | + | + |
| YW | Exp | + | | + | + | | | + | + | + |
| | Obs | + | | + | + | | | + | + | + |
| T7527 | Exp | + | + | + | + | + | *** | + | + | + |
| | Obs | + | + | + | + | + | B | + | + | + |
| HOR | Exp | + | | + | + | + | A | | + | + |
| | Obs | + | | + | + | + | A | | + | + |
| DU145 | Exp | | + | | + | + | A | | + | + |
| | Obs | | + | | + | + | A | | + | + |
| FC | Exp | + | + | | + | | | + | + | + |
| | Obs | + | + | | + | | | + | + | + |

| | | 2DS1 | 2DS2 | 2DS3 | 2DS4 | 2DS4 *del | 2DS5 | 3DS1 | 2DP1 | 3DP1 |
|---|---|---|---|---|---|---|---|---|---|---|
| | | Number of probes/locus | | | | | | | | |
| | | 2 | 2 | 2 | 2 | 1 | 2 | 3 | 1 | 1 |
| BM16 | Exp | | | | + | *** | | | + | + |
| | Obs | | | | + | + | | | + | + |
| PITOUT | Exp | | + | | + | *** | | | + | + |
| | Obs | | + | | + | + | | | + | + |
| BM92 | Exp | + | + | + | + | *** | + | + | + | + |
| | Obs | + | + | + | + | | + | + | + | + |
| OLGA | Exp | + | | | + | *** | + | + | + | + |
| | Obs | + | | | + | + | + | + | + | + |
| RML | Exp | + | + | | + | *** | + | + | + | + |
| | Obs | + | + | | + | | + | + | + | + |
| HS | Exp | | | | + | + | | | + | + |
| | Obs | | | | + | + | | | + | + |
| NV | Exp | + | + | + | + | | + | + | + | + |
| | Obs | + | + | + | + | | + | + | + | + |
| WC | Exp | + | + | | + | + | + | | + | + |
| | Obs | + | + | | + | + | + | | + | + |
| WT47 | Exp | + | + | + | | | + | + | + | + |
| | Obs | + | + | + | | | + | + | + | + |
| RR | Exp | | + | + | + | + | | | + | + |
| | Obs | | + | + | + | + | | | + | + |
| YW | Exp | | | | + | + | | | + | + |
| | Obs | | | | + | + | | | + | + |
| T7527 | Exp | + | + | + | + | *** | | + | + | + |
| | Obs | + | + | + | + | | | + | + | + |
| HOR | Exp | + | | | | | + | + | + | + |
| | Obs | + | | | | | + | + | + | + |
| DU145 | Exp | + | + | | | | + | + | | + |
| | Obs | + | + | | | | + | + | | + |
| FC | Exp | | + | + | + | + | | | + | + |
| | Obs | | + | + | + | + | | | + | + |

Abbreviations: Exp = expected; Obs = observed.

A generic assay for the presence of KIR 2DL5 is combined with a higher resolution assay capable of resolving 2DL5 A and B. A generic assay for 2DS4 is combined with an assay for detection of the deletion variants 2DS4*003/*004/*006.

+ in the expected row signifies that the locus is expected to be present;

blank signifies that locus is not expected to be present.

*** indicates that the sample had not been previously typed at allelic level resolution.

"NEW" is a putative novel alleles found for "OLGA" at 2DL5 A/B.

TABLE 11

| Concordance between typing methods for samples used in validating KIR MALDI typing | | | | |
|---|---|---|---|---|
| Population | No. Samples (N) | Methods | Concordance | Novel Freq (% samples with "new" alleles) |
| IHWC/PP | 15 | SSOP vs. MALDI | 100% (99.6%) | 1/15 (6.6%) |
| NMDP | 120 | SSOP vs. MALDI | 100% (99.8%) | 4/120 (3.3%) |
| MACS | 98 | SSP/SSOP vs. MALDI | 100% (99.8%) | 4/98 (4.2%) |

The concordance between typing methods is 100%. Concordance numbers in parentheses indicate higher level of discordance due to putative novel alleles discovered with the KIR/MALDI method. The average novel allele frequency per sample for these populations was 4% using the KIR/MALDI method.

Example 3

Discovery of Novel KIR Alleles by SNP/MALDI-TOF Typing

Certain KIR allele differences have profound functional consequences. For example common KIR2DS4 alleles are inactivated by a deletion of 18 nucleotides. The present SNP/MALDI-TOF typing system was designed to distinguish the 2DS4 deletion variants from the full-length forms and provided results that were concordant with those obtained by the SSOP and SSP methods (see Tables 10 and 11).

A more complicated situation is presented by KIR2DL5, for which the gene can variably be found in either the centromeric and telemetric parts of KIR haplotypes or in both regions of the chromosome. Although these genes have been designated as 2DL5B and 2DL5A according to their centromeric or telemetric position, respectively, their sequences show no A-specific or B-specific character and form a single lineage of seven 'alleles'. Consequently, in order to distinguish the two 2DL5A subtypes from the five 2DL5B subtypes it was necessary to perform allele-specific typing. hME subtyping assays were designed to distinguish the 2DL5A and 2DL5B subtypes, based on six SNPs, previously used in SSP typing to discriminate 2DL5 variants (32). In the 15 member panel, eight donors in the panel were previously subtyped for 2DL5A and 2DL5B, and these included individuals who had only 2DL5A, only 2DL5B. For seven of the donors the results were concordat between SNP/MALDI-TOF and SSP typing (Table 10). The eighth donor. OLGA, had a combination of SNPs that did not correspond to any of the known 2DL5A or 2DL5B alleles. This data showed that OLGA has a novel variant of 2DL5.

To test this hypothesis, the 2DL5 gene from OLGA was isolated and characterized. Long-range PCR amplification of genomic DNA was used to obtain a fragment spanning the 5' untranslated region (UTR) through to the 3' UTR. This 9.3 kb fragment was cloned and sequences determined for exons 1 through 9 (see FIGS. 12 and 13 for exons 3 and 5 sequences). This analysis shows that OLGA has a KIR2DL5 allele that contains a novel combination of nucleotide substitutions in exons 3 and 5, different from all previously known 2DL5 subtypes (see Table 12), and undetectable using current SSP or SSOP methods.

TABLE 12

| Nucleotides that distinguish OLGA from other 2DL5 alleles. | | | | | | | | |
|---|---|---|---|---|---|---|---|---|
| Nucleotide: | | 139 Sub6 | 173 Sub1 | 364 | 385 Sub2 | 410 Sub3 | 581 | 647 Sub4 |
| 2DL5A | 001 | **T** | **G** | A | **A** | **G** | A | **G** |
| 2DL5B | 002 | **A** | **G** | G | **G** | **G** | G | **A** |
| | 003 | **T** | **G** | A | **A** | **A** | A | **G** |
| | 004 | **T** | **A** | A | **A** | **G** | A | **G** |
| | 005 | **A** | **G** | G | **G** | **G** | G | **A** |
| | 006 | **T** | **G** | A | **A** | **G** | A | **G** |
| | 007 | **T** | **G** | A | **A** | **A** | A | **G** |
| OLGA | | **T** | **G** | A | **G** | **G** | A | **G** |

Nucleotides positions shown in bold and underline were queried by KIR/MALDI method.

Numbering system follows Vilches, et al J. Immunol 164: 5797-5804 (2000).

Additional novel KIR alleles were identified from analysis of 120 individuals from the sample repository of the National Marrow Donor Program (NMDP). At the level of KIR gene content SNP/MALDI-TOF typing gave results that were in full agreement with the KIR types we had previously obtained using the SSOP method. The increased resolution of the SNP/MALDI-TOF analysis identified four novel combinations of SNPs that correspond to putative novel alleles at the 2DL1, 3DL1, 2DS5 and 2DL5 genes (Table 13). In addition one Hispanic individual was found to have the same KIR2DL5 allele as OLGA.

TABLE 13

| Expected/observed MALDI-TOF MS hit patterns for putative novel alleles of 2DL1, 3DL1 and 2DS5 | | | | |
|---|---|---|---|---|
| A Unexpected hit patterns observed through locus-specific resolution two-hit/two-domain strategy | | | | |
| Domain | D0 | D1 | D2 | Trans Cyt |
| 2DL1 expected hit pattern | | + | + | + |
| Putative novel 2DL1 allele | | + | missing | missing |
| 3DL1 expected hit pattern | | + | | + |
| Putative novel 3DL1 allele | | + | | missing |

TABLE 13-continued

| Expected/observed MALDI-TOF MS hit patterns for putative novel alleles of 2DL1, 3DL1 and 2DS5 | | | | | | |
|---|---|---|---|---|---|---|
| 2DS5 expected hit pattern | + | + | | | | |
| Putative novel 2DS5 allele | + | missing | | | | |
| B Expected hit pattern for known 2DL5 alleles with intermediate resolution subtyping hMEs. Expected hit pattern for all known 2DL5 alleles with 6 subtyping assays | | | | | | |
| Probe | 2DL5sub1 | 2DL5sub2 | 2DL5sub3 | 2DL5sub4 | 2DL5sub5 | 2DL5sub6 |
| Nt Position | 173 | 385 | 410 | 947 | 1325 | 139 |
| 2DL5A*001 | G | A | G | G | A | T |
| 2DL5B*002 | G | G | G | A | A | A |
| 2DL5B*003 | G | A | A | G | A | T |
| 2DL5B*004 | A | A | G | G | A | T |
| 2DL5A*005 | G | G | G | A | A | A |
| 2DL5B*006 | G | A | G | G | A | T |
| 2DL5B*007 | G | A | A | G | A | T |
| C Novel hit pattern found in OLGA AND which identified a putative new allele. | | | | | | |
| 2DL5*novel | G | G | G | G | A | T |

+ indicates expected hME SNP hit pattern, 'Missing" indicates aberrant hME SNP hit pattern.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A high-throughput method for determining a killer cell immunoglobulin-like receptor (KIR) genotype of a subject, comprising:

co-amplifying a plurality of target sequences of a plurality of query KIR genes and a target sequence of at least one anchor KIR gene selected from the group consisting of 3DL3, 3DL2, 2DL4, and 3DP1, wherein the target sequences are suspected of comprising single nucleotide polymorphisms (SNPs) and wherein the amplification is by using a plurality of 3' primers and a plurality of 5' primers, wherein each pair of 3' primer and 5' primer are selected to amplify a sequence flanking the SNP, extending a plurality of extension primers in an extension reaction, wherein each extension primer is complementary to a nucleic acid sequence of an amplified target sequence at a 5' end of a SNP wherein the extension primer for 3DL3 is SEQ ID NO:196 or SEQ ID NO:203, the extension primer for 3DL2 is SEQ ID NO: 211 or SEQ ID NO: 197, the extension primer for 3DL3 is SEQ ID NO:194 OR SEQ ID NO:195, and the extension primer for 3DP1 is SEQ ID NO:214, and detecting in the extension reaction the presence or absence of the plurality of SNPs of the plurality of query KIR genes and the presence of a SNP of the at least one anchor KIR gene by matrix-assisted laser desorption/ionization time-of-flight (MALDI-TOF) mass spectrometry, wherein detection of the presence or absence of the plurality of SNPs of query KIR genes is indicative of the KIR genotype of the subject.

2. The method of claim 1, wherein said method comprises determining the genotype of six or more query KIR genes.

3. The method of claim 1, wherein said at least one anchor KIR gene is 2DL4.

4. The method of claim 1, wherein the plurality of query KIR genes are selected from 2DL1, 2DL2, 2DL3, 2DL5A, 2DL5B, 2DS1, 2DS2, 2DS3, 2DS4, 2DS5, 3DL1, 3DS1, and 2DP1.

5. A method for identifying a transplant donor, comprising:

determining the killer cell immunoglobulin-like receptor (KIR) genotype of a candidate donor, comprising co-amplifying a plurality of target sequences of a plurality of query KIR genes, and a target sequence of at least one anchor KIR gene selected from the group consisting of 3DL3, 3DL2, 2DL4, and 3DP1, wherein the target sequences are suspected of comprising single nucleotide polymorphisms (SNPs) and wherein the amplification is by using a plurality of 3' primers and a plurality of 5' primers selected to amplify a sequence flanking the SNP, extending a plurality of extension primers in an extension reaction, wherein each extension primer is complementary to a nucleic acid sequence of an amplified target sequence at a 5' end of a SNP wherein the extension primer for 3DL3 is SEQ ID NO:196 or SEQ ID NO:203, the extension primer for 3DL2 is SEQ ID NO: 211 or SEQ ID NO: 197, the extension primer for 3DL3 is SEQ ID NO:194 OR SEQ ID NO:195, and the extension primer for 3DP1 is SEQ ID NO:214, and detecting in the extension reaction the presence or absence of the plurality of SNPs of the plurality of query KIR genes and the presence of a SNP of the at least one anchor KIR gene by matrix-assisted laser desorption/ionization time-of-flight (MALDI-TOF) mass spectrometry, wherein detection of the presence or absence of the plurality of SNPs of query KIR genes is indicative of the KIR genotype of the subject; and comparing the KIR genotype of the candidate donor to a transplant recipient's KIR genotype, wherein the comparison indicates whether the candidate donor is a transplant donor.

6. The method of claim 5, wherein said method comprises determining the genotype of six or more query KIR genes.

7. The method of claim 5, wherein said at least one anchor KIR gene is 2DL4.

8. The method of claim 5, wherein the plurality of query KIR genes are selected from 2DL1, 2DL2, 2DL3, 2DL5A, 2DL5B, 2DS1, 2DS2, 2DS3, 2DS4, 2DS5, 3DL1, 3DS1, and 2DP1.

9. A kit comprising;

a first addressable array comprising a solid substrate comprising a plurality of addressable features, wherein each feature comprises a 5' primer and a 3' primer for use in co-amplification of a target sequence of a killer cell immunoglobulin-like receptor (KIR) gene, wherein, for at least one of said addressable features, the target sequences is a target sequence of an anchor KIR gene selected from the group consisting of 3DL3, 3DL2, 2DL4, and 3DP1, and wherein, for a plurality of the addressable features, the target sequence is a target sequence of a query KIR gene other than the anchor KIR gene, and a second addressable array comprising a solid substrate comprising a plurality of addressable features, wherein each feature comprises an extension primer for use in detecting the presence or absence of a single nucleotide polymorphism of a KIR gene, in a target sequence amplified using the first addressable array, wherein the second addressable array comprises an extension primer for at least one anchor KIR gene selected from the group consisting of 3DL3, 3DL2, 2DL4, and 3DP1, wherein the extension primer for 3DL3 is SEQ ID NO:196 or SEQ ID NO:203, the extension primer for 3DL2 is SEQ ID NO:211 or SEQ ID NO:197, the extension primer for 3DL3 is SEQ ID NO:194 or SEQ ID NO:195, and the extension primer for 3DP1 is SEQ ID NO:214.

10. The kit of claim 9, wherein the first addressable array is a microtiter plate.

11. The kit of claim 9, wherein the second addressable array is a microtiter plate.

12. The kit of claim 9, wherein the plurality of query KIR genes are selected from 2DL1, 2DL2, 2DL3, 2DL5A, 2DL5B, 2DS1, 2DS2, 2DS3, 2DS4, 2DS5, 3DL1, 3DS1, and 2DP1.

* * * * *

SEQUENCE LISTING

<160> NUMBER OF SEQ ID NOS: 305

<210> SEQ ID NO 1
<211> LENGTH: 1368
<212> TYPE: DNA
<213> ORGANISM: Homo sapiens

<400> SEQUENCE: 1
atgtcgctca tggtcgtcag catggcgtgt gttgggttct tcttgctgca gggggcctgg 60
ccacacgagg gtggtcagga caagcccttc ctgtctgcct ggcccagcgc tgtggtgcct 120
cgaggaggac acgtgactct tcggtgtcac tatcgtcata ggtttaacaa tttcatgcta 180
tacaaagaag acagaatcca cgttcccatc ttccatggca gaatattcca ggagagcttc 240
aacatgagcc ctgtgaccac agcacatgca gggaactaca catgtcgggg ttcacaccca 300
cactccccca ctgggtggtc ggcacccagc aaccccgtgg tgatcatggt cacaggaatc 360
cacagaaaac cttccctcct ggcccaccca ggtcccctgg tgaaatcaga agagacagtc 420
atcctgcaat gttggtcaga tgtcatgttt gagcacttcc ttctgcacag agaggggatg 480
tctaaggaca ctttgcgcct cattggagag caccatgatg gggtctccaa ggccaacttc 540
tccatcggtc ccatgatgca tgaccttgca gggacctaca gatgctacgg ttctgttact 600
cactccccct atcagttgtc agctcccagt gaccctctgg acatcgtgat cacaggtcta 660

-continued

```
tatgagaaac cttctctctc agcccagccg ggccccacgg ttcaggcagg agagagcgtg    720

accttgtcct gcagctcccg gagctcctat gacatgtacc atctatccag ggagggggag    780

gcccatgaac gtaggctccc tgcagtgccc aaggtcaacg gaacattcca ggccgacttt    840

cctctgggcc ctgccaccca cggagggacc tacagatgct tcggctcttt ccgtgactct    900

ccctacgagt ggtcaaactc gagtgaccca ctgcttgttt ctgtcacagg aaacccttca    960

agtagttggc cttcacccac tgaaccaagc tccaaaactg gtaaccccag acacctgcat   1020

gttctgattg ggacctcagt ggtcatcatc ctcttcatcc tcctcctctt ctttctcctt   1080

catcgctggt gctccaacaa aaaaaatgct gctgtaatgg accaagagcc tgcagggaac   1140

agaacagtga acagcgagga ctctgatgaa caagaccctc aggaggtgac atacgcacag   1200

ttggatcact gcgttttcac acagagaaaa atcactcgcc cttctcagag gcccaagaca   1260

cccccaacag ataccagcgt gtacacggaa cttccaaatg ctgagcccag atccaaagtt   1320

gtctcctgcc catgagcacc acagtcaggc cttgagggga tcttctag                1368
```

```
<210> SEQ ID NO 2
<211> LENGTH: 1368
<212> TYPE: DNA
<213> ORGANISM: Homo sapiens

<400> SEQUENCE: 2

atgtcgctca cggtcgtcag catggcgtgc gttgggttct tcttgctgca gggggcctgg     60

ccactcatgg gtggtcagga caaacccttc ctgtctgccc ggcccagcac tgtggtgcct    120

cgaggaggac acgtggctct tcagtgtcac tatcgtcgtg ggtttaacaa tttcatgctg    180

tacaaagaag acagaagcca cgttcccatc ttccacggca gaatattcca ggagagcttc    240

atcatgggcc ctgtgacccc agcacatgca gggacctaca gatgtcgggg ttcacgccca    300

cactccctca ctgggtggtc ggcacccagc aacccccctgg tgatcatggt cacaggaaac    360

cacagaaaac cttccctcct ggcccaccca gggcccctgc tgaaatcagg agagacagtc    420

atcctgcaat gttggtcaga tgtcatgttt gagcacttct ttctgcacag agaggggatc    480

tctgaggacc cctcacgcct cgttggacag atccatgatg ggtctccaa ggccaacttc    540

tccatcggtc ccttgatgcc tgtccttgca ggaacctaca gatgttatgg ttctgttcct    600

cactccccct atcagttgtc agctcccagt gaccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgac gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                1368
```

<210> SEQ ID NO 3
<211> LENGTH: 1365
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1333)...(1365)
<223> OTHER INFORMATION: n = A,T,C or G

<400> SEQUENCE: 3
atgtcgctct tggtcgtcag catggcgtgt gttgggttct tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctcct ggcccaccca ggtcccctgg tgaaatcaga agagacagtc 420
atcctgcaat gttggtcaga tgtcatgttt gaacacttcc ttctgcacag agaggggatg 480
tttaacgaca ctttgcgcct cattggagaa caccatgatg gggtctccaa ggccaacttc 540
tccatcagtc gcatgacgca agacctggca gggacctaca gatgctacgg ttctgttact 600
cactccccct atcaggtgtc agctcccagt gaccctctgg acatcgtgat cataggtcta 660
tatgagaaac cttctctctc agcccagccg ggccccacgg ttctggcagg agagaatgtg 720
accttgtcct gcagctcccg gagctcctat gacatgtacc atctatccag ggaaggggag 780
gcccatgaac gtaggctccc tgcagggccc aaggtcaacg gaacattcca ggctgacttt 840
cctctgggcc ctgccaccca cggagggacc tacagatgct tcggctcttt ccatgactct 900
ccatacgagt ggtcaaagtc aagtgaccca ctgcttgttt ctgtcacagg aaacccttca 960
aatagttggc cttcacccac tgaaccaagc tccaaaaccg gtaacccccg acacctgcac 1020
attctgattg ggacctcagt ggtcatcatc ctcttcatcc tcctcttctt tctccttcat 1080
cgctggtgct ccaacaaaaa aaatgctgcg gtaatggacc aagagtctgc aggaaacaga 1140
acagcgaata gcgaggactc tgatgaacaa gaccctcagc aggtgacata cacacagttg 1200
aatcactgcg ttttcacaca gagaaaaatc actcgccctt ctcagaggcc caagacaccc 1260
ccaacagata tcatcgtgta cacggaactt ccaaatgctg agtccagatc caaagttgtc 1320
tcctgcccat gannnnnnnn nnnnnnnnnn nnnnnnnnnn nnnnn 1365

<210> SEQ ID NO 4
<211> LENGTH: 1365
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1333)...(1365)
<223> OTHER INFORMATION: n = A,T,C or G

<400> SEQUENCE: 4
atgtcgctct tgttcgtcag catggcgtgt gttgggttct tcttgctgca gggggcctgg 60
ccacatgagg nnnnnnnnnn nnnnnnnnnn nnnnnnnnnn nnnnnnnnnn nnnnnnnnnn 120

-continued

```
nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccctcct ggcccaccca ggtcccctgg tgaaatcaga agagacagtc    420

atcctgcaat gttggtcaga tgtcatgttt gaacacttcc ttctgcacag agaggggatg    480

tttaacgaca ctttgcgcct cattggagaa caccatgatg ggtctccaa ggccaacttc    540

tccatcagtc gcatgacgca agacctggca gggacctaca gatgctacgg ttctgttact    600

cactccccct atcaggtgtc agctcccagt gaccctctgg acatcgtgat cataggtcta    660

tatgagaaac cttctctctc agcccagccg ggccccacgg ttctggcagg agagaatgtg    720

accttgtcct gcagctcccg gagctcctat gacatgtacc atctatccag ggaaggggag    780

gcccatgaac gtaggctccc tgcagggccc aaggtcaacg gaacattcca ggctgacttt    840

cctctgggcc ctgccaccca cggagggacc tacagatgct tcggctcttt ccatgactct    900

ccatacgagt ggtcaaagtc aagtgaccca ctgcttgttt ctgtcacagg aaacccttca    960

aatagttggc cttcacccac tgaaccaagc tccaaaaccg gtaacccccg acacctgcac   1020

attctgattg ggacctcagt ggtcatcatc ctcttcatcc tcctcttctt tctccttcat   1080

cgctggtgct ccaacaaaaa aaatgctgcg gtaatggacc aagagtctgc aggaaacaga   1140

acagcgaata gcgaggactc tgatgaacaa gaccctcagc aggtgacata cacacagttg   1200

aatcactgcg ttttcacaca gagaaaaatc actcgccctt ctcagaggcc caagacaccc   1260

ccaacagata tcatcgtgta cacggaactt ccaaatgctg agtccagatc caaagttgtc   1320

tcctgcccat gannnnnnnn nnnnnnnnnn nnnnnnnnnn nnnnn                   1365
```

<210> SEQ ID NO 5
<211> LENGTH: 1365
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1333)...(1365)
<223> OTHER INFORMATION: n = A,T,C or G

<400> SEQUENCE: 5

```
atgtcgctct tggtcgtcag catggcgtgt gttgggttct tcttgctgca gggggcctgg     60

ccacatgagg nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccctcct ggcccaccca ggtcgcctgg tgaaatcaga agagacagtc    420

atcctgcagt gttggtcaga tgtcatgttt gaacacttcc ttctgcacag agaggggatg    480

tttaacgaca ctttgcgcct cattggagaa caccatgatg ggtctccaa ggccaacttc    540

tccatcagtc gcatgacgca agacctggca gggacctaca gatgctacgg ttctgttact    600

cactccccct atcaggtgtc agctcccagt gaccctctgg acatcgtgat cataggtcta    660
```

tatgagaaac cttctctctc agcccagctg ggccccacgg ttctggcagg agagaatgtg 720
accttgtcct gcagctcccg gagctcctat gacatgtacc atctatccag ggaaggggag 780
gcccatgaac gtaggctccc tgcagggccc aaggtcaacg gaacattcca ggctgacttt 840
cctctgggcc ctgccaccca cggagggacc tacagatgct tcggctcttt ccatgactct 900
ccatacgagt ggtcaaagtc aagtgaccca ctgcttgttt ctgtcacagg aaacccttca 960
aatagttggc cttcacccac tgaaccaagc tccaaaacgg gtaacccccg acacctgcac 1020
attctgattg ggacctcagt ggtcatcatc ctcttcatcc tcctcttctt tctccttcat 1080
cgctggtgct ccaacaaaaa aaatgctgcg gtaatggacc aagagtctgc aggaaacaga 1140
acagcgaata gcgaggactc tgatgaacaa gaccctcagc aggtgacata cacacagttg 1200
aatcactgcg ttttcacaca gagaaaaatc actcgccctt ctcagaggcc caagacaccc 1260
ccaacagata tcatcgtgta cacggaactt ccaaatgctg agtccagatc caaagttgtc 1320
tcctgcccat gannnnnnnn nnnnnnnnnn nnnnnnnnnn nnnnn 1365

<210> SEQ ID NO 6
<211> LENGTH: 1365
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1333)...(1365)
<223> OTHER INFORMATION: n = A,T,C or G

<400> SEQUENCE: 6
atgtcgctct tggtcgtcag catggcgtgt gttgggttct tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctcct ggcccaccca ggtcgcctgg tgaaatcaga agagacagtc 420
atcctgcagt gttggtcaga tgtcatgttt gaacacttcc ttctgcacag agaggggatg 480
tttaacgaca ctttgcgcct cattggagaa caccatgatg gggtctccaa ggccaacttc 540
tccatcagtc gcatgacgca agacctggca gggacctaca gatgctacgg ttctgttact 600
cactccccct atcaggtgtc agctcccagt gaccctctgg acatcgtgat cataggtcta 660
tatgagaaac cttctctctc agcccagctg ggccccacgg ttctggcagg agagaatgtg 720
accttgtcct gcagctcccg gagctcctat gacatgtacc atctatccag ggaaggggag 780
gcccatgaac gtaggctccc tgcagggccc aaggtcaacg gaacattcca ggctgacttt 840
cctctgggcc ctgccaccca cggagggacc tacagatgct tcggctcttt ccatgactct 900
ccatacgagt ggtcaaagtc aagtgaccca ctgcttgttt ctgtcacagg aaacccttca 960
aatagttggc cttcacccac tgaaccaagc tccaaaaccg gtaacccccg acacctgcac 1020
attctgattg ggacctcagt ggtcatcatc ctcttcatcc tcctcttctt tctccttcat 1080
cgctggtgct ccaacaaaaa aaatgctgcg gtaatggacc aagagtctgc aggaaacaga 1140
acagcgaata gcgaggactc tgatgaacaa gaccctcagc aggtgacata cacacagttg 1200

```
aatcactgcg ttttcacaca gagaaaaatc actcgccctt ctcagaggcc caagacaccc   1260

ccaacagata tcatcgtgta cacggaactt ccaaatgctg agtccagatc caaagttgtc   1320

tcctgcccat gannnnnnnn nnnnnnnnnn nnnnnnnnnn nnnnn                   1365


<210> SEQ ID NO 7
<211> LENGTH: 1362
<212> TYPE: DNA
<213> ORGANISM: Homo sapiens
<220> FEATURE:
<221> NAME/KEY: misc_feature
<222> LOCATION: (1330)...(1362)
<223> OTHER INFORMATION: n = A,T,C or G

<400> SEQUENCE: 7

atgtcgctct tggtcgtcag catggcgtgt gttgggttct tcttgctgca gggggcctgg     60

ccacatgagg gtggtcagga caagcccttg ctgtctgcct ggccaagccc tgtggtgcct    120

ccaggacatg tgattcttca gtgtcattct tatcttgggt ttaacaactt cagtctgtaa    180

aaggaagatg gggtgcctgt ccctgagctc tacaacataa tattctggaa cagccttttc    240

atgggccctg tgaccccagc acacgcaggg acctatacat gtcggggttc acaaccacac    300

taccccagtg ggtggtcggc acccagcaac cccctggaga tcacggtcac aggagtccac    360

agaaaacctt ccctcctggc ccacccaggt cgcctggtga aatcagaaga gacagtcatc    420

ctgcaatgtt ggtcagatgt catgtttgaa cacttccttc tgcacagaga ggggatgttt    480

aacgacactt tgcgcctcat tggagaacac catgatgggg tctccaaggc caacttctcc    540

atcagtcgca tgacgcaaga cctggcaggg acctacagat gctacggttc tgttactcac    600

tccccctatc aggtgtcagc tcccagtgac cctctggaca tcgtgatcat aggtctatat    660

gagaaacctt ctctctcagc ccagccgggc cccacggttc tggcaggaga gaatgtgacc    720

ttgtcctgca gctcccggag ctcctatgac atgtaccatc tatccaggga aggggaggcc    780

catgaacgta ggctccctgc agggaccaag gtcaacggaa cattccaggc caactttcct    840

ctgggccctg ccacccatgg agggacctac agatgcttcg gctctttccg tgactctcca    900

tacgagtggt caaagtcaag tgacccactg cttgtttctg tcacaggaaa cccttcaaat    960

agttggcctt cacccactga accaagctcc gaaaccggta acccccgaca cctgcacatt   1020

ctgattggga cctcagtggt catcatcctc ttcatcctcc tcttctttct ccttcattgc   1080

tggtgctcca acaaaaaaaa tgctgcggta atggaccaag agtctgcagg aaacagaaca   1140

gcgaatagcg aggactctga tgaacaagac cctcagcagg tgacatacac acagttgaat   1200

cactgcgttt tcacacagag aaaaatcact cgcccttctc agaggcccaa gacaccccca   1260

acagatatca tcgtgtacac ggaacttcca aatgctgagt ccagatccaa agttgtctcc   1320

tgcccatgan nnnnnnnnnn nnnnnnnnnn nnnnnnnnnn nn                      1362


<210> SEQ ID NO 8
<211> LENGTH: 1365
<212> TYPE: DNA
<213> ORGANISM: Homo sapiens
<220> FEATURE:
<221> NAME/KEY: misc_feature
<222> LOCATION: (1)...(40)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
```

<222> LOCATION: (1333)...(1365)
<223> OTHER INFORMATION: n = A,T,C or G

<400> SEQUENCE: 8

```
nnnnnnnnnn nnnnnnnnnn nnnnnnnnnn nnnnnnnnnn tcttgctgca gggggcctgg      60

ccacatgagg nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnngagtc     360

cacagaaaac cttccctcct ggcccaccca ggtcgcctgg tgaaatcaga agagacagtc     420

atcctgcaat gttggtcaga tgtcatgttt gaacacttcc ttctgcacag agaggggatg     480

tttaacgaca ctttgcgcct cattggagaa caccatgatg ggtctccaa ggccaacttc      540

tccatcagtc gcatgacgca agacctggca gggacctaca gatgctacgg ttctgttact     600

cactccccct atcaggtgtc agctcccagt gaccctctgg acatcgtgat cataggtcta     660

tatgagaaac cttctctctc agcccagctg ggccccacgg ttctggcagg agagaatgtg     720

accttgtcct gcagctcccg gagctcctat gacatgtacc atctatccag ggaaggggag     780

gcccatgaac gtaggctccc tgcagggccc aaggtcaacg gaacattcca ggctgacttt     840

cctctgggcc ctgccaccca cggagggacc tacagatgct tcggctcttt ccatgactct     900

ccatacgagt ggtcaaagtc aagtgaccca ctgcttgttt ctgtcacagg aaacccttca     960

aatagttggc cttcacccac tgaaccaagc tccaaaaccg gtaacccccg acacctgcac    1020

attctgattg ggacctcagt ggtcatcatc ctcttcatcc tcctcttctt tctccttcat    1080

cgctggtgct ccaacaaaaa aaatgctgcg gtaatggacc aagagtctgc agggaacaga    1140

acagcgaata gcgaggactc tgatgaacaa gaccctcagc aggtgacata cacacagttg    1200

aatcactgcg ttttcacaca gagaaaaatc actcgccctt ctcagaggcc caagacaccc    1260

ccaacagata tcatcgtgta cgcggaactt ccaaatgctg agtccagatc caaagttgtc    1320

tcctgcccat gannnnnnnn nnnnnnnnnn nnnnnnnnnn nnnnn                    1365
```

<210> SEQ ID NO 9
<211> LENGTH: 1362
<212> TYPE: DNA
<213> ORGANISM: Homo sapiens
<220> FEATURE:
<221> NAME/KEY: misc_feature
<222> LOCATION: 264
<223> OTHER INFORMATION: n = A,T,C or G
<220> FEATURE:
<221> NAME/KEY: misc_feature
<222> LOCATION: (1330)...(1362)
<223> OTHER INFORMATION: n = A,T,C or G

<400> SEQUENCE: 9

```
atgtcgctca tggtcgtcag catggcgtgt gttgggttct tcttgctgca gggggcctgg      60

ccacatgagg gtggtcagga caagcccttg ctgtctgcct ggcccagcct tgtggtgcct     120

ctaggacatg tcattcttcg gtgtcactct tatcttgggt ttaacaactt cagtctgtac     180

aaggaaggtg gggtgcctgt ccctgagctc tacaacagaa tattctggaa cagccttttc     240

atgggccctg tgacccccgc acanacaggg acatacagat gtcggggttc acacacacac     300

tcccccagtg ggtggtcagc acccagcaac cccgtggtga tcgtggtcat aggagtccac     360

agaaaacctt ccctcctggc ccacccaggt cgcctggtga aatcagaaga gacagtcatc     420
```

```
ctgcaatgtt ggtcagatgt caggtttgag cacttccttc tgcacagaga agggaagttt    480

aaggacactt tgcacctcat tggagagcac catgatgggg tctccaaagc caacttctcc    540

atcggtccca tgatgcaaga ccttgcaggg acctacagat gctacggttc tgttactcac    600

tcccccctatc agttgtcagc tcccagtgac cctctggaca tcgtcatcac aggtctatat   660

gagaaacctt ctctctcagc ccagccgggc cccacggttc tggcaggaga gagcgtgacc    720

ttgtcctgca gctcccggag ctcctatgac atgtaccatc tatccaggga gggggaggcc    780

catgaatgta ggttctctgc agggcccaag gtcaacggaa cattccaggc cgactttcct    840

ctgggccctg ccacccacgg aggaacctac agatgcttcg gctctttccg tgactctcca    900

tacgagtggt caaactcgag tgacccactg cttgtttctg tcataggaaa cccttcaaat    960

agttggcctt cacccactga accaagctct aaaaccggta acccccgaca cctgcacatt   1020

ctgattggga cctcagtggt catcatcctc ttcatcctcc tcttctttct ccttcatcgc   1080

tggtgctcca acaaaaaaaa tgctgcggta atggaccaag agtctgcagg gaacagaaca   1140

gcgaatagcg aggactctga tgaacaagac cctcaggagg tgacatacac acagttgaat   1200

cactgcgttt tcacacagag aaaaatcact cgcccttctc agaggcccaa gacaccccca   1260

acagatatca tcgtgtacgc ggaacttcca aatgctgagt ccagatccaa agttgtctcc   1320

tgcccatgan nnnnnnnnnn nnnnnnnnnn nnnnnnnnnn nn                      1362
```

<210> SEQ ID NO 10
<211> LENGTH: 1365
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1333)...(1365)
<223> OTHER INFORMATION: n = A,T,C or G

<400> SEQUENCE: 10

```
atgtcgctca tggtcgtcag catggcgtgt gttgggttct tcttgctgca gggggcctgg     60

ccacatgagg nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccctcct ggcccaccca ggtcgcctgg tgaaatcaga agagacagtc    420

atcctgcaat gttggtcaga tgtcaggttt gagcacttcc ttctgcacag agaagggaag    480

tttaaggaca ctttgcacct cattggagag caccatgatg ggtctccaa agccaacttc     540

tccatcggtc ccatgatgca agaccttgca gggacctaca gatgctacgg ttctgttact    600

cactcccccct atcagttgtc agctcccagt gaccctctgg acatcgtcat cacaggtcta   660

tatgagaaac cttctctctc agcccagccg ggccccacgg ttctggcagg agagagcgtg    720

accttgtcct gcagctcccg gagctcctat gacatgtacc atctatccag ggagggggag    780

gcccatgaat gtaggttctc tgcagggccc aaggtcaacg gaacattcca ggccgacttt    840

cctctgggcc ctgccaccca cggaggaacc tacagatgct tcggctcttt ccgtgactct    900

ccatacgagt ggtcaaactc gagtgaccca ctgcttgttt ctgtcatagg aaacccttca    960
```

aatagttggc cttcacccac tgaaccaagc tctaaaaccg gtaacccccg acacctgcac 1020
attctgattg ggacctcagt ggtcatcatc ctcttcatcc tcctcttctt tctccttcat 1080
cgctggtgct ccaacaaaaa aaatgctgcg gtaatggacc aagagtctgc agggaacaga 1140
acagcgaaca ggcaggactc tgatgaacaa gaccctcagg aggtgacata cacacagttg 1200
aatcactgcg ttttcacaca gagaaaaatc actcgccctt ctcagaggcc caagacaccc 1260
ccaacagata tcatcgtgta cgcggaactt ccaaatgctg agtccagatc caaagttgtc 1320
tcctgcccat gannnnnnnn nnnnnnnnnn nnnnnnnnnn nnnnn 1365

<210> SEQ ID NO 11
<211> LENGTH: 1365
<212> TYPE: DNA
<213> ORGANISM: Homo sapiens
<220> FEATURE:
<221> NAME/KEY: misc_feature
<222> LOCATION: (1)...(40)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1333)...(1365)
<223> OTHER INFORMATION: n = A,T,C or G

<400> SEQUENCE: 11
nnnnnnnnnn nnnnnnnnnn nnnnnnnnnn nnnnnnnnnn tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctcct ggcccaccca ggtcgcctgg tgaaatcaga agagacagtc 420
atcctgcaat gttggtcaga tgtcaggttt gagcacttcc ttctgcacag agaagggaag 480
tttaaggaca ctttgcacct cattggagag caccatgatg gggtctccaa agccaacttc 540
tccatcggtc ccatgatgca agaccttgca gggacctaca gatgctacgg ttctgttact 600
cactccccct atcagttgtc agctcccagt gaccctctgg acatcgtcat cacaggtcta 660
tatgagaaac cttctctctc agcccagccg ggccccacgg ttctggcagg agagagcgtg 720
accttgtcct gcagctcccg gagctcctat gacatgtacc atctatccag ggagggggag 780
gcccatgaat gtaggttctc tgcagggccc aaggtcaacg gaacattcca ggccgacttt 840
cctctgggcc ctgccaccca cggaggaacc tacagatgct tcggctcttt ccgtgactct 900
ccatacgagt ggtcaaactc gagtgaccca ctgcttgttt ctgtcacagg aaacccttca 960
aatagttggc cttcacccac tgaaccaagc tctaaaaccg gtaacccccg acacctgcac 1020
attctgattg ggacctcagt ggtcatcatc ctcttcatcc tcctcttctt tctccttcat 1080
cgctggtgct ccaacaaaaa aaatgctgcg gtaatggacc aagagtctgc agggaacaga 1140
acagcgaata gcgaggactc tgatgaacaa gaccctcagg aggtgacata cacacagttg 1200
aatcactgcg ttttcacaca gagaaaaatc actcgccctt ctcagaggcc caagacaccc 1260
ccaacagata tcatcgtgta cacggaactt ccaaatgctg agtccagatc caaagttgtc 1320
tcctgcccat gannnnnnnn nnnnnnnnnn nnnnnnnnnn nnnnn 1365

<210> SEQ ID NO 12
<211> LENGTH: 1365
<212> TYPE: DNA
<213> ORGANISM: Homo sapiens
<220> FEATURE:
<221> NAME/KEY: misc_feature
<222> LOCATION: (1)...(40)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1333)...(1365)
<223> OTHER INFORMATION: n = A,T,C or G

<400> SEQUENCE: 12

```
nnnnnnnnnn nnnnnnnnnn nnnnnnnnnn nnnnnnnnnn tcttgctgca gggggcctgg      60

ccacatgagg nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnngagtc     360

cacagaaaac cttccctcct ggcccaccca ggtcccctgg tgaaatcaga agagacagtc     420

atcctgcaat gttggtcaga tgtcaggttt cagcacttcc ttctgcacac agaagggaag     480

tttaaggaca ctttgcacct cattggagag caccatgatg gggtctccaa ggccaacttc     540

tccattggtc ccatgatgca agaccttgca gggacctaca gatgctacgg ttctgttact     600

cactccccct atcagttgtc agctcccagt gaccctctgg acatcgtcat cacaggtcta     660

tatgagaaac cttctctctc agcccagccg ggccccacgg ttctggcagg agagagcgtg     720

accttgtcct gcagctcccg gagctcctat gacatgtacc atctatccag ggagggggag     780

gcccatgaat gtaggttctc tgcagggccc aaggtcaacg gaacattcca ggccgacttt     840

cctctggacc ctgccaccca cggaggaacg tacagatgct tcggctcttt ccgtgactct     900

ccatacgagt ggtcaaactc gagtgaccca ctgcttgttt ctgtcacagg aaacccttca     960

aatagttggc cttcacccac tgaaccaagc tccgaaaccg gtaacccccg acacctgcac    1020

attctgattg ggacctcagt ggtcatcatc ctcttcatcc tcctcttctt tctccttcat    1080

cgctggtgct ccaacaaaaa aaatgctgct gtaatggacc aagagtctgc aggaaacaga    1140

acagcgaata tcgaggactc tgatgaacaa gaccctcagg aggtgacata cacacagttg    1200

aatcactgcg ttttcacaca gagaaaaatc actcaccctt ctcagaggcc caagacaccc    1260

ccaacagata tcatcgtgta cacggaactt ccaagtgctg agtccagatc caaagttgtc    1320

tcctgcccat gannnnnnnn nnnnnnnnnn nnnnnnnnnn nnnnn                    1365
```

<210> SEQ ID NO 13
<211> LENGTH: 1368
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 13
atgtcgctca tggtcgtcag catggtgtgt gttgggttct tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctcct ggcccaccca ggtcccctgg tgaaatcaga agagacagtc 420
atcctgcaat gttggtcaga tgtcaggttt cagcacttct ttctgcacag agaagggaag 480
tttaaggaca ctttgcacct cattggagag caccatgatg ggtctccaa ggccaacttc 540 tccatcggtc ccatgatgca agaccttgca gggacctaca gatgctacgg ttctgttact 600
cactccccct atcagttgtc agctcccagt gaccctctgg acatcgtcat cacaggtcta 660
tatgagaaac cttctctctc agcccagccg ggccccacgg ttctggcagg agagagcgtg 720
accttgtcct gcagctcccg gagctcctat gacatgtacc atctatccag ggagggggag 780
gcccatgaac gtaggttctc tgcagggccc aaggtcaacg gaacattcca ggccgacttt 840
cctctgggcc ctgccaccca cggaggaacc tacagatgct tcggctcttt ccgtgactct 900
ccatacgagt ggtcaaactc gagtgaccca ctgcttgttt ctgtcacagg aaacccttca 960
aatagttggc cttcacccac tgaaccaagc tccgaaaccg gtaaccccag acacctgcat 1020
gttctgattg ggacctcagt ggtcatcatc ctcttcatcc tcctcctctt ctttctcctt 1080
catcgctggt gctgcaacaa aaaaaatgct gttgtaatgg accaagagcc tgcagggaac 1140
agaacagtga acagggagga ctctgatgaa caagaccctc aggaggtgac atatgcacag 1200
ttgaatcact gcgttttcac acagagaaaa atcactcgcc cttctcagag gcccaagaca 1260
cccccaacag atatcatcgt gtacacggaa cttccaaatg ctgagccctg atccaaagtt 1320
gtctcctgcc catgannnnn nnnnnnnnnn nnnnnnnnnn nnnnnnnn 1368

<210> SEQ ID NO 14
<211> LENGTH: 1365
<212> TYPE: DNA
<213> ORGANISM: Homo sapiens
<220> FEATURE:
<221> NAME/KEY: misc_feature
<222> LOCATION: (1333)...(1365)
<223> OTHER INFORMATION: n = A,T,C or G

<400> SEQUENCE: 14
atgtcgctca tggtcgtcag catggtgtgt gttgggttct tcttgctgca gggggcctgg 60
ccacatgagg gtggtcagga caagcccttg ctgtctgcct ggcccagcct tgtggtgcct 120
ctaggacatg tcattcttcg gtgtcactct tatcttgggt ttaacaactt cagtctgtac 180
aaggaaggtg gggtgcctgt ccctgagctc tacaacagaa tattctggaa cagccttttc 240
atgggccctg tgacccccgc acacacaggg acatacagat gtcggggttc acacacacac 300
tcccccagtg ggtggtcagc acccagcaac cccgtggtga tcgtggtcat aggagtccac 360
agaaaacctt ccctcctggc ccacccaggt cccctggtga aatcagaaga gacagtcatc 420
ctgcaatgtt ggtcagatgt caggtttcag cacttccttc tgcacagaga agggaagttt 480
aaggacactt tgcacctcat tggagagcac catgatgggg tctccaaggc caacttctcc 540
atcggtccca tgatgcaaga ccttgcaggg acctacagat gctacggttc tgttactcac 600
tccccctatc agttgtcagc tcccagtgac cctctggaca tcgtcatcac aggtctatat 660
gagaaacctt ctctctcagc ccagccgggc cccacggttc tggcaggaga gagcgtgacc 720
ttgtcctgca gctcccggag ctcctatgac atgtaccatc tatccaggga gggggaggcc 780
catgaacgta ggttctctgc agggcccaag gtcaacggaa cattccaggc cgactttcct 840
ctgggccctg ccacccacgg aggaacctac agatgcttcg gctctttccg tgactctcca 900
tacgagtggt caaactcgag tgacccactg cttgtttctg tcacaggaaa cccttcaaat 960
agttggcttt cacccactga accaagctcc gaaaccggta accccagaca cctgcatgtt 1020
ctgattggga cctcagtggt catcatcctc ttcatcctcc tcctcttctt tctccttcat 1080
cgctggtgct gcaacaaaaa aaatgctgtg gtaatggacc aagagcctgc agggaacaga 1140
acagtgaaca gggaggactc tgatgaacaa gaccctcagg aggtgacata tgcacagttg 1200
aatcactgcg ttttcacaca gagaaaaatc actcaccctt ctcagaggcc caagacaccc 1260
ccaacagata tcatcgtgta cacggaactt ccaaatgctg agccctgatc caaagttgtc 1320
tcctgcccat gannnnnnnn nnnnnnnnnn nnnnnnnnnn nnnnn 1365

<210> SEQ ID NO 15
<211> LENGTH: 1368
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 15
atgtcgctca tggtcgtcag catggtgtgt gttgggttct tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctcct ggcccaccca ggtcccctgg tgaaatcaga agagacagtc 420
atcctgcaat gttggtcaga tgtcaggttt cagcacttcc ttctgcacag agaagggaag 480
tttaaggaca ctttgcacct cattggagag caccatgatg ggtctccaa ggccaacttc 540 tccatcggtc ccatgatgca agaccttgca gggacctaca gatgctacgg ttctgttact 600
cactccccct atcagttgtc agctcccagt gaccctctgg acatcgtcat cacaggtcta 660
tatgagaaac cttctctctc agcccagccg ggccccacgg ttctggcagg agagagcgtg 720
accttgtcct gcagctcccg gagctcctat gacatgtacc atctatccag ggagggggag 780
gcccatgaac gtaggttctc tgcagggccc aaggtcaacg gaacattcca ggccgacttt 840
cctctgggcc ctgccaccca cggaggaacc tacagatgct tcggctcttt ccgtgactct 900
ccatacgagt ggtcaaactc gagtgaccca ctgcttgttt ctgtcacagg aaacccttca 960
aatagttggc cttcacccac tgaaccaagc tccgaaaccg gtaaccccag acacctgcat 1020
gttctgattg ggacctcagt ggtcatcatc ctcttcatcc tcctcctctt ctttctcctt 1080
catcgctggt gctgcaacaa aaaaaatgct gtggtaatgg accaagagcc tgcagggaac 1140
agaacagtga acagggagga ctctgatgaa caagaccctc aggaggtgac atacacacag 1200
ttgaatcact gcgttttcac acagagaaaa atcactcgcc cttctcagag gcccaagaca 1260
cccccaacag atatcatcgt gtacacggaa cttccaaatg ctgagccctg atccaaagtt 1320
gtctcctgcc catgannnnn nnnnnnnnnn nnnnnnnnnn nnnnnnnn 1368

<210> SEQ ID NO 16
<211> LENGTH: 1368
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 16
atgtcgctca tggtcgtcag catggcgtgt gttgggttct tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctccg ggcccaccca ggtcccctgg tgaaatcaga agagacagtc 420
atcctgcaat gttggtcaga tgtcaggttt gagcacttcc ttctgcacag agaagggaag 480
tttaaggaca ctttgcgcct cattggagag caccatgatg ggggtctccaa ggccaacttc 540 tccatcggtc ccatgatgca agaccttgca gggacctaca gatgctacgg ttctgttact 600
cactccccct atcagttgtc agctcccagt gaccctctgg acatcgtcat cacaggtcta 660
tatgagaaac cttctctctc agcccagccg ggccccacgg ttctggcagg agagagcgtg 720
accttgtcct gcagctcccg gagctcctat gacatgtacc atctatccag ggagggggag 780
gcccatgaac gtaggttctc tgcagggccc aaggtcaacg gaacattcca ggccgacttt 840
cctctgggcc ctgccaccca cggaggaacc tacagatgct tcggctcttt ccgtgactct 900
ccatacgagt ggtcaaactc gagtgaccca ctgcttgttt ctgtcacagg aaacccttca 960
aatagttggc cttcacccac tgaaccaagc tccgaaaccg gtaaccccat acacctgcat 1020
gttctgattg ggacctcagt ggtcatcatc ctcttcatcc tcctcctctt ctttctcctt 1080
catcgctggt gctgcaacaa aaaaaatgct gtggtaatgg accaagagcc tgcagggaac 1140
agaacagtga acagggagga ctctgatgaa caagaccctc aggaggtgac atatgcacag 1200
ttgaatcact gcgttttcac acagagaaaa atcactcacc cttctcagag gcccaagaca 1260
cccccaacag atatcatcgt gtacacggaa cttccaaatg ctgagccctg atccaaagtt 1320
gtctcctgcc catgannnnn nnnnnnnnnn nnnnnnnnnn nnnnnnnn 1368

<210> SEQ ID NO 17
<211> LENGTH: 1365
<212> TYPE: DNA
<213> ORGANISM: Homo sapiens
<220> FEATURE:
<221> NAME/KEY: misc_feature
<222> LOCATION: (1333)...(1365)
<223> OTHER INFORMATION: n = A,T,C or G

<400> SEQUENCE: 17
atgtcgctca tggtcgtcag catggcgtgt gttgggttct tcttgctgca gggggcctgg 60
ccacatgagg gtggtcagga caagcccttg ctgtctgcct ggcccagcct tgtggtgcct 120
ctaggacatg tcattcttcg gtgtcactct tatcttgggt ttaacaactt cagtctgtac 180
aaggaaggtg gggtgcctgt ccctgagctc tacaacagaa tattctggaa cagccttttc 240
atgggccctg tgacccccgc acacacaggg acatacagat gtcggggttc acacacacac 300
tcccccagtg ggtggtcagc acccagcaac cccgtggtga tcgtggtcat aggagtccac 360
agaaaacctt ccctccgggc ccacccaggt cccctggtga aatcagaaga gacagtcatc 420
ctgcaatgtt ggtcagatgt caggtttgag cacttccttc tgcacagaga agggaagttt 480
aaggacactt tgcgcctcat tggagagcac catgatgggg tctccaaggc caacttctcc 540
atcggtccca tgatgcaaga ccttgcaggg acctacagat gctacggttc tgttactcac 600 tcccccctatc agttgtcagc tcccagtgac cctctggaca tcgtcatcac aggtctatat 660
gagaaacctt ctctctcagc ccagccgggc cccacggttc tggcaggaga gagcgtgacc 720
ttgtcctgca gctcccggag ctcctatgac atgtaccatc tatccaggga gggggaggcc 780
catgaacgta ggttctctgc agggcccaag gtcaacggaa cattccaggc cgactttcct 840
ctgggccctg ccacccacgg agggacctac agatgcttcg gctctttccg tgactctcca 900
tacgagtggt caaactcgag tgacccactg cttgtttctg tcacaggaaa cccttcaaat 960
agttggcttt cacccactga accaagctcc gaaaccggta accccagaca cctgcatgtt 1020
ctgattggga cctcagtggt catcatcctc ttcatcctcc tcctcttctt tctccttcat 1080
cgctggtgct gcaacaaaaa aaatgctgtg gtaatggacc aagagcctgc agggaacaga 1140
acagtgaaca gggaggactc tgatgaacaa gaccctcagg aggtgacata tgcacagttg 1200
aatcactgcg ttttcacaca gagaaaaatc actcaccctt ctcagaggcc caagacaccc 1260
ccaacagata tcatcgtgta cacggaactt ccaaatgctg agccctgatc caaagttgtc 1320
tcctgcccat gannnnnnnn nnnnnnnnnn nnnnnnnnnn nnnnn 1365

<210> SEQ ID NO 18
<211> LENGTH: 1368
<212> TYPE: DNA
<213> ORGANISM: Homo sapiens
<220> FEATURE:
<221> NAME/KEY: misc_feature
<222> LOCATION: (1)...(40)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 18
nnnnnnnnnn nnnnnnnnnn nnnnnnnnnn nnnnnnnnnn tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360

```
cacagaaaac cttccctcct ggcccaccca ggtcccctgg tgaaatcaga agagacagtc    420
atcctgcaat gttggtcaga tgtcaggttt cagcacttcc ttctgcacag agaagggaag    480
tttaaggaca ctttgcacct cattggagag caccatgatg gggtttccaa ggccaacttc    540
tccatcggtc ccatgatgca agaccttgca gggacctaca gatgctacgg ttctgttact    600
cactccccct atcagttgtc agctcccagt gaccctctgg acatcgtcat cacaggtcta    660
tatgagaaac cttctctctc agcccagccg ggccccacgg ttctggcagg agagagcgtg    720
accttgtcct gcagctcccg gagctcctat gacatgtacc atctatccag ggagggggag    780
gcccatgaac gtaggttctc tgcagggccc aaggtcaacg gaacattcca ggccgacttt    840
cctctgggcc ctgccaccca cggaggaacc tacagatgct tcggctcttt ccgtgactct    900
ccatacgagt ggtcaaactc gagtgaccca ctgcttgttt ctgtcacagg aaacccttca    960
aatagttggc tttcacccac tgaaccaagc tccgaaaccg gtaaccccag acacctgcat   1020
gttctgattg ggacctcagt ggtcatcatc ctcttcatcc tcctcctctt ctttctcctt   1080
catcgctggt gctgcaacaa aaaaaatgct gtggtaatgg accaagagcc tgcagggaac   1140
agaacagtga acagggagga ctctgatgaa caagaccctc aggaggtgac atatgcacag   1200
ttgaatcact gcgttttcac acagagaaaa atcactcacc cttctcagag gcccaagaca   1260
cccccaacag atatcatcgt gtacacggaa cttccaaatg ctgagccctg atccaaagtt   1320
gtctcctgcc catganannnn nnnnnnnnnn nnnnnnnnnn nnnnnnnn              1368
```

<210> SEQ ID NO 19
<211> LENGTH: 1368
<212> TYPE: DNA
<213> ORGANISM: Homo sapiens

<400> SEQUENCE: 19

```
atgtcgctca cggtcgtcag catggcgtgc gttgggttct tcttgctgca gggggcctgg     60
ccactcatgg gtggtcagga caaacccttc ctgtctgccc ggcccagcac tgtggtgcct    120
cgaggaggac acgtggctct tcagtgtcac tatcgtcgtg ggtttaacaa tttcatgctg    180
tacaaagaag acagaagcca cgttcccatc ttccacggca gaatattcca ggagagcttc    240
atcatgggcc ctgtgacccc agcacatgca gggacctaca gatgtcgggg ttcacgccca    300
cactccctca ctgggtggtc ggcacccagc aaccccctgg tgatcatggt cacaggaaac    360
cacagaaaac cttccctcct ggcccaccca gggcccctgc tgaaatcagg agagacagtc    420
atcctgcaat gttggtcaga tgtcatgttt gagcacttct ttctgcacag agaggggatc    480
tctgaggacc cctcacgcct cgttggacag atccatgatg ggtctccaa ggccaacttc    540
tccatcggtc ccttgatgcc tgtccttgca ggaacctaca gatgttatgg ttctgttcct    600
cactccccct atcagttgtc agctcccagt gacccctgg acatcgtgat cacaggtcta    660
tatgagaaac cttctctctc agcccagccg ggccccacgg ttcaggcagg agagaacgtg    720
accttgtcct gtagctcctg gagctcctat gacatctacc atctgtccag ggaaggggag    780
gcccatgaac gtaggctccg tgcagtgccc aaggtcaaca gaacattcca ggcagacttt    840
cctctgggcc ctgccaccca cggagggacc tacagatgct tcggctcttt ccgtgccctg    900
ccctgcgtgt ggtcaaactc aagtgaccca ctgcttgttt ctgtcacagg aaacccttca    960
agtagttggc cttcacccac agaaccaagc tccaaatctg gtatctgcag acacctgcat   1020
gttctgattg ggacctcagt ggtcatcttc ctcttcatcc tcctcctctt ctttctcctt   1080
tatcgctggt gctccaacaa aaagaatgct gctgtaatgg accaagagcc tgcgggggac   1140
```

agaacagtga ataggcagga ctctgatgaa caagaccctc aggaggtgac gtacgcacag 1200
ttggatcact gcgttttcat acagagaaaa atcagtcgcc cttctcagag gcccaagaca 1260
cccctaacag ataccagcgt gtacacggaa cttccaaatg ctgagcccag atccaaagtt 1320
gtctcctgcc cacgagcacc acagtcaggt cttgaggggg ttttctag 1368

<210> SEQ ID NO 20
<211> LENGTH: 1134
<212> TYPE: DNA
<213> ORGANISM: Homo sapiens

<400> SEQUENCE: 20
atgtccatgt cacccacggt catcatcctg gcatgtcttg ggttcttctt ggaccagagt 60
gtgtgggcac acgtgggtgg tcaggacaag cccttctgct ctgcctggcc cagcgctgtg 120
gtgcctcaag gaggacacgt gactcttcgg tgtcactatc gtcgtgggtt taacatcttc 180
acgctgtaca agaaagatgg ggtccctgtc cctgagctct acaacagaat attctggaac 240
agtttcctca ttagccctgt gaccccagca cacgcaggga cctacagatg tcgaggtttt 300
cacccgcact cccccactga gtggtcggca cccagcaacc ccctggtgat catggtcaca 360
ggtctatatg agaaaccttc gcttacagcc cggccgggcc ccacggttcg cacaggagag 420
aacgtgacct tgtcctgcag ctcccagagc tcctttgaca tctaccatct atccagggaa 480
ggggaagccc atgaacttag gctccctgca gtgcccagca tcaatggaac attccaggcc 540
gacttccctc tgggtcctgc cacccacgga gagacctaca gatgcttcgg ctctttccat 600
ggatctccct acgaatggtc agacgcgagt gacccactgc ctgtttctgt cacaggaaac 660
ccttctagta gttggccttc acccactgaa ccaagcttca aaactggtat cgccagacac 720
ctgcatgctg tgattaggta ctcagtggcc atcatcctct ttaccatcct tcccttcttt 780
ctccttcatc gctggtgctc caaaaaaaaa aatgctgctg taatgaacca agagcctgcg 840
ggacacagaa cagtgaacag ggaggactct gatgaacaag accctcagga ggtgacatac 900
gcacagttgg atcactgcat tttcacacag agaaaaatca ctggcccttc tcagaggagc 960
aagagaccct caacagatac cagcgtgtgt atagaacttc caaatgctga gcccagagcg 1020
ttgtctcctg cccatgagca ccacagtcag gccttgatgg gatcttctag ggagacaaca 1080
gccctgtctc aaacccagct tgccagctct aatgtaccag cagctggaat ctga 1134

<210> SEQ ID NO 21
<211> LENGTH: 1134
<212> TYPE: DNA
<213> ORGANISM: Homo sapiens

<400> SEQUENCE: 21
atgtccatgt cacccacggt catcatcctg gcatgtcttg ggttcttctt ggaccagagt 60
gtgtgggcac acgtgggtgg tcaggacaag cccttctgct ctgcctggcc cagcgctgtg 120
gtgcctcaag gaggacacgt gactcttcgg tgtcactatc gtcgtgggtt taacatcttc 180
acgctgtaca agaaagatgg ggtccctgtc cctgagctct acaacagaat attctggaac 240
agtttcctca ttagccctgt gaccccagca cacgcaggga cctacagatg tcgaggtttt 300
cacccgcact cccccactga gtggtcggca cccagcaacc ccctggtgat catggtcaca 360
ggtctatatg agaaaccttc gcttacagcc cggccgggcc ccacggttcg cacaggagag 420
aacgtgacct tgtcctgcag ctcccagagc tcctttgaca tctaccatct atccagggag 480
ggggaagccc atgaacttag gctccctgca gtgcccagca tcaatggaac attccaggcc 540

```
gacttccctc tgggtcctgc cacccacgga gagacctaca gatgcttcgg ctctttccat    600

ggatctccct acgagtggtc agacgcgagt gacccactgc ctgtttctgt cacaggaaac    660

ccttctagta gttggccttc acccactgaa ccaagcttca aaactggtat cgccagacac    720

ctgcatgctg tgattaggta ctcagtggcc atcatcctct tcaccatcct tcccttcttt    780

ctccttcatc gctggtgctc caaaaaaaaa aatgctgctg taatgaacca agagcctgcg    840

ggacacagaa cagtgaacag ggaggactct gatgaacaag accctcagga ggtgacatac    900

gcacagttgg atcactgcat tttcacacag agaaaaatca ctggcccttc tcagaggagc    960

aagagaccct caacagatac cagcgtgtgt atagaacttc caaatgctga gcccagagcg   1020

ttatctcctg cccatgagca ccacagtcag gccttgatgg gatcttctag ggagacaaca   1080

gccctgtctc aaacccagct tgccagctct aatgtaccag cagctggaat ctga         1134
```

```
<210> SEQ ID NO 22
<211> LENGTH: 1134
<212> TYPE: DNA
<213> ORGANISM: Homo sapiens

<400> SEQUENCE: 22

atgtccatgt cacccacggt catcatcctg gcatgtcttg ggttcttctt ggaccagagt     60

gtgtgggcac acgtgggtgg tcaggacaag cccttctgct ctgcctggcc cagcgctgtg    120

gtgcctcaag gaggacacgt gactcttcgg tgtcactatc gtcgtgggtt taacatcttc    180

acgctgtaca agaaagatgg ggtccctgtc cctgagctct acaacagaat attctggaac    240

agtttcctca ttagccctgt gaccccagca cacgcaggga cctacagatg tcgaggtttt    300

cacccgcact cccccactga gtggtcggca cccagcaacc ccctggtgat catggtcaca    360

ggtctatatg agaaaccttc gcttacagcc cggccgggcc ccacggttcg cgcaggagag    420

aacgtgacct tgtcctgcag ctcccagagc tcctttgaca tctaccatct atccagggaa    480

ggggaagccc atgaacttag gctccctgca gtgcccagca tcaatggaac attccaggcc    540

gacttccctc tgggtcctgc cacccacgga gagacctaca gatgcttcgg ctctttccat    600

ggatctccct acgagtggtc agacccgagt gacccactgc ctgtttctgt cacaggaaac    660

ccttctagta gttggccttc acccactgaa ccaagcttca aaactggtat cgccagacac    720

ctgcatgctg tgattaggta ctcagtggcc atcatcctct ttaccatcct tcccttcttt    780

ctccttcatc gctggtgctc caaaaaaaaa aatgctgctg taatgaacca agagcctgcg    840

ggacacagaa cagtgaacag ggaggactct gatgaacaag accctcagga ggtgacatac    900

gcacagttgg atcactgcat tttcacacag agaaaaatca ctggcccttc tcagaggagc    960

aagagaccct caacagatac cagcgtgtgt atagaacttc caaatgctga gcccagagcg   1020

ttgtctcctg cccatgagca ccacagtcag gccttgatgg gatcttctag ggagacaaca   1080

gccctgtctc aaacccagct tgccagctct aatgtaccag cagctggaat ctga         1134
```

```
<210> SEQ ID NO 23
<211> LENGTH: 1134
<212> TYPE: DNA
<213> ORGANISM: Homo sapiens

<400> SEQUENCE: 23

atgtccatgt cacccacggt catcatcctg gcatgtcttg ggttcttctt ggaccagagt     60

gtgtgggcac acgtgggtgg tcaggacaag cccttctgct ctgcctggcc cagcgctgtg    120

gtgcctcaag gaggacacgt gactcttcgg tgtcactatc gtcgtgggtt taacatcttc    180
```

acgctgtaca agaaagatgg ggtccctgtc cctgagctct acaacagaat attctggaac 240
agtttcctca ttagccctgt gaccccagca cacgcaggga cctacagatg tcgaggtttt 300
cacccgcact cccccactga gtggtcggca cccagcaacc ccctggtgat catggtcaca 360
ggtctatatg agaaaccttc gcttacagcc cggccgggcc ccacggttcg cgcaggagag 420
aacgtgacct tgtcctgcag ctcccagagc tcctttgaca tctaccatct atccagggag 480
ggggaagccc atgaacttag gctccctgca gtgcccagca tcaatggaac attccaggcc 540
gacttccctc tgggtcctgc cacccacgga gagacctaca gatgcttcgg ctctttccat 600
ggatctccct acgagtggtc agacccgagt gacccactgc ctgtttctgt cacaggaaac 660
ccttctagta gttggccttc acccactgaa ccaagcttca aaactggtat cgccagacac 720
ctgcatgctg tgattaggta ctcagtggcc atcatcctct ttaccatcct tcccttcttt 780
ctccttcatc gctggtgctc caaaaaaaaa aatgctgctg taatgaacca agagcctgcg 840
ggacacagaa cagtgaacag ggaggactct gatgaacaag accctcagga ggtgacatac 900
gcacagttgg atcactgcat tttcacacag agaaaaatca ctggcccttc tcagaggagc 960
aagagaccct caacagatac cagcgtgtgt atagaacttc caaatgctga gcccagagcg 1020
ttgtctcctg cccatgagca ccacagtcag gccttgatgg gatcttctag ggagacaaca 1080
gccctgtctc aaacccagct tgccagctct aatgtaccag cagctggaat ctga 1134

<210> SEQ ID NO 24
<211> LENGTH: 1134
<212> TYPE: DNA
<213> ORGANISM: Homo sapiens

<400> SEQUENCE: 24
atgtccatgt cacccacggt catcatcctg gcatgtcttg ggttcttctt ggaccagagt 60
gtgtgggcac acgtgggtgg tcaggacaag cccttctgct ctgcctggcc cagcgctgtg 120
gtgcctcaag gaggacacgt gactcttcgg tgtcactatc gtcgtgggtt taacatcttc 180
acgctgtaca agaaagatgg ggtccctgtc cctgagctct acaacagaat attctggaac 240
agtttcctca ttagccctct gacccctgca cacgcaggga cctacagatg tcgaggtttt 300
cacccgcact cccccactga gtggtcggca cccagcaacc ccctggtgat catggtcaca 360
ggtctatatg agaaaccttc gcttacagcc cggccgggcc ccacggttcg cacaggagag 420
aacgtgacct tgtcctgcag ctcccagagc tcctttgaca tctaccatct atccagggag 480
ggggaagccc atgaacttag gctccctgca gtgcccagca tcaatggaac attccaggcc 540
gacttccctc tgggtcctgc cacccacgga gagacctaca gatgcttcgg ctctttccat 600
ggatctccct acgagtggtc agacgcgagt gacccactgc ctgtttctgt cacaggaaac 660
ccttctagta gttggccttc acccacagaa ccaagcttca aaactggtat cgccagacac 720
ctgcatgctg tgattaggta ctcagtggcc atcatcctct tcaccatcct ccccttcttt 780
ctccttcatc gctggtgctc caaaaaaaaa gatgctgctg taatgaacca agagcctgcg 840
ggacacagaa cagtgaacag ggaggactct gatgaacaag accctcagga ggtgacatac 900
gcacagttgg atcactgcat tttcacacag agaaaaatca ctggcccttc tcagaggagc 960
aagagaccct caacagatac cagcgtgtgt atagaacttc caaatgctga gcccagagcg 1020
ttatctcctg cgcatgagca ccacagtcag gccttgatgg gatcttctag ggagacaaca 1080
gccctgtctc aaacccagct tgccagctcc catgtaccag cagctggaat ctga 1134

<210> SEQ ID NO 25
<211> LENGTH: 1134
<212> TYPE: DNA
<213> ORGANISM: Homo sapiens

<400> SEQUENCE: 25
atgtccatgt cacccacggt catcatcctg gcatgtcttg ggttcttctt ggaccagagt 60
gtgtgggcac acgtgggtgg tcaggacaag cccttctgct ctgcctggcc cagcgctgtg 120
gtgcctcaag gaggacacgt gactcttcgg tgtcactatc gtcgtgggtt taacatcttc 180
acgctgtaca agaaagatgg ggtccctgtc cctgagctct acaacagaat attctggaac 240
agtttcctca ttagccctct gaccccagca cacgcaggga cctacagatg tcgaggtttt 300
cacccgcact cccccactga gtggtcggca cccagcaacc ccctggtgat catggtcaca 360
ggtctatatg agaaaccttc gcttacagcc cggccgggcc ccacggttcg cgcaggagag 420
aacgtgacct tgtcctgcag ctcccagagc tcctttgaca tctaccatct atccagggag 480
ggggaagccc atgaacttag gctccctgca gtgcccagca tcaatggaac attccaggcc 540
gacttccctc tgggtcctgc cacccacgga gagacctaca gatgcttcgg ctctttccat 600
ggatctccct acgagtggtc agacccgagt gacccactgc ctgtttctgt cacaggaaac 660
ccttctagta gttggccttc acccacagaa ccaagcttca aaactggtat cgccagacac 720
ctgcatgctg tgattaggta ctcagtggcc atcatcctct tcaccatcct tcccttcttt 780
ctccttcatc gctggtgctc caaaaaaaaa aatgctgctg taatgaacca agagcctgcg 840
ggacacagaa cagtgaacag ggaggactct gatgaacaag accctcagga ggtgacatac 900
gcacagttgg atcactgcat tttcacacag agaaaaatca ctggcccttc tcagaggagc 960
aagagaccct caacagatac cagcgtgtgt atagaacttc caaatgctga gcccagagcg 1020
ttgtctcctg cgcatgagca ccacagtcag gccttgatgg gatcttctag ggagacaaca 1080
gccctgtctc aaacccagct tgccagctcc catgtaccag cagctggaat ctga 1134

<210> SEQ ID NO 26
<211> LENGTH: 1134
<212> TYPE: DNA
<213> ORGANISM: Homo sapiens

<400> SEQUENCE: 26
atgtccatgt cacccacggt catcatcctg gcatgtcttg ggttcttctt ggaccagagt 60
gtgtgggcac acgtgggtgg tcaggacaag cccttctgct ctgcctggcc cagcgctgtg 120
gtgcctcaag gaggacacgt gactcttcgg tgtcactgtc gtcgtgggtt taacatcttc 180
acgctgtaca agaaagatgg ggtccctgtc cctgagctct acaacagaat attctggaac 240
agtttcctca ttagccctct gaccccagca cacgcaggga cctacagatg tcgaggtttt 300
cacccgcact cccccactga gtggtcggca cccagcaacc ccctggtgat catggtcaca 360
ggtctatatg agaaaccttc gcttacagcc cggccgggcc ccacggttcg cgcaggagag 420
aacgtgacct tgtcctgcag ctcccagagc tcctttgaca tctaccatct atccagggag 480
ggggaagccc atgaacttag gctccctgca gtgcccagca tcaatggaac attccaggcc 540
gacttccctc tgggtcctgc cacccacgga gagacctaca gatgcttcgg ctctttccat 600
ggatctccct acgagtggtc agacccgagt gacccactgc ctgtttctgt cacaggaaac 660
ccttctagta gttggccttc acccactgaa ccaagcttca aaactggtat cgccagacac 720
ctgcatgctg tgattaggta ctcagtggcc atcatcctct tcaccatcct tcccttcttt 780
ctccttcatc gctggtgctc caaaaaaaaa aatgctgctg taatgaacca agagcctgcg 840

-continued

```
ggacacagaa cagtgaacag ggaggactct gatgaacaag accctcagga ggtgacatac    900

gcacagttgg atcactgcat tttcacacag agaaaaatca ctggcccttc tcagaggagc    960

aagagaccct caacagatac cagcgtgtgt atagaacttc caaatgctga gcccagagcg   1020

ttgtctcctg cccatgagca ccacagtcag gccttgatgg gatcttctag ggagacaaca   1080

gccctgtctc aaacccagct tgccagctct aatgtaccag cagctggaat ctga         1134
```

<210> SEQ ID NO 27
<211> LENGTH: 1134
<212> TYPE: DNA
<213> ORGANISM: Homo sapiens

<400> SEQUENCE: 27

```
atgtccatgt cacccacggt catcatcctg gcatgtcttg ggttcttctt ggaccagagt     60

gtgtgggcac acgtgggtgg tcaggacaag cccttctgct ctgcctggcc cagcgctgtg    120

gtgcctcaag gaggacacgt gactcttcgg tgtcactatc gtcgtgggtt taacatcttc    180

acgctgtaca agaaagatgg ggtccctgtc cctgagctct acaacagaat attctggaac    240

agtttcctca ttagccctct gaccccagca cacgcaggga cctacagatg tcgaggtttt    300

cacccgcact cccccactga gtggtcggca cccagcaacc ccctggtgat catggtcaca    360

ggtctatatg agaaaccttc gcttacagcc cggctgggcc ccacggttcg cgcaggagag    420

aacgtgacct tgtcctgcag ctcccagagc tcctttgaca tctaccatct atccagggag    480

ggggaagccc atgaacttag gctccctgca gtgcccagca tcaatggaac attccaggcc    540

gacttccctc tgggtcctgc cacccacgga gagacctaca gatgcttcgg ctctttccat    600

ggatctccct acgagtggtc agacccgagt gacccactgc ctgtttctgt cacaggaaac    660

ccttctagta gttggccttc acccacagaa ccaagcttca aaactggtat cgccagacac    720

ctgcatgctg tgattaggta ctcagtggcc atcatcctct tcaccatcct tcccttcttt    780

ctccttcatc gctggtgctc caaaaaaaaa aatgctgctg taatgaacca agagcctgcg    840

ggacacagaa cagtgaacag ggaggactct gatgaacaag accctcagga ggtgacatac    900

gcacagttgg atcactgcat tttcacacag agaaaaatca ctggcccttc tcagaggagc    960

aagagaccct caacagatac cagcgtgtgt atagaacttc caaatgctga gcccagagcg   1020

ttgtctcctg cccatgagca ccacagtcag gccttgatgg gatcttctag ggagacaaca   1080

gccctgtctc aaacccagct tgccagctct aatgtaccag cagctggaat ctga         1134
```

<210> SEQ ID NO 28
<211> LENGTH: 1133
<212> TYPE: DNA
<213> ORGANISM: Homo sapiens
<220> FEATURE:
<221> NAME/KEY: misc_feature
<222> LOCATION: (1107)...(1133)
<223> OTHER INFORMATION: n = A,T,C or G

<400> SEQUENCE: 28

```
atgtccatgt cacccacggt catcatcctg gcatgtcttg ggttcttctt ggaccagagt     60

gtgtgggcac acgtgggtgg tcaggacaag cccttctgct ctgcctggcc cagcgctgtg    120

gtgcctcaag gaggacacgt gactcttcgg tgtcactatc gtcgtgggtt taacatcttc    180

acgctgtaca agaaagatgg ggtccctgtc cctgagctct acaacagaat attctggaac    240

agtttcctca ttagccctct gaccccagca cacgcaggga ccaacagatg tcgaggtttt    300

cacccgcact cccccactga gtggtcggca cccagcaacc ccctggtgat catggtcaca    360
```

ggtctatatg agaaaccttc gcttacagcc cggccgggcc ccacggttcg cgcaggagag 420
aacgtgacct tgtcctgcag ctcccagagc tcctttgaca tctaccatct atccagggag 480
ggggaagccc atgaacttag gctccctgca gtgcccagca tcaatggaac attccaggcc 540
gacttccctc tgggtcctgc cacccacgga gagacctaca gatgcttcgg ctctttccat 600
ggatctccct acgagtggtc agacccgagt gacccactgc ctgtttctgt cacaggaaac 660
ccttctagta gttggccttc acccactgaa ccaagcttca aaactggtat cgccagacac 720
ctgcatgctg tgattaggta ctcagtggcc atcatcctct ttaccatcct tcccttcttt 780
ctccttcatc gctggtgctc caaaaaaaaa atgctgctgt aatgaaccaa gagcctgcgg 840
gacacagaac agtgaacagg gaggactctg atgaacaaga ccctcaggag gtgacatacg 900
cacagttgga tcactgcatt ttcacacaga gaaaaatcac tggcccttct cagaggagca 960
agagaccctc aacagatacc agcgtgtgta tagaacttcc aaatgctgag cccagtgcgt 1020
tgtctcctgc ccatgagcac cacagtcagg ccttgatggg atcttctagg gagacaacag 1080
ccctgtctca aacccagctt gccagcnnnn nnnnnnnnnn nnnnnnnnnn nnn 1133

<210> SEQ ID NO 29
<211> LENGTH: 1368
<212> TYPE: DNA
<213> ORGANISM: Homo sapiens

<400> SEQUENCE: 29
atgtcgctca cggtcgtcag catggcgtgc gttgggttct tcttgctgca gggggcctgg 60
ccactcatgg gtggtcagga caaacccttc ctgtctgccc ggcccagcac tgtggtgcct 120
cgaggaggac acgtggctct tcagtgtcac tatcgtcgtg ggtttaacaa tttcatgctg 180
tacaaagaag acagaagcca cgttcccatc ttccacggca gaatattcca ggagagcttc 240
atcatgggcc ctgtgacccc agcacatgca gggacctaca gatgtcgggg ttcacgccca 300
cactccctca ctgggtggtc ggcacccagc aaccccctgg tgatcatggt cacaggaaac 360
cacagaaaac cttccctcct ggcccaccca gggcccctgc tgaaatcagg agagacagtc 420
atcctgcaat gttggtcaga tgtcatgttt gagcacttct ttctgcacag agaggggatc 480
tctgaggacc cctcacgcct cgttggacag atccatgatg ggtctccaa ggccaacttc 540 tccatcggtc ccttgatgcc tgtccttgca ggaacctaca gatgttatgg ttctgttcct 600
cactccccct atcagttgtc agctcccagt gaccccctgg acatcgtgat cacaggtcta 660
tatgagaaac cttctctctc agcccagccg ggccccacgg ttcaggcagg agagaacgtg 720
accttgtcct gtagctcctg gagctcctat gacatctacc atctgtccag ggaaggggag 780
gcccatgaac gtaggctccg tgcagtgccc aaggtcaaca gaacattcca ggcagacttt 840
cctctgggcc ctgccaccca cggagggacc tacagatgct tcggctcttt ccgtgccctg 900
ccctgcgtgt ggtcaaactc aagtgaccca ctgcttgttt ctgtcacagg aaacccttca 960
agtagttggc cttcacccac agaaccaagc tccaaatctg gtatctgcag acacctgcat 1020
gttctgattg ggacctcagt ggtcatcttc ctcttcatcc tcctcctctt ctttctcctt 1080
tatcgctggt gctccaacaa aaagaatgct gctgtaatgg accaagagcc tgcgggggac 1140
agaacagtga ataggcagga ctctgatgaa caagaccctc aggaggtgac gtacgcacag 1200
ttggatcact gcgttttcat acagagaaaa atcagtcgcc cttctcagag gcccaagaca 1260
cccctaacag ataccagcgt gtacacggaa cttccaaatg ctgagcccag atccaaagtt 1320
gtctcctgcc cacgagcacc acagtcaggt cttgaggggg ttttctag 1368

<210> SEQ ID NO 30
<211> LENGTH: 1128
<212> TYPE: DNA
<213> ORGANISM: Homo sapiens

<400> SEQUENCE: 30
atgtcgctca tggtcatcag catggcgtgt gttgggttct tcttgctgca gggggcctgg 60
acacatgagg gtggtcagga caagcccttg ctgtctgcct ggcccagcgc tgtggtgcct 120
cgaggaggac atgtgactct tctgtgtcgc tctcgtcttg ggtttaccat cttcagtctg 180
tacaaagaag atggggtgcc tgtccctgag ctctacaaca aaatattctg gaagagcatc 240
ctcatgggcc ctgtgacccc tgcacacgca gggacctaca gatgtcgggg ttcacaccca 300
cgctccccca ttgagtggtc agcacccagc aaccccctgg tgatcgtggt cacaggtcta 360
tttgggaaac cttcactctc agcccagccg ggccccacgg ttcgcacagg agagaacgtg 420
accttgtcct gcagctccag gagctcatat gacatgtacc atctatccag ggaggggagg 480
gcccatgaac ctaggctccc tgcagtgccc agcgtcaatg gaacattcca ggctgacttt 540
cctctgggcc ctgccaccca cggagggacc tacacatgct tcggctctct ccatgactca 600
ccctatgagt ggtcagaccc gagtgaccca ctgcttgttt ctgtcacagg aaactcttca 660
agtagttcat cttcacccac tgaaccaagc tccaaaactg gtatccgcag acacctgcac 720
attctgattg ggacctcagt ggctatcatc ctcttcatca tcctcttctt ctttctcctt 780
cattgctgct gctccaacaa aaagaatgct gctgtaatgg accaagagcc tgccggggac 840
agaacagtga acagggagga ctctgatgat caagaccctc aggaggtgac atatgcacag 900
ttggatcact gcgttttcac acagacaaaa atcacttccc cttctcagag gcccaagaca 960
cctccaacag ataccaccat gtacatggaa cttccaaatg ctaagccaag atcattgtct 1020
cctgcccata agcaccacag tcaggccttg aggggatctt ctagggagac aacagccctg 1080
tctcaaaacc gggttgctag ctcccatgta ccagcagctg gaatctga 1128

<210> SEQ ID NO 31
<211> LENGTH: 1128
<212> TYPE: DNA
<213> ORGANISM: Homo sapiens

<400> SEQUENCE: 31
atgtcgctca tggtcgtcag catggcgtgt gttgggttct tcttgctgca gggggcctgg 60
acacatgagg gtggacagga caagcccttg ctgtctgcct ggcccagcgc tgtggtgcct 120
cgaggaggac atgtgactct tctgtgtcgc tctcgtcttg ggtttaccat cttcagtctg 180
tacaaagaag atggggtgcc tgtccctgag ctctacaaca aaatattctg gaagagcatc 240
ctcatgggcc ctgtgacccc tgcacacgca gggacctaca gatgtcgggg ttcacacccg 300
cgctccccca ttgagtggtc ggcacccagc aaccccctgg tgatcgtggt cacaggtcta 360
tttgggaaac cttcactctc agcccagccg ggccccacgg ttcgcacagg agagaacgtg 420
accttgtcct gcagctccag gagctcatat gacatgtacc atctatccag ggaggggagg 480
gcccatgaac ctaggctccc tgcagtgccc agcgtcgatg gaacattcca ggctgacttt 540
cctctgggcc ctgccaccca cggagggacc tacacatgct tcagctctct ccatgactca 600
ccctatgagt ggtcagaccc gagtgaccca ctgcttgttt ctgtcacagg aaactcttca 660
agtagttcat cttcacccac tgaaccaagc tccaaaactg gtatccgcag acacctgcac 720
attctgattg ggacctcagt ggctatcatc ctcttcatca tcctcttctt ctttctcctt 780

```
cattgctgct gctccaacaa aaagaatgct gctgtaatgg accaagagcc tgccggggac    840

agaacagtga acagggagga ctctgatgat caagaccctc aggaggtgac atatgcacag    900

ttggatcact gcgttttcac acagacaaaa atcacttccc cttctcagag gcccaagaca    960

cctccaacag ataccaccat gtacatggaa cttccaaatg ctaagccaag atcattgtct   1020

cctgcccata agcaccacag tcaggccttg aggggatctt ctagggagac aacagccctg   1080

tctcaaaacc gggttgctag ctcccatgta ccagcagctg gaatctga                1128
```

<210> SEQ ID NO 32
<211> LENGTH: 1128
<212> TYPE: DNA
<213> ORGANISM: Homo sapiens

<400> SEQUENCE: 32

```
atgtcgctca tggtcgtcag catggcgtgt gttgggttct tcttgctgca gggggcctgg     60

ccacatgagg gtggtcagga caagcccttg ctgtctgcct ggcccagcgc tgtggtgcct    120

cgaggaggac atgtgactct tctgtgtcgc tctcgtcttg ggtttaccat cttcagtctg    180

tacaaagaag atggggtgcc tgtccctgag ctctacaaca aaatattctg gaagagcatc    240

ctcatgggcc ctgtgacccc tgcacacgca gggacctaca gatgtcgggg ttcacaccca    300

cgctccccca ttgagtggtc agcacccagc aacccccctgg tgatcatggt cacaggtcta    360

tttgggaaac cttcactctc agcccagccg ggccccacgg ttcgcacagg agagaacgtg    420

accttgtcct gcagctccag gagctcatat gacatgtacc atctatccag ggagggggagg    480

gcccatgaac ctaggctccc tgcagtgccc agcgtcaatg gaacattcca ggctgacttt    540

cctctgggcc ctgccaccca cggagggacc tacacatgct tcggctctct ccatgactca    600

ccctatgagt ggtcagaccc gagtgaccca ctgcttgttt ctgtcacagg aaactcttca    660

agtagttcat cttcacccac tgaaccaagc tccaaaactg gtatccgcag acacctgcac    720

attctgattg ggacctcagt ggctatcatc ctcttcatca tcctcttctt ctttctcctt    780

cattgctgct gctccaacaa aaagaatgct gctgtaatgg accaagagcc tgccggggac    840

agaacagtga acagggagga ctctgatgat caagaccctc aggaggtgac atatgcacag    900

ttggatcact gcgttttcac acagacaaaa atcacttccc cttctcagag gcccaagaca    960

cctccaacag ataccaccat gtacatggaa cttccaaatg ctaagccaag atcattgtct   1020

cctgcccata agcaccacag tcaggccttg aggggatctt ctagggagac aacagccctg   1080

tctcaaaacc gggttgctag ctcccatgta ccagcagctg gaatctga                1128
```

<210> SEQ ID NO 33
<211> LENGTH: 1131
<212> TYPE: DNA
<213> ORGANISM: Homo sapiens
<220> FEATURE:
<221> NAME/KEY: misc_feature
<222> LOCATION: (29)...(34)
<223> OTHER INFORMATION: n = A,T,C or G
<220> FEATURE:
<221> NAME/KEY: misc_feature
<222> LOCATION: (600)...(1131)
<223> OTHER INFORMATION: n = A,T,C or G

<400> SEQUENCE: 33

```
atgtcgctca tggtcgtcag catggcgtnn nnnnggttct tcttgctgca gggggcctgg     60

acacatgagg gtggtcagga caagcccttg ctgtctgcct ggcccagcac tgtggtgcct    120

cgaggaggac atgtgactct tctgtgtcgc tctcgtcttg ggtttaccat cttcagtctg    180
```

```
tacaaagaag atggggtgcc tgtccctgag ctctacaaca aaatattctg gaagagcatc    240

ctcatgggcc ctgtgacccc tgcacacgca gggacctaca gatgtcgggg ttcacaccca    300

cgctccccca ttgagtggtc agcacccagc aacccccctgg tgatcgtggt cacaggtcta    360

tttgggaaac cttcactctc agcccagccg ggccccacgg ttcgcacagg agagaacgtg    420

accttgtcct gcagctccag gagctcatat gacatgtacc atctatccag ggaggggagg    480

gcccatgaac ctaggctccc tgcagtgccc agcgtcaatg gaacattcca ggctgacttt    540

cctctgggcc ctgccaccca cggagggacc tacacatgct tcggctctct ccatgactcn    600

nnnnnnnnnn nnnnnnnnnn nnnnnnnnnn nnnnnnnnnn nnnnnnnnnn nnnnnnnnnn    660

nnnnnnnnnn nnnnnnnnnn nnnnnnnnnn nnnnnnnnnn nnnnnnnnnn nnnnnnnnnn    720

nnnnnnnnnn nnnnnnnnnn nnnnnnnnnn nnnnnnnnnn nnnnnnnnnn nnnnnnnnnn    780

nnnnnnnnnn nnnnnnnnnn nnnnnnnnnn nnnnnnnnnn nnnnnnnnnn nnnnnnnnnn    840

nnnnnnnnnn nnnnnnnnnn nnnnnnnnnn nnnnnnnnnn nnnnnnnnnn nnnnnnnnnn    900

nnnnnnnnnn nnnnnnnnnn nnnnnnnnnn nnnnnnnnnn nnnnnnnnnn nnnnnnnnnn    960

nnnnnnnnnn nnnnnnnnnn nnnnnnnnnn nnnnnnnnnn nnnnnnnnnn nnnnnnnnnn   1020

nnnnnnnnnn nnnnnnnnnn nnnnnnnnnn nnnnnnnnnn nnnnnnnnnn nnnnnnnnnn   1080

nnnnnnnnnn nnnnnnnnnn nnnnnnnnnn nnnnnnnnnn nnnnnnnnnn n            1131


<210> SEQ ID NO 34
<211> LENGTH: 1128
<212> TYPE: DNA
<213> ORGANISM: Homo sapiens

<400> SEQUENCE: 34

atgtcgctca tggtcatcag catggcgtgt gttgggttct tcttgctgca gggggcctgg     60

acacatgagg gtggacagga caagcccttg ctgtctgcct ggcccagcgc tgtggtgcct    120

cgaggaggac atgtgactct tctgtgtcgc tctcgtcttg ggtttaccat cttcagtctg    180

tacaaagaag atggggtgcc tgtccctgag ctctacaaca aaatattctg gaagagcatc    240

ctcatgggcc ctgtgacccc tgcacacgca gggacctaca gatgtcgggg ttcacacccg    300

cgctccccca ttgagtggtc ggcacccagc aacccccctgg tgatcgtggt cacaggtcta    360

tttgggaaac cttcactctc agcccagccg ggccccacgg ttcgcacagg agagaacgtg    420

accttgtcct gcagctccag gagctcatat gacatgtacc atctatccag ggaggggagg    480

gcccatgaac ctaggctccc tgcagtgccc agcgtcgatg gaacattcca ggctgacttt    540

cctctgggcc ctgccaccca cggagggacc tacacatgct tcagctctct ccatgactca    600

ccctatgagt ggtcagaccc gagtgaccca ctgcttgttt ctgtcacagg aaactcttca    660

agtagttcat cttcacccac tgaaccaagc tccaaaactg gtatccgcag acacctgcac    720

attctgattg ggacctcagt ggctatcatc ctcttcatca tcctcttctt ctttctcctt    780

cattgctgct gctccaacaa aaagaatgct gctgtaatgg accaagagcc tgccggggac    840

agaacagtga acagggagga ctctgatgat caagaccctc aggaggtgac atatgcacag    900

ttggatcact gcgttttcac acagacaaaa atcacttccc cttctcagag gcccaaggca    960

cctccaacag ataccaccat gtacatggaa cttccaaatg ctaagccaag atcattgtct   1020

cctgcccata agcaccacag tcaggccttg aggggatctt ctagggagac aacagccctg   1080

tctcaaaacc gggttgctag ctcccatgta ccagcagctg gaatctga                1128
```

<210> SEQ ID NO 35
<211> LENGTH: 1128
<212> TYPE: DNA
<213> ORGANISM: Homo sapiens

<400> SEQUENCE: 35
atgtcgctca tggtcatcag catggcgtgt gttgggttct tcttgctgca gggggcctgg 60
acacatgagg gtggacagga caagcccttg ctgtctgcct ggcccagcgc tgtggtgcct 120
cgaggaggac atgtgactct tctgtgtcgc tctcgtcttg ggtttaccat cttcagtctg 180
tacaaagaag atggggtgcc tgtccctgag ctctacaaca aaatattctg gaagagcatc 240
ctcatgggcc ctgtgacccc tgcacacgca gggacctaca gatgtcgggg ttcacacccg 300
cgctccccca ttgagtggtc ggcacccagc aaccccctgg tgatcgtggt cacaggtcta 360
tttgggaaac cttcactctc agcccagccg ggccccacgg ttcgcacagg agagaacgtg 420
gccttgtcct gcagctccag gagctcatat gacatgtacc atctatccag ggaggggagg 480
gcccatgaac ctaggctccc tgcagtgccc agcgtcgatg gaacattcca ggctgacttt 540
cctctgggcc ctgccaccca cggagggacc tacacatgct tcagctctct ccatgactca 600
ccctatgagt ggtcagaccc gagtgaccca ctgcttgttt ctgtcacagg aaactcttca 660
agtagttcat cttcacccac tgaaccaagc tccaaaactg gtatccgcag acacctgcac 720
attctgattg ggacctcagt ggctatcatc ctcttcatca tcctcttctt ctttctcctt 780
cattgctgct gctccaacaa aaagaatgct gctgtaatgg accaagggcc tgccggggac 840
agaacagtga acagggagga ctctgatgat caagaccctc aggaggtgac atatgcacag 900
ttggatcact gcgttttcac acagacaaaa atcacttccc cttctcagag gcccaaggca 960
cctccaacag ataccaccat gtacatggaa cttccaaatg ctaagccaag atcattgtct 1020
cctgcccata agcaccacag tcaggccttg aggggatctt ctagggagac aacagccctg 1080
tctcaaaacc gggttgctag ctcccatgta ccagcagctg gaatctga 1128

<210> SEQ ID NO 36
<211> LENGTH: 1364
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 36
atgtcgctca cggtcgtcag catggcgtgt gttgggttct tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctcct ggcccaccca ggtcgcctgg tgaaatcaga agagacagtc 420
atcctgcaat gttggtcaga tgtcatgttt gaacacttcc ttctgcacag agaggggatg 480
tttaacgaca ctttgcgcct cattggagaa caccatgatg ggtctccaa ggccaacttc 540 tccatcagtc gcatgaggca agacctggca gggacctaca gatgctacgg ttctgttact 600 cactcccccct atcagttgtc agctcccagt gaccctctgg acatcgtgat cataggtcta 660
tatgagaaac cttctctctc agcccagccg ggccccacgg ttctggcagg agagagtgtg 720
accttgtcct gcagctcccg gagctcctat gacatgtacc atctatccag ggagggggag 780
gcccatgaac gtaggctccc tgcagggacc aaggtcaacg gaacattcca ggccaacttt 840
cctctgggcc ctgccaccca tggagggacc tacagatgct tcggctcttt ccgtgactct 900
ccatacgagt ggtcaaagtc aagtgaccca ctgcttgttt ctgtcacagg aaacccttca 960
aatagttggc cttcacccac tgaaccaagc tccgaaaccg gtaaccccag acacctacat 1020
gttctgattg ggacctcagt ggtcaaaatc cctttcacca tcctcctctt ctttctcctt 1080
catcgctggt gctccgacaa aaaaaatgct gctgtaatgg accaagagcc tgcagggaac 1140
agaacagtga acagcgagga ttctgatgaa caagaccatc aggaggtgtc atacgcataa 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnn 1364

<210> SEQ ID NO 37
<211> LENGTH: 1361
<212> TYPE: DNA
<213> ORGANISM: Homo sapiens
<220> FEATURE:
<221> NAME/KEY: misc_feature
<222> LOCATION: (1198)...(1361)
<223> OTHER INFORMATION: n = A,T,C or G

<400> SEQUENCE: 37
atgtcgctca cggtcgtcag catggcgtgt gttgggttct tcttgctgca gggggcctgg 60
ccacatgagg gtggtcagga caagcccttg ctgtctgcct ggccaagccc tgtggtgcct 120
ccaggatatg tgattcttca gtgtcattct tatcttgggt ttaacaactt cagtctgtaa 180
aaggaagatg gggtgcctgt ccctgagctc tacaacataa tattctggaa cagccttttc 240
atgggccctg tgaccccagc acatgcaggg acctatacat gtcggggttc acaaccacac 300
taccccagtg ggtggtcggc acccagcaac cccctggaga tcacggtcac aggagtccac 360
agaaaacctt ccctcctggc ccacccaggt cgcctggtga aatcagaaga gacagtcatc 420
ctgcaatgtt ggtcagatgt catgtttgaa cacttccttc tgcacagaga ggggatgttt 480
aacgacactt tgcgcctcat tggagaacac catgatgggg tctccaaggc caacttctcc 540
atcagtcgca tgaagcaaga cctggcaggg acctacagat gctacggttc tgttactcac 600
tccccctatc agttgtcagc tcccagtgac cctctggaca tcgtgatcat aggtctatat 660
gagaaacctt ctctctcagc ccagccgggc cccacggttc tggcaggaga gagtgtgacc 720
ttgtcctgca gctcccggag ctcctatgac atgtaccatc tatccaggga gggggaggcc 780
catgaacgta ggctccctgc agggaccaag gtcaacggaa cattccaggc caactttcct 840
ctgggccctg ccacccatgg agggacctac agatgcttcg gctctttccg tgactctcca 900
tacgagtggt caaagtcaag tgacccactg cttgtttctg tcacaggaaa cccttcaaat 960
agttggcctt cacccactga accaagctcc gaaaccggta accccagaca cctacatgtt 1020
ctgattggga cctcagtggt caaaatccct ttcaccatcc tcctcttctt tctccttcat 1080
cgctggtgct ccgacaaaaa aaatgctgct gtaatggacc aagagcctgc agggaacaga 1140
acagtgaaca gcgaggattc tgatgaacaa gaccatcagg aggtgtcata cgcataannn 1200
nnnnnnnnnn nnnnnnnnnn nnnnnnnnnn nnnnnnnnnn nnnnnnnnnn nnnnnnnnnn 1260

```
nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn n                       1361


<210> SEQ ID NO 38
<211> LENGTH: 1364
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 38

atgtcgctca tggtcgtcag catggcgtgt gttgggttct tcttgctgca gggggcctgg     60

ccacatgagg nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccctcct ggcccaccca ggtcgcctgg tgaaatcaga agagacagtc    420

atcctgcaat gttggtcaga tgtcatgttt gaacacttcc ttctgcacag agaggggatg    480

tttaacgaca ctttgcgcct cattggagaa caccacgatg ggtctccaa ggccaacttc     540

tccatcagtc gcatgaagca agacctggca gggacctaca gatgctacgg ttctgttact    600

cactccccct atcagttgtc agctcccagt gaccctctgg acatcgtgat cataggtcta    660

tatgagaaac cttctctctc agcccagccg ggccccacgg ttctggcagg agagagtgtg    720

accttgtcct gcagctcccg gagctcctat gacatgtacc atctatccag ggagggggag    780

gcccatgaac gtaggctccc tgcagggacc aaggtcaacg gaacattcca ggccaacttt    840

cctctgggcc ctgccaccca tggagggacc tacagatgct tcggctcttt ccgtgactct    900

ccatacgagt ggtcaaagtc aagtgaccca ctgcttgttt ctgtcacagg aaacccttca    960

aatagttggc cttcacccac tgaaccaagc tccgaaaccg gtaaccccag acacctacat   1020

gttctgattg ggacctcagt ggtcaaaatc cctttcacca tcctcctctt ctttctcctt   1080

catcgctggt gctccgacaa aaaaaatgct gctgtaatgg accaagagcc tgcagggaac   1140

agaacagtga acagcgagga ttctgatgaa caagaccatc aggaggtgtc atacgcataa   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnn                    1364


<210> SEQ ID NO 39
<211> LENGTH: 1364
<212> TYPE: DNA
<213> ORGANISM: Homo sapiens
<220> FEATURE:
<221> NAME/KEY: misc_feature
<222> LOCATION: (1)...(40)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
```

<220> FEATURE:
<221> NAME/KEY: misc_feature
<222> LOCATION: (1201)...(1364)
<223> OTHER INFORMATION: n = A,T,C or G

<400> SEQUENCE: 39

```
nnnnnnnnnn nnnnnnnnnn nnnnnnnnnn nnnnnnnnnn tcttgctgca gggggcctgg      60

ccacatgagg nnnnnnnnnn nnnnnnnnnn nnnnnnnnnn nnnnnnnnnn nnnnnnnnnn     120

nnnnnnnnnn nnnnnnnnnn nnnnnnnnnn nnnnnnnnnn nnnnnnnnnn nnnnnnnnnn     180

nnnnnnnnnn nnnnnnnnnn nnnnnnnnnn nnnnnnnnnn nnnnnnnnnn nnnnnnnnnn     240

nnnnnnnnnn nnnnnnnnnn nnnnnnnnnn nnnnnnnnnn nnnnnnnnnn nnnnnnnnnn     300

nnnnnnnnnn nnnnnnnnnn nnnnnnnnnn nnnnnnnnnn nnnnnnnnnn nnnnngagtc     360

cacagaaaac cttccctcct ggcccaccca ggtcgcctgg tgaaatcaga agagacagtc     420

atcctgcaat gttggtcaga tgtcatgttt gaacacttcc ttctgcacag agaggggatg     480

tttaacgaca ctttgcgcct cattggagaa caccatgatg ggtctccaa ggccaacttc     540

tccatcagtc gcatgaagca agacctggca gggacctaca gatgctacgg ttctgttact     600

cactccccct atcaggtgtc agctcccagt gaccctctgg acatcgtgat cataggtcta     660

tatgagaaac cttctctctc agcccagccg ggccccacgg ttctggcagg agagagtgtg     720

accttgtcct gcagctcccg gagctcctat gacatgtacc atctatccag ggagggggag     780

gcccatgaac gtaggctccc tgcagggacc aaggtcaacg gaacattcca ggccaacttt     840

cctctgggcc ctgccaccca tggagggacc tacagatgct tcggctcttt ccgtgactct     900

ccatacgagt ggtcaaagtc aagtgaccca ctgcttgttt ctgtcacagg aaacccttca     960

aatagttggc cttcacccac tgaaccaagc tccaaaaccg gtaaccccag acacctacat    1020

gttctgattg ggacctcagt ggtcaaaatc cctttcacca tcctcctctt ctttctcctt    1080

catcgctggt gctccgacaa aaaaaatgct gctgtaatgg accaagagcc tgcagggaac    1140

agaacagtga acagcgagga ttctgatgaa caagaccatc aggaggtgtc atacgcataa    1200

nnnnnnnnnn nnnnnnnnnn nnnnnnnnnn nnnnnnnnnn nnnnnnnnnn nnnnnnnnnn    1260

nnnnnnnnnn nnnnnnnnnn nnnnnnnnnn nnnnnnnnnn nnnnnnnnnn nnnnnnnnnn    1320

nnnnnnnnnn nnnnnnnnnn nnnnnnnnnn nnnnnnnnnn nnnn                     1364
```

<210> SEQ ID NO 40
<211> LENGTH: 1360
<212> TYPE: DNA
<213> ORGANISM: Homo sapiens
<220> FEATURE:
<221> NAME/KEY: misc_feature
<222> LOCATION: (1197)...(1360)
<223> OTHER INFORMATION: n = A,T,C or G

<400> SEQUENCE: 40

```
atgtcgctca tggtcgtcag catggcgtgt gttgggttct tcttgctgca gggggcctgg      60

ccacatgagg gtggtcagga caagcccttg ctgtctgcct ggcccagcct tgtggtgcct     120

ctaggacatg tcattcttcg gtgtcactct tatcttgggt ttaacaactt cagtctgtac     180

aaggaaggtg ggtgcctgt ccctgagctc tacaacagaa tattctggaa cagccttttc     240

atgggccctg tgacccccgc acaacaggga catatacatg tcggggttca cacacacact     300

cccccagtgg gtggtcagca cccagcaacc ccctggtgat cgtggtcata ggagtccaca     360

gaaaaccttc cctcctggcc cacccaggtc ccctggtgaa atcagaagag acagtcatcc     420

tgcaatgttg gtcagatgtc aggtttgagc acttccttct gcacagagag gggaagtata     480
```

```
aggacacttt gcacctcatt ggagagcacc atgatggggt ctccaaggcc aacttctcca    540
tcggtcccat gatgcaagac cttgcaggga cctacagatg ctacggttct gttactcact    600
ccccctatca gttgtcagct cccagtgacc ctctggacat cgtcatcaca ggtctatatg    660
agaaaccttc tctctcagcc cagccgggcc ccacggtttt ggcaggagag agcgtgacct    720
tgtcctgcag ctcccggagc tcctatgaca tgtaccatct atccagggag gggggaggccc   780
atgaacgtag gttctctgca gggcccaagg tcaacggaac attccaggcc gactttcctc    840
tgggccctgc cacccacgga ggaacctaca gatgcttcgg ctctttccgt gactctccct    900
atgagtggtc aaactcgagt gacccactgc ttgtttctgt cacaggaaac ccttcaaata    960
gttggccttc acccactgaa ccaagctcca aaaccggtaa ccccagacac ctgcatgttc   1020
tgattgggac ctcagtggtc aaaatccctt tcaccatcct cctcttcttt ctccttcatc   1080
gctggtgctc caacaaaaaa aatgctgctg taatggacca agagcctgca gggaacagaa   1140
cagtgaacag cgaggattct gatgaacaag accatcagga ggtgtcatac gcataannnn   1200
nnnnnnnnnn nnnnnnnnnn nnnnnnnnnn nnnnnnnnnn nnnnnnnnnn nnnnnnnnnn   1260
nnnnnnnnnn nnnnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn                         1360
```

```
<210> SEQ ID NO 41
<211> LENGTH: 1364
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 41

atgtcgctca tggtcgtcag catggcgtgt gttgggttct tcttgctgca gggggccggg     60
ccacatgagg nnnnnnnnnn nnnnnnnnnn nnnnnnnnnn nnnnnnnnnn nnnnnnnnnn    120
nnnnnnnnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnnnnnnn nnnnnnnnnn nnnnnnnnnn nnnnnnnnnn    300
nnnnnnnnnn nnnnnnnnnn nnnnnnnnnn nnnnnnnnnn nnnnnnnnnn nnnnngagtc    360
cacagaaaac cttccctcct ggcccaccca ggtcccctgg tgaaatcaga agagacagtc    420
atcctgcaat gttggtcaga tgtcaggttt gagcacttcc ttctgcacag agaggggaag    480
tataaggaca ctttgcacct cattggagag caccatgatg ggtctccaa ggccaacttc     540
tccatcggtc ccatgatgca agaccttgca gggacctaca gatgctacgg ttctgttact    600
cactccccct atcagttgtc agctcccagt gaccctctgg acatcgtcat cacaggtcta    660
tatgagaaac cttctctctc agcccagccg ggccccacgg ttttggcagg agagagcgtg    720
accttgtcct gcagctcccg gagctcctat gacatgtacc atctatccag ggagggggag    780
gcccatgaac gtaggttctc tgcagggccc aaggtcaacg gaacattcca ggccgacttt    840
cctctgggcc ctgccaccca cggaggaacc tacagatgct tcggctcttt ccgtgactct    900
ccctatgagt ggtcaaactc gagtgaccca ctgcttgttt ctgtcacagg aaacccttca    960
aatagttggc cttcacccac tgaaccaagc tccaaaaccg gtaaccccag acacctgcat   1020
```

```
gttctgattg ggacctcagt ggtcaaaatc cctttcacca tcctcctctt ctttctcctt   1080

catcgctggt gctccaacaa aaaaaatgct gctgtaatgg accaagagcc tgcagggaac   1140

agaacagtga acagcgagga ttctgatgaa caagaccatc aggaggtgtc atacgcataa   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnn                    1364


<210> SEQ ID NO 42
<211> LENGTH: 1364
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 42

atgtcgctca tggtcgtcag catggcgtgt gttgggttct tcttgctgca gggggcctgg     60

ccacatgagg nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccctcct ggcccaccca ggtcccctgg tgaaatcaga agagacagtc    420

atcctgcaat gttggtcaga tgtcaggttt gagcacttcc ttctgcacag agaggggaag    480

tataaggaca ctttgcacct cattggagag caccatgatg ggtctccaa ggccaacttc    540

tccatcggtc ccatgatgca agaccttgca gggacctaca gatgctacgg ttctgttact    600

cactccccct atcagttgtc agctcccagt gaccctctgg acatcgtcat cacaggtcta    660

tatgagaaac cttctctctc agcccagccg ggccccacgg ttttggcagg agagagcgtg    720

accttgtcct gcagctcccg gagctcctat gacatgtacc atctatccag ggagggggag    780

gcccatgaac gtaggttctc tgcagggccc aaggtcaacg gaacattcca ggccgacttt    840

cctctgggcc ctgccaccca cggaggaacc tacagatgct tcggctcttt ccgtgactct    900

ccctatgagt ggtcaaactc gagtgaccca ctgcttgttt ctgtcacagg aaacccttca    960

aatagttggc cttcacccac tgaaccaagc tccaaaaccg gtaactccag atacctgcac   1020

gctctgattg ggacctcagt ggtcatcatc ccctttgcta tcctcctctt ctttctcctt   1080

catcgctggt gtgccaacaa aaaaaatgct gctgtaatgg accaagagcc tgcagggaac   1140

agaacagtga acagcgagga ttctgatgaa caagaccatc aggaggtgtc atacgcataa   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnn                    1364


<210> SEQ ID NO 43
<211> LENGTH: 1364
<212> TYPE: DNA
<213> ORGANISM: Homo sapiens
```

<220> FEATURE:
<221> NAME/KEY: misc_feature
<222> LOCATION: (1)...(40)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 43
nnnnnnnnnn nnnnnnnnnn nnnnnnnnnn nnnnnnnnnn tcttgctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngagtc 360
cacagaaaac cttccctcct ggcccaccca ggtcccctgg tgaaatcaga agagacagtc 420
atcctgcaat gttggtcaga tgtcaggttt gagcacttcc ttctgcacag agaggggaag 480
tataaggaca ctttgcacct cattggagag caccatgatg ggtctccaa ggccaacttc 540 tccatcggtc ccatgatgca agaccttgca gggacctaca gatgctacgg ttctgttact 600
cactccccct atcagttgtc agctcccagt gaccctctgg acatcgtcat cacaggtcta 660
tatgagaaac cttctctctc agcccagccg ggccccacgg ttttggcagg agagagcgtg 720
accttgtcct gcagctcccg gagctcctat gacatgtacc atctatccag ggagggggag 780
gcccatgaac gtaggttctc tgcagggccc aaggtcaacg gaacattcca ggccgacttt 840
cctctgggcc ctgccaccca cggaggaacc tacagatgct tcggctcttt ccgtgactct 900
ccctatgagt ggtcaaactc gagtgaccca ctgcttgttt ctgtcacagg aaacccttca 960
aatagttggc cttcacccac tgaaccaagc tccgaaaccg gtaaccccag acacctgcac 1020
gttctgattg ggacctcagt ggtcaaaatc cctttcacca tcctcctctt ctttctcctt 1080
catcgctggt gctccaacaa aaaaaatgct gctgtaatgg accaagagcc tgcagggaac 1140
agaacagtga acagcgagga ttctgatgaa caagaccatc aggaggtgtc atacgcataa 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnn 1364

<210> SEQ ID NO 44
<211> LENGTH: 1364
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 44
atgtcgctca tggtcgtcag catggcgtgt gttgggttct tcttgctgca gggggccggg 60
ccacatgagg nnnnnnnnnn nnnnnnnnnn nnnnnnnnnn nnnnnnnnnn nnnnnnnnnn 120

```
nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccctcct ggcccaccca ggtcccctgg tgaaatcaga agagacagtc    420

atcctgcaat gttggtcaga tgtcaggttt gagcacttcc ttctgcacag agaggggaag    480

tataaggaca ctttgcacct cattggagag caccatgatg ggtctccaa ggccaacttc    540

tccatcggtc ccatgatgca agaccttgca gggacctaca gatgctacgg ttctgttact    600

cactccccct atcagttgtc agctcccagt gaccctctgg acatcgtcat cacaggtcta    660

tatgagaaac cttctctctc agcccagccg ggccccacgg ttttggcagg agagagcgtg    720

accttgtcct gcagctcccg gagctcctat gacatgtacc atctatccag ggagggggag    780

gcccatgaac gtaggttctc tgcagggccc aaggtcaacg gaacattcca ggccgacttt    840

cctctgggcc ctgccaccca cggaggaacc tacagatgct tcggctcttt ccgtgactct    900

ccctatgagt ggtcaaactc gagtgaccca ctgcttgttt ctgtcacagg aaacccttca    960

aatagttggc cttcacccac tgaaccaagc tccaaaaccg gtaaccccag acacctacac   1020

gttctgattg ggacctcagt ggtcaaactc cctttcacca tcctcctctt ctttctcctt   1080

catcgctggt gctccgacaa aaaaaatgca tctgtaatgg accaagggcc tgcagggaac   1140

agaacagtga acagggagga ttctgatgaa caggaccatc aggaggtgtc atacgcataa   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnn                    1364


<210> SEQ ID NO 45
<211> LENGTH: 1364
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 45

atgtcgctca tggtcatcag catggcatgt gttgggttct tctggctgca gggggccggg      60

ccacatgagg nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngattc    360

cgcagaaaac cttccctcct ggcccaccca ggtcgcctgg tgaaatcaga agagacagtc    420

atcctgcaat gttggtcaga tgtcatgttt gagcacttcc ttctgcacag agaggggacg    480

tttaacgaca ctttgcgcct cattggagag cacattgatg ggtctccaa ggccaacttc    540

tccatcggtc gcatgaggca agacctggca gggacctaca gatgctacgg ttctgttcct    600

cactccccct atcagttttc agctcccagt gaccctctgg acatcgtgat cacaggtcta    660
```

tatgagaaac cttctctctc agcccagccg ggccccacgg ttctggcagg agagagcgtg 720
accttgtcct gcagctcctg gagctcctat gacatgtacc atctatccac ggaaggggag 780
gcccatgaac gtaggttctc tgcagggccc aaggtcaacg gaacattcca ggccgacttt 840
cctctgggcc ctgccaccca aggaggaacc tacagatgct tcggctcttt ccatgactct 900
ccctacgagt ggtcaaagtc aagtgaccca ctgcttgttt ctgtcacagg aaacccttca 960
aatagttggc cttcacccac tgaaccaagc tccaaaaccg gtaaccccag acacctacac 1020
gttctgattg ggacctcagt ggtcaaactc cctttcacca tcctcctctt ctttctcctt 1080
catcgctggt gctccgacaa aaaaaatgca tctgtaatgg accaagggcc tgcagggaac 1140
agaacagtga acagggagga ttctgacgaa caggaccatc aggaggtgtc atacgcataa 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnn 1364

<210> SEQ ID NO 46
<211> LENGTH: 1364
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1364)
<223> OTHER INFORMATION: n = A,T,C or G

<400> SEQUENCE: 46
atgtcgctca tggtcatcag catggcatgt gttgggttct tctggctgca gggggccggg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngattc 360
cgcagaaaac cttccctcct ggcccaccca ggtcgcctgg tgaaatcaga agagacagtc 420
atcctgcaat gttggtcaga tgtcatgttt gagcacttcc ttctgcacag agaggggacg 480
tttaacgaca ctttgcgcct cattggagag cacattgatg gggtctccaa ggccaacttc 540
tccatcggtc gcatgaggca agacctggca gggacctaca gatgctacgg ttctgttcct 600 cactcccccct atcagttttc agctcccagt gaccctctgg acatcgtgat cacaggtcta 660
tatgagaaac cttctctctc agcccagccg ggccccacgg ttctggcagg agagagcgtg 720
accttgtcct gcagctcctg gagctcctat gacatgtacc atctatccac ggaaggggag 780
gcccatgaac gtaggttctc tgcagggccc aaggtcaacg gaacattcca ggccgacttt 840
cctctgggcc ctgccaccca aggaggaacc tacagatgct tcggctcttt ccatgactct 900
ccctacgagt ggtcaaagtc aagtgaccca ctgcttgttt ctgtcacagg aaacccttca 960
aatagttggc cttcacccac tgaaccaagc tccaaaaccg gtaaccccag acacctacac 1020
gttctgattg ggacctcagt ggtcaaactc cctttcacca tcctcctctt ctttctcctt 1080
catcgctggt gctccgacaa aaaaaatgca tctgtaatgg accaagggcc tgcagggaac 1140
agaacggtga acagggagga ttctgatgaa caggaccatc aggaggtgtc atacgcataa 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnn 1364

<210> SEQ ID NO 47
<211> LENGTH: 1361
<212> TYPE: DNA
<213> ORGANISM: Homo sapiens
<220> FEATURE:
<221> NAME/KEY: misc_feature
<222> LOCATION: (1198)...(1361)
<223> OTHER INFORMATION: n = A,T,C or G

<400> SEQUENCE: 47
atgtcgctca tggtcatcag catggcatgt gttgggttct tctggctgca gggggccggg 60
ccacatgagg gtggtcagga caagcccttg ctttctacct ggcccagcct tgtggtgcct 120
ccagaacatg tgactcttcg gtgtcactct aatcttgggt ttaacaactt cagtctgtac 180
aaggatgatg gggtgcctgt ccctgaacac tacaacagaa tattctggaa aagccttttc 240
atgggccctg tgaccccgtc acacacaggg acctatagat gccggggttc acacccacac 300
tcccccagtg ggtggtcggc acccagcaac cccctgctga tcatggtcac aggattccgc 360
agaaaacctt ccctcctggc ccacccaggt cgcctggtga aatcagaaga gacagtcatc 420
ctgcaatgtt ggtcagatgt catgtttgag cacttccttc tgcacagaga ggggacgttt 480
aacgacactt tgcgcctcat tggagagcac attgatgggg tctccaaggc caacttctcc 540
atcggtcgca tgaggcaaga cctggcaggg acctacagat gctacggttc tgttcctcac 600
tccccctatc agttttcagc tcccagtgac cctctggaca tcgtgatcac aggtctatat 660
gagaaacctt ctctctcagc ccagccgggc cccacggttc tggcaggaga gagcgtgacc 720
ttgtcctgca gctcctggag ctcctatgac atgtaccatc tatccacgga aggggaggcc 780
catgaacgta ggttctctgc agggcccaag gtcaacggaa cattccaggc cgactttcct 840
ctgggccctg ccacccaagg aggaacctac agatgcttcg gctctttcca tgactctccc 900
tacgagtggt caaagtcaag tgacccactg cttgtttctg tcacaggaaa cccttcaaat 960
agttggcctt cacccactga accaagctcc aaaaccggta accccagaca cctacacgtt 1020
ctgattggga cctcagtggt caaactccct ttcaccatcc tcctcttctt tctccttcat 1080
cgctggtgct ccgacaaaaa aaatgcatct gtaatggacc aagggcctgc agggaacaga 1140
acagtgaaca gggaggattc tgatgaacag gaccatcagg aggtgtcata cgcataannn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn n 1361

<210> SEQ ID NO 48
<211> LENGTH: 1365
<212> TYPE: DNA
<213> ORGANISM: Homo sapiens
<220> FEATURE:
<221> NAME/KEY: misc_feature
<222> LOCATION: (1198)...(1365)
<223> OTHER INFORMATION: n = A,T,C or G

<400> SEQUENCE: 48
atgtcgctca tggtcatcat catggcatgt gttgggttct tctggctgca gggggcctgg 60
ccacaggagg gtggtcagga caagcccttg ctttctacct ggcccagcct tgtggtgcct 120

```
ccagaacatg tgactcttca gtgtcactct aatcttgggt ttaacaactt cagtctgtac    180

aaggatgatg ggtgcctgt ccctgagctg tacaacagaa tattctggaa aagccttttc    240

atgggccctg tgaccccgtc acacgcaggg acctatagat gccggggttc acacccacac    300

tcccccagtg ggtggtcggc acccagcaac cccctggtga tcatggtcac aggagtccac    360

agaaaacctt ccttcctggc cctcccaggt cacctggtga aatcagaaga gacagtcatc    420

ctgcaatgtt ggtcggatgt catgtttgag cacttccttc tgcacagaga ggggaagttt    480

aacaacactt tgcacctcat tggagagcac catgatgggg tttccaaggc caacttctcc    540

attggtccca tgatgcctgt ccttgcagga acctacagat gctacggttc tgttcctcac    600

tccccctatc agttgtcagc tcccagtgac cctctggaca tggtgatcat aggtctatat    660

gagaaacctt ctctctcagc ccagccgggc cccacggttc aggcaggaga gaatgtgacc    720

ttgtcctgca gctcccggag ctcctatgac atgtaccatc tatccaggga aggggaggcc    780

catgaacgta ggctccctgc agtgcgcagc atcaacggaa cattccaggc cgactttcct    840

ctgggccctg ccacccacgg agggacctac agatgcttcg gctctttccg tgacgctccc    900

tacgagtggt caaactcgag tgatccactg cttgtttccg tcacaggaaa cccttcaaat    960

agttggcctt cacccactga accaagctcc aaaaccggta accccagaca cctacatgtt   1020

ctgattggga cctcagtggt caaaatccct ttcaccatcc tcctcttctt tctccttcat   1080

cgctggtgct ccgacaaaaa aaatgctgct gtaatggacc aagagcctgc agggaacaga   1140

acagtgaaca gcgaggattc tgatgaacaa gaccatcagg aggtgtcata cgcataannn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnn                    1365
```

```
<210> SEQ ID NO 49
<211> LENGTH: 1368
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1368)
<223> OTHER INFORMATION: n = A,T,C or G

<400> SEQUENCE: 49

atgtcgctca tggtcatcat catggcatgt gttgggttct tctggctgca gggggcctgg     60

ccacaggagg nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccttcct ggccctccca ggtcacctgg tgaaatcaga agagacagtc    420

atcctgcaat gttggtcgga tgtcatgttt gagcacttcc ttctgcacag agaggggaag    480

tttaacaaca ctttgcacct cattggagag caccatgatg ggtttccaa ggccaacttc     540

tccattggtc ccatgatgcc tgtccttgca ggaacctaca gatgctacgg ttctgttcct    600

cactccccct atcagttgtc agctcccagt gaccctctgg acatggtgat cataggtcta    660
```

```
tatgagaaac cttctctctc agcccagccg ggccccacgg ttcaggcagg agagaatgtg    720

accttgtcct gcagctcccg gagctcctat gacatgtacc atctatccag ggagggggag    780

gcccatgaac gtaggctccc tgcagtgcgc agcatcaacg gaacattcca ggccgacttt    840

cctctgggcc ctgccaccca cggagggacc tacagatgct tcggctcttt ccgtgacgct    900

ccctacgagt ggtcaaactc gagtgatcca ctgcttgttt ccgtcacagg aaacccttca    960

aatagttggc cttcacccac tgaaccaagc tccaaaaccg gtaaccccag acacctacat   1020

gttctgattg ggacctcagt ggtcaaaatc cctttcacca tcctcctctt ctttctcctt   1080

catcgctggt gctccgacaa aaaaaatgct gctgtaatgg accaagagcc tgcagggaac   1140

agaacagtga acagcgagga ttctgatgaa caagaccatc aggaggtgtc atacgcataa   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnnnnn               1368


<210> SEQ ID NO 50
<211> LENGTH: 1365
<212> TYPE: DNA
<213> ORGANISM: Homo sapiens
<220> FEATURE:
<221> NAME/KEY: misc_feature
<222> LOCATION: (1198)...(1365)
<223> OTHER INFORMATION: n = A,T,C or G

<400> SEQUENCE: 50

atgtcgctca tggtcatcat catggcatgt gttgggttct tctggctgca gggggcctgg     60

ccacaggagg gtggtcagga caagcccttg ctttctacct ggcccagcct tgtggtgcct    120

ccagaacatg tgactcttcg gtgtcactct aatcttgggt ttaacaactt cagtctgtac    180

aaggatgatg gggtgcctgt ccctgagctc tacaacagaa tattctggaa aagccttttc    240

atgggccctg tgaccccgtc acacacaggg acctatagat gccggggttc acacccacac    300

tcccccagtg gggggtcggc acccagcaac cccctgctga tcgtggtcac aggagtccac    360

agaaaacctt ccttcctggc cctcccaggt cacctggtga aatcagaaga gacagtcatc    420

ctgcaatgtt ggtcggatgt catgtttgag cacttccttc tgcacagaga ggggaagttt    480

aacaacactt tgcacctcat tggagagcac catgatgggg tttccaaggc caacttctcc    540

attggtccca tgatgcctgt ccttacagga acctacagat gctacagttc tgttcctcac    600

tcccccctatc agttgtcagc tcccagtgac cctctggaca tggtgatcat aggtctatat    660

gagaaacctt ctctctcagc ccagccgggc cccacggttc aggcaggaga gaatgtgtcc    720

ttgtcctgca gctcccggag ctcctatgac atgtaccatc tatccaggga gggggaggcc    780

catgaacgta ggctccctgc agtgcgcagc atccacggaa cattccaggc cgactttcct    840

ctgggccctg ccacccacgg agggacctac agatgcttcg gctctttccg tgacgctccc    900

tacgagtggt caaactcgag tgatccactg cttgtttccg tcacaggaaa cccttcaaat    960

agttggcctt cacccactga accaagctcc aaaaccggta accccagaca cctacatgtt   1020

ctgattggga cctcagtggt caaaatccct ttcaccatcc tcctcttctt tctccttcat   1080

cgctggtgct ccgacaaaaa aaatgctgct gtaatggacc aagagcctgc agggaacaga   1140

acagtgaaca gcgaggattc tgatgaacaa gaccatcagg aggtgtcata cgcataannn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320
```

```
nnnnnnnnnn nnnnnnnnnn nnnnnnnnnn nnnnnnnnnn nnnnn                  1365


<210> SEQ ID NO 51
<211> LENGTH: 1346
<212> TYPE: DNA
<213> ORGANISM: Homo sapiens
<220> FEATURE:
<221> NAME/KEY: misc_feature
<222> LOCATION: (1)...(20)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1178)...(1346)
<223> OTHER INFORMATION: n = A,T,C or G

<400> SEQUENCE: 51

nnnnnnnnnn nnnnnnnnnn catggcatgt gttgggttct tctggctgca gggggcctgg     60

ccacaggagg nnnnnnnnnn nnnnnnnnnn nnnnnnnnnn nnnnnnnnnn nnnnnnnnnn    120

nnnnnnnnnn nnnnnnnnnn nnnnnnnnnn nnnnnnnnnn nnnnnnnnnn nnnnnnnnnn    180

nnnnnnnnnn nnnnnnnnnn nnnnnnnnnn nnnnnnnnnn nnnnnnnnnn nnnnnnnnnn    240

nnnnnnnnnn nnnnnnnnnn nnnnnnnnnn nnnnnnnnnn nnnnnnnnnn nnnnnnnnnn    300

nnnnnnnnnn nnnnnnnnnn nnnnnnnnnn nnnnnnnnnn nnnnnnnnnn nnnnngagtc    360

cacagaaaac cttccttcct ggccctccca ggtcacctgg tgaaatcaga agagacagtc    420

atcctgcaat gttggtcgga tgtcatgttt gagcacttcc ttctgcacag agaggggaag    480

tttaacaaca ctttgcacct cattggagag caccatgatg gggtttccaa ggccaacttc    540

tccattggtc ccatgatgcc tgtccttgca ggaacctaca gatgctacgg ttctgttcct    600

cactcccccct atcagttgtc agctcccagt gaccctctgg acatggtgat cataggtcta    660

tatgagaaac cttctctctc agcccagccg ggccccacgg ttcaggcagg agagaatgtg    720

accttgtcct gcagctccat ctatccaggg aaggggaggc ccatgaacgt aggctccctg    780

cagtgcgcag catcaacgga acattccagg ccgactttcc tctgggccct gccacccacg    840

gagggaccta cagatgcttc ggctctttcc gtgacgctcc ctacgagtgg tcaaactcga    900

gtgatccact gcttgtttcc gtcacaggaa acccttcaaa tagttggcct tcacccactg    960

aaccaagctc caaaaccggt aaccccagac acctacatgt tctgattggg acctcagtgg   1020

tcaaaatccc tttcaccatc ctcctcttct ttctccttca tcgctggtgc tccgacaaaa   1080

aaaatgctgc tgtaatggac caagagcctg cagggaacag aacagtgaac agcgaggatt   1140

ctgatgaaca agaccatcag gaggtgtcat acgcataann nnnnnnnnnn nnnnnnnnnn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnn                                         1346


<210> SEQ ID NO 52
<211> LENGTH: 1368
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
```

<222> LOCATION: (1201)...(1368)
<223> OTHER INFORMATION: n = A,T,C or G

<400> SEQUENCE: 52

```
atgttgctca tggtcatcag catggcgtgt gttgcgttct tctggctgca gggggcctgg      60
ccacatgagg nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnngattc     360
cgcagaaaac cttccctcct ggccctccca ggtcccctgg tgaaatcaga agagacagtc     420
atcctgcaat gttggtcaga tgtcatgttt gagcacttcc ttctgcacag agaggggacg     480
tttaaccaca ctttgcgcct cattggagag cacattgatg ggtctccaa gggcaacttc     540
tccatcggtc gcatgacaca agacctggca gggacctaca gatgctacgg ttctgttact     600
cactccccct atcagttgtc agcgcccagt gaccctctgg acatcgtgat cacaggtcta     660
tatgagaaac cttctctccc agcccagccg ggccccacgg ttctggcagg agagagcgtg     720
accttgtcct gcagctcccg gagctcctat gacatgtacc atctatccag ggaaggggag     780
gcccatgaac gtaggctccc tgcagggccc aaggtcaaca gaacattcca ggccgactct     840
cctctggacc ctgccaccca cggaggggcc tacagatgct tcggctcttt ccgtgactct     900
ccatacgagt ggtcaaagtc gagtgaccca ctgcttgttt ctgtcacagg aaactcttca     960
aatagttggc cttcacccac tgaaccaagc tccgaaaccg gtaaccccag acacctacac    1020
gttctgattg ggacctcagt ggtcaaactc cctttcacca tcctcctctt ctttctcctt    1080
catcgctggt gctccaacaa aaaaaatgca tctgtaatgg accaagggcc tgcggggaac    1140
agaacagtga acagcgagga ttctgatgaa caggaccatc aggaggtgtc gtacgcataa    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnn                1368
```

<210> SEQ ID NO 53
<211> LENGTH: 1368
<212> TYPE: DNA
<213> ORGANISM: Homo sapiens
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1368)
<223> OTHER INFORMATION: n = A,T,C or G

<400> SEQUENCE: 53

```
atgtcgctca tggtcatcag catggcgtgt gttgcgttct tctggctgca gggggcctgg      60
ccacatgagg nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnngattc     360
cgcagaaaac cttccctcct ggccctccca ggtcccctgg tgaaatcaga agagacagtc     420
```

atcctgcaat gttggtcaga tgtcatgttt gagcacttcc ttctgcacag agaggggacg 480
tttaaccaca ctttgcgcct cattggagag cacattgatg ggtctccaa gggcaacttc 540 tccatcggtc gcatgacaca agacctggca gggacctaca gatgctacgg ttctgttact 600
cactccccct atcagttgtc agcgcccagt gaccctctgg acatcgtgat cacaggtcta 660
tatgagaaac cttctctctc agcccagccg ggccccacgg ttctggcagg agagagcgtg 720
accttgtcct gcagctcccg gagctcctat gacatgtacc atctatccag ggaaggggag 780
gcccatgaac gtaggctccc tgcagggccc aaggtcaaca gaacattcca ggccgacttt 840
cctctggacc ctgccaccca cggagggacc tacagatgct tcggctcttt ccgtgactct 900
ccatacgagt ggtcaaagtc gagtgaccca ctgcttgttt ctgtcacagg aaactcttca 960
aatagttggc cttcacccac tgaaccaagc tccgaaaccg gtaaccccag acacctacac 1020
gttctgattg ggacctcagt ggtcaaactc cctttcacca tcctcctctt ctttctcctt 1080
catcgctggt gctccaacaa aaaaaatgca tctgtaatgg accaagggcc tgcggggaac 1140
agaacagtga acagcgagga ttctgatgaa caggaccatc aggaggtgtc gtacgcataa 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnn 1368

<210> SEQ ID NO 54
<211> LENGTH: 1368
<212> TYPE: DNA
<213> ORGANISM: Homo sapiens
<220> FEATURE:
<221> NAME/KEY: misc_feature
<222> LOCATION: (1)...(16)
<223> OTHER INFORMATION: n = A,T,C or G
<220> FEATURE:
<221> NAME/KEY: misc_feature
<222> LOCATION: (71)...(355)
<223> OTHER INFORMATION: n = A,T,C or G
<220> FEATURE:
<221> NAME/KEY: misc_feature
<222> LOCATION: (1201)...(1368)
<223> OTHER INFORMATION: n = A,T,C or G

<400> SEQUENCE: 54
nnnnnnnnnn nnnnnntcag catggcgtgt gttgcgttct tctggctgca gggggcctgg 60
ccacatgagg nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnnnnnn 180
nnnnnnnnnn nnnnnnnnnn nnnnnnnnnn nnnnnnnnnn nnnnnnnnnn nnnnnnnnnn 240
nnnnnnnnnn nnnnnnnnnn nnnnnnnnnn nnnnnnnnnn nnnnnnnnnn nnnnnnnnnn 300
nnnnnnnnnn nnnnnnnnnn nnnnnnnnnn nnnnnnnnnn nnnnnnnnnn nnnnngattc 360
cgcagaaaac cttccctcct ggccctccca ggtcccctgg tgaaatcaga agagacagtc 420
atcctgcaat gttggtcaga tgtcatgttt gagcacttcc ttctgcacag agaggggacg 480
tttaaccaca ctttgcgcct cattggagag cacattgatg ggtctccaa gggcaacttc 540 tccatcggtc gcatgacaca agacctggca gggacctaca gatgctacgg ttctgttact 600
cactccccct atcagttgtc agctcccagt gaccctctgg acatcgtgat cacaggtcta 660
tatgagaaac cttctctctc agcccagccg ggccccacgg ttctggcagg agagaatgtg 720
accttgtcct gcagctcccg gagctcctat gacatgtacc atctatccag ggaaggggag 780
gcccatgaac gtaggctccc tgcagggccc aaggtcaacg gaacattcca ggccgacttt 840

```
cctctggacc ctgccaccca cggagggacc tacagatgct tcggctcttt ccgtgactct    900

ccatacgagt ggtcaaagtc gagtgaccca ctgcttgttt ctgtcacagg aaactcttca    960

aatagttggc cttcacccac tgaaccaagc tccgaaaccg gtaaccccag acacctacac   1020

gttctgattg ggacctcagt ggtcaaactc cctttcacca tcctcctctt ctttctcctt   1080

catcgctggt gctccaacaa aaaaaatgca tctgtaatgg accaagggcc tgcggggaac   1140

agaacagtga acagcgagga ttctgatgaa caggaccatc aggaggtgtc gtacgcataa   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnnnnn               1368
```

<210> SEQ ID NO 55
<211> LENGTH: 1368
<212> TYPE: DNA
<213> ORGANISM: Homo sapiens
<220> FEATURE:
<221> NAME/KEY: misc_feature
<222> LOCATION: (1336)...(1368)
<223> OTHER INFORMATION: n = A,T,C or G

<400> SEQUENCE: 55

```
atgtcgctca tggtcgtcag catggcgtgt gttgggttgt tcttggtcca gagggccggt     60

ccacacatgg gtggtcagga caaacccttc ctgtctgcct ggcccagcgc tgtggtgcct    120

cgaggaggac acgtgactct tcggtgtcac tatcgtcata ggtttaacaa tttcatgcta    180

tacaaagaag acagaatcca cattcccatc ttccatggca gaatattcca ggagagcttc    240

aacatgagcc ctgtgaccac agcacatgca gggaactaca catgtcgggg ttcacaccca    300

cactccccca ctgggtggtc ggcacccagc aaccccgtgg tgatcatggt cacaggaaac    360

cacagaaaac cttccctcct ggcccaccca ggtcccctgg tgaaatcagg agagagagtc    420

atcctgcaat gttggtcaga tatcatgttt gagcacttct ttctgcacaa agaggggatc    480

tctaaggacc cctcacgcct cgttggacag atccatgatg ggtctccaa ggccaatttc     540

tccatcggtc ccatgatgct tgcccttgca gggacctaca gatgctacgg ttctgttact    600

cacacccccct atcagttgtc agctcccagt gatcccctgg acatcgtggt cacaggtcca   660

tatgagaaac cttctctctc agcccagccg ggccccaagg ttcaggcagg agagagcgtg    720

accttgtcct gtagctcccg gagctcctat gacatgtacc atctatccag ggagggggga    780

gcccatgaac gtaggctccc tgcagtgcgc aaggtcaaca gaacattcca ggcagatttc    840

cctctgggcc ctgccaccca cggagggacc tacagatgct tcggctcttt ccgtcactct    900

ccctacgagt ggtcagaccc gagtgaccca ctgcttgttt ctgtcacagg aaacccttca    960

agtagttggc cttcacccac agaaccaagc tccaaatctg gtaaccccag acacctgcac   1020

attctgattg ggacctcagt ggtcatcatc ctcttcatcc tcctcctctt ctttctcctt   1080

catctctggt gctccaacaa aaaaaatgct gctgtaatgg accaagagcc tgcagggaac   1140

agaacagcca acagcgagga ctctgatgaa caagaccctg aggaggtgac atacgcacag   1200

ttggatcact gcgttttcac acagagaaaa atcactcgcc cttctcagag gcccaagaca   1260

ccccttacag ataccatctt gtacacggaa cttccaaatg ctaagcccag atccaaagtt   1320

gtctcctgcc catgannnnn nnnnnnnnnn nnnnnnnnnn nnnnnnnn               1368
```

<210> SEQ ID NO 56
<211> LENGTH: 1368

<212> TYPE: DNA
<213> ORGANISM: Homo sapiens
<220> FEATURE:
<221> NAME/KEY: misc_feature
<222> LOCATION: (1)...(81)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 56

```
nnnnnnnnnn nnnnnnnnnn nnnnnnnnnn nnnnnnnnnn nnnnnnnnnn nnnnnnnnnn     60

nnnnnnnnnn nnnnnnnnnn naaacccttc ctgtctgcct ggcccagcgc tgtggtgcct    120

cgaggaggac acgtgactct tcggtgtcac tatcgtcata ggtttaacaa tttcatgcta    180

tacaaagaag acagaatcca cattcccatc ttccatggca gaatattcca ggagagcttc    240

aacatgagcc ctgtgaccac agcacatgca gggaactaca catgtcgggg ttcacaccca    300

cactccccca ctgggtggtc ggcacccagc aaccccgtgg tgatcatggt cacaggaaac    360

cacagaaaac cttccctcct ggcccaccca ggtcccctgg tgaaatcagg agagagagtc    420

atcctgcaat gttggtcaga tatcatgttt gagcacttct ttctgcacaa agaggggatc    480

tctaaggacc cctcacgcct cgttggacag atccatgatg gggtctccaa ggccaatttc    540

tccatcggtc ccatgatgct tgcccttgca gggacctaca gatgctacgg ttctgttact    600

cacacccccct atcagttgtc agctcccagt gatcccctgg acatcgtggt cacgggtcca    660

tatgagaaac cttctctctc agcccagccg ggccccaagg ttcaggcagg agagagcgtg    720

accttgtcct gtagctcccg gagctcctat gacatgtacc atctatccag ggagggggga    780

gcccatgaac gtaggctccc tgcagtgcgc aaggtcaaca gaacattcca ggcagatttc    840

cctctgggcc ctgccaccca cggagggacc tacagatgct tcggctcttt ccgtcactct    900

ccctacgagt ggtcagaccc gagtgaccca ctgcttgttt ctgtcacagg aaacccttca    960

agtagttggc cttcacccac agaaccaagc tccaaatctg gtaaccccag acacctgcac   1020

attctgattg ggacctcagt ggtcatcatc ctcttcatcc tcctcctctt ctttctcctt   1080

catctctggt gctccaacaa aaaaaatgct gctgtaatgg accaggagcc tgcagggaac   1140

agaacagcca acagcgagga ctctgatgaa caagaccctg aggaggtgac atacgcacag   1200

ttggatcact gcgttttcac acagagaaaa atcactcgcc cttctcagag gcccaagaca   1260

ccccttacag ataccatctt gtacacggaa cttccaaatg ctaagcccag atccaaagtt   1320

gtctcctgcc catganannnn nnnnnnnnnn nnnnnnnnnn nnnnnnnn              1368
```

<210> SEQ ID NO 57
<211> LENGTH: 1368
<212> TYPE: DNA
<213> ORGANISM: Homo sapiens
<220> FEATURE:
<221> NAME/KEY: misc_feature
<222> LOCATION: (1336)...(1368)
<223> OTHER INFORMATION: n = A,T,C or G

<400> SEQUENCE: 57

```
atgttgctca tggtcgtcag catggcgtgt gttgggttct tcttggtcca gagggccggt     60

ccacacgtgg gtggtcagga caagcccttc ctgtctgcct ggcccagcgc tgtggtgcct    120

cgaggaggac acgtgactct tcggtgtcac tatcgtcata ggtttaacaa tttcatgcta    180

tacaaagaag acagaatcca cgttcccatc ttccatggca gattattcca ggagagcttc    240

aacatgagcc ctgtgaccac agcacatgca gggaactaca catgtcgggg ttcacaccca    300
```

cactccccca ctgggtggtc ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg ggtctccaa ggccaatttc 540 tccatcggtc ccatgatgct tgcccttgca gggacctaca gatgctacgg ttctgttact 600
cacaccccct atcagttgtc agctcccagt gatcccctgg acatcgtggt cacaggtcca 660
tatgagaaac cttctctctc agcccagccg ggccccaagg ttcaggcagg agagagcgtg 720
accttgtcct gcagctcccg gagctcctat gacatgtacc atctatccag ggagcgggga 780
gcccatgaac gtaggctccc tgcagtgcgc aaggtcaaca gaacattcca ggcagatttc 840
cctctgggcc ctgccaccca cggagggacc tacagatgct tcggctcttt ccgtcactct 900
ccctacgagt ggtcagaccc gagtgaccca ctgcttgttt ctgtcacagg aaacccttca 960
agtagttggc cttcacccac agaaccaagc tccaaatctg gtaaccccag acacctgcac 1020
attctgattg ggacctcagt ggtcatcatc ctcttcatcc tcctcctctt ctttctcctt 1080
catctctggt gctccaacaa aaaaaatgct gctgtaatgg accaggagcc tgcagggaac 1140
agaacagcca acagcgagga ctctgatgaa caagaccctg aggaggtgac atacgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 58
<211> LENGTH: 1368
<212> TYPE: DNA
<213> ORGANISM: Homo sapiens
<220> FEATURE:
<221> NAME/KEY: misc_feature
<222> LOCATION: (1336)...(1368)
<223> OTHER INFORMATION: n = A,T,C or G

<400> SEQUENCE: 58
atgttgctca tggtcgtcag catggcgtgt gttgggttct tcttggtcca gagggccggt 60
ccacacgtgg gtggtcagga caagcccttc ctgtctgcct ggcccagcgc tgtggtgcct 120
cgaggaggac acgtgactct tcggtgtcac tatcgtcata ggtttaacaa tttcatgcta 180
tacaaagaag acagaatcca cgttcccatc ttccatggca gattattcca ggagagcttc 240
aacatgagcc ctgtgaccac agcacatgca gggaactaca catgtcgggg ttcacaccca 300
cactccccca ctgggtggtc ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg ggtctccaa ggccaatttc 540 tccatcggtc ccatgatgct tgcccttgca gggacctaca gatgctacgg ttctgttact 600
cacaccccct atcagttgtc agctcccagt gatcccctgg acatcgtggt cacaggtcca 660
tatgagaaac cttctctctc agcccagccg ggccccaagg ttcaggcagg agagagcgtg 720
accttgtcct gcagctcccg gagctcctat gacatgtacc atctatccag ggaggggga 780 gcccatgaac gtaggctccc tgcagtgcgc aaggtcaaca gaacattcca ggcagatttc 840
cctctgggcc ctgccaccca cggagggacc tacagatgct tcggctcttt ccgtcactct 900
ccctacgagt ggtcagaccc gagtgaccca ctgcttgttt ctgtcacagg aaacccttca 960
agtagttggc cttcacccac agaaccaagc tccaaatgtg gtaaccccag acacctgcac 1020
attctgattg ggacctcagt ggtcatcatc ctcttcatcc tcctcctctt ctttctcctt 1080
catctctggt gctccaacaa aaaaaatgct gctgtaatgg accaggagcc tgcagggaac 1140
agaacagcca acagcgagga ctctgatgaa caagaccctg aggaggtgac atacgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 59
<211> LENGTH: 1368
<212> TYPE: DNA
<213> ORGANISM: Homo sapiens
<220> FEATURE:
<221> NAME/KEY: misc_feature
<222> LOCATION: (1)...(81)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 59
nnnnnnnnnn nnnnnnnnnn nnnnnnnnnn nnnnnnnnnn nnnnnnnnnn nnnnnnnnnn 60
nnnnnnnnnn nnnnnnnnnn naaacccttc ctgtctgcct ggcccagcgc tgtggtgcct 120
cgaggaggac acgtgactct tcggtgtcac tatcatcata ggtttaacaa tttcatgcta 180
tacaaagaag acggaatcca cattcccatc ttccatggca gaatattcca ggagagcttc 240
aacatgagcc ctgtgaccac agcacatgca gggaactaca catgtcgggg ttcacaccca 300
cactccccca ctgggtggtt ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg ggtctccaa ggccaatttc 540 tccatcggtc ccatgatgct tgcccttgca gggacctaca gatgctacgg ttctgttact 600
cacacctcct atcagttgtc agctcccagt gatcccctgg acatcgtggt cacaggtcca 660
tatgagaaac cttctctctc agcccagccg ggccccaagg ttcaggcagg agagagcgtg 720
accttgtcct gtagctcccg gagctcctat gacatgtacc atctatccag ggaggggga 780 gcccatgaac gtaggctccc tgcagtgcgc aaggtcaaca gaacattcca ggcagatttc 840
cctctgggcc ctgccaccca cggagggacc tacagatgct ttggctcttt ccgtcactct 900
ccctacgagt tgtcagaccc gagtgaccca ctgcttgttt ctgtcacagg aaacccttca 960
agtagttggc cttcacccac agaaccaagc tccaaatctg gtaaccccag acacctgcat 1020
gttctcattg ggacctcagt ggtcatcatc ctcttcatcc tcctcctctt ctttctcctt 1080
catctctggt actccaacaa aaaaaatgct gctgtaatgg accaagagcc tgcagggaac 1140
agaacagcca acagcgagga ttctgatgaa caagaccctc aggaggtgac atacgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 60
<211> LENGTH: 1368

<212> TYPE: DNA
<213> ORGANISM: Homo sapiens
<220> FEATURE:
<221> NAME/KEY: misc_feature
<222> LOCATION: (1)...(81)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 60
nnnnnnnnnn nnnnnnnnnn nnnnnnnnnn nnnnnnnnnn nnnnnnnnnn nnnnnnnnnn 60
nnnnnnnnnn nnnnnnnnnn naaacccttc ctgtctgcct ggcccagcgc tgtggtgcct 120
cgaggaggac acgtgactct tcggtgtcac tatcatcata ggtttaacaa tttcatgcta 180
tacaaagaag acggaatcca cattcccatc ttccatggca gaatattcca ggagagcttc 240
aacatgagcc ctgtgaccac agcacatgca gggaactaca catgtcgggg ttcacaccca 300
cactccccca ctgggtggtt ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg gggtctccaa ggccaatttc 540
tccatcggtc ccatgatgct tgcccttgca gggacctaca gatgctacgg ttctgttact 600
cacacctcct atcagttgtc agctcccagt gatcccctgg acatcgtggt cacaggtcca 660
tatgagaaac cttctctctc agcccagccg ggccccaagg ttcaggcagg agagagcgtg 720
accttgtcct gtagctcccg gagctcctat gacatgtacc atctatccag ggagggggga 780
gcccatgaac gtaggctccc tgcagtgcgc aaggtcaaca gaacattcca ggcagatttc 840
cctctgggcc ctgccaccca cggagggacc tacagatgct ttggctcttt ccgtcactct 900
ccctacgagt tgtcagaccc gagtgaccca ctgcttgttt ctgtcacagg aaacccttca 960
agtagttggc cttcacccac agaaccaagc tccaaatctg gtaaccccag acacctgcat 1020
gttctcattg ggacctcagt ggtcatcatc ctcttcatcc tcctcctctt ctttctcctt 1080
catctctggt actccaacaa aaaaaatgct gctgtaatgg accaagagcc tgcagggaac 1140
agaacagcca acagcgagga ctctgatgaa caagaccctc aggaggtgac atacgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 61
<211> LENGTH: 1368
<212> TYPE: DNA
<213> ORGANISM: Homo sapiens
<220> FEATURE:
<221> NAME/KEY: misc_feature
<222> LOCATION: (1)...(81)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 61
nnnnnnnnnn nnnnnnnnnn nnnnnnnnnn nnnnnnnnnn nnnnnnnnnn nnnnnnnnnn 60
nnnnnnnnnn nnnnnnnnnn naaacccttc ctgtctgcct ggcccagcgc tgtggtgcct 120
cgaggaggac acgtgactct tcggtgtcac tatcgtcata ggtttaacaa tttcatgcta 180
tacaaagaag acagaatcca cattcccatc ttccatggca gaatattcca ggagagcttc 240
aacatgagcc ctgtgaccac agcacatgca gggaactaca catgtcgggg ttcacaccca 300
cactccccca ctgggtggtc ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg ggtctccaa ggccaatttc 540 tccatcggtc ccatgatgct tgcccttgca gggacctaca gatgctacgg ttctgttact 600
cacacctcct atcagttgtc agctcccagt gatcccctgg acatcgtggt cacaggtcca 660
tatgagaaac cttctctctc agcccagccg ggccccaagg ttcaggcagg agagagcgtg 720
accttgtcct gtagctcccg gagctcctat gacatgtacc atctatccag ggagggggga 780
gcccatgaac gtaggctccc tgcagtgcgc aaggtcaaca gaacattcca ggcagatttc 840
cctctgggcc ctgccaccca cggagggacc tacagatgct ttggctcttt ccgtcactct 900
ccctacgagt tgtcagaccc gagtgaccca ctgcttgttt ctgtcacagg aaacccttca 960
agtagttggc cttcacccac agaaccaagc tccaaatctg gtaaccccag acacctgcac 1020
attctgattg ggacctcagt ggtcatcatc ctcttcatcc tcctcctctt ctttctcctt 1080
catctctggt gctccaacaa aaaaaatgct gctgtaatgg accaagagcc tgcagggaac 1140
agaacagcca acagcgagga ctctgatgaa caagaccctg aggaggtgac atacgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 62
<211> LENGTH: 1368
<212> TYPE: DNA
<213> ORGANISM: Homo sapiens
<220> FEATURE:
<221> NAME/KEY: misc_feature
<222> LOCATION: (1)...(81)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 62
nnnnnnnnnn nnnnnnnnnn nnnnnnnnnn nnnnnnnnnn nnnnnnnnnn nnnnnnnnnn 60
nnnnnnnnnn nnnnnnnnnn naagcccttc ctgtctgcct ggcccagcgc tgtggtgcct 120
cgaggaggac acgtgactct tcggtgtcac tatcgtcata ggtttaacaa tttcatgcta 180
tacaaagaag acagaatcca cgttcccatc ttccatggca gattattcca ggagagcttc 240
aacatgagcc ctgtgaccac agcacatgca gggaactaca catgtcgggg ttcacaccca 300
cactccccca ctgggtggtc ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg ggtctccaa ggccaatttc 540 tccattggtc ccatgatgct tgcccttgca gggacctaca gatgctacgg ttctgttact 600 cacacccccct atcagttgtc agctcccagt gatcccctgg acatcgtggt cacaggtcca 660
tatgagaaac cttctctctc agcccagccg ggccccaagg ttcaggcagg agagagcgtg 720
accttgtcct gtagctcccg gagctcctat gacatgtacc atctatccag ggaggggga 780 gcccatgaac gtaggctccc tgcagtgcgc aaggtcaaca gaacattcca ggcagatttc 840
cctctgggcc ctgccaccca cggagggacc tacagatgct tcggctcttt ctgtcactct 900
ccctacgagt tgtcagaccc gagtgaccca ctgcttgttt ctgtcacagg aaacccttca 960
agtagttggc cttcacccac agaaccaagc tccaaatctg gtaaccccag acacctgcac 1020
attctgattg ggacctcagt ggtcatcatc ctcttcatcc tcctcctctt ctttctcctt 1080
catctctggt gctccaacaa aaaaaatgct gctgtaatgg accaagagcc tgcagggaac 1140
agaacagcca acagcgagga ctctgatgaa caagaccctg aggaggtgac atacgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 63
<211> LENGTH: 1368
<212> TYPE: DNA
<213> ORGANISM: Homo sapiens
<220> FEATURE:
<221> NAME/KEY: misc_feature
<222> LOCATION: (1336)...(1368)
<223> OTHER INFORMATION: n = A,T,C or G

<400> SEQUENCE: 63
atgttgctca tggtcgtcag catggcgtgt gttgggttct tcttggtcca gagggccggt 60
ccacacgtgg gtggtcagga caagcccttc ctgtctgcct ggcccagcgc tgtggtgcct 120
cgaggaggac acgtgactct tcggtgtcac tatcgtcata ggtttaacaa tttcatgcta 180
tacaaagaag acagaatcca cgttcccatc ttccatggca gattattcca ggagagcttc 240
aacatgagcc ctgtgaccac agcacatgca gggaactaca catgtcgggg ttcacaccca 300
cactccccca ctgggtggtc ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg ggtctccaa ggccaatttc 540 tccatcggtc ccatgatgct tgcccttgca gggacctaca gatgctacgg ttctgttact 600 cacacccct atcagttgtc agctcccagt gatcccctgg acatcgtggt cacaggtcca 660
tatgagaaac cttctctctc agcccagccg ggccccaagg ttcaggcagg agagagcgtg 720
accttgtcct gtagctcccg gagctcctat gacatgtacc atctatccag ggaggggga 780 gcccatgaac gtaggctccc tgcagtgcgc aaggtcaaca gaacattcca ggcagatttc 840
cctctgggcc ctgccaccca cggagggacc tacagatgct tcggctcttt ccgtcactct 900
ccctacgagt ggtcagaccc gagtgaccca ctgcttgttt ctgtcacagg aaacccttca 960
agtagttggc cttcacccac agaaccaagc tccaaatctg gtaaccccag acacctgcac 1020
gttctgattg ggacctcagt ggtcatcatc ctcttcatcc tcctcctctt ctttctcctt 1080
catctctggt gctccaacaa aaaaaatgct gctgtaatgg accaagagcc tgcagggaac 1140
agaacagcca acagcgagga ctctgatgaa caagaccctc aggaggtgac atatgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 64
<211> LENGTH: 1368
<212> TYPE: DNA
<213> ORGANISM: Homo sapiens
<220> FEATURE:
<221> NAME/KEY: misc_feature
<222> LOCATION: (1336)...(1368)
<223> OTHER INFORMATION: n = A,T,C or G

<400> SEQUENCE: 64
atgttgctca tggtcgtcag catggcgtgt gttgggttct tcttggtcca gagggccggt 60
ccacacgtgg gtggtcagga caagcccttc ctgtctgcct ggcccagcgc tgtggtgcct 120
cgaggaggac acgtgactct tcggtgtcac tatcatcata ggtttaacaa tttcatgcta 180
tacaaagaag acagaatcca cgttcccatc ttccatggca gattattcca ggagagcttc 240
aacatgagcc ctgtgaccac agcacatgca gggaactaca catgtcgggg ttcacaccca 300
cactccccca ctgggtggtc ggcacccagc aaccccgtgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg gggtctccaa ggccaatttc 540
tccatcggtc ccatgatgct tgcccttgca gggacctaca gatgctacgg ttctgttact 600 cacacccccct atcagttgtc agctcccagt gatcccctgg acatcgtggt cacaggtcca 660
tatgagaaac cttctctctc agcccagccg ggccccaagg ttcaggcagg agagagcgtg 720
accttgtcct gtagctcccg gagctcctat gacatgtacc atctatccag ggagggggga 780
gcccatgaac gtaggctccc tgcagtgcgc aaggtcaaca gaacattcca ggcagatttc 840
cctctgggcc ctgccaccca cggagggacc tacagatgct tcggctcttt ccgtcactct 900
ccctacgagt ggtcagaccc gagtgaccca ctgcttgttt ctgtcacagg aaacccttca 960
agtagttggc cttcacccac agaaccaagc tccaaatctg gtaaccccag acacctgcac 1020
attctgattg ggacctcagt ggtcatcatc ctcttcatcc tcctcctctt ctttctcctt 1080
catctctggt gctccaacaa aaaaaatgct gctgtaatgg accaagagcc tgcagggaac 1140
agaacagcca acagcgagga ctctgatgaa caagaccctg aggaggtgac atacgcacag 1200
ttggatcact gcgttttcac acagagaaaa atcactcgcc cttctcagag gcccaagaca 1260
ccccttacag ataccatctt gtacacggaa cttccaaatg ctaagcccag atccaaagtt 1320
gtctcctgcc catgannnnn nnnnnnnnnn nnnnnnnnnn nnnnnnnn 1368

<210> SEQ ID NO 65
<211> LENGTH: 1368
<212> TYPE: DNA
<213> ORGANISM: Homo sapiens
<220> FEATURE:
<221> NAME/KEY: misc_feature
<222> LOCATION: (1)...(51)
<223> OTHER INFORMATION: n = A,T,C or G
<220> FEATURE:
<221> NAME/KEY: misc_feature
<222> LOCATION: (1336)...(1368)
<223> OTHER INFORMATION: n = A,T,C or G

<400> SEQUENCE: 65
nnnnnnnnnn nnnnnnnnnn nnnnnnnnnn nnnnnnnnnn nnnnnnnnnn nagggccggt 60
ccacacatgg gtggtcagga caagcccttc ctgtctgcct ggcccagcgc tgtggtgcct 120
cgcggaggac acgtgactct tcggtgtcac tatcgtcata ggtttaacaa tttcatgcta 180

-continued

| | |
|---|---|
| tacaaagaag acagaatcca cgttcccatc ttccatggca gaatattcca ggagggcttc | 240 |
| aacatgagcc ctgtgaccac agcacatgca gggaactaca catgtcgggg ttcacaccca | 300 |
| cactccccca ctgggtggtc ggcacccagc aaccccatgg tgatcatggt cacaggaaac | 360 |
| cacagaaaac cttccctcct ggcccaccca ggtcccctgg tgaaatcagg agagagagtc | 420 |
| atcctgcaat gttggtcaga tatcatgttt gagcacttct ttctgcacaa agaggggatc | 480 |
| tctaaggacc cctcacgcct cgttggacag atccatgatg gggtctccaa ggccaatttc | 540 |
| tccatcggtc ccatgatgct tgcccttgca gggacctaca gatgctacgg ttctgttact | 600 |
| cacacccct atcagttgtc agctcccagt gatcccctgg acatcgtggt cacaggtcca | 660 |
| tatgagaaac cttctctctc agcccagccg ggccccaagg ttcaggcagg agagagcgtg | 720 |
| accttgtcct gtagctcccg gagctcctat gacatgtacc atctatccag ggaggggga | 780 |
| gcccatgaac gtaggctccc tgcagtgcgc aaggtcaaca gaacattcca ggcagatttc | 840 |
| cctctgggcc ctgccaccca cggagggacc tacagatgct tcggctcttt ccgtcactct | 900 |
| ccctacgagt ggtcagaccc gagtgaccca ctgcttgttt ctgtcacagg aaacccttca | 960 |
| agtagttggc cttcacccac agaaccaagc tccaaatctg gtaaccccag acacctgcac | 1020 |
| attctgattg ggacctcagt ggtcatcatc ctcttcatcc tcctcctctt ctttctcctt | 1080 |
| catctctggt gctccaacaa aaaaaatgct gctgtaatgg accaagagcc tgcagggaac | 1140 |
| agaacagcca acagcgagga ctctgatgaa caagaccctg aggaggtgac atacgcacag | 1200 |
| ttggatcact gcgttttcac acagagaaaa atcactcgcc cttctcagag gcccaagaca | 1260 |
| ccccttacag ataccatctt gtacacggaa cttccaaatg ctaagcccag atccaaagtt | 1320 |
| gtctcctgcc catgannnnn nnnnnnnnnn nnnnnnnnnn nnnnnnnn | 1368 |

<210> SEQ ID NO 66
<211> LENGTH: 1368
<212> TYPE: DNA
<213> ORGANISM: Homo sapiens

<400> SEQUENCE: 66

| | |
|---|---|
| atgtcgctca cggtcgtcag catggcgtgc gttgggttct tcttgctgca ggggcctgg | 60 |
| ccactcatgg gtggtcagga caaacccttc ctgtctgccc ggcccagcac tgtggtgcct | 120 |
| cgaggaggac acgtggctct tcagtgtcac tatcgtcgtg ggtttaacaa tttcatgctg | 180 |
| tacaaagaag acagaagcca cgttcccatc ttccacggca gaatattcca ggagagcttc | 240 |
| atcatgggcc ctgtgacccc agcacatgca gggacctaca gatgtcgggg ttcacgccca | 300 |
| cactccctca ctgggtggtc ggcacccagc aaccccctgg tgatcatggt cacaggaaac | 360 |
| cacagaaaac cttccctcct ggcccaccca gggcccctgc tgaaatcagg agagacagtc | 420 |
| atcctgcaat gttggtcaga tgtcatgttt gagcacttct ttctgcacag agggggatc | 480 |
| tctgaggacc cctcacgcct cgttggacag atccatgatg gggtctccaa ggccaacttc | 540 |
| tccatcggtc ccttgatgcc tgtccttgca ggaacctaca gatgttatgg ttctgttcct | 600 |
| cactccccct atcagttgtc agctcccagt gaccccctgg acatcgtgat cacaggtcta | 660 |
| tatgagaaac cttctctctc agcccagccg ggcccacggg ttcaggcagg agagaacgtg | 720 |
| accttgtcct gtagctcctg gagctcctat gacatctacc atctgtccag ggaagggag | 780 |
| gcccatgaac gtaggctccg tgcagtgccc aaggtcaaca gaacattcca ggcagactt | 840 |
| cctctgggcc ctgccaccca cggagggacc tacagatgct tcggctcttt ccgtgccctg | 900 |
| ccctgcgtgt ggtcaaactc aagtgaccca ctgcttgttt ctgtcacagg aaacccttca | 960 |

-continued

```
agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgac gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                1368
```

<210> SEQ ID NO 67
<211> LENGTH: 1366
<212> TYPE: DNA
<213> ORGANISM: Homo sapiens
<220> FEATURE:
<221> NAME/KEY: misc_feature
<222> LOCATION: (1165)...(1366)
<223> OTHER INFORMATION: n = A,T,C or G

<400> SEQUENCE: 67

```
atgtcgctca tggtcgtcag catggcgtgt gttgggttgt tcttggtcca gagggccggt     60

ccacacatgg gtggtcagga caagcccttc ctgtctgcct ggcccagcgc tgtggtgcct    120

cgcggaggac acgtgactct tcggtgtcac tatcgtcata ggtttaacaa tttcatgcta    180

tacaaagaag acagaatcca cgttcccatc ttccatggca gaatattcca ggagggcttc    240

aacatgagcc ctgtgaccac agcacatgca gggaactaca catgtcgggg ttcacaccca    300

cactccccca ctgggtggtc ggcacccagc aaccccatgg tgatcatggt cacaggaaac    360

cacagaaaac cttccctcct ggcccaccca ggtcccctgg tgaaatcagg agagagagtc    420

atcctgcaat gttggtcaga tatcatgttt gagcacttct ttctgcacaa agagtggatc    480

tctaaggacc cctcacgcct cgttggacag atccatgatg gggtctccaa ggccaatttc    540

tccatcggtt ccatgatgct tgcccttgca gggacctaca gatgctacgg ttctgttact    600

cacacccccct atcagttgtc agctcccagt gatcccctgg acatcgtggt cacaggtcta   660

tatgagaaac cttctctctc agcccagccg ggccccaagg ttcaggcagg agagagcgtg    720

accttgtcct gtagctcccg gagctcctat gacatgtacc atctatccag ggagggggga    780

gcccatgaac gtaggctccc tgcagtgcgc aaggtcaaca gaacattcca ggcagatttc    840

cctctgggcc ctgccaccca cggagggacc tacagatgct tcggctcttt ccgtcactct    900

ccctacgagt ggtcagaccc gagtgaccca ctgcttgttt ctgtcacagg aaacccttca    960

agtagttggc cttcacccac agaaccaagc tccaaatctg gtaacctcag acacctgcac   1020

attctgattg ggacctcagt ggtcaaaatc cctttcacca tcctcctctt ctttctcctt   1080

catcgctggt gctccaacaa aaaaaatgct gctgtaatgg accaagagcc tgcagggaac   1140

agaagtgaac agcgaggatt ctgannnnnn nnnnnnnnnn nnnnnnnnnn nnnnnnnnnn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnnn                  1366
```

<210> SEQ ID NO 68
<211> LENGTH: 1367
<212> TYPE: DNA
<213> ORGANISM: Homo sapiens
<220> FEATURE:
<221> NAME/KEY: misc_feature
<222> LOCATION: (1150)...(1367)
<223> OTHER INFORMATION: n = A,T,C or G

<400> SEQUENCE: 68
atgtcgctca tggtcgtcag catggcgtgt gttgggttgt tcttggtcca gagggccggt 60
ccacacatgg gtggtcagga caagcccttc ctgtctgcct ggcccagcgc tgtggtgcct 120
cgcggaggac acgtgactct tcggtgtcac tatcgtcata ggtttaacaa tttcatgcta 180
tacaaagaag acagaatcca cgttcccatc ttccatggca gaatattcca ggagggcttc 240
aacatgagcc ctgtgaccac agcacatgca gggaactaca catgtcgggg ttcacaccca 300
cactccccca ctgggtggtc ggcacccagc aaccccatgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agagtggatc 480
tctaaggacc cctcacgcct cgttggacag atccatgatg ggtctccaa ggccaatttc 540 tccatcggtt ccatgatgct tgcccttgca gggacctaca gatgctacgg ttctgttact 600 cacacccccct atcagttgtc agctcccagt gatcccctgg acatcgtggt cacaggtcta 660
tatgagaaac cttctctctc accgcagccg ggccccaagg ttcaggcagg agagagcgtg 720
accttgtcct gtagctcccg gagctcctat gacatgtacc atctatccag ggagggggga 780
gcccatgaac gtaggctccc tgcagtgcgc aaggtcaaca gaacattcca ggcagatttc 840
cctctgggcc ctgccaccca cggagggacc tacagatgct tcggctcttt ccgtcactct 900
ccctacgagt ggtcagaccc gagtgaccca ctgcttgttt ctgtcacagg aaacccttca 960
agtagttggc cttcacccac agaaccaagc tccaaatctg gtaacctcag acacctgcac 1020
attctgattg ggacctcagt ggtcaaaatc cctttcacca tcctcctctt ctttctcctt 1080
catcgctggt gctccaacaa aaaaaaatgc tgctgtaatg gaccaagagc ctgcagggaa 1140
cagaagtgan nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnn 1367

<210> SEQ ID NO 69
<211> LENGTH: 1367
<212> TYPE: DNA
<213> ORGANISM: Homo sapiens
<220> FEATURE:
<221> NAME/KEY: misc_feature
<222> LOCATION: (1150)...(1367)
<223> OTHER INFORMATION: n = A,T,C or G

<400> SEQUENCE: 69
atgtcgctca tggtcgtcag catggcgtgt gttgggttgt tcttggtcca gagggccggt 60
ccacacatgg gtggtcagga caagcccttc ctgtctgcct ggcccagcgc tgtggtgcct 120
cgcggaggac acgtgactct tcggtgtcac tatcgtcata ggtttaacaa tttcatgcta 180
tacaaagaag acagaatcca cgttcccatc ttccatggca gaatattcca ggagggcttc 240
aacatgagcc ctgtgaccac agcacatgca gggaactaca catgtcgggg ttcacaccca 300
cactccccca ctgggtggtc ggcacccagc aaccccatgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agagtggatc 480
tctaaggacc cctcacacct cgttggacag atccatgatg ggtctccaa ggccaatttc 540

-continued

```
tccatcggtt ccatgatgct tgcccttgca gggacctaca gatgctacgg ttctgttact    600

cacacccccct atcagttgtc agctcccagt gatcccctgg acatcgtggt cacaggtcta    660

tatgagaaac cttctctctc agcccagccg ggccccaagg ttcaggcagg agagagcgtg    720

accttgtcct gtagctcccg gagctcctat gacatgtacc atctatccag ggagggggga    780

gcccatgaac gtaggctccc tgcagtgcgc aaggtcaaca gaacattcca ggcagatttc    840

cctctgggcc ctgccaccca cggagggacc tacagatgct tcggctcttt ccgtcactct    900

ccctacgagt ggtcagaccc gagtgaccca ctgcttgttt ctgtcacagg aaacccttca    960

agtagttggc cttcacccac agaaccaagc tccaaatctg gtaacctcag acacctgcac   1020

attctgattg ggacctcagt ggtcaaaatc cctttcacca tcctcctctt ctttctcctt   1080

catcgctggt gctccaacaa aaaaaaatgc tgctgtaatg gaccaagagc ctgcagggaa   1140

cagaagtgan nnnnnnnnnn nnnnnnnnnn nnnnnnnnnn nnnnnnnnnn nnnnnnnnnn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnnnn                 1367


<210> SEQ ID NO 70
<211> LENGTH: 1367
<212> TYPE: DNA
<213> ORGANISM: Homo sapiens
<220> FEATURE:
<221> NAME/KEY: misc_feature
<222> LOCATION: (1150)...(1367)
<223> OTHER INFORMATION: n = A,T,C or G

<400> SEQUENCE: 70

atgttgctca tggtcgtcag catggcgtgt gttgggttgt tcttggtcca gagggccggt     60

ccacacatgg gtggtcagga caagcccttc ctgtctgcct ggcccagcgc tgtggtgcct    120

cgcggaggac acgtgactct tcggtgtcac tatcgtcata ggtttaacaa tttcatgcta    180

tacaaagaag acagaatcca cgttcccatc ttccatggca gaatattcca ggagggcttc    240

aacatgagcc ctgtgaccac agcacatgca gggaactaca catgtcgggg ttcacaccca    300

cactccccca ctgggtggtc ggcacccagc aaccccatgg tgatcatggt cacaggaaac    360

cacagaaaac cttccctcct ggcccaccca ggtcccctgg tgaaatcagg agagagagtc    420

atcctgcaat gttggtcaga tatcatgttt gagcacttct ttctgcacaa agagtggatc    480

tctaaggacc cctcacgcct cgttggacag atccatgatg gggtctccaa ggccaatttc    540

tccatcggtt ccatgatgct tgcccttgca gggacctaca gatgctacgg ttctgttact    600

cacacccccct atcagttgtc agctcccagt gatcccctgg acatcgtggt cacaggtcta    660

tatgagaaac cttctctctc agcccagccg ggccccaagg ttcaggcagg agagagcgtg    720

accttgtcct gtagctcccg gagctcctat gacatgtacc atctatccag ggagggggga    780

gcccatgaac gtaggctccc tgcagtgcgc aaggtcaaca gaacattcca ggcagatttc    840

cctctgggcc ctgccaccca cggagggacc tacagatgct tcggctcttt ccgtcactct    900

ccctacgagt ggtcagaccc gagtgaccca ctgcttgttt ctgtcacagg aaacccttca    960

agtagttggc cttcacccac agaaccaagc tccaaatctg gtaacctcag acacctgcac   1020

attctgattg ggacctcagt ggtcaaaatc cctttcacca tcctcctctt ctttctcctt   1080

catcgctggt gctccaacaa aaaaaaatgc tgctgtaatg gaccaagagc ctgcagggaa   1140

cagaagtgan nnnnnnnnnn nnnnnnnnnn nnnnnnnnnn nnnnnnnnnn nnnnnnnnnn   1200
```

nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnn 1367

<210> SEQ ID NO 71
<211> LENGTH: 1366
<212> TYPE: DNA
<213> ORGANISM: Homo sapiens
<220> FEATURE:
<221> NAME/KEY: misc_feature
<222> LOCATION: (1)...(51)
<223> OTHER INFORMATION: n = A,T,C or G
<220> FEATURE:
<221> NAME/KEY: misc_feature
<222> LOCATION: (1165)...(1366)
<223> OTHER INFORMATION: n = A,T,C or G

<400> SEQUENCE: 71
nnnnnnnnnn nnnnnnnnnn nnnnnnnnnn nnnnnnnnnn nnnnnnnnnn nagggccggt 60
ccacacatgg gtggtcagga caagcccttc ctgtctgcct ggcccagcgc tgtggtgcct 120
cgaggaggac acgtgactct tcggtgtcac tatcgtcata ggtttaacaa tttcatgcta 180
tacaaagaag acagaatcca cgttcccatc ttccatggca gaatattcca ggagggcttc 240
aacatgagcc ctgtgaccac agcacatgca gggaactaca catgtcgggg ttcacaccca 300
cactccccca ctgggtggtc ggcacccagc aaccccatgg tgatcatggt cacaggaaac 360
cacagaaaac cttccctcct ggcccaccca ggtcccctgg tgaaatcagg agagagagtc 420
atcctgcaat gttggtcaga tatcatgttt gagcacttct ttctgcacaa agaggggatc 480
tctaaggacc cctcacgcct cgttggacag atccatgatg gggtctccaa ggccaatttc 540
tccatcggtt ccatgatgct tgcccttgca gggacctaca gatgctacgg ttctgttact 600
cacaccccct atcagttgtc agctcccagt gatcccctgg acatcgtggt cacaggtcta 660
tatgagaaac cttctctctc agcccagccg ggccccaagg ttcaggcagg agagagcgtg 720
accttgtcct gtagctcccg gagctcctat gacatgtacc atctatccag ggagggggga 780
gcccatgaac gtaggctccc tgcagtgcgc aaggtcaaca gaacattcca ggcagatttc 840
cctctgggcc ctgccaccca cggagggacc tacagatgct tcggctcttt ccgtcactct 900
ccctacgagt ggtcagaccc gagtgaccca ctgcttgttt ctgtcacagg aaacccttca 960
agtagttggc cttcacccac agaaccaagc tccaaatctg gtaacctcag acacctgcac 1020
attctgattg ggacctcagt ggtcaaaatc cctttcacca tcctcctctt ctttctcctt 1080
catcgctggt gctccaacaa aaaaaatgct gctgtaatgg accaagagcc tgcagggaac 1140
agaagtgaac agcgaggatt ctgannnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnn 1366

<210> SEQ ID NO 72
<211> LENGTH: 1368
<212> TYPE: DNA
<213> ORGANISM: Homo sapiens

<400> SEQUENCE: 72
atgtcgctca cggtcgtcag catggcgtgc gttgggttct tcttgctgca gggggcctgg 60
ccactcatgg gtggtcagga caaacccttc ctgtctgccc ggcccagcac tgtggtgcct 120

```
cgaggaggac acgtggctct tcagtgtcac tatcgtcgtg ggtttaacaa tttcatgctg    180
tacaaagaag acagaagcca cgttcccatc ttccacggca gaatattcca ggagagcttc    240
atcatgggcc ctgtgacccc agcacatgca gggacctaca gatgtcgggg ttcacgccca    300
cactccctca ctgggtggtc ggcacccagc aaccccctgg tgatcatggt cacaggaaac    360
cacagaaaac cttccctcct ggcccaccca gggcccctgc tgaaatcagg agagacagtc    420
atcctgcaat gttggtcaga tgtcatgttt gagcacttct ttctgcacag agaggggatc    480
tctgaggacc cctcacgcct cgttggacag atccatgatg ggtctccaa ggccaacttc     540
tccatcggtc ccttgatgcc tgtccttgca ggaacctaca gatgttatgg ttctgttcct    600
cactccccct atcagttgtc agctcccagt gacccccctgg acatcgtgat cacaggtcta   660
tatgagaaac cttctctctc agcccagccg ggccccacgg ttcaggcagg agagaacgtg    720
accttgtcct gtagctcctg gagctcctat gacatctacc atctgtccag ggaaggggag    780
gcccatgaac gtaggctccg tgcagtgccc aaggtcaaca gaacattcca ggcagacttt    840
cctctgggcc ctgccaccca cggagggacc tacagatgct tcggctcttt ccgtgccctg    900
ccctgcgtgt ggtcaaactc aagtgaccca ctgcttgttt ctgtcacagg aaacccttca    960
agtagttggc cttcacccac agaaccaagc tccaaatctg gtatctgcag acacctgcat   1020
gttctgattg ggacctcagt ggtcatcttc ctcttcatcc tcctcctctt ctttctcctt   1080
tatcgctggt gctccaacaa aaagaatgct gctgtaatgg accaagagcc tgcgggggac   1140
agaacagtga ataggcagga ctctgatgaa caagaccctc aggaggtgac gtacgcacag   1200
ttggatcact gcgttttcat acagagaaaa atcagtcgcc cttctcagag gcccaagaca   1260
cccctaacag ataccagcgt gtacacggaa cttccaaatg ctgagcccag atccaaagtt   1320
gtctcctgcc cacgagcacc acagtcaggt cttgaggggg ttttctag                1368
```

```
<210> SEQ ID NO 73
<211> LENGTH: 1368
<212> TYPE: DNA
<213> ORGANISM: Homo sapiens

<400> SEQUENCE: 73
```

```
atgtcgctca cggtcgtcag catggcgtgc gttgggttct tcttgctgca gggggcctgg     60
ccactcatgg gtggtcagga caaacccttc ctgtctgccc ggcccagcac tgtggtgcct    120
cgaggaggac acgtggctct tcagtgtcac tatcgtcgtg ggtttaacaa tttcatgctg    180
tacaaagaag acagaagcca cgttcccatc ttccacggca gaatattcca ggagagcttc    240
atcatgggcc ctgtgacccc agcacatgca gggacctaca gatgtcgggg ttcacgccca    300
cactccctca ctgggtggtc ggcacccagc aaccccctgg tgatcatggt cacaggaaac    360
cacagaaaac cttccctcct ggcccaccca gggcccctgc tgaaatcagg agagacagtc    420
atcctgcaat gttggtcaga tgtcatgttt gagcacttct ttctgcacag agaggggatc    480
tctgaggacc cctcacgcct cgttggacag atccatgatg ggtctccaa ggccaacttc     540
tccatcggtc ccttgatgcc tgtccttgca ggaacctaca gatgttatgg ttctgttcct    600
cactccccct atcagttgtc agctcccagt gacccccctgg acatcgtgat cacaggtcta   660
tatgagaaac cttctctctc agcccagccg ggccccacgg ttcaggcagg agagaacgtg    720
accttgtcct gtagctcctg gagctcctat gacatctacc atctgtccag ggaaggggag    780
gcccatgaac gtaggctccg tgcagtgccc aaggtcaaca gaacattcca ggcagacttt    840
cctctgggcc ctgccaccca cggagggacc tacagatgct tcggctcttt ccgtgccctg    900
```

```
ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgac gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                1368
```

<210> SEQ ID NO 74
<211> LENGTH: 1368
<212> TYPE: DNA
<213> ORGANISM: Homo sapiens

<400> SEQUENCE: 74

```
atgtcgctca ctgtcgtcag catggcgtgc gttgggttct tcttgctgca gggggcctgg     60

ccactcatgg gtggtcagga caaacccttc ctgtctgccc ggcccagcac tgtggtgcct    120

cgaggaggac acgtggctct tcagtgtcac tatcgtcgtg ggtttaacaa tttcatgctg    180

tacaaagaag acagaagcca cgttcccatc ttccacggca gaatattcca ggagagcttc    240

atcatgggcc ctgtgacccc agcacatgca gggacctaca gatgtcgggg ttcacgccca    300

cactccctca ctgggtggtc ggcacccagc aacccccctgg tgatcatggt cacaggaaac    360

cacagaaaac cttccctcct ggcccaccca gggcccctgc tgaaatcagg agagacagtc    420

atcctgcaat gttggtcaga tgtcatgttt gagcacttct ttctgcacag agatgggatc    480

tctgaggacc cctcacgcct cgttggacag atccatgatg ggtctccaa ggccaacttc    540

tccatcggtc ccttgatgcc tgtccttgca ggaacctaca gatgttatgg ttctgttcct    600

cactcccct atcagttgtc agctcccagt gacccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgac gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                1368
```

<210> SEQ ID NO 75
<211> LENGTH: 1368
<212> TYPE: DNA
<213> ORGANISM: Homo sapiens

<400> SEQUENCE: 75

```
atgtcgctca cggtcgtcag catggcgtgc gttgggttct tcttgctgca gggggcctgg     60
```

ccactcatgg gtggtcagga caaacccttc ctgtctgccc ggcccagcac tgtggtgcct 120
cgaggaggac acgtggctct tcagtgtcac tatcgtcgtg ggtttaacaa tttcatgctg 180
tacaaagaag acagaagcca cgttcccatc ttccacggca gaatattcca ggagagcttc 240
atcatgggcc ctgtgacccc agcacatgca gggacctaca gatgtcgggg ttcacgccca 300
cactccctca ctgggtggtc ggcacccagc aaccccgtgg tgatcatggt cacaggaaac 360
cacagaaaac cttccctcct ggcccaccca gggcccctgc tgaaatcagg agagacagtc 420
atcctgcaat gttggtcaga tgtcatgttt gagcacttct ttctgcacag agaggggatc 480
tctgaggacc cctcacgcct cgttggacag atccatgatg ggtctccaa ggccaacttc 540 tccatcggtc ccttgatgcc tgtccttgca ggaacctaca gatgttatgg ttctgttcct 600
cactccccct atcagttgtc agctcccagt gacccccctgg acatcgtgat cacaggtcta 660
tatgagaaac cttctctctc agcccagccg ggccccacgg ttcaggcagg agagaacgtg 720
accttgtcct gtagctcctg gagctcctat gacatctacc atctgtccag ggaaggggag 780
gcccatgaac gtaggctccg tgcagtgccc aaggtcaaca gaacattcca ggcagacttt 840
cctctgggcc ctgccaccca cggagggacc tacagatgct tcggctcttt ccgtgccctg 900
ccctgcgtgt ggtcaaactc aagtgaccca ctgcttgttt ctgtcacagg aaacccttca 960
agtagttggc cttcacccac agaaccaagc tccaaatctg gtatctgcag acacctgcat 1020
gttctgattg ggacctcagt ggtcatcttc ctcttcatcc tcctcctctt ctttctcctt 1080
tatcgctggt gctccaacaa aaagaatgct gctgtaatgg accaagagcc tgcgggggac 1140
agaacagtga ataggcagga ctctgatgaa caagaccctc aggaggtgac gtacgcacag 1200
ttggatcact gcgttttcat acagagaaaa atcagtcgcc cttctcagag gcccaagaca 1260
cccctaacag ataccagcgt gtacacggaa cttccaaatg ctgagcccag atccaaagtt 1320
gtctcctgcc cacgagcacc acagtcaggt cttgaggggg ttttctag 1368

<210> SEQ ID NO 76
<211> LENGTH: 1368
<212> TYPE: DNA
<213> ORGANISM: Homo sapiens

<400> SEQUENCE: 76
atgtcgctca cggtcgtcag catggcgtgc gttgggttct tcttgctgca gggggcctgg 60
ccactcatgg gtggtcagga caaacccttc ctgtctgccc ggcccagcac tgtggtcgct 120
cgaggaggac acgtggctct tcagtgtcac tatcgtcgtg ggtttaacaa tttcatgctg 180
tacaaagaag acagaagcca cgttcccatc ttccacggca gaatattcca ggagagcttc 240
atcatgggcc ctgtgacccc agcacatgca gggacctaca gatgtcgggg ttcacgccca 300
cactccctca ctgggtggtc ggcacccagc aaccccgtgg tgatcatggt cacaggaaac 360
cacagaaaac cttccctcct ggcccaccca gggcccctgc tgaaatcagg agagacagtc 420
atcctgcaat gttggtcaga tgtcatgttt gagcacttct ttctgcacag agaggggatc 480
tctgaggacc cctcacacct cgttggacag atccatgatg ggtctccaa ggccaacttc 540 tccatcggtc ccttgatgcc tgtccttgca ggaacctaca gatgttatgg ttctgttcct 600
cactccccct atcagttgtc agctcccagt gacccccctgg acatcgtgat cacaggtcta 660
tatgagaaac cttctctctc accgcagccg ggccccacgg ttcaggcagg agagaacgtg 720
accttgtcct gtagctcctg gagctcctat gacacctacc atctgtccag ggaaggggag 780
gcccatgaac gtaggctccg tgcagtgccc aaggtcaaca gaacattcca ggcagacttt 840
cctctgggcc ctgccaccca cggagggacc tacagatgct tcggctcttt ccgtgccctg 900
ccctgcgtgt ggtcaaactc aagtgaccca ctgcttgttt ctgtcacagg aaacccttca 960
agtagttggc cttcacccac agaaccaagc tccaaatctg gtatctgcag acacctgcat 1020
gttctgattg ggacctcagt ggtcatcttc ctcttcatcc tcctcctctt ctttctcctt 1080
tatcgctggt gctccaacaa aaagaatgct gctgtaatgg accaagagcc tgcgggggac 1140
agaacagtga ataggcagga ctctgatgaa caagaccctc aggaggtgac gtacgcacag 1200
ttggatcact gcgttttcat acagagaaaa atcagtcgcc cttctcagag gcccaagaca 1260
cccctaacag ataccagcgt gtacacggaa cttccaaatg ctgagcccag atccaaagtt 1320
gtctcctgcc cacgagcacc acagtcaggt cttgaggggg ttttctag 1368

<210> SEQ ID NO 77
<211> LENGTH: 1368
<212> TYPE: DNA
<213> ORGANISM: Homo sapiens

<400> SEQUENCE: 77
atgtcgctca cggtcgtcag catggcgtgc gttgggttct tcttgctgca gggggcctgg 60
ccactcatgg gtggtcagga caaacccttc ctgtctgccc ggcccagcac tgtggtgcct 120
cgaggaggac acgtggctct tcagtgtcac tatcgtcgtg ggtttaacaa tttcatgctg 180
tacaaagaag acagaagcca cgttcccatc ttccacggca gaatattcca ggagagcttc 240
atcatgggcc ctgtgacccc agcacatgca gggacctaca gatgtcgggg ttcacgccca 300
cactccctca ctgggtggtc ggcacccagc aaccccgtgg tgatcatggt cacaggaaac 360
cacagaaaac cttccctcct ggcccaccca gggcccctgc tgaaatcagg agagacagtc 420
atcctgcaat gttggtcaga tgtcatgttt gagcacttct ttctgcacag agaggggatc 480
tctgaggacc cctcacacct cgttggacag atccatgatg gggtctccaa ggccaacttc 540
tccatcggtc ccttgatgcc tgtccttgca ggaacctaca gatgttatgg ttctgttcct 600
cactccccct atcagttgtc agctcccagt gaccccctgg acatcgtgat cacaggtcta 660
tatgagaaac cttctctctc agcccagccg ggccccacgg ttcaggcagg agagaacgtg 720
accttgtcct gtagctcctg gagctcctat gacatctacc atctgtccag ggaaggggag 780
gcccatgaac gtaggctccg tgcagtgccc aaggtcaaca gaacattcca ggcagacttt 840
cctctgggcc ctgccaccca cggagggacc tacagatgct tcggctcttt ccgtgccctg 900
ccctgcgtgt ggtcaaactc aagtgaccca ctgcttgttt ctgtcacagg aaacccttca 960
agtagttggc cttcacccac agaaccaagc tccaaatctg gtatctgcag acacctgcat 1020
gttctgattg ggacctcagt ggtcatcttc ctcttcatcc tcctcctctt ctttctcctt 1080
tatcgctggt gctccaacaa aaagaatgct gctgtaatgg accaagagcc tgcgggggac 1140
agaacagtga ataggcagga ctctgatgaa caagaccctc aggaggtgac gtacgcacag 1200
ttggatcact gcgttttcat acagagaaaa atcagtcgcc cttctcagag gcccaagaca 1260
cccctaacag ataccagcgt gtacacggaa cttccaaatg ctgagcccag atccaaagtt 1320
gtctcctgcc cacgagcacc acagtcaggt cttgaggggg ttttctag 1368

<210> SEQ ID NO 78
<211> LENGTH: 1368
<212> TYPE: DNA
<213> ORGANISM: Homo sapiens
<220> FEATURE:
<221> NAME/KEY: misc_feature
<222> LOCATION: (1)...(81)
<223> OTHER INFORMATION: n = A,T,C or G

<400> SEQUENCE: 78

```
nnnnnnnnnn nnnnnnnnnn nnnnnnnnnn nnnnnnnnnn nnnnnnnnnn nnnnnnnnnn     60
nnnnnnnnnn nnnnnnnnnn naaacccttc ctgtctgccc ggcccagcac tgtggtgcct    120
cgaggaggac acgtggctct tcagtgtcac tatcgtcgtg ggtttaacaa tttcatgctg    180
tacaaagaag acagaagcca cgttcccatc ttccacggca gaatattcca ggagagcttc    240
atcatgggcc ctgtgacccc agcacatgca gggacctaca gatgtcgggg ttcacgccca    300
cactccctca ctgggtggtc gacacccagc aaccccctgg tgatcatggt cacaggaaac    360
cacagaaaac cttccctcct ggcccaccca gggcccctgc tgaaatcagg agagacagtc    420
atcctgcaat gttggtcaga tgtcatgttt gagcacttct ttctgcacag agaggggatc    480
tctgaggacc cctcacgcct cgttggacag atccatgatg gggtctccaa ggccaacttc    540
tccatcggtc ccttgatgcc tgtccttgca ggaacctaca gatgttatgg ttctgttcct    600
cactccccct atcagttgtc agctcccagt gacccccctgg acatcgtgat cacaggtcta    660
tatgagaaac cttctctctc agcccagccg ggccccacgg ttcaggcagg agagaacgtg    720
accttgtcct gtagctcctg gagctcctat gacatctacc atctgtccag ggaaggggag    780
gcccatgaac gtaggctccg tgcagtgccc aaggtcaaca gaacattcca ggcagacttt    840
cctctgggcc ctgccaccca cggagggacc tacagatgct tcggctcttt ccgtgccctg    900
ccctgcgtgt ggtcaaactc aagtgaccca ctgcttgttt ctgtcacagg aaacccttca    960
agtagttggc cttcacccac agaaccaagc tccaaatctg gtatctgcag acacctgcat   1020
gttctgattg ggacctcagt ggtcatcttc ctcttcatcc tcctcctctt ctttctcctt   1080
tatcgctggt gctccaacaa aaagaatgct gctgtaatgg accaagagcc tgcgggggac   1140
agaacagtga ataggcagga ctctgatgaa caagaccctc aggaggtgac gtacgcacag   1200
ttggatcact gcgttttcat acagagaaaa atcagtcgcc cttctcagag gcccaagaca   1260
cccctaacag ataccagcgt gtacacggaa cttccaaatg ctgagcccag atccaaagtt   1320
gtctcctgcc cacgagcacc acagtcaggt cttgaggggg ttttctag                1368
```

<210> SEQ ID NO 79
<211> LENGTH: 1368
<212> TYPE: DNA
<213> ORGANISM: Homo sapiens
<220> FEATURE:
<221> NAME/KEY: misc_feature
<222> LOCATION: (1)...(81)
<223> OTHER INFORMATION: n = A,T,C or G

<400> SEQUENCE: 79

```
nnnnnnnnnn nnnnnnnnnn nnnnnnnnnn nnnnnnnnnn nnnnnnnnnn nnnnnnnnnn     60
nnnnnnnnnn nnnnnnnnnn naaacccttc ctgtctgccc ggcccagcac tgtggtgcct    120
cgaggaggac acgtggctct tcagtgtcac tatcgtcgtg ggtttaacaa tttcatgctg    180
tacaaagaag acagaagcca cgttcccatc ttccacggca gaatattcca ggagagcttc    240
atcatgggcc ctgtgacccc agcacatgca gggacctaca gatgtcgggg ttcacgccca    300
cactccctca ctgggtggtc gacacccagc aaccccctgg tgatcatggt cacaggaaac    360
cacagaaaac cttccctcct ggcccaccca gggcccctgc tgaaatcagg agagacagtc    420
atcctgcaat gttggtcaga tgtcatgttt gagcacttct ttctgcacag agaggggatc    480
tctgaggacc cctcacgcct cgttggacag atccatgatg gggtctccaa ggccaacttc    540
```

```
tccatcggtc ccttgatgcc tgtccttgca ggaacctaca gatgttatgg ttctgttcct    600

cactccccct atcagttgtc agctcccagt gacccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgat gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                 1368
```

<210> SEQ ID NO 80
<211> LENGTH: 1368
<212> TYPE: DNA
<213> ORGANISM: Homo sapiens

<400> SEQUENCE: 80

```
atgtcgctca ctgtcgtcag catggcgtgc gttgggttct tcttgctgca gggggcctgg     60

ccactcatgg gtggtcagga caaacccttc ctgtctgccc ggcccagcac tgtggtgcct    120

caaggaggac acgtggctct tcagtgtcac tatcgtcgtg ggtttaacaa tttcatgctg    180

tacaaagaag acagaagcca cgttcccatc ttccacggca gaatattcca ggagagcttc    240

atcatgggcc ctgtgacccc agcacatgca gggacctaca gatgtcgggg ttcacgccca    300

cactccctca ctgggtggtc ggcacccagc aaccccctgg tgatcatggt cacaggaaac    360

cacagaaaac cttccctcct ggcccaccca gggaccctgc tgaaatcagg agagacagtc    420

atcctgcaat gttggtcaga tgtcatgttt gagcacttct ttctgcacag agaggggatc    480

tctgaggacc cctcacgcct cgttggacag atccatgatg ggtctccaa ggccaacttc     540

tccatcggtc ccttgatgcc tgtccttgca ggaacctaca gatgttatgg ttctgttcct    600

cactccccct atcagttgtc agctcccagt gacccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgac gtacgcacag   1200

ttggatcact gcgttttcat acagagaaaa atcagtcgcc cttctcagag gcccaagaca   1260

cccccaacag ataccagcgt gtacacggaa cttccaaatg ctgagcccag atccaaagtt   1320
```

gtctcctgcc cacgagcacc acagtcaggt cttgaggggg ttttctag 1368

<210> SEQ ID NO 81
<211> LENGTH: 1368
<212> TYPE: DNA
<213> ORGANISM: Homo sapiens

<400> SEQUENCE: 81
atgtcgctca cggtcgtcag catggcgtgc gttgggttct tcttgctgca gggggcctgg 60
ccactcatgg gtggtcagga caaacccttc ctgtctgccc ggcccagcac tgtggtgcct 120
cgaggaggac acgtggctct tcagtgtcac tatcgtcgtg ggtttaacaa tttcatgctg 180
tacaaagaag acagaagcca cgttcccatc ttccacggca gaatattcca ggagagcttc 240
atcatgggcc ctgtgacccc agcacatgca gggacctaca gatgtcgggg ttcacgccca 300
cactccctca ctgggtggtc ggcacccagc aacccccctgg tgatcatggt cacaggaaac 360
cacagaaaac cttccctcct ggcccaccca gggcccctgc tgaaatcagg agagacagtc 420
atcctgcaat gttggtcaga tgtcatgttt gagcatttct ttctgcacag agaggggatc 480
tctgaggacc cctcacgcct cgttggacag atccatgatg ggtctccaa ggccaacttc 540 tccatcggtc ccttgatgcc tgtccttgca ggaacctaca gatgttatgg ttctgttcct 600
cactccccct atcagttgtc agctcccagt gacccccctgg acatcgtgat cacaggtcta 660
tatgagaaac cttctctctc agcccagccg ggccccacgg ttcaggcagg agagaacgtg 720
accttgtcct gtagctcctg gagctcctat gacatctacc atctgtccag ggaaggggag 780
gcccatgaac gtaggctccg tgcagtgccc aaggtcaaca gaacattcca ggcagacttt 840
cctctgggcc ctgccaccca cggagggacc tacagatgct tcggctcttt ccatgccctg 900
ccctgcgtgt ggtcaaactc aagtgaccca ctgcttgttt ctgtcacagg aaacccttca 960
agtagttggc cttcacccac agaaccaagc tccaaatctg gtatctgcag acacctgcat 1020
gttctgattg ggacctcagt ggtcatcttc ctcttcatcc tcctcctctt ctttctcctt 1080
tatcgctggt gctccaacaa aaagaatgct gctgtaatgg accaagagcc tgcgggggac 1140
agaacagtga ataggcagga ctctgatgaa caagaccctc aggaggtgac gtacgcacag 1200
ttggatcact gcgttttcat acagagaaaa atcagtcgcc cttctcagag gcccaagaca 1260
cccctaacag ataccagcgt gtacacggaa cttccaaatg ctgagcccag atccaaagtt 1320
gtctcctgcc cacgagcacc acagtcaggt cttgaggggg ttttctag 1368

<210> SEQ ID NO 82
<211> LENGTH: 1368
<212> TYPE: DNA
<213> ORGANISM: Homo sapiens
<220> FEATURE:
<221> NAME/KEY: misc_feature
<222> LOCATION: (1)...(69)
<223> OTHER INFORMATION: n = A,T,C or G

<400> SEQUENCE: 82
nnnnnnnnnn nnnnnnnnnn nnnnnnnnnn nnnnnnnnnn nnnnnnnnnn nnnnnnnnnn 60
nnnnnnnnng gtggtcagga caaacccttc ctgtctgccc ggcccagcac tgtggtgcct 120
cgaggaggac acgtggctct tcagtgtcac tatcgtcgtg ggtttaacaa tttcatgctg 180
tacaaagaag acagaagcca cgttcccatc ttccacggca gaatattcca ggagagcttc 240
atcatgggcc ctgtgacccc agcacatgca gggacctaca gatgtcgggg ttcacgccca 300
cactccctca ctgggtggtc ggcacccagc aacccccctgg tgatcatggt cacaggaaac 360

```
cacagaaaac cttccctcct ggcccaccca gggcccctgc tgaaatcagg agagacagtc    420

atcctgcaat gttggtcaga tgtcatgttt gagcacttct ttctgcacag agaggggatc    480

tctgaggacc cctcacgcct cgttggacag atccatgatg gggtctccaa ggccaacttc    540

tccatcggtc ccttgatgcc tgtccttgca ggaacctaca gatgttatgg ttctgttcct    600

cactccccct atcagttgtc agctcccagt gaccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgat gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                1368
```

<210> SEQ ID NO 83
<211> LENGTH: 1368
<212> TYPE: DNA
<213> ORGANISM: Homo sapiens
<220> FEATURE:
<221> NAME/KEY: misc_feature
<222> LOCATION: (1)...(69)
<223> OTHER INFORMATION: n = A,T,C or G

<400> SEQUENCE: 83

```
nnnnnnnnnn nnnnnnnnnn nnnnnnnnnn nnnnnnnnnn nnnnnnnnnn nnnnnnnnnn     60

nnnnnnnnng gtggtcagga caaacccttc ctgtctgccc ggcccagcac tgtggtgcct    120

cgaggaggac acgtggctct tcagtgtcac tatcgtcgtg ggtttaacaa tttcatgctg    180

tacaaagaag acagaagcca cgttcccatc ttccacggca gaatattcca ggagagcttc    240

atcatgggcc ctgtgacccc agcacatgca gggacctaca gatgtcgggg ttcacgccca    300

cactccctca ctgggtggtc ggcacccagc aaccccgtgg tgatcatggt cacaggaaac    360

cacagaaaac cttccctcct ggcccaccca gggcccctgc tgaaatcagg agagacagtc    420

atcctgcaat gttggtcaga tgtcatgttt gagcacttct ttctgcacag agaggggatc    480

tctgaggacc cctcacgcct cgttggacag atccatgatg gggtctccaa ggccaacttc    540

tccatcggtc ccttgatgcc tgtccttgca ggaacctaca gatgttatgg ttctgttcct    600

cactccccct atcagttgtc agctcccagt gaccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020
```

```
gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgat gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                 1368
```

<210> SEQ ID NO 84
<211> LENGTH: 1368
<212> TYPE: DNA
<213> ORGANISM: Homo sapiens
<220> FEATURE:
<221> NAME/KEY: misc_feature
<222> LOCATION: (1)...(69)
<223> OTHER INFORMATION: n = A,T,C or G

<400> SEQUENCE: 84

```
nnnnnnnnnn nnnnnnnnnn nnnnnnnnnn nnnnnnnnnn nnnnnnnnnn nnnnnnnnnn     60

nnnnnnnnng gtggtcagga caaacccttc ctgtctgccc ggcccagcac tgtggtgcct    120

caaggaggac acgtggctct tcagtgtcac tatcgtcgtg ggtttaacaa tttcatgctg    180

tacaaagaag acagaagcca cgttcccatc ttccacggca gaatattcca ggagagcttc    240

atcatgggcc ctgtgacccc agcacatgca gggacctaca gatgtcgggg ttcacgccca    300

cactccctca ctgggtggtc ggcacccagc aacccccctgg tgatcatggt cacaggaaac    360

cacagaaaac cttccctcct ggcccaccca gggcccctgc tgaaatcagg agagacagtc    420

atcctgcaat gttggtcaga tgtcatgttt gagcacttct ttctgcacag agaggggatc    480

tctgaggacc cctcacacct cgttggacag atccatgatg ggtctccaa ggccaacttc    540

tccatcggtc ccttgatgcc tgtccttgca ggaacctaca gatgttatgg ttctgttcct    600

cactccccct atcagttgtc agctcccagt gacccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgac gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag                 1368
```

<210> SEQ ID NO 85
<211> LENGTH: 1368
<212> TYPE: DNA
<213> ORGANISM: Homo sapiens

<400> SEQUENCE: 85

```
atgtcgctca cggtcgtcag catggcgtgc gttgggttct tcttgctgca gggggcctgg     60
```

```
ccactcatgg gtggtcagga caaacccttc ctgtctgccc ggcccagcac tgtggtgcct    120
cgaggaggac acgtggctct tcagtgtcac tatcgtcgtg ggtttaacaa tttcatgctg    180
tacaaagaag acagaagcca cgttcccatc ttccacggca gaatattcca ggagagcttc    240
atcatgggcc ctgtgacccc agcacatgca gggacctaca gatgtcgggg ttcacgccca    300
cactccctca ctgggtggtc ggcacccagc aaccccctgg tgatcatggt cacaggaaac    360
cacagaaaac cttccctcct ggcccaccca gggcccctgc tgaaatcagg agagacagtc    420
atcctgcaat gttggtcaga tgtcatgttt gagcacttct ttctgcacag agaggggatc    480
tctgaggacc cctcacgcct cgttggacag atccatgatg ggtctccaa ggccaacttc    540
tccatcggtc ccttgatgcc tgtccttgca ggaacctaca gatgttatgg ttctgttcct    600
cactccccct atcagttgtc agctcccagt gaccccctgg acatcgtgat cacaggtcta    660
tatgagaaac cttctctctc agcccagccg ggccccacgg ttcaggcagg agagaacgtg    720
accttgtcct gtagctcctg gagctcctat gacatctacc atctgtccag ggaaggggag    780
gcccatgaac gtaggctccg tgcagtgccc aaggtcaaca gaacattcca ggcagacttt    840
cctctgggcc ctgccaccca cggagggacc tacagatgct tcggctcttt ccgtgccctg    900
ccctgcgtgt ggtcaaactc aagtgaccca ctgcttgttt ctgtcacagg aaacccttca    960
agtagttggc cttcacccac agaaccaagc tccaaatctg gtatctgcag acacctgcat   1020
gttctgattg ggacctcagt ggtcatcttc ctcttcatcc tcctcctctt ctttctcctt   1080
tatcgctggt gctccaacaa aaagaatgct gctgtaatgg accaagagcc tgcgggggac   1140
agaacagtga ataggcagga ctctgatgaa caagaccctc aggaggtgac gtacgcacag   1200
ttggatcact gcgttttcat acagagaaaa atcagtcgcc cttctcagag gcccaagaca   1260
cccctaacag ataccagcgt gtacacggaa cttccaaatg ctgagcccag atccaaagtt   1320
gtctcctgcc cacgagcacc acagtcaggt cttgaggggg ttttctag               1368
```

<210> SEQ ID NO 86
<211> LENGTH: 1317
<212> TYPE: DNA
<213> ORGANISM: Homo sapiens
<220> FEATURE:
<221> NAME/KEY: misc_feature
<222> LOCATION: (1234)...(1317)
<223> OTHER INFORMATION: n = A,T,C or G

<400> SEQUENCE: 86

```
atgtcgctca tggtcgtcag catggcgtgt gttgggttct tcttgctgga ggggccctgg     60
ccacatgtgg gtggtcagga caagcccttc ctctctgcct ggcccggcac tgtggtgtct    120
gaaggacaac atgtgactct tcagtgtcgc tctcgtcttg ggtttaacga attcagtctg    180
tccaaagaag acgggatgcc tgtccctgag ctctacaaca gaatattccg gaacagcttt    240
ctcatgggcc ctgtgacccc agcacatgca gggacctaca gatgttgcag ttcacaccca    300
cactccccca ctgggtggtc ggcacccagc aaccctgtgg tgatcatggt cacaggagtc    360
cacagaaaac cttccctcct ggcccaccca ggtcccctgg tgaaatcggg agagacggtc    420
atcctgcaat gttggtcaga tgtcaggttt gagcgcttcc ttctgcacag agaggggatc    480
actgaggacc ccttgcgcct cattggacag ctccacgatg cgggttccca ggtcaactat    540
tccatgggtc ccatgacacc tgcccttgca gggacctaca gatgctatgg ttctgtcact    600
cacttaccct atgagttgtc ggctcccagt gaccctctgg acatcgtggt cgtaggtcta    660
tatgggaaac cttctctctc agcccagccg ggccccacgg ttcaggcagg agagaatgtg    720
```

```
accttgtcct gcagctcccg gagctcgttt gacatttacc atctatccag ggaggcagag    780

gccggtgaac ttaggctcac tgcggtgctg agggtcaatg gaacattcca ggccaacttc    840

cctctgggcc ctgtgaccca cggagggaac tacagatgct tcggctcttt ccgtgccctg    900

ccccacgcgt ggtcagaccc gagtgaccca ctgcccgttt ctgtcacagg taactccaga    960

aacctgcacg ttctgattgg gacctcagtg gtcatcatcc cctttgctat cctcctcttc   1020

tttctccttc atcgctggtg tgccaacaaa aagaatgctg ttgtaatgga ccaagagcct   1080

gcagggaaca gaacagtgaa cagggaggac tctgatgaac aagaccctca ggaggtgaca   1140

tacgcacagt tgaatcactg cgttttcaca cagagaaaaa tcactcgccc ttctcagagg   1200

cccaagacac ccccaacaga taccagcgtg taannnnnnn nnnnnnnnnn nnnnnnnnnn   1260

nnnnnnnnnn nnnnnnnnnn nnnnnnnnnn nnnnnnnnnn nnnnnnnnnn nnnnnnn      1317
```

```
<210> SEQ ID NO 87
<211> LENGTH: 1317
<212> TYPE: DNA
<213> ORGANISM: Homo sapiens
<220> FEATURE:
<221> NAME/KEY: misc_feature
<222> LOCATION: (1234)...(1317)
<223> OTHER INFORMATION: n = A,T,C or G

<400> SEQUENCE: 87

atgtcgctca tggtcgtcag catggcgtgt gttgggttct tcttgctgga ggggccctgg     60

ccacatgtgg gtggtcagga caagcccttc ctctctgcct ggcccggcac tgtggtgtct    120

gaaggacaac atgtgactct tcagtgtcgc tctcgtcttg ggtttaacga attcagtctg    180

tccaaagaag acgggatgcc tgtccctgag ctctacaaca gaatattccg gaacagcttt    240

ctcatgggcc ctgtgacccc agcacatgca gggacctaca gatgttgcag ttcacaccca    300

cactccccca ctgggtggtc ggcacccagc aaccctgtgg tgatcatggt cacaggagtc    360

cacagaaaac cttccctcct ggcccaccca ggtcccctgg tgaaatcggg agagacggtc    420

atcctgcaat gttggtcaga tgtcaggttt gagcgcttcc ttctgcacag agaggggatc    480

actgaggacc ccttgcgcct cgttggacag ctccacgatg cgggttccca ggtcaactat    540

tccatgggtc ccatgacacc tgcccttgca gggacctaca gatgctatgg ttctgtcact    600

cacttaccct atgagttgtc ggctcccagt gaccctctgg acatcgtggt cgtaggtcta    660

tatgggaaac cttctctctc agcccagccg ggccccacgg ttcaggcagg agagaatgtg    720

accttgtcct gcagctcccg gagctcgttt gacatttacc atctatccag ggaggcagag    780

gccggtgaac ttaggctcac tgcggtgctg agggtcaatg gaacattcca ggccaacttc    840

cctctgggcc ctgtgaccca cggagggaac tacagatgct tcggctcttt ccgtgccctg    900

ccccacgcgt ggtcagaccc gagtgaccca ctgcccgttt ctgtcacagg taactccaga    960

cacctgcacg ttctgattgg gacctcagtg gtcatcatcc cctttgctat cctcctcttc   1020

tttctccttc atcgctggtg tgccaacaaa aagaatgctg ttgtaatgga ccaagagcct   1080

gcagggaaca gaacagtgaa cagggaggac tctgatgaac aagaccctca ggaggtgaca   1140

tacgcacagt tgaatcactg cgttttcaca cagagaaaaa tcactcgccc ttctcagagg   1200

cccaagacac ccccaacaga taccagcgtg taannnnnnn nnnnnnnnnn nnnnnnnnnn   1260

nnnnnnnnnn nnnnnnnnnn nnnnnnnnnn nnnnnnnnnn nnnnnnnnnn nnnnnnn      1317

<210> SEQ ID NO 88
<211> LENGTH: 1368
```

<212> TYPE: DNA
<213> ORGANISM: Homo sapiens
<220> FEATURE:
<221> NAME/KEY: misc_feature
<222> LOCATION: (1)...(34)
<223> OTHER INFORMATION: n = A,T,C or G
<220> FEATURE:
<221> NAME/KEY: misc_feature
<222> LOCATION: (892)...(1368)
<223> OTHER INFORMATION: n = A,T,C or G

<400> SEQUENCE: 88
nnnnnnnnnn nnnnnnnnnn nnnnnnnnnn nnnnggttct tcttgctgga ggggccctgg 60
ccacatgtgg gtggtcagga caagcccttc ctctctgcct ggcccggcac tgtggtgtct 120
gaaggacaac atgtgactct tcagtgtcgc tctcgtcttg ggtttaatga attcagtctg 180
tccaaagaag acgggatgcc tgtccctgag ctctacaaca gaatattccg gaacagcttt 240
ctcatgggcc ctgtgacccc agcacatgca gggacctaca gatgttgcag ttcacaccca 300
cactccccca ctgggtggtc ggcacccagc aaccctgtgg tgatcatggt cacaggagtc 360
cacagaaaac cttccctcct ggcccaccca ggtcccctgg tgaaatcagg agagacggtc 420
atcctgcaat gttggtcaga tgtcaggttt gagcgcttcc ttctgcacag agaggggatc 480
actgaggacc ccttgcgcct cgttggacag ctccacgatg cgggttccca ggtcaactat 540
tccatgggtc ccatgacacc tgcccttgca gggacctaca gatgctatgg ttctgtcact 600
cacttaccct atgagttgtc ggctcccagt gaccctctgg acatcgtggt cgtaggtcta 660
tatgggaaac cttctctctc agcccagccg ggccccacgg ttcaggcagg agagaatgtg 720
accttgtcct gcagctcccg gagctcgttt gacatttacc atctatccag ggagcggagg 780
ccggtgaact taggctcact gcagtgctga gggtcaatgg aacattccag gccaacttcc 840
ctctgggccc tgtgacccac ggagggaact acagatgctt cggctctttc cnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnn 1368

<210> SEQ ID NO 89
<211> LENGTH: 1317
<212> TYPE: DNA
<213> ORGANISM: Homo sapiens
<220> FEATURE:
<221> NAME/KEY: misc_feature
<222> LOCATION: (1234)...(1317)
<223> OTHER INFORMATION: n = A,T,C or G

<400> SEQUENCE: 89
atgtcgctca tggtcgtcag catggcgtgt gttgggttct tcttgctgga ggggccctgg 60
ccacatgtgg gtggtcagga caagcccttc ctctctgcct ggcccggcac tgtggtgtct 120
gaaggacaac atgtgactct tcagtgtcgc tctcgtcttg ggtttaacga attcagtctg 180
tccaaagaag acgggatgcc tgtccctgag ctctacaaca gaatattccg gaacagcttt 240
ctcatgggcc ctgtgacccc agcacatgca gggacctaca gatgttgcag ttcacaccca 300

-continued

```
cactccccca ctgggtggtc ggcacccagc aaccctgtgg tgatcatggt cacaggagtc    360

cacagaaaac cttccctcct ggcccaccca ggtcccctgg tgaaatcggg agagacggtc    420

atcctgcaat gttggtcaga tgtcaggttt gagcgcttcc ttctgcacag agaggggatc    480

actgaggacc ccttgcgcct cattggacag ctccacgatg cgggttccca ggtcaactat    540

tccatgggtc ccatgacacc tgcccttgca gggacctaca gatgctatgg ttctgtcact    600

cacttaccct atgagttgtc ggctcccagt gaccctctgg acatcgtggt cgtaggtcta    660

tatgggaaac cttctctctc agcccagccg ggccccacgg ttcaggcagg agagaatgtg    720

accttgtcct gcagctcccg gagctcgttt gacatttacc atctatccag ggaggcagag    780

gccggtgaac ttaggctcac tgcggtgctg agggtcaatg gaacattcca ggccaacttc    840

cctctgggcc ctgtgaccca cggagggaac tacagatgct tcggctcttt ccgtgccctg    900

ccccacgcgt ggtcagaccc gagtgaccca ctgcccgttt ctgtcacagg taactccaga    960

tacctgcacg ctctgattgg gacctcagtg gtcatcatcc cctttgctat cctcctcttc   1020

tttctccttc atcgctggtg tgccaacaaa aagaatgctg ttgtaatgga ccaagagcct   1080

gcagggaaca gaacagtgaa cagggaggac tctgatgaac aagaccctca ggaggtgaca   1140

tacgcacagt tgaatcactg cgttttcaca cagagaaaaa tcactcgccc ttctcagagg   1200

cccaagacac ccccaacaga taccagcgtg taannnnnnn nnnnnnnnnn nnnnnnnnnn   1260

nnnnnnnnnn nnnnnnnnnn nnnnnnnnnn nnnnnnnnnn nnnnnnnnnn nnnnnnn      1317


<210> SEQ ID NO 90
<211> LENGTH: 1317
<212> TYPE: DNA
<213> ORGANISM: Homo sapiens
<220> FEATURE:
<221> NAME/KEY: misc_feature
<222> LOCATION: (1234)...(1317)
<223> OTHER INFORMATION: n = A,T,C or G

<400> SEQUENCE: 90

atgtcgctca tggtcgtcag catggcgtgt gttgggttct tcttgctgga ggggccctgg     60

ccacatgtgg gtggtcagga caagcccttc ctctctgcct ggcccggcac tgtggtgtct    120

gaaggacaac atgtgactct tcagtgtcgc tctcatcttg ggtttaacga attcagtctg    180

tccaaagaag acgggatgcc tgtccctgag ctctacaaca gaatattccg gaacagcttt    240

ctcatgggcc ctgtgacccc agcacatgca gggacctaca gatgttgcag ttcacaccca    300

cactccccca ctgggtggtc ggcacccagc aaccctgtgg tgatcatggt cacgggagtc    360

cacagaaaac cttccctcct ggcccaccca ggtcccctgg tgaaatcggg agagacggtc    420

atcctgcaat gttggtcaga tgtcaggttt gagcgcttcc ttctgcacag agaggggatc    480

actgaggacc ccttgcgcct cgttggacag ctccacgatg cgggttccca ggtcaactat    540

tccatgggtc ccatgacacc tgcccttgca gggacctaca gatgctatgg ttctgtcact    600

cacttaccct atgagttgtc ggctcccagt gaccctctgg acatcgtggt cgtaggtcta    660

tatgggaaac cttctctctc agcccagccg ggccccacgg ttcaggcagg agagaatgtg    720

accttgtcct gcagctcccg gagctcgttt gacatttacc atctatccag ggaggcagag    780

gccggtgaac ttaggctcac tgcggtgctg agggtcaatg gaacattcca ggccaacttc    840

cctctgggcc ctgtgaccca cggagggaac tacagatgct tcggctcttt ccgtgccctg    900

ccccacgcgt ggtcagaccc gagtgaccca ctgcccgttt ctgtcacagg taactccaga    960

tacctgcacg ctctgattgg gacctcagtg gtcatcatcc cctttgctat cctcctcttc   1020
```

```
tttctccttc atcgctggtg tgccaacaaa aagaatgctg ttgtaatgga ccaagagcct   1080

gcagggaaca gaacagtgaa cagggaggac tctgatgaac aagaccctca ggaggtgaca   1140

tacgcacagt tgaatcactg cgttttcaca cagagaaaaa tcactcgccc ttctcagagg   1200

cccaagacac ccccaacaga taccagcgtg taannnnnnn nnnnnnnnnn nnnnnnnnnn   1260

nnnnnnnnnn nnnnnnnnnn nnnnnnnnnn nnnnnnnnnn nnnnnnnnnn nnnnnnn      1317
```

```
<210> SEQ ID NO 91
<211> LENGTH: 1368
<212> TYPE: DNA
<213> ORGANISM: Homo sapiens

<400> SEQUENCE: 91

atgtcgctca cggtcgtcag catggcgtgc gttgggttct tcttgctgca gggggcctgg     60

ccactcatgg gtggtcagga caaacccttc ctgtctgccc ggcccagcac tgtggtgcct    120

cgaggaggac acgtggctct tcagtgtcac tatcgtcgtg ggtttaacaa tttcatgctg    180

tacaaagaag acagaagcca cgttcccatc ttccacggca gaatattcca ggagagcttc    240

atcatgggcc ctgtgacccc agcacatgca gggacctaca gatgtcgggg ttcacgccca    300

cactccctca ctgggtggtc ggcacccagc aaccccctgg tgatcatggt cacaggaaac    360

cacagaaaac cttccctcct ggcccaccca gggcccctgc tgaaatcagg agagacagtc    420

atcctgcaat gttggtcaga tgtcatgttt gagcacttct ttctgcacag agaggggatc    480

tctgaggacc cctcacgcct cgttggacag atccatgatg ggtctccaa ggccaacttc     540

tccatcggtc ccttgatgcc tgtccttgca ggaacctaca gatgttatgg ttctgttcct    600

cactccccct atcagttgtc agctcccagt gaccccctgg acatcgtgat cacaggtcta    660

tatgagaaac cttctctctc agcccagccg ggccccacgg ttcaggcagg agagaacgtg    720

accttgtcct gtagctcctg gagctcctat gacatctacc atctgtccag ggaaggggag    780

gcccatgaac gtaggctccg tgcagtgccc aaggtcaaca gaacattcca ggcagacttt    840

cctctgggcc ctgccaccca cggagggacc tacagatgct tcggctcttt ccgtgccctg    900

ccctgcgtgt ggtcaaactc aagtgaccca ctgcttgttt ctgtcacagg aaacccttca    960

agtagttggc cttcacccac agaaccaagc tccaaatctg gtatctgcag acacctgcat   1020

gttctgattg ggacctcagt ggtcatcttc ctcttcatcc tcctcctctt ctttctcctt   1080

tatcgctggt gctccaacaa aaagaatgct gctgtaatgg accaagagcc tgcgggggac   1140

agaacagtga ataggcagga ctctgatgaa caagaccctc aggaggtgac gtacgcacag   1200

ttggatcact gcgttttcat acagagaaaa atcagtcgcc cttctcagag gcccaagaca   1260

cccctaacag ataccagcgt gtacacggaa cttccaaatg ctgagcccag atccaaagtt   1320

gtctcctgcc cacgagcacc acagtcaggt cttgaggggg ttttctag               1368
```

```
<210> SEQ ID NO 92
<211> LENGTH: 1368
<212> TYPE: DNA
<213> ORGANISM: Homo sapiens
<220> FEATURE:
<221> NAME/KEY: misc_feature
<222> LOCATION: (1)...(34)
<223> OTHER INFORMATION: n = A,T,C or G
<220> FEATURE:
<221> NAME/KEY: misc_feature
<222> LOCATION: (893)...(1368)
<223> OTHER INFORMATION: n = A,T,C or G

<400> SEQUENCE: 92
```

```
nnnnnnnnnn nnnnnnnnnn nnnnnnnnnn nnnnggttct tcttgctgca gggggcctgg      60

acacatgagg gtggtcagga caagcccttc ctctctgcct ggcccagccc tgtggtgtct     120

gaaggagaac atgtggctct tcagtgtcgc tctcgtcttg ggtttaacga attcagtctg     180

tccaaagaag acgggatgcc tgtccctgag ctctacaaca gagtattccg aaacaccgtt     240

ttcataggcc ctgtgacccc agcacatgca gggacctaca gatgtcgggg ttcacaccca     300

cacttcctca ctgggtggtc agcacccagc aaccccctgg tgatcatggt cacaggagtc     360

cacagaaaac cttccctcct ggcccaccca ggtcccctgc tgaaatcaga agagacagtc     420

atcctgcaat gttggtcaga tgtcatgttt gagcacttcc ttctgcacag agaggggaag     480

tttaatgaca ctttgcgcct cactggagag ctccatgatg ggtctccaa ggccaacttc     540

tccatcggtc gcatgacgca agaccttgca gggacctaca gatgctacgg ttctgttcct     600

cattccccct atcagttgtc agctcccagt gaccctctgg acatcgtgat tacaggtcta     660

tgtgggaaac cttctctctc agcccagccg cgccccatgg ttaaggcagg agagagcgtg     720

accttgtcct gcagctcccg gagctcctat gacatctacc atctatcaag ggagggggag     780

gctcatgaac ttaggttccc tgcagtgccc aaggtcaatg gaaccttcca ggccaacttt     840

cctctgggcc ctgccaccca cggagggacc tacagatgct tcggctcttt ccnnnnnnnn     900

nnnnnnnnnn nnnnnnnnnn nnnnnnnnnn nnnnnnnnnn nnnnnnnnnn nnnnnnnnnn     960

nnnnnnnnnn nnnnnnnnnn nnnnnnnnnn nnnnnnnnnn nnnnnnnnnn nnnnnnnnnn    1020

nnnnnnnnnn nnnnnnnnnn nnnnnnnnnn nnnnnnnnnn nnnnnnnnnn nnnnnnnnnn    1080

nnnnnnnnnn nnnnnnnnnn nnnnnnnnnn nnnnnnnnnn nnnnnnnnnn nnnnnnnnnn    1140

nnnnnnnnnn nnnnnnnnnn nnnnnnnnnn nnnnnnnnnn nnnnnnnnnn nnnnnnnnnn    1200

nnnnnnnnnn nnnnnnnnnn nnnnnnnnnn nnnnnnnnnn nnnnnnnnnn nnnnnnnnnn    1260

nnnnnnnnnn nnnnnnnnnn nnnnnnnnnn nnnnnnnnnn nnnnnnnnnn nnnnnnnnnn    1320

nnnnnnnnnn nnnnnnnnnn nnnnnnnnnn nnnnnnnnnn nnnnnnnn                1368


<210> SEQ ID NO 93
<211> LENGTH: 1368
<212> TYPE: DNA
<213> ORGANISM: Homo sapiens
<220> FEATURE:
<221> NAME/KEY: misc_feature
<222> LOCATION: (893)...(1368)
<223> OTHER INFORMATION: n = A,T,C or G

<400> SEQUENCE: 93

atgtcgctca tggtcgtcag catggcgtgt gttgggttct tcttgctgca gggggcctgg      60

ccacatgagg gtggtcagga caagcccttc ctctctgcct ggcccagccc tgtggtgtct     120

gaaggagaac atgtggctct tcagtgtcgc tctcgtcttg ggtttaacga attcagtctg     180

tccaaagaag acgggatgcc tgtccctgag ctctacaaca gagtattccg aaacaccgtt     240

ttcataggcc ctgtgacccc agcacatgca gggacctaca gatgtcgggg ttcacaccca     300

cacttcctca ctgggtggtc agcacccagc aaccccctgg tgatcatggt cacaggagtc     360

cacagaaaac cttccctcct ggcccaccca ggtcccctgc tgaaatcaga agagacagtc     420

atcctgcaat gttggtcaga tgtcatgttt gagcacttcc ttctgcacag agaggggaag     480

tttaatgaca ctttgcgcct cactggagag ctccatgatg ggtctccaa ggccaacttc     540

tccatcggtc gcatgacgca agaccttgca gggacctaca gatgctacgg ttctgttcct     600

cattccccct atcagttgtc agctcccagt gaccctctgg acatcgtgat tacaggtcta     660
```

```
tgtgggaaac cttctctctc agcccagccg cgccccatgg ttaaggcagg agagagcgtg    720

accttgtcct gcagctcccg gagctcctat gacatctacc atctatcaag ggagggggag    780

gctcatgaac ttaggttccc tgcagtgccc aaggtcaatg gaaccttcca ggccaacttt    840

cctctgggcc ctgccaccca cggagggacc tacagatgct tcggctcttt ccnnnnnnnn    900

nnnnnnnnnn nnnnnnnnnn nnnnnnnnnn nnnnnnnnnn nnnnnnnnnn nnnnnnnnnn    960

nnnnnnnnnn nnnnnnnnnn nnnnnnnnnn nnnnnnnnnn nnnnnnnnnn nnnnnnnnnn   1020

nnnnnnnnnn nnnnnnnnnn nnnnnnnnnn nnnnnnnnnn nnnnnnnnnn nnnnnnnnnn   1080

nnnnnnnnnn nnnnnnnnnn nnnnnnnnnn nnnnnnnnnn nnnnnnnnnn nnnnnnnnnn   1140

nnnnnnnnnn nnnnnnnnnn nnnnnnnnnn nnnnnnnnnn nnnnnnnnnn nnnnnnnnnn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320

nnnnnnnnnn nnnnnnnnnn nnnnnnnnnn nnnnnnnnnn nnnnnnnn                1368
```

<210> SEQ ID NO 94
<211> LENGTH: 1332
<212> TYPE: DNA
<213> ORGANISM: Homo sapiens
<220> FEATURE:
<221> NAME/KEY: misc_feature
<222> LOCATION: (857)...(1332)
<223> OTHER INFORMATION: n = A,T,C or G

<400> SEQUENCE: 94

```
atgtcgctca tggtcgtcag catggcgtgt gttggtggtc aggacaagcc cctcctctct     60

gcctggccca gccccgtggt gtctgaagga gaacatgtgg ctcttcagtg tcgctctcgt    120

cttgggttta acgaattcag tctgtccaaa gaagacggga tgcctgtccc tgagctctac    180

aacagagtat tccgaaacac cgttttcata ggccctgtga ccccagcaca tgcagggacc    240

tacagatgtc ggggttcaca cccacacttc ctcactgggt ggtcagcacc cagcaacccc    300

ctggtgatca tggtcacagg agtccacaga aaaccttccc tcctggccca cccaggtccc    360

ctgctgaaat cagaagagac agtcatcctg caatgttggt cagatgtcat gtttgagcac    420

ttccttctgc acagagaggg gaagtttaat gacactttgc gcctcactgg agagctccat    480

gatggggtct ccaaggccaa cttctccatc ggtcgcatga cgcaagacct tgcagggacc    540

tacagatgct acggttctgt tcctcattcc ccctatcagt tgtcagctcc cagtgaccct    600

ctggacatcg tgattacagg tctatgtggg aaaccttctc tctcagccca gccgcgcccc    660

atggttaagg caggagagag cgtgaccttg tcctgcagct cccggagctc ctatgacatc    720

taccatctat caagggaggg ggaggctcat gaacttaggt tccctgcagt gcccaaggtc    780

aatggaacct tccaggccaa ctttcctctg ggccctgcca cccacggagg gacctacaga    840

tgcttcggct ctttccnnnn nnnnnnnnnn nnnnnnnnnn nnnnnnnnnn nnnnnnnnnn    900

nnnnnnnnnn nnnnnnnnnn nnnnnnnnnn nnnnnnnnnn nnnnnnnnnn nnnnnnnnnn    960

nnnnnnnnnn nnnnnnnnnn nnnnnnnnnn nnnnnnnnnn nnnnnnnnnn nnnnnnnnnn   1020

nnnnnnnnnn nnnnnnnnnn nnnnnnnnnn nnnnnnnnnn nnnnnnnnnn nnnnnnnnnn   1080

nnnnnnnnnn nnnnnnnnnn nnnnnnnnnn nnnnnnnnnn nnnnnnnnnn nnnnnnnnnn   1140

nnnnnnnnnn nnnnnnnnnn nnnnnnnnnn nnnnnnnnnn nnnnnnnnnn nnnnnnnnnn   1200

nnnnnnnnnn nnnnnnnnnn nnnnnnnnnn nnnnnnnnnn nnnnnnnnnn nnnnnnnnnn   1260

nnnnnnnnnn nnnnnnnnnn nnnnnnnnnn nnnnnnnnnn nnnnnnnnnn nnnnnnnnnn   1320
```

nnnnnnnnnn nn 1332

<210> SEQ ID NO 95
<211> LENGTH: 1332
<212> TYPE: DNA
<213> ORGANISM: Homo sapiens
<220> FEATURE:
<221> NAME/KEY: misc_feature
<222> LOCATION: (914)...(1332)
<223> OTHER INFORMATION: n = A,T,C or G

<400> SEQUENCE: 95
atgtcgctca tggtcgtcag catggcgtgt gttggtggtc aggacaagcc cctcctctct 60
gcctggccca gccctgtggt gtctgaagga gaacatgtgg ctcttcagtg tcgctctcgt 120
cttgggttta acgaattcag tctgtccaaa gaagacggga tgcctgtccc tgagctctac 180
aacagagtat tccgaaacac cgttttcata ggccctgtga ccccagcaca tgcagggacc 240
tacagatgtc ggggttcaca cccacacttc ctcactgggt ggtcagcacc cagcaacccc 300
ctggtgatca tggtcacagg agtccacaga aaaccttccc tcctggccca cccaggtccc 360
ctgctgaaat cagaagagac agtcatcctg caatgttggt cagatgtcat gtttgagcac 420
ttccttctgc acagagaggg gaagtttaat gacactttgc gcctcactgg agagctccat 480
gatggggtct ccaaggccaa cttctccatc ggtcgcatga cgcaagacct tgcagggacc 540
tacagatgct acggttctgt tcctcattcc ccctatcagt tgtcagctcc cagtgaccct 600
ctggacatcg tgattacagg tctatgtggg aaaccttctc tctcagccca gccgcgcccc 660
atggttaagg caggagagag cgtgaccttg tcctgcagct cccggagctc ctatgacatc 720
taccatctat caagggaggg ggaggctcat gaacttaggt tccctgcagt gcccaaggtc 780
aatggaacct tccaggccaa ctttcctctg ggccctgcca cccacggagg gacctacaga 840
tgcttcggct ctttccgtga ctctccctac gagtggtcag accttagtga cccactgctt 900
gtttctgtca cagnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nn 1332

<210> SEQ ID NO 96
<211> LENGTH: 1367
<212> TYPE: DNA
<213> ORGANISM: Homo sapiens
<220> FEATURE:
<221> NAME/KEY: misc_feature
<222> LOCATION: (1)...(34)
<223> OTHER INFORMATION: n = A,T,C or G
<220> FEATURE:
<221> NAME/KEY: misc_feature
<222> LOCATION: (892)...(1367)
<223> OTHER INFORMATION: n = A,T,C or G

<400> SEQUENCE: 96
nnnnnnnnnn nnnnnnnnnn nnnnnnnnnn nnnnggttct tcttgctgca gggggcctgg 60
ccacatgagg gtggtcagga caagcccttg ctgtctgcct ggcccagctc tgtggtgtct 120
ccaggaggac atgtgattct tcggtgtcat tcttatcttg ggtttaacaa cttcagtctg 180
taaaaggaag atggggtgcc tggcactgag ctctacaaca gaatattctg gaagagcctt 240
atcatgggcc ctgtgacccc agcacacaca gggacgtaca gatgtcgggg ttcacaccca 300
cactccccca gtgggtggtc ggcacccagc aaccccctgg tgatcatggc cacaggagtc 360
cacagaaaac cttccctcct ggcccaccca ggtcccctgg tgaaatcaga agagacagtc 420
atcctgcaat gttggtcaga tgtcaggttt gagcacttcc ttctgcacag agaggggaca 480
tttaacgaca ctttgcacct cactggagag caccatgatg gggtctccaa ggccaacttc 540
tccatcggtc ccatgatgga agacctggca gggacctaca gatgctacgg ttctgttact 600
cactccccca tcagttgtca gctcccagtg accctctgga catcgtcatt acaggtctat 660
atgagaaacc ttctctctca gcccagccgg gccccacggt tctggcagga gagagcgtga 720
ccttgtcctg cagctcccgg agctcctatg acatgtacca tctatccacg gaggggaagg 780
cccatgaacg taggttctct gcagggacca aggtcaacgg aacattccag gctgactttc 840
ctctgggccc tgccacccac ggaggaacct acagatgctt cggctctttc cnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnn 1367

<210> SEQ ID NO 97
<211> LENGTH: 1367
<212> TYPE: DNA
<213> ORGANISM: Homo sapiens
<220> FEATURE:
<221> NAME/KEY: misc_feature
<222> LOCATION: 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367
<223> OTHER INFORMATION: n = A,T,C or G

<400> SEQUENCE: 97
atgtcgctca cggtcgtcag catggcgtgt gttgggttct tcttgctgca gggggcctgg 60
ccacatgagg gtggtcagga caagcccttg ctgtctgcct ggcccagctc tgtggtgtct 120
ccaggaggac atgtgattct tcggtgtcat tcttatcttg ggtttaacaa cttcagtctg 180
taaaaggaag atggggtgcc tggcactgag ctctacaaca gaatattctg gaagagcctt 240
atcatgggcc ctgtgacccc agcacacaca gggacgtaca gatgtcgggg ttcacaccca 300
cactacccca gtgggtggtc ggcacccagc aacaccctgg tgatcatggc cacaggagtc 360
cacagaaaac cttccctcct ggcccaccca ggtcccctgg tgaaatcaga agagacagtc 420
atcctgcaat gttggtcaga tgtcaggttt cagcacttcc ttctgcacag agaagggaca 480
tttaacgaca ctttgcacct cactggagag caccatgatg gggtttccaa ggccaacttc 540
tccatcggtc ccatgatgga agacctggca gggacctaca gatgctacgg ttctgttact 600
cactccccca tcagttgtca gctcccagtg accctctgga catcgtcatt acaggtctat 660
atgagaaacc ttctctctca gcccagccgg gccccacggt tctggcagga gagagcgtga 720
ccttgtcctg cagctcccgg agctcctatg acatgtacca tctatccagg gagggggagg 780
cccatgaacg taggttctct gcagggccca aggtcaacgg aacattccag gctgactttc 840
ctctgggccc tgccacccac ggaggaacct acagatgctt cggctctttc cgtgactctc 900
cctacgagtg gtcaaactcg agtgacccac tgcttgtttc tgtcacagga aacccttcaa 960
atagttggcc ttcacccact gaaccaagct ccaaaaccgg taacccaaga cacctgcacg 1020
ttctgattgg gacctcagtg gtcatcatcc tcttcatcct cctcctcttc tttctccttc 1080
atcgctggtg ctccaacaag aaaaatgctg ctgtaatgga ccaagagcct gcagggaaca 1140
gaacagcgaa tagcgaggac tctgatgaac aagaccctca ggaggtgaca tacgtacagt 1200
tggatcactg cgttttcaca cagagaaaaa tcactcgccc ttctcagagg cccaagacac 1260
ccccaacaga taccagagtg tacacggaac ttccaaatgc tgagtccaga tccaaagttg 1320
tctcctgccc atgannnnnn nnnnnnnnnn nnnnnnnnnn nnnnnnn 1367

<210> SEQ ID NO 98
<211> LENGTH: 285
<212> TYPE: DNA
<213> ORGANISM: Homo sapiens

<400> SEQUENCE: 98
gtggtcagga caagcccttg ctgtctgcct ggcccagcgc tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacaccca cgctccccca 240
ttgagtggtc agcacccagc aaccccctgg tgatcgtggt cacag 285

<210> SEQ ID NO 99
<211> LENGTH: 285
<212> TYPE: DNA
<213> ORGANISM: Homo sapiens

<400> SEQUENCE: 99
gtggacagga caagcccttg ctgtctgcct ggcccagcgc tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacacccg cgctccccca 240
ttgagtggtc ggcacccagc aaccccctgg tgatcgtggt cacag 285

<210> SEQ ID NO 100
<211> LENGTH: 285
<212> TYPE: DNA
<213> ORGANISM: Homo sapiens

<400> SEQUENCE: 100
gtggacagga caagcccttg ctgtctgcct ggcccagcgc tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacacccg cgctccccca 240
ttgagtggtc ggcacccagc aaccccctgg tgatcgtggt cacag 285

<210> SEQ ID NO 101

<211> LENGTH: 285
<212> TYPE: DNA
<213> ORGANISM: Homo sapiens

<400> SEQUENCE: 101
gtggtcagga caagcccttg ctgtctgcct ggcccagcgc tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacaccca cgctccccca 240
ttgagtggtc agcacccagc aaccccctgg tgatcatggt cacag 285

<210> SEQ ID NO 102
<211> LENGTH: 285
<212> TYPE: DNA
<213> ORGANISM: Homo sapiens

<400> SEQUENCE: 102
gtggtcagga caagcccttg ctgtctgcct ggcccagcac tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacaccca cgctccccca 240
ttgagtggtc agcacccagc aaccccctgg tgatcgtggt cacag 285

<210> SEQ ID NO 103
<211> LENGTH: 285
<212> TYPE: DNA
<213> ORGANISM: Homo sapiens

<400> SEQUENCE: 103
gtggtcagga caagcccttg ctgtctgcct ggcccagcgc tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacaccca cgctccccca 240
ttgagtggtc agcacccagc aaccccctgg tgatcgtggt cacag 285

<210> SEQ ID NO 104
<211> LENGTH: 285
<212> TYPE: DNA
<213> ORGANISM: Homo sapiens

<400> SEQUENCE: 104
gtggtcagga caagcccttg ctgtctgcct ggcccagcgc tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacaccca cgctccccca 240
ttgagtggtc agcacccagc aaccccctgg tgatcatggt cacag 285

<210> SEQ ID NO 105
<211> LENGTH: 285
<212> TYPE: DNA
<213> ORGANISM: Homo sapiens

<400> SEQUENCE: 105
gtggtcagga caagcccttg ctgtctgcct ggcccagcgc tgtggtgcct cgaggaggac 60
atgtgactct tctgtgtcgc tctcgtcttg ggtttaccat cttcagtctg tacaaagaag 120
atggggtgcc tgtccctgag ctctacaaca aaatattctg gaagagcatc ctcatgggcc 180
ctgtgacccc tgcacacgca gggacctaca gatgtcgggg ttcacaccca cgctccccca 240
ttgagtggtc ggcacccagc aaccccctgg tgatcgtggt cacag 285

<210> SEQ ID NO 106
<211> LENGTH: 294
<212> TYPE: DNA
<213> ORGANISM: Homo sapiens

<400> SEQUENCE: 106
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt caatggaaca ttccaggctg 180
actttcctct gggccctgcc acccacggag ggacctacac atgcttcggc tctctccatg 240
actcacccta tgagtggtca gacccgagtg acccactgct tgtttctgtc acag 294

<210> SEQ ID NO 107
<211> LENGTH: 294
<212> TYPE: DNA
<213> ORGANISM: Homo sapiens

<400> SEQUENCE: 107
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt cgatggaaca ttccaggctg 180
actttcctct gggccctgcc acccacggag ggacctacac atgcttcagc tctctccatg 240
actcacccta tgagtggtca gacccgagtg acccactgct tgtttctgtc acag 294

<210> SEQ ID NO 108
<211> LENGTH: 294
<212> TYPE: DNA
<213> ORGANISM: Homo sapiens

<400> SEQUENCE: 108
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt cgatggaaca ttccaggctg 180
actttcctct gggccctgcc acccacggag ggacctacac atgcttcagc tctctccatg 240
actcacccta tgagtggtca gacccgagtg acccactgct tgtttctgtc acag 294

<210> SEQ ID NO 109
<211> LENGTH: 294
<212> TYPE: DNA
<213> ORGANISM: Homo sapiens

<400> SEQUENCE: 109
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt caatggaaca ttccaggctg 180
actttcctct gggccctgcc acccacggag ggacctacac atgcttcggc tctctccatg 240
actcacccta tgagtggtca gacccgagtg acccactgct tgtttctgtc acag 294

<210> SEQ ID NO 110
<211> LENGTH: 294
<212> TYPE: DNA
<213> ORGANISM: Homo sapiens

<400> SEQUENCE: 110
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt caatggaaca ttccaggctg 180
actttcctct gggccctgcc acccacggag ggacctacac atgcttcggc tctctccatg 240
actcacccta tgagtggtca gacccgagtg acccactgct tgtttctgtc acag 294

<210> SEQ ID NO 111
<211> LENGTH: 294
<212> TYPE: DNA
<213> ORGANISM: Homo sapiens

<400> SEQUENCE: 111
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt caatggaaca ttccaggctg 180
actttcctct gggccctgcc acccacggag ggacctacac atgcttcggc tctctccatg 240
actcacccta tgagtggtca gacccgagtg acccactgct tgtttctgtc acag 294

<210> SEQ ID NO 112
<211> LENGTH: 294
<212> TYPE: DNA
<213> ORGANISM: Homo sapiens

<400> SEQUENCE: 112
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt caatggaaca ttccaggctg 180
actttcctct gggccctgcc acccacggag ggacctacac atgcttcggc tctctccatg 240
actcacccta tgagtggtca gacccgagtg acccactgct tgtttctgtc acag 294

<210> SEQ ID NO 113
<211> LENGTH: 294
<212> TYPE: DNA
<213> ORGANISM: Homo sapiens

<400> SEQUENCE: 113
gtctatttgg gaaaccttca ctctcagccc agccgggccc cacggttcgc acaggagaga 60
acgtgacctt gtcctgcagc tccaggagct catttgacat gtaccatcta tccagggagg 120
ggagggccca tgaacctagg ctccctgcag tgcccagcgt caatggaaca ttccaggctg 180
actttcctct gggccctgcc acccacggag ggacctacac atgcttcggc tctctccatg 240
actcacccta tgagtggtca gacccgagtg acccactgct tgtttctgtc acag 294

<210> SEQ ID NO 114
<211> LENGTH: 8
<212> TYPE: DNA
<213> ORGANISM: Homo sapiens

<400> SEQUENCE: 114 aaggctaa                                                                  8

<210> SEQ ID NO 115
<211> LENGTH: 8
<212> TYPE: DNA
<213> ORGANISM: Homo sapiens

<400> SEQUENCE: 115 atggctaa                                                                  8

<210> SEQ ID NO 116
<211> LENGTH: 29
<212> TYPE: DNA
<213> ORGANISM: Homo sapiens

<400> SEQUENCE: 116
acgttggatg ctgtgatcac gatgtccag                                          29

<210> SEQ ID NO 117
<211> LENGTH: 30
<212> TYPE: DNA
<213> ORGANISM: Homo sapiens

<400> SEQUENCE: 117
acgttggatg gagctcctat gacatgtacc                                         30

<210> SEQ ID NO 118
<211> LENGTH: 30
<212> TYPE: DNA
<213> ORGANISM: Homo sapiens

<400> SEQUENCE: 118
acgttggatg gatgactaag gaccccttgc                                         30

<210> SEQ ID NO 119
<211> LENGTH: 30
<212> TYPE: DNA
<213> ORGANISM: Homo sapiens

<400> SEQUENCE: 119
acgttggatg agaatgtgac cttgtcctgc                                         30

<210> SEQ ID NO 120
<211> LENGTH: 28
<212> TYPE: DNA
<213> ORGANISM: Homo sapiens

<400> SEQUENCE: 120
acgttggatg tgccgaccac tcagtggg                                           28

<210> SEQ ID NO 121
<211> LENGTH: 34
<212> TYPE: DNA
<213> ORGANISM: Homo sapiens

<400> SEQUENCE: 121
acgttggatg gatgaacaag accctcagga ggtg                                    34

<210> SEQ ID NO 122
<211> LENGTH: 30
<212> TYPE: DNA
<213> ORGANISM: Homo sapiens

<400> SEQUENCE: 122
acgttggatg caaggccaat ttctccatcg 30

<210> SEQ ID NO 123
<211> LENGTH: 30
<212> TYPE: DNA
<213> ORGANISM: Homo sapiens

<400> SEQUENCE: 123
acgttggatg tgacagaaac aagcagtggg 30

<210> SEQ ID NO 124
<211> LENGTH: 29
<212> TYPE: DNA
<213> ORGANISM: Homo sapiens

<400> SEQUENCE: 124
acgttggatg cttgggcctc tgagaaggg 29

<210> SEQ ID NO 125
<211> LENGTH: 31
<212> TYPE: DNA
<213> ORGANISM: Homo sapiens

<400> SEQUENCE: 125
acgttggatg agagacagtc atcctgcaat g 31

<210> SEQ ID NO 126
<211> LENGTH: 28
<212> TYPE: DNA
<213> ORGANISM: Homo sapiens

<400> SEQUENCE: 126
acgttggatg gactttgacc actcgtat 28

<210> SEQ ID NO 127
<211> LENGTH: 30
<212> TYPE: DNA
<213> ORGANISM: Homo sapiens

<400> SEQUENCE: 127
acgttggatg atctgttgag ggtctcttgc 30

<210> SEQ ID NO 128
<211> LENGTH: 29
<212> TYPE: DNA
<213> ORGANISM: Homo sapiens

<400> SEQUENCE: 128
acgttggatg ggccgaggag tacctacct 29

<210> SEQ ID NO 129
<211> LENGTH: 30
<212> TYPE: DNA
<213> ORGANISM: Homo sapiens

<400> SEQUENCE: 129
acgttggatg agaagttggc cttggagacc 30

<210> SEQ ID NO 130
<211> LENGTH: 30
<212> TYPE: DNA
<213> ORGANISM: Homo sapiens

<400> SEQUENCE: 130
acgttggatg atgggcagga gacaactttg 30

<210> SEQ ID NO 131
<211> LENGTH: 31
<212> TYPE: DNA
<213> ORGANISM: Homo sapiens

<400> SEQUENCE: 131
acgttggatg aggcccatga acgtaggctc c 31

<210> SEQ ID NO 132
<211> LENGTH: 30
<212> TYPE: DNA
<213> ORGANISM: Homo sapiens

<400> SEQUENCE: 132
acgttggatg gtaatggacc aagagtctgc 30

<210> SEQ ID NO 133
<211> LENGTH: 34
<212> TYPE: DNA
<213> ORGANISM: Homo sapiens

<400> SEQUENCE: 133
acgttggatg gagtccacag aaaaccttcc ctcc 34

<210> SEQ ID NO 134
<211> LENGTH: 30
<212> TYPE: DNA
<213> ORGANISM: Homo sapiens

<400> SEQUENCE: 134
acgttggatg tcatgctata caaagaagac 30

<210> SEQ ID NO 135
<211> LENGTH: 30
<212> TYPE: DNA
<213> ORGANISM: Homo sapiens

<400> SEQUENCE: 135
acgttggatg ggagctgaca actgataggg 30

<210> SEQ ID NO 136
<211> LENGTH: 34
<212> TYPE: DNA
<213> ORGANISM: Homo sapiens

<400> SEQUENCE: 136
acgttggatg aggtcaacgg aacattccag gccg 34

<210> SEQ ID NO 137
<211> LENGTH: 29
<212> TYPE: DNA
<213> ORGANISM: Homo sapiens

<400> SEQUENCE: 137
acgttggatg aactgctatg attagcttc 29

<210> SEQ ID NO 138
<211> LENGTH: 30
<212> TYPE: DNA
<213> ORGANISM: Homo sapiens

<400> SEQUENCE: 138

-continued acgttggatg gagctgcagg acaaggtcac 30

<210> SEQ ID NO 139
<211> LENGTH: 30
<212> TYPE: DNA
<213> ORGANISM: Homo sapiens

<400> SEQUENCE: 139
acgttggatg gatcttggct tagcatttgg 30

<210> SEQ ID NO 140
<211> LENGTH: 28
<212> TYPE: DNA
<213> ORGANISM: Homo sapiens

<400> SEQUENCE: 140
acgttggatg ccacggaggg acctacac 28

<210> SEQ ID NO 141
<211> LENGTH: 30
<212> TYPE: DNA
<213> ORGANISM: Homo sapiens

<400> SEQUENCE: 141
acgttggatg aggacaagcc cttgctgtct 30

<210> SEQ ID NO 142
<211> LENGTH: 31
<212> TYPE: DNA
<213> ORGANISM: Homo sapiens

<400> SEQUENCE: 142
acgttggatg acactttgcg cctcattgga g 31

<210> SEQ ID NO 143
<211> LENGTH: 32
<212> TYPE: DNA
<213> ORGANISM: Homo sapiens

<400> SEQUENCE: 143
acgttggatg gggtttaaca acttcagtct gt 32

<210> SEQ ID NO 144
<211> LENGTH: 29
<212> TYPE: DNA
<213> ORGANISM: Homo sapiens

<400> SEQUENCE: 144
acgttggatg gtctatatga gaaaccttc 29

<210> SEQ ID NO 145
<211> LENGTH: 29
<212> TYPE: DNA
<213> ORGANISM: Homo sapiens

<400> SEQUENCE: 145
acgttggatg aaggccaact tctccatca 29

<210> SEQ ID NO 146
<211> LENGTH: 30
<212> TYPE: DNA
<213> ORGANISM: Homo sapiens

<400> SEQUENCE: 146

-continued acgttggatg gacatgagtc ctctgacctg 30

<210> SEQ ID NO 147
<211> LENGTH: 30
<212> TYPE: DNA
<213> ORGANISM: Homo sapiens

<400> SEQUENCE: 147
acgttggatg gacatgagtc ctctgacctg 30

<210> SEQ ID NO 148
<211> LENGTH: 29
<212> TYPE: DNA
<213> ORGANISM: Homo sapiens

<400> SEQUENCE: 148
acgttggatg ttgaccactc gtagggagc 29

<210> SEQ ID NO 149
<211> LENGTH: 30
<212> TYPE: DNA
<213> ORGANISM: Homo sapiens

<400> SEQUENCE: 149
acgttggatg gagctctgtg acggaaacaa 30

<210> SEQ ID NO 150
<211> LENGTH: 30
<212> TYPE: DNA
<213> ORGANISM: Homo sapiens

<400> SEQUENCE: 150
acgttggatg ctgcttcgtg agacttactt 30

<210> SEQ ID NO 151
<211> LENGTH: 30
<212> TYPE: DNA
<213> ORGANISM: Homo sapiens

<400> SEQUENCE: 151
acgttggatg ggagctgaca actgataggg 30

<210> SEQ ID NO 152
<211> LENGTH: 30
<212> TYPE: DNA
<213> ORGANISM: Homo sapiens

<400> SEQUENCE: 152
acgttggatg acttgacttt gaccactcgt 30

<210> SEQ ID NO 153
<211> LENGTH: 30
<212> TYPE: DNA
<213> ORGANISM: Homo sapiens

<400> SEQUENCE: 153
acgttggatg taaggtggcg cctccttctc 30

<210> SEQ ID NO 154
<211> LENGTH: 30
<212> TYPE: DNA
<213> ORGANISM: Homo sapiens

<400> SEQUENCE: 154
acgttggatg aaggccaact tctccatcgg 30

<210> SEQ ID NO 155
<211> LENGTH: 34
<212> TYPE: DNA
<213> ORGANISM: Homo sapiens

<400> SEQUENCE: 155
acgttggatg gcctggaatg ttccgttgac cttg 34

<210> SEQ ID NO 156
<211> LENGTH: 30
<212> TYPE: DNA
<213> ORGANISM: Homo sapiens

<400> SEQUENCE: 156
acgttggatg tcatgggacc catggaatag 30

<210> SEQ ID NO 157
<211> LENGTH: 30
<212> TYPE: DNA
<213> ORGANISM: Homo sapiens

<400> SEQUENCE: 157
acgttggatg cagtgagcct aagttcaccg 30

<210> SEQ ID NO 158
<211> LENGTH: 30
<212> TYPE: DNA
<213> ORGANISM: Homo sapiens

<400> SEQUENCE: 158
acgttggatg ccctgagctc tacaacagaa 30

<210> SEQ ID NO 159
<211> LENGTH: 28
<212> TYPE: DNA
<213> ORGANISM: Homo sapiens

<400> SEQUENCE: 159
acgttggatg tacacgctgg tatctgtt 28

<210> SEQ ID NO 160
<211> LENGTH: 30
<212> TYPE: DNA
<213> ORGANISM: Homo sapiens

<400> SEQUENCE: 160
acgttggatg gggagctgac aactgatagg 30

<210> SEQ ID NO 161
<211> LENGTH: 29
<212> TYPE: DNA
<213> ORGANISM: Homo sapiens

<400> SEQUENCE: 161
acgttggatg gactttcctc tgggccctg 29

<210> SEQ ID NO 162
<211> LENGTH: 30
<212> TYPE: DNA
<213> ORGANISM: Homo sapiens

<400> SEQUENCE: 162
acgttggatg caagaccctc aggaggtgac 30

<210> SEQ ID NO 163
<211> LENGTH: 30
<212> TYPE: DNA
<213> ORGANISM: Homo sapiens

<400> SEQUENCE: 163
acgttggatg atggagaagt tggccttgga 30

<210> SEQ ID NO 164
<211> LENGTH: 28
<212> TYPE: DNA
<213> ORGANISM: Homo sapiens

<400> SEQUENCE: 164
acgttggatg cagggcccaa ggtcaacg 28

<210> SEQ ID NO 165
<211> LENGTH: 30
<212> TYPE: DNA
<213> ORGANISM: Homo sapiens

<400> SEQUENCE: 165
acgttggatg aggtgacata cgcacagttg 30

<210> SEQ ID NO 166
<211> LENGTH: 30
<212> TYPE: DNA
<213> ORGANISM: Homo sapiens

<400> SEQUENCE: 166
acgttggatg gtaatggacc aagagtctgc 30

<210> SEQ ID NO 167
<211> LENGTH: 30
<212> TYPE: DNA
<213> ORGANISM: Homo sapiens

<400> SEQUENCE: 167
acgttggatg cctgcaatgt tggtcagatg 30

<210> SEQ ID NO 168
<211> LENGTH: 30
<212> TYPE: DNA
<213> ORGANISM: Homo sapiens

<400> SEQUENCE: 168
acgttggatg cactgcgttt tcacacagag 30

<210> SEQ ID NO 169
<211> LENGTH: 30
<212> TYPE: DNA
<213> ORGANISM: Homo sapiens

<400> SEQUENCE: 169
acgttggatg aagagccgaa gcatctgtag 30

<210> SEQ ID NO 170
<211> LENGTH: 31
<212> TYPE: DNA
<213> ORGANISM: Homo sapiens

<400> SEQUENCE: 170

-continued acgttggatg cgggccgagg agtacctacc t 31

<210> SEQ ID NO 171
<211> LENGTH: 33
<212> TYPE: DNA
<213> ORGANISM: Homo sapiens

<400> SEQUENCE: 171
acgttggatg agtgtcctta aacttccctt ctc 33

<210> SEQ ID NO 172
<211> LENGTH: 30
<212> TYPE: DNA
<213> ORGANISM: Homo sapiens

<400> SEQUENCE: 172
acgttggatg tgtgtagttc cctgcatgtg 30

<210> SEQ ID NO 173
<211> LENGTH: 30
<212> TYPE: DNA
<213> ORGANISM: Homo sapiens

<400> SEQUENCE: 173
acgttggatg ccaaggccaa cttctccatc 30

<210> SEQ ID NO 174
<211> LENGTH: 30
<212> TYPE: DNA
<213> ORGANISM: Homo sapiens

<400> SEQUENCE: 174
acgttggatg aagagccgaa gcatctgtag 30

<210> SEQ ID NO 175
<211> LENGTH: 34
<212> TYPE: DNA
<213> ORGANISM: Homo sapiens

<400> SEQUENCE: 175
acgttggatg gatgaaggag aaagaagagg agga 34

<210> SEQ ID NO 176
<211> LENGTH: 32
<212> TYPE: DNA
<213> ORGANISM: Homo sapiens

<400> SEQUENCE: 176
acgttggatg tgggaaacct tctctctcag cc 32

<210> SEQ ID NO 177
<211> LENGTH: 28
<212> TYPE: DNA
<213> ORGANISM: Homo sapiens

<400> SEQUENCE: 177
acgttggatg ctgcgttttc acacagac 28

<210> SEQ ID NO 178
<211> LENGTH: 30
<212> TYPE: DNA
<213> ORGANISM: Homo sapiens

<400> SEQUENCE: 178
acgttggatg gtgacagaaa caagcagtgg 30

<210> SEQ ID NO 179
<211> LENGTH: 28
<212> TYPE: DNA
<213> ORGANISM: Homo sapiens

<400> SEQUENCE: 179
acgttggatg caagacgaga gcgacaca 28

<210> SEQ ID NO 180
<211> LENGTH: 29
<212> TYPE: DNA
<213> ORGANISM: Homo sapiens

<400> SEQUENCE: 180
acgttggatg gtgagtaaca gaaccgtag 29

<210> SEQ ID NO 181
<211> LENGTH: 30
<212> TYPE: DNA
<213> ORGANISM: Homo sapiens

<400> SEQUENCE: 181
acgttggatg tgtgctgggg tcacagggcc 30

<210> SEQ ID NO 182
<211> LENGTH: 30
<212> TYPE: DNA
<213> ORGANISM: Homo sapiens

<400> SEQUENCE: 182
acgttggatg ggacaaggtc acgctctctc 30

<210> SEQ ID NO 183
<211> LENGTH: 30
<212> TYPE: DNA
<213> ORGANISM: Homo sapiens

<400> SEQUENCE: 183
acgttggatg gtgagtaaca gaaccgtagc 30

<210> SEQ ID NO 184
<211> LENGTH: 28
<212> TYPE: DNA
<213> ORGANISM: Homo sapiens

<400> SEQUENCE: 184
acgttggatg ccctgagctc tacaacaa 28

<210> SEQ ID NO 185
<211> LENGTH: 28
<212> TYPE: DNA
<213> ORGANISM: Homo sapiens

<400> SEQUENCE: 185
acgttggatg ccctgagctc tacaacaa 28

<210> SEQ ID NO 186
<211> LENGTH: 30
<212> TYPE: DNA
<213> ORGANISM: Homo sapiens

<400> SEQUENCE: 186

-continued acgttggatg cggttcaggc aggagagaat 30

<210> SEQ ID NO 187
<211> LENGTH: 33
<212> TYPE: DNA
<213> ORGANISM: Homo sapiens

<400> SEQUENCE: 187
acgttggatg gcatcaacgg aacattccag gcc 33

<210> SEQ ID NO 188
<211> LENGTH: 31
<212> TYPE: DNA
<213> ORGANISM: Homo sapiens

<400> SEQUENCE: 188
acgttggatg gtaaccccag acacctgcat g 31

<210> SEQ ID NO 189
<211> LENGTH: 30
<212> TYPE: DNA
<213> ORGANISM: Homo sapiens

<400> SEQUENCE: 189
acgttggatg cctgcaatgt tggtcagatg 30

<210> SEQ ID NO 190
<211> LENGTH: 30
<212> TYPE: DNA
<213> ORGANISM: Homo sapiens

<400> SEQUENCE: 190
acgttggatg cctatgacat gtaccatcta 30

<210> SEQ ID NO 191
<211> LENGTH: 28
<212> TYPE: DNA
<213> ORGANISM: Homo sapiens

<400> SEQUENCE: 191
acgttggatg caagacgaga gcgacaca 28

<210> SEQ ID NO 192
<211> LENGTH: 17
<212> TYPE: DNA
<213> ORGANISM: Homo sapiens

<400> SEQUENCE: 192
cactccccct atcagtt 17

<210> SEQ ID NO 193
<211> LENGTH: 17
<212> TYPE: DNA
<213> ORGANISM: Homo sapiens

<400> SEQUENCE: 193
ccctgcagag aacctac 17

<210> SEQ ID NO 194
<211> LENGTH: 20
<212> TYPE: DNA
<213> ORGANISM: Homo sapiens

<400> SEQUENCE: 194
aatagttgac ctgggaaccc 20

<210> SEQ ID NO 195
<211> LENGTH: 21
<212> TYPE: DNA
<213> ORGANISM: Homo sapiens

<400> SEQUENCE: 195
ggatagatgg taaatgtcaa a 21

<210> SEQ ID NO 196
<211> LENGTH: 17
<212> TYPE: DNA
<213> ORGANISM: Homo sapiens

<400> SEQUENCE: 196
tggaacagtt tcctcat 17

<210> SEQ ID NO 197
<211> LENGTH: 17
<212> TYPE: DNA
<213> ORGANISM: Homo sapiens

<400> SEQUENCE: 197
gcctctgaga agggcga 17

<210> SEQ ID NO 198
<211> LENGTH: 21
<212> TYPE: DNA
<213> ORGANISM: Homo sapiens

<400> SEQUENCE: 198
ctgtaggtcc ctgcaagggc a 21

<210> SEQ ID NO 199
<211> LENGTH: 17
<212> TYPE: DNA
<213> ORGANISM: Homo sapiens

<400> SEQUENCE: 199
ccacggaggg acctaca 17

<210> SEQ ID NO 200
<211> LENGTH: 19
<212> TYPE: DNA
<213> ORGANISM: Homo sapiens

<400> SEQUENCE: 200
cactgcgttt tcacacaga 19

<210> SEQ ID NO 201
<211> LENGTH: 21
<212> TYPE: DNA
<213> ORGANISM: Homo sapiens

<400> SEQUENCE: 201
gaagtgctca aacatgacat c 21

<210> SEQ ID NO 202
<211> LENGTH: 17
<212> TYPE: DNA
<213> ORGANISM: Homo sapiens

<400> SEQUENCE: 202
atgcttcggc tctttcc 17

<210> SEQ ID NO 203
<211> LENGTH: 17
<212> TYPE: DNA
<213> ORGANISM: Homo sapiens

<400> SEQUENCE: 203
cacagttgga tcactgc 17

<210> SEQ ID NO 204
<211> LENGTH: 18
<212> TYPE: DNA
<213> ORGANISM: Homo sapiens

<400> SEQUENCE: 204
gaaacagaac agcgaata 18

<210> SEQ ID NO 205
<211> LENGTH: 17
<212> TYPE: DNA
<213> ORGANISM: Homo sapiens

<400> SEQUENCE: 205
gcacagagag gggaagt 17

<210> SEQ ID NO 206
<211> LENGTH: 18
<212> TYPE: DNA
<213> ORGANISM: Homo sapiens

<400> SEQUENCE: 206
gaggcccaag acaccccc 18

<210> SEQ ID NO 207
<211> LENGTH: 17
<212> TYPE: DNA
<213> ORGANISM: Homo sapiens

<400> SEQUENCE: 207
ctccgtgggt ggcaggg 17

<210> SEQ ID NO 208
<211> LENGTH: 19
<212> TYPE: DNA
<213> ORGANISM: Homo sapiens

<400> SEQUENCE: 208
cgctattcgc tgttctgtt 19

<210> SEQ ID NO 209
<211> LENGTH: 17
<212> TYPE: DNA
<213> ORGANISM: Homo sapiens

<400> SEQUENCE: 209
cttctgattt caccagg 17

<210> SEQ ID NO 210
<211> LENGTH: 17
<212> TYPE: DNA
<213> ORGANISM: Homo sapiens

<400> SEQUENCE: 210
agggctcatg ttgaagc 17

<210> SEQ ID NO 211
<211> LENGTH: 20
<212> TYPE: DNA
<213> ORGANISM: Homo sapiens

<400> SEQUENCE: 211
cttgcaggaa cctacagatg 20

<210> SEQ ID NO 212
<211> LENGTH: 17
<212> TYPE: DNA
<213> ORGANISM: Homo sapiens

<400> SEQUENCE: 212
catctgtagg ttcctcc 17

<210> SEQ ID NO 213
<211> LENGTH: 17
<212> TYPE: DNA
<213> ORGANISM: Homo sapiens

<400> SEQUENCE: 213
gaatgtgcag gtgtctg 17

<210> SEQ ID NO 214
<211> LENGTH: 17
<212> TYPE: DNA
<213> ORGANISM: Homo sapiens

<400> SEQUENCE: 214
ctctctcagc ccagccg 17

<210> SEQ ID NO 215
<211> LENGTH: 17
<212> TYPE: DNA
<213> ORGANISM: Homo sapiens

<400> SEQUENCE: 215
cttctcagag gcccaag 17

<210> SEQ ID NO 216
<211> LENGTH: 18
<212> TYPE: DNA
<213> ORGANISM: Homo sapiens

<400> SEQUENCE: 216
gtgagtcatg gagagagc 18

<210> SEQ ID NO 217
<211> LENGTH: 21
<212> TYPE: DNA
<213> ORGANISM: Homo sapiens

<400> SEQUENCE: 217
gtcctcctcg aggcaccaca g 21

<210> SEQ ID NO 218
<211> LENGTH: 17
<212> TYPE: DNA
<213> ORGANISM: Homo sapiens

<400> SEQUENCE: 218

```
gaccgatgga gaagttg                                                  17

<210> SEQ ID NO 219
<211> LENGTH: 19
<212> TYPE: DNA
<213> ORGANISM: Homo sapiens

<400> SEQUENCE: 219

attctgttgt agagctcag                                                19

<210> SEQ ID NO 220
<211> LENGTH: 17
<212> TYPE: DNA
<213> ORGANISM: Homo sapiens

<400> SEQUENCE: 220

cacgctctct cctgcca                                                  17

<210> SEQ ID NO 221
<211> LENGTH: 19
<212> TYPE: DNA
<213> ORGANISM: Homo sapiens

<400> SEQUENCE: 221

ggtccctgcc aggtcttgc                                                19

<210> SEQ ID NO 222
<211> LENGTH: 17
<212> TYPE: DNA
<213> ORGANISM: Homo sapiens

<400> SEQUENCE: 222

gcaaccccct ggtgatc                                                  17

<210> SEQ ID NO 223
<211> LENGTH: 20
<212> TYPE: DNA
<213> ORGANISM: Homo sapiens

<400> SEQUENCE: 223

cgctccccca ttgagtggtc                                               20

<210> SEQ ID NO 224
<211> LENGTH: 17
<212> TYPE: DNA
<213> ORGANISM: Homo sapiens

<400> SEQUENCE: 224

ccttgtcctg cagctcc                                                  17

<210> SEQ ID NO 225
<211> LENGTH: 17
<212> TYPE: DNA
<213> ORGANISM: Homo sapiens

<400> SEQUENCE: 225

tcggctcttt ccgtgac                                                  17

<210> SEQ ID NO 226
<211> LENGTH: 20
<212> TYPE: DNA
<213> ORGANISM: Homo sapiens

<400> SEQUENCE: 226
```

tctccttcat cgctggtgct 20

<210> SEQ ID NO 227
<211> LENGTH: 17
<212> TYPE: DNA
<213> ORGANISM: Homo sapiens

<400> SEQUENCE: 227
catgatgggg tctccaa 17

<210> SEQ ID NO 228
<211> LENGTH: 19
<212> TYPE: DNA
<213> ORGANISM: Homo sapiens

<400> SEQUENCE: 228
caacggaaca ttccaggcc 19

<210> SEQ ID NO 229
<211> LENGTH: 17
<212> TYPE: DNA
<213> ORGANISM: Homo sapiens

<400> SEQUENCE: 229
agcaagggct tgtcctg 17

<210> SEQ ID NO 230
<211> LENGTH: 19
<212> TYPE: DNA
<213> ORGANISM: Homo sapiens

<400> SEQUENCE: 230
ctgtgatcac gatgtccag 19

<210> SEQ ID NO 231
<211> LENGTH: 20
<212> TYPE: DNA
<213> ORGANISM: Homo sapiens

<400> SEQUENCE: 231
gagctcctat gacatgtacc 20

<210> SEQ ID NO 232
<211> LENGTH: 20
<212> TYPE: DNA
<213> ORGANISM: Homo sapiens

<400> SEQUENCE: 232
gatgactaag gaccccttgc 20

<210> SEQ ID NO 233
<211> LENGTH: 20
<212> TYPE: DNA
<213> ORGANISM: Homo sapiens

<400> SEQUENCE: 233
agaatgtgac cttgtcctgc 20

<210> SEQ ID NO 234
<211> LENGTH: 18
<212> TYPE: DNA
<213> ORGANISM: Homo sapiens

<400> SEQUENCE: 234
tgccgaccac tcagtggg 18

<210> SEQ ID NO 235
<211> LENGTH: 24
<212> TYPE: DNA
<213> ORGANISM: Homo sapiens

<400> SEQUENCE: 235
gatgaacaag accctcagga ggtg 24

<210> SEQ ID NO 236
<211> LENGTH: 20
<212> TYPE: DNA
<213> ORGANISM: Homo sapiens

<400> SEQUENCE: 236
caaggccaat ttctccatcg 20

<210> SEQ ID NO 237
<211> LENGTH: 20
<212> TYPE: DNA
<213> ORGANISM: Homo sapiens

<400> SEQUENCE: 237
tgacagaaac aagcagtggg 20

<210> SEQ ID NO 238
<211> LENGTH: 19
<212> TYPE: DNA
<213> ORGANISM: Homo sapiens

<400> SEQUENCE: 238
cttgggcctc tgagaaggg 19

<210> SEQ ID NO 239
<211> LENGTH: 21
<212> TYPE: DNA
<213> ORGANISM: Homo sapiens

<400> SEQUENCE: 239
agagacagtc atcctgcaat g 21

<210> SEQ ID NO 240
<211> LENGTH: 20
<212> TYPE: DNA
<213> ORGANISM: Homo sapiens

<400> SEQUENCE: 240
ggagctgaca actgataggg 20

<210> SEQ ID NO 241
<211> LENGTH: 18
<212> TYPE: DNA
<213> ORGANISM: Homo sapiens

<400> SEQUENCE: 241
gactttgacc actcgtat 18

<210> SEQ ID NO 242
<211> LENGTH: 20
<212> TYPE: DNA
<213> ORGANISM: Homo sapiens

<400> SEQUENCE: 242
atctgttgag ggtctcttgc 20

<210> SEQ ID NO 243
<211> LENGTH: 19
<212> TYPE: DNA
<213> ORGANISM: Homo sapiens

<400> SEQUENCE: 243
ggccgaggag tacctacct 19

<210> SEQ ID NO 244
<211> LENGTH: 20
<212> TYPE: DNA
<213> ORGANISM: Homo sapiens

<400> SEQUENCE: 244
agaagttggc cttggagacc 20

<210> SEQ ID NO 245
<211> LENGTH: 20
<212> TYPE: DNA
<213> ORGANISM: Homo sapiens

<400> SEQUENCE: 245
atgggcagga gacaactttg 20

<210> SEQ ID NO 246
<211> LENGTH: 21
<212> TYPE: DNA
<213> ORGANISM: Homo sapiens

<400> SEQUENCE: 246
aggcccatga acgtaggctc c 21

<210> SEQ ID NO 247
<211> LENGTH: 20
<212> TYPE: DNA
<213> ORGANISM: Homo sapiens

<400> SEQUENCE: 247
gtaatggacc aagagtctgc 20

<210> SEQ ID NO 248
<211> LENGTH: 24
<212> TYPE: DNA
<213> ORGANISM: Homo sapiens

<400> SEQUENCE: 248
gagtccacag aaaaccttcc ctcc 24

<210> SEQ ID NO 249
<211> LENGTH: 24
<212> TYPE: DNA
<213> ORGANISM: Homo sapiens

<400> SEQUENCE: 249
aggtcaacgg aacattccag gccg 24

<210> SEQ ID NO 250
<211> LENGTH: 19
<212> TYPE: DNA
<213> ORGANISM: Homo sapiens

<400> SEQUENCE: 250
aactgctatg attagcttc 19

<210> SEQ ID NO 251
<211> LENGTH: 20
<212> TYPE: DNA
<213> ORGANISM: Homo sapiens

<400> SEQUENCE: 251
gagctgcagg acaaggtcac 20

<210> SEQ ID NO 252
<211> LENGTH: 20
<212> TYPE: DNA
<213> ORGANISM: Homo sapiens

<400> SEQUENCE: 252
tcatgctata caaagaagac 20

<210> SEQ ID NO 253
<211> LENGTH: 20
<212> TYPE: DNA
<213> ORGANISM: Homo sapiens

<400> SEQUENCE: 253
gatcttggct tagcatttgg 20

<210> SEQ ID NO 254
<211> LENGTH: 18
<212> TYPE: DNA
<213> ORGANISM: Homo sapiens

<400> SEQUENCE: 254
ccacggaggg acctacac 18

<210> SEQ ID NO 255
<211> LENGTH: 20
<212> TYPE: DNA
<213> ORGANISM: Homo sapiens

<400> SEQUENCE: 255
aggacaagcc cttgctgtct 20

<210> SEQ ID NO 256
<211> LENGTH: 21
<212> TYPE: DNA
<213> ORGANISM: Homo sapiens

<400> SEQUENCE: 256
acactttgcg cctcattgga g 21

<210> SEQ ID NO 257
<211> LENGTH: 22
<212> TYPE: DNA
<213> ORGANISM: Homo sapiens

<400> SEQUENCE: 257
gggtttaaca acttcagtct gt 22

<210> SEQ ID NO 258
<211> LENGTH: 19
<212> TYPE: DNA
<213> ORGANISM: Homo sapiens

<400> SEQUENCE: 258
gtctatatga gaaaccttc 19

<210> SEQ ID NO 259
<211> LENGTH: 19
<212> TYPE: DNA
<213> ORGANISM: Homo sapiens

<400> SEQUENCE: 259
aaggccaact tctccatca 19

<210> SEQ ID NO 260
<211> LENGTH: 20
<212> TYPE: DNA
<213> ORGANISM: Homo sapiens

<400> SEQUENCE: 260
gacatgagtc ctctgacctg 20

<210> SEQ ID NO 261
<211> LENGTH: 20
<212> TYPE: DNA
<213> ORGANISM: Homo sapiens

<400> SEQUENCE: 261
gacatgagtc ctctgacctg 20

<210> SEQ ID NO 262
<211> LENGTH: 19
<212> TYPE: DNA
<213> ORGANISM: Homo sapiens

<400> SEQUENCE: 262
ttgaccactc gtagggagc 19

<210> SEQ ID NO 263
<211> LENGTH: 20
<212> TYPE: DNA
<213> ORGANISM: Homo sapiens

<400> SEQUENCE: 263
taaggtggcg cctccttctc 20

<210> SEQ ID NO 264
<211> LENGTH: 20
<212> TYPE: DNA
<213> ORGANISM: Homo sapiens

<400> SEQUENCE: 264
gagctctgtg acggaaacaa 20

<210> SEQ ID NO 265
<211> LENGTH: 20
<212> TYPE: DNA
<213> ORGANISM: Homo sapiens

<400> SEQUENCE: 265
ctgcttcgtg agacttactt 20

<210> SEQ ID NO 266
<211> LENGTH: 20
<212> TYPE: DNA
<213> ORGANISM: Homo sapiens

<400> SEQUENCE: 266
ggagctgaca actgataggg 20

<210> SEQ ID NO 267
<211> LENGTH: 20
<212> TYPE: DNA
<213> ORGANISM: Homo sapiens

<400> SEQUENCE: 267
acttgacttt gaccactcgt 20

<210> SEQ ID NO 268
<211> LENGTH: 20
<212> TYPE: DNA
<213> ORGANISM: Homo sapiens

<400> SEQUENCE: 268
aaggccaact tctccatcgg 20

<210> SEQ ID NO 269
<211> LENGTH: 24
<212> TYPE: DNA
<213> ORGANISM: Homo sapiens

<400> SEQUENCE: 269
gcctggaatg ttccgttgac cttg 24

<210> SEQ ID NO 270
<211> LENGTH: 20
<212> TYPE: DNA
<213> ORGANISM: Homo sapiens

<400> SEQUENCE: 270
tcatgggacc catggaatag 20

<210> SEQ ID NO 271
<211> LENGTH: 20
<212> TYPE: DNA
<213> ORGANISM: Homo sapiens

<400> SEQUENCE: 271
cagtgagcct aagttcaccg 20

<210> SEQ ID NO 272
<211> LENGTH: 20
<212> TYPE: DNA
<213> ORGANISM: Homo sapiens

<400> SEQUENCE: 272
ccctgagctc tacaacagaa 20

<210> SEQ ID NO 273
<211> LENGTH: 18
<212> TYPE: DNA
<213> ORGANISM: Homo sapiens

<400> SEQUENCE: 273
tacacgctgg tatctgtt 18

<210> SEQ ID NO 274
<211> LENGTH: 20
<212> TYPE: DNA
<213> ORGANISM: Homo sapiens

<400> SEQUENCE: 274
gggagctgac aactgatagg 20

<210> SEQ ID NO 275
<211> LENGTH: 19
<212> TYPE: DNA
<213> ORGANISM: Homo sapiens

<400> SEQUENCE: 275
gactttcctc tgggccctg 19

<210> SEQ ID NO 276
<211> LENGTH: 20
<212> TYPE: DNA
<213> ORGANISM: Homo sapiens

<400> SEQUENCE: 276
caagaccctc aggaggtgac 20

<210> SEQ ID NO 277
<211> LENGTH: 20
<212> TYPE: DNA
<213> ORGANISM: Homo sapiens

<400> SEQUENCE: 277
atggagaagt tggccttgga 20

<210> SEQ ID NO 278
<211> LENGTH: 20
<212> TYPE: DNA
<213> ORGANISM: Homo sapiens

<400> SEQUENCE: 278
ccaaggccaa cttctccatc 20

<210> SEQ ID NO 279
<211> LENGTH: 18
<212> TYPE: DNA
<213> ORGANISM: Homo sapiens

<400> SEQUENCE: 279
cagggcccaa ggtcaacg 18

<210> SEQ ID NO 280
<211> LENGTH: 20
<212> TYPE: DNA
<213> ORGANISM: Homo sapiens

<400> SEQUENCE: 280
aggtgacata cgcacagttg 20

<210> SEQ ID NO 281
<211> LENGTH: 20
<212> TYPE: DNA
<213> ORGANISM: Homo sapiens

<400> SEQUENCE: 281
gtaatggacc aagagtctgc 20

<210> SEQ ID NO 282
<211> LENGTH: 20
<212> TYPE: DNA
<213> ORGANISM: Homo sapiens

<400> SEQUENCE: 282
cctgcaatgt tggtcagatg 20

<210> SEQ ID NO 283
<211> LENGTH: 20
<212> TYPE: DNA
<213> ORGANISM: Homo sapiens

<400> SEQUENCE: 283
cactgcgttt tcacacagag 20

<210> SEQ ID NO 284
<211> LENGTH: 20
<212> TYPE: DNA
<213> ORGANISM: Homo sapiens

<400> SEQUENCE: 284
aagagccgaa gcatctgtag 20

<210> SEQ ID NO 285
<211> LENGTH: 21
<212> TYPE: DNA
<213> ORGANISM: Homo sapiens

<400> SEQUENCE: 285
cgggccgagg agtacctacc t 21

<210> SEQ ID NO 286
<211> LENGTH: 23
<212> TYPE: DNA
<213> ORGANISM: Homo sapiens

<400> SEQUENCE: 286
agtgtcctta aacttccctt ctc 23

<210> SEQ ID NO 287
<211> LENGTH: 20
<212> TYPE: DNA
<213> ORGANISM: Homo sapiens

<400> SEQUENCE: 287
aagagccgaa gcatctgtag 20

<210> SEQ ID NO 288
<211> LENGTH: 24
<212> TYPE: DNA
<213> ORGANISM: Homo sapiens

<400> SEQUENCE: 288
gatgaaggag aaagaagagg agga 24

<210> SEQ ID NO 289
<211> LENGTH: 22
<212> TYPE: DNA
<213> ORGANISM: Homo sapiens

<400> SEQUENCE: 289
tgggaaacct tctctctcag cc 22

<210> SEQ ID NO 290
<211> LENGTH: 20
<212> TYPE: DNA
<213> ORGANISM: Homo sapiens

<400> SEQUENCE: 290
tgtgtagttc cctgcatgtg 20

<210> SEQ ID NO 291
<211> LENGTH: 18
<212> TYPE: DNA
<213> ORGANISM: Homo sapiens

<400> SEQUENCE: 291
ctgcgttttc acacagac 18

<210> SEQ ID NO 292
<211> LENGTH: 20
<212> TYPE: DNA
<213> ORGANISM: Homo sapiens

<400> SEQUENCE: 292
gtgacagaaa caagcagtgg 20

<210> SEQ ID NO 293
<211> LENGTH: 18
<212> TYPE: DNA
<213> ORGANISM: Homo sapiens

<400> SEQUENCE: 293
caagacgaga gcgacaca 18

<210> SEQ ID NO 294
<211> LENGTH: 19
<212> TYPE: DNA
<213> ORGANISM: Homo sapiens

<400> SEQUENCE: 294
gtgagtaaca gaaccgtag 19

<210> SEQ ID NO 295
<211> LENGTH: 20
<212> TYPE: DNA
<213> ORGANISM: Homo sapiens

<400> SEQUENCE: 295
tgtgctgggg tcacagggcc 20

<210> SEQ ID NO 296
<211> LENGTH: 20
<212> TYPE: DNA
<213> ORGANISM: Homo sapiens

<400> SEQUENCE: 296
ggacaaggtc acgctctctc 20

<210> SEQ ID NO 297
<211> LENGTH: 20
<212> TYPE: DNA
<213> ORGANISM: Homo sapiens

<400> SEQUENCE: 297
gtgagtaaca gaaccgtagc 20

<210> SEQ ID NO 298
<211> LENGTH: 18
<212> TYPE: DNA
<213> ORGANISM: Homo sapiens

<400> SEQUENCE: 298

-continued ccctgagctc tacaacaa 18

<210> SEQ ID NO 299
<211> LENGTH: 18
<212> TYPE: DNA
<213> ORGANISM: Homo sapiens

<400> SEQUENCE: 299
ccctgagctc tacaacaa 18

<210> SEQ ID NO 300
<211> LENGTH: 20
<212> TYPE: DNA
<213> ORGANISM: Homo sapiens

<400> SEQUENCE: 300
cggttcaggc aggagagaat 20

<210> SEQ ID NO 301
<211> LENGTH: 18
<212> TYPE: DNA
<213> ORGANISM: Homo sapiens

<400> SEQUENCE: 301
caagacgaga gcgacaca 18

<210> SEQ ID NO 302
<211> LENGTH: 23
<212> TYPE: DNA
<213> ORGANISM: Homo sapiens

<400> SEQUENCE: 302
gcatcaacgg aacattccag gcc 23

<210> SEQ ID NO 303
<211> LENGTH: 21
<212> TYPE: DNA
<213> ORGANISM: Homo sapiens

<400> SEQUENCE: 303
gtaaccccag acacctgcat g 21

<210> SEQ ID NO 304
<211> LENGTH: 20
<212> TYPE: DNA
<213> ORGANISM: Homo sapiens

<400> SEQUENCE: 304
cctgcaatgt tggtcagatg 20

<210> SEQ ID NO 305
<211> LENGTH: 20
<212> TYPE: DNA
<213> ORGANISM: Homo sapiens

<400> SEQUENCE: 305
cctatgacat gtaccatcta 20